US011661418B2

(12) United States Patent
Cutshall et al.

(10) Patent No.: US 11,661,418 B2
(45) Date of Patent: May 30, 2023

(54) MASP-2 INHIBITORS AND METHODS OF USE

(71) Applicant: Omeros Corporation, Seattle, WA (US)

(72) Inventors: Neil S. Cutshall, Snohomish, WA (US); Jennifer Lynn Gage, Kenmore, WA (US); Sara Rebecca Goldstein, Seattle, WA (US); Santosh Kumar Keshipeddy, Bellevue, WA (US); Do Yeon Kwon, Seattle, WA (US); Robert Huerta Lemus, Seattle, WA (US); Thomas L. Little, Seattle, WA (US); Markus Metz, Bellevue, WA (US); Peter Kurt Nollert Von Specht, Bainbridge Island, WA (US); Loren Michael Price, Seattle, WA (US); Jennifer Tsoung, Seattle, WA (US)

(73) Assignee: OMEROS CORPORATION, Seattle, WA (US)

( * ) Notice: Subject to any disclaimer, the term of this patent is extended or adjusted under 35 U.S.C. 154(b) by 0 days.

(21) Appl. No.: 17/112,887

(22) Filed: Dec. 4, 2020

(65) Prior Publication Data

US 2021/0171512 A1    Jun. 10, 2021

Related U.S. Application Data

(60) Provisional application No. 62/943,622, filed on Dec. 4, 2019.

(51) Int. Cl.
| | | |
|---|---|---|
| *C07D 413/12* | (2006.01) | |
| *C07D 211/60* | (2006.01) | |
| *C07D 401/06* | (2006.01) | |
| *C07D 401/14* | (2006.01) | |
| *C07D 409/12* | (2006.01) | |
| *C07F 9/6561* | (2006.01) | |

(52) U.S. Cl.
CPC .......... *C07D 413/12* (2013.01); *C07D 211/60* (2013.01); *C07D 401/06* (2013.01); *C07D 401/14* (2013.01); *C07D 409/12* (2013.01); *C07F 9/6561* (2013.01)

(58) Field of Classification Search
CPC ................ C07D 413/12; C07D 211/60; C07D 401/06; C07D 401/14; C07D 409/12; C07F 9/6561
See application file for complete search history.

(56) References Cited

U.S. PATENT DOCUMENTS

| | | |
|---|---|---|
| 6,653,316 B1 | 11/2003 | South et al. |
| 7,015,230 B1 | 3/2006 | South et al. |
| 7,919,094 B2 | 4/2011 | Schwaeble et al. |
| 8,652,477 B2 | 2/2014 | Schwaeble et al. |
| 8,840,893 B2 | 9/2014 | Schwaeble et al. |
| 8,889,712 B2 | 11/2014 | Borzilleri et al. |
| 8,951,522 B2 | 2/2015 | Demopulos et al. |
| 9,011,860 B2 | 4/2015 | Dudler et al. |
| 9,475,885 B2 | 10/2016 | Dudler et al. |
| 9,644,035 B2 | 5/2017 | Demopulos et al. |
| 2013/0266560 A1 | 10/2013 | Demopulos et al. |
| 2013/0344073 A1 | 12/2013 | Schwaeble et al. |
| 2015/0166675 A1 | 6/2015 | Demopulos et al. |
| 2015/0315141 A1 | 11/2015 | Chobanian et al. |
| 2017/0137537 A1 | 5/2017 | Demopulos et al. |
| 2017/0166660 A1 | 6/2017 | Schwaeble et al. |
| 2017/0189525 A1 | 7/2017 | Brunskill et al. |
| 2017/0253667 A1 | 9/2017 | Brunskill et al. |
| 2017/0267781 A1 | 9/2017 | Demopulos et al. |
| 2017/0283508 A1 | 10/2017 | Demopulos et al. |
| 2018/0105604 A1 | 4/2018 | Brunskill et al. |
| 2021/0171461 A1 | 6/2021 | Cutshall et al. |
| 2021/0171531 A1 | 6/2021 | Cicirelli et al. |
| 2021/0179612 A1 | 6/2021 | Cutshall et al. |

FOREIGN PATENT DOCUMENTS

| | | | |
|---|---|---|---|
| WO | WO 1994/29336 A1 | 12/1994 | |
| WO | WO 95/23609 | 9/1995 | |
| WO | 99/61442 A1 | 12/1999 | |
| WO | WO 2000/55188 A1 | 9/2000 | |
| WO | 00/69834 A1 | 11/2000 | |
| WO | WO 2002/50056 A1 | 6/2002 | |
| WO | 03/029224 A1 | 4/2003 | |
| WO | 2006/101860 A1 | 9/2006 | |
| WO | 2008/085608 A1 | 7/2008 | |
| WO | 2012/151481 A1 | 11/2012 | |
| WO | 2017/173290 A1 | 10/2017 | |
| WO | 2018/045054 A1 | 3/2018 | |
| WO | 2019/036460 A1 | 2/2019 | |
| WO | WO 2019/055590 A1 | 3/2019 | |
| WO | 2019/186164 A1 | 10/2019 | |
| WO | WO-2019186164 A1 * | 10/2019 | ............. A61K 31/40 |

(Continued)

OTHER PUBLICATIONS

2021/0171461, Jun. 10, 2021.
2021/0171531, Jun. 10, 2021.
2021/0179612, Jun. 17, 2021.
Ambrus et al., "Natural Substrates and Inhibitors of Mannan-Binding Lectin-Associated Serine Protease-1 and -2: A Study on Recombinant Catalytic Fragments," *J. Immunol.* 170:1374-1382, 2003.
Berge et al., "Pharmaceutical salts," *J. Pharm. Sci.* 66(1):1-19, Jan. 1977.
Berthoux et al., "Predicting the Risk for Dialysis or Death in IgA Nephropathy," *J. Am. Soc. Nephrol.* 22:752-761, 2011.
Goto et al., "A scoring system to predict renal outcome in IgA nephropathy: a nationwide 10-year prospective cohort study," *Nephrol. Dial. Transplant.* 24:3068-3074, Jun. 10, 2009.

(Continued)

*Primary Examiner* — Daniel R Carcanague
*Assistant Examiner* — Gillian A Hutter
(74) *Attorney, Agent, or Firm* — Christensen O'Connor Johnson Kindness

(57) ABSTRACT

The present disclosure provides, inter alia, compounds with MASP-2 inhibitory activity, compositions of such compounds, and methods of making and using such compounds.

21 Claims, No Drawings

Specification includes a Sequence Listing.

(56) References Cited

FOREIGN PATENT DOCUMENTS

| WO | 2019/211585 A1 | 11/2019 | | |
|---|---|---|---|---|
| WO | 2019/231933 A2 | 12/2019 | | |
| WO | WO-2019231933 A2 | * | 12/2019 | ........... A61K 31/397 |

OTHER PUBLICATIONS

Ho et al., "Blood and Marrow Transplant Clinical Trials Network Toxicity Committee Consensus Summary: Thrombotic Microangiopathy after Hematopoietic Stem Cell Transplantation," *Biology of Blood and Marrow Transplantation* 11:571-575, 2005.

Kozarcanin et al., "The lectin complement pathway serine proteases (MASPs) represent a possible crossroad between the coagulation and complement system in thromboinflammation," *Journal of Thrombosis & Haemostasis* 14:531-545, 2015.

Lange et al., "Orally active thrombin inhibitors. Part 2: Optimization of the P2-moiety," *Biorganic & Medicinal Chemistry Letters* 16:2648-2653, Feb. 3, 2006.

Noris et al., "Genetic Atypical Hemolytic-Uremic Syndrome," *GeneReviews®*, eds. Adam et al., University of Washington, Seattle, WA, Nov. 16, 2007, 32 pages.

Parlow et al., "Design, Parallel Synthesis, and Crystal Structures of Pyrazinone Antithrombotics as Selective Inhibitors of the Tissue Factor VIIa Complex," *Journal of Medicinal Chemistry* 46(19):4050-4062, 2003.

Peterlin-Masic et al., "Metabolism-Directed Optimisation of Antithrombotics: The Prodrug Principle," *Curr. Pharm. Des.* 12(1):73-91, 2006.

Pétursson, "Protecting Groups in Carbohydrate Chemistry," *Journal of Chemical Education* 74(11):1297, Nov. 1997.

Rambaldi et al., "Endothelial injury and thrombotic microangiopathy in COVID-19: Treatment with the lectin-pathway inhibitor narsoplimab," *Immunobiology* 225(152001):1-10, 2020.

Reich et al., "Remission of Proteinuria Improves Prognosis in IgA Nephropathy," *J. Am. Soc. Nephrol.* 18:3177-3183, 2007.

Ricklin et al., "Complement—a key system for immune surveillance and homeostasis," *Nat. Immunol.* 11(9):785-797, Sep. 2010.

Sanderson et al., "Azaindoles: Moderately Basic P1 Groups for Enhancing the Selectivity of Thrombin Inhibitors," *Bioorganic & Medicinal Chemistry Letters* 13:795-798, 2003.

Schwaeble et al., "Targeting of mannan-binding lectin-associated serine protease-2 confers protection from myocardial and gastrointestinal ischemia/reperfusion injury," *PNAS* 108(18):7523-7528, May 3, 2011.

Staas et al., "Discovery of potent, selective 4-fluoroproline-based thrombin inhibitors with improved metabolic stability," *Bioorganic & Medicinal Chemistry* 14(20):6900-6916, Jul. 25, 2006.

Trost et al., eds., "Comprehensive Organic Synthesis: Selectivity, Strategy & Efficiency in Modern Organic Chemistry" vol. 1, Pergamon Press, Oxford, United Kingdom, 1991.

Vomp-Jensen et al., "Distinct Pathways of Mannan-Binding Lectin (MBL)- and C1-Complex Autoactivation Revealed by Reconstitution of MBL with Recombinant MBL-Associated Serine Protease-2," *J. Immunol.* 165(4):2093-2100, 2000.

Wyatt et al., "IgA Nephropathy," *N. Engl. J. Med.* 368(25):2402-2414, Jun. 20, 2013.

Zipfel et al., "Deletion of Complement Factor H-Related Genes CFHR1 and CFHR3 Is Associated with Atypical Hemolytic Uremic Syndrome," *PLoS Genet.* 3(3):0387-0392, e41, Mar. 2007.

Ronn, et al., "Exploration of acyl sulfonamides as carboxylic acid replacements in protease inhibitors of the hepatitis C virus full-length NS3," *Biorganic & Medicinal Chemistry*, 14: 544-559 (2006).

Extended European Search Report, dated Mar. 14, 2022 for PCT/US2019/034220.

* cited by examiner

SEQUENCE LISTING

```
<160> NUMBER OF SEQ ID NOS: 1

<210> SEQ ID NO 1
<211> LENGTH: 686
<212> TYPE: PRT
<213> ORGANISM: Homo sapiens

<400> SEQUENCE: 1

Met Arg Leu Leu Thr Leu Leu Gly Leu Leu Cys Gly Ser Val Ala Thr
1               5                   10                  15

Pro Leu Gly Pro Lys Trp Pro Glu Pro Val Phe Gly Arg Leu Ala Ser
            20                  25                  30

Pro Gly Phe Pro Gly Glu Tyr Ala Asn Asp Gln Glu Arg Arg Trp Thr
        35                  40                  45

Leu Thr Ala Pro Pro Gly Tyr Arg Leu Arg Leu Tyr Phe Thr His Phe
    50                  55                  60

Asp Leu Glu Leu Ser His Leu Cys Glu Tyr Asp Phe Val Lys Leu Ser
65                  70                  75                  80
```

-continued

```
Ser Gly Ala Lys Val Leu Ala Thr Leu Cys Gly Gln Glu Ser Thr Asp
            85                  90                  95

Thr Glu Arg Ala Pro Gly Lys Asp Thr Phe Tyr Ser Leu Gly Ser Ser
            100                 105                 110

Leu Asp Ile Thr Phe Arg Ser Asp Tyr Ser Asn Glu Lys Pro Phe Thr
            115                 120                 125

Gly Phe Glu Ala Phe Tyr Ala Ala Glu Asp Ile Asp Glu Cys Gln Val
            130                 135                 140

Ala Pro Gly Glu Ala Pro Thr Cys Asp His His Cys His Asn His Leu
145                 150                 155                 160

Gly Gly Phe Tyr Cys Ser Cys Arg Ala Gly Tyr Val Leu His Arg Asn
            165                 170                 175

Lys Arg Thr Cys Ser Ala Leu Cys Ser Gly Gln Val Phe Thr Gln Arg
            180                 185                 190

Ser Gly Glu Leu Ser Ser Pro Glu Tyr Pro Arg Pro Tyr Pro Lys Leu
            195                 200                 205

Ser Ser Cys Thr Tyr Ser Ile Ser Leu Glu Glu Gly Phe Ser Val Ile
            210                 215                 220

Leu Asp Phe Val Glu Ser Phe Asp Val Glu Thr His Pro Glu Thr Leu
225                 230                 235                 240

Cys Pro Tyr Asp Phe Leu Lys Ile Gln Thr Asp Arg Glu Glu His Gly
            245                 250                 255

Pro Phe Cys Gly Lys Thr Leu Pro His Arg Ile Glu Thr Lys Ser Asn
            260                 265                 270

Thr Val Thr Ile Thr Phe Val Thr Asp Glu Ser Gly Asp His Thr Gly
            275                 280                 285

Trp Lys Ile His Tyr Thr Thr Ala Gln Pro Cys Pro Tyr Pro Met
            290                 295                 300

Ala Pro Pro Asn Gly His Val Ser Pro Val Gln Ala Lys Tyr Ile Leu
305                 310                 315                 320

Lys Asp Ser Phe Ser Ile Phe Cys Glu Thr Gly Tyr Glu Leu Leu Gln
            325                 330                 335

Gly His Leu Pro Leu Lys Ser Phe Thr Ala Val Cys Gln Lys Asp Gly
            340                 345                 350

Ser Trp Asp Arg Pro Met Pro Ala Cys Ser Ile Val Asp Cys Gly Pro
            355                 360                 365

Pro Asp Asp Leu Pro Ser Gly Arg Val Glu Tyr Ile Thr Gly Pro Gly
            370                 375                 380

Val Thr Thr Tyr Lys Ala Val Ile Gln Tyr Ser Cys Glu Glu Thr Phe
385                 390                 395                 400

Tyr Thr Met Lys Val Asn Asp Gly Lys Tyr Val Cys Glu Ala Asp Gly
            405                 410                 415

Phe Trp Thr Ser Ser Lys Gly Glu Lys Ser Leu Pro Val Cys Glu Pro
            420                 425                 430

Val Cys Gly Leu Ser Ala Arg Thr Thr Gly Gly Arg Ile Tyr Gly Gly
            435                 440                 445

Gln Lys Ala Lys Pro Gly Asp Phe Pro Trp Gln Val Leu Ile Leu Gly
            450                 455                 460

Gly Thr Thr Ala Ala Gly Ala Leu Leu Tyr Asp Asn Trp Val Leu Thr
465                 470                 475                 480

Ala Ala His Ala Val Tyr Glu Gln Lys His Asp Ala Ser Ala Leu Asp
            485                 490                 495
```

```
Ile Arg Met Gly Thr Leu Lys Arg Leu Ser Pro His Tyr Thr Gln Ala
            500                 505                 510
Trp Ser Glu Ala Val Phe Ile His Glu Gly Tyr Thr His Asp Ala Gly
        515                 520                 525
Phe Asp Asn Asp Ile Ala Leu Ile Lys Leu Asn Asn Lys Val Val Ile
    530                 535                 540
Asn Ser Asn Ile Thr Pro Ile Cys Leu Pro Arg Lys Glu Ala Glu Ser
545                 550                 555                 560
Phe Met Arg Thr Asp Asp Ile Gly Thr Ala Ser Gly Trp Gly Leu Thr
                565                 570                 575
Gln Arg Gly Phe Leu Ala Arg Asn Leu Met Tyr Val Asp Ile Pro Ile
            580                 585                 590
Val Asp His Gln Lys Cys Thr Ala Ala Tyr Glu Lys Pro Pro Tyr Pro
            595                 600                 605
Arg Gly Ser Val Thr Ala Asn Met Leu Cys Ala Gly Leu Glu Ser Gly
        610                 615                 620
Gly Lys Asp Ser Cys Arg Gly Asp Ser Gly Gly Ala Leu Val Phe Leu
625                 630                 635                 640
Asp Ser Glu Thr Glu Arg Trp Phe Val Gly Gly Ile Val Ser Trp Gly
                645                 650                 655
Ser Met Asn Cys Gly Glu Ala Gly Gln Tyr Gly Val Tyr Thr Lys Val
            660                 665                 670
Ile Asn Tyr Ile Pro Trp Ile Glu Asn Ile Ile Ser Asp Phe
        675                 680                 685
```

MASP-2 INHIBITORS AND METHODS OF USE

STATEMENT REGARDING SEQUENCE LISTING

The sequence listing associated with this application is provided in text format in lieu of a paper copy and is hereby incorporated by reference into the specification. The name of the text file containing the sequence listing is 700128_422_SEQUENCE_LISTING. The text file is 6 KB, was created on Dec. 3, 2020, and is being submitted via EFS-Web with the filing of the specification.

TECHNICAL FIELD

The present disclosure is directed generally to compositions and methods that are useful in the field of medicine. More specifically, the disclosure provides synthetic inhibitors of mannan-binding lectin-associated serine protease-2 (MASP-2), including inhibitors that selectively inhibit MASP-2 over thrombin, compositions thereof, and methods for the manufacture and use thereof.

BACKGROUND

The complement system plays a role in the inflammatory response and becomes activated because of tissue damage or microbial infection. Complement activation must be tightly regulated to ensure selective targeting of invading microorganisms and avoid self-inflicted damage (Ricklin et al., Nat. Immunol. 11:785-797, 2010). Currently, it is widely accepted that the complement system can be activated through three distinct pathways: the classical pathway, the lectin pathway, and the alternative pathway. The classical pathway is usually triggered by a complex composed of host antibodies bound to a foreign particle (i.e., an antigen) and generally requires prior exposure to an antigen for the generation of a specific antibody response. Since activation of the classical pathway depends on a prior adaptive immune response by the host, the classical pathway is part of the acquired immune system. In contrast, both the lectin and alternative pathways are independent of adaptive immunity and are part of the innate immune system.

Mannan-binding lectin-associated serine protease-2 (MASP-2) has been shown to be required for the function of the lectin pathway, one of the principal complement activation pathways (Vorup-Jensen et al., J. Immunol 165:2093-2100, 2000; Ambrus et al., J Immunol. 170: 1374-1382, 2003; Schwaeble et al., PNAS 108:7523-7528, 2011). Importantly, inhibition of MASP-2 does not appear to interfere with the antibody-dependent classical complement activation pathway, which is a critical component of the acquired immune response to infection. As described in U.S. Pat. No. 9,011,860 (assigned to Omeros Corporation), which is hereby incorporated by reference, discloses a fully human monoclonal antibody targeting human MASP-2 has been generated which binds to human MASP-2 with high affinity and blocks the lectin pathway complement activity and is therefore useful to treat various lectin complement pathway-associated diseases and disorders.

MASP-2-dependent complement activation has been implicated as contributing to the pathogenesis of numerous acute and chronic disease states. Therefore, a need exists for compounds that are suitable for administration/treatment of subject suffering from MASP-2 complement pathway-associated diseases and disorders, including diseases that are not suitably or efficiently treated with large molecule biologic inhibitors.

BRIEF SUMMARY

One embodiment provides a compound having the following Structure (I):

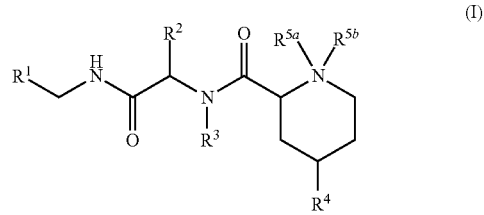

(I)

or a stereoisomer, tautomer, or pharmaceutically acceptable salt thereof, wherein $R^1$, $R^2$, $R^3$, $R^4$, $R^{5a}$, and $R^{5b}$ are as defined herein.

Another embodiment provides a compound having the following Structure (II):

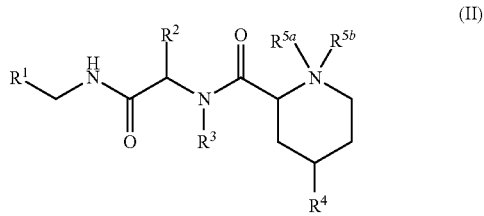

(II)

or a stereoisomer, tautomer, or pharmaceutically acceptable salt thereof, wherein $R^1$, $R^2$, $R^3$, $R^4$, $R^{5a}$, and $R^{5b}$ are as defined herein.

Yet another embodiment provides a compound having the following Structure (III):

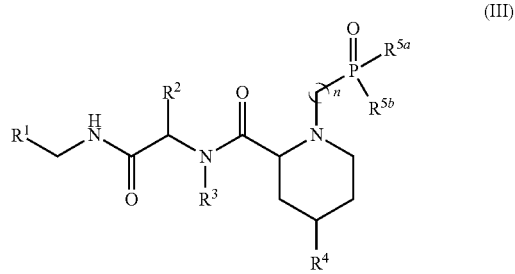

(III)

or a stereoisomer, tautomer, or pharmaceutically acceptable salt thereof, wherein $R^1$, $R^2$, $R^3$, $R^4$, $R^{5a}$, $R^{5b}$ and n are as defined herein.

Additional embodiments of the present disclosure provide a pharmaceutical composition comprising a compound of Structure (I), Structure (II), or Structure (III), or a stereoisomer, tautomer, or pharmaceutically acceptable salt thereof, and at least one pharmaceutically acceptable carrier or excipient.

The compounds of Structures (I), (II), and (III) are useful in the treatment of MASP-2-associated diseases and disorders, and in the manufacture of medicaments for treating MASP-2-associated diseases and disorders. Accordingly, other embodiments of the disclosure provide methods of treating a MASP-2-associated disease and disorder comprising administering to a patient a therapeutically effective amount of a compound of Structure (I), Structure (II), or Structure (III), or a stereoisomer, tautomer, or pharmaceutically acceptable salt thereof.

These and other aspects, objects and embodiments will become more apparent when read with the detailed description and figures which follow.

DETAILED DESCRIPTION

I. Definitions

Unless otherwise defined, all technical and scientific terms used herein have the same meaning as commonly understood by one of ordinary skill in the art to which this disclosure belongs. Although methods and materials similar or equivalent to those described herein can be used in the practice or testing of the subject matter of the present disclosure, suitable methods and materials are described below. In addition, the materials, methods, and examples are illustrative only and not intended to be limiting.

In certain embodiments herein, reference is made to features and aspects of the disclosure, including method steps. All possible combinations of such features and aspects within the embodiments of the disclosure are included, at least to the extent that such combinations are non-contradictory. For example, if an embodiment presents aspects A, B, and C, it is understood that this also discloses embodiments including both aspects A and B, both aspects B and C, and both aspects A and C, as well as an embodiment with aspects A, B, and C.

The terms "a," "an," or "the" not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art.

The terms "about" and "approximately" refer to an acceptable degree of error for the quantity measured given the nature or precision of the measurements. Typical, exemplary degrees of error are within ±20 percent (%); preferably, within ±10%; and more preferably, within ±c5% of a given value or range of values. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written support for a claim limitation of, e.g., "0.98X." Alternatively, in biological systems, the terms "about" and "approximately" may mean values that are within an order of magnitude, preferably within 5-fold, and more preferably within 2-fold of a given value. Numerical quantities given herein are approximate unless stated otherwise, meaning that the term "about" or "approximately" can be inferred when not expressly stated. When "about" is applied to the beginning of a numerical range, it applies to both ends of the range. Thus, "from about 5 to 20%" is equivalent to "from about 5% to about 20%." When "about" is applied to the first value of a set of values, it applies to all values in that set. Thus, "about 7, 9, or 11 mg/kg" is equivalent to "about 7, about 9, or about 11 mg/kg."

The term "MASP-2" refers to mannan-binding lectin-associated serine protease-2. Human MASP-2 protein with UniProt accession code 000187 (SEQ ID NO:1). The Serine Protease Domain ('B-chain'=Mannan-binding lectin serine protease 2 B chain, based on UniProtKB-000187 (MASP-2 HUMAN)) includes residues 445 to 686 (or consists of residues 445 to 686).

The term "MASP-2-dependent complement activation" refers to MASP-2-dependent activation of the lectin pathway, which occurs under physiological conditions (i.e., in the presence of $Ca^{++}$) leading to the formation of the lectin pathway C3 convertase C4b2a and upon accumulation of the C3 cleavage product C3b subsequently to the C5 convertase C4b2a(C3b)n.

The term "MASP-2-dependent complement-associated disease or disorder" refers to a disease or disorder that is associated with MASP-2-dependent complement activation.

The term "MASP-2-associated disease or disorder" refers to a disease or disorder that is associated with activation or activity of MASP-2, including MASP-2-dependent complement-associated disease or disorders, and wherein inhibition of MASP-2 is or is expected to be therapeutically beneficial.

The term "lectin pathway" refers to complement activation that occurs via the specific binding of serum and non-serum carbohydrate-binding proteins including mannan-binding lectin (MBL), CL-11 and the ficolins (H-ficolin, M-ficolin, or L-ficolin).

The term "classical pathway" refers to complement activation that is triggered by an antibody bound to a foreign particle and requires binding of the recognition molecule C1q.

Amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gin; Q), glycine (Gly; G), histidine (His; H), isoleucine (lie), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

In the broadest sense, the naturally occurring amino acids can be divided into groups based upon the chemical characteristic of the side chain of the respective amino acids. By "hydrophobic" amino acid is meant either His, Leu, Met, Phe, Trp, Tyr, Val, Ala, Cys or Pro. By "hydrophilic" amino acid is meant either Gly, Asn, Gin, Ser, Thr, Asp, Glu, Lys, Arg or His. This grouping of amino acids can be further sub-classed as follows: by "uncharged hydrophilic" amino acid is meant either Ser, Thr, Asn or Gin. By "acidic" amino acid is meant either Glu or Asp. By "basic" amino acid is meant either Lys, Arg or His.

The term "conservative amino acid substitution" is illustrated by a substitution among amino acids within each of the following groups:
  (1) glycine, alanine, valine, leucine, and isoleucine;
  (2) phenylalanine, tyrosine, and tryptophan;
  (3) serine and threonine;
  (4) aspartate and glutamate;
  (5) glutamine and asparagine; and
  (6) lysine, arginine and histidine.

The term "a subject" includes all mammals, including without limitation, humans, non-human primates, dogs, cats, horses, sheep, goats, cows, rabbits, pigs, and rodents.

"Mammal" includes humans and both domestic animals such as laboratory animals and household pets, (e.g., cats, dogs, swine, cattle, sheep, goats, horses, rabbits), and non-domestic animals such as wildlife and the like.

The terms "small molecule" and "small organic molecule" refers to a small carbon-containing molecule that has a molecular weight of about 2500 daltons or lower. In some embodiments, a small molecule has a molecular weight of about 2000 daltons or lower. In some embodiments, a small molecule has a molecular weight of about 1500 daltons or lower. In some embodiments, a small molecule has a molecular weight of about 1000 daltons or lower. In some embodiments, a small molecule has a molecular weight of about 750 daltons or lower. In some embodiments, a small molecule has a molecular weight of about 500 daltons or lower. In some embodiments, a small molecule has a molecular weight of about 50 daltons or greater. In some embodiments, a small molecule has a molecular weight of about 75 daltons or greater. In some embodiments, a small molecule has a molecular weight of about 100 daltons or greater. In some embodiments, a small molecule has a molecular weight of about 150 daltons or greater. In some embodiments, a small molecule has a molecular weight of about 250 daltons or greater. In some embodiments, small molecules may have a molecular weight in the range from about 50 daltons to about 500 daltons, from about 50 daltons to about 750 daltons, from about 50 daltons to about 1000 daltons, from about 50 daltons to about 1500 daltons, from about 50 daltons to about 2000 daltons, or from about 50 daltons to about 2500 daltons. When the term "compound" is used herein, the term is explicitly intended to include small molecule compounds as defined herein (including any of the embodiments thereof).

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians. In some embodiments, a disease is a pathological condition of an organ, a body part, or a system resulting from various causes, such as infection, genetic defect, or environmental stress that is characterized by an identifiable group of symptoms.

"Therapeutically effective amount," "effective amount," or "effective dose" refers to that amount of a compound of the disclosure that, when administered to a mammal (e.g., a human), is sufficient to effect treatment, as defined below, of a disease or condition in the mammal, preferably a human. The amount of a compound of the disclosure which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

The term "subcutaneous administration" refers to administration of a formulation under all layers of the skin of a subject.

The term "histidine" specifically includes L-histidine unless otherwise specified.

The term "isotonic" refers to a formulation that has essentially the same osmotic pressure as human blood. Isotonic formulations will generally have an osmotic pressure from about 250 to about 350 mOsmol/L. Isotonicity can be measured using a vapor pressure or freezing point depression osmometer, for example.

The term "hypertonic" refers to a formulation with an osmotic pressure above that of human (i.e., greater than 350 mOsm/L).

The term "hydrogen-bonding" is a partially electrostatic attraction between a hydrogen (H) which is bound to a more electronegative atom such as nitrogen (N) or oxygen (O) and another adjacent atom bearing a lone pair of electrons. For example, when it is stated that the nitrogen acts as a "hydrogen bond donor" it means that a hydrogen (H) bound to a nitrogen (N) is donated by the nitrogen as it electrostatically attracted to or accepted by an adjacent atom bearing a lone pair of electrons such as an oxygen. Similarly, when it is stated that an oxygen acts as a "hydrogen bond acceptor," it means that a hydrogen (H) bound to a more electronegative atom such as nitrogen (N) is electrostatically attracted to or "accepted by" an adjacent atom such as oxygen bearing a lone pair of electrons. Sometimes the hydrogen bonded atoms are called out without explicitly stating the origin and presence of an intermediate hydrogen atom. The term "hydrogen bonding" is used wherever LigPlot+ software predicts a hydrogen bonding interaction using its algorithm and applied parameters of 3.35 Å for maximum distance between hydrogen bond donor and acceptor. Not all hydrogen bonds may actually be in place simultaneously; this is evident for atoms that are shown to form 4 putative hydrogen bonds, where however, at any given time only 3 hydrogen bonds are chemically possible. In general, although crystal structures such as the co-crystal structural information herein does not directly show or detect hydrogen bonding, the software used to describe the co-crystal does predict such H-bonding exists. Therefore, throughout the disclosure when a H-bond is present and described, it may be said to be "predicted" by software to be present.

The term ionic bonding includes a type of chemical bond that involves the electrostatic attraction between oppositely charged ions, and is the primary interaction occurring in ionic compounds.

The term "van der Waals" interaction includes weak, short-range electrostatic attractive forces between uncharged molecules, arising from the interaction of permanent or transient electric dipole moments. As determined by LigPlot+ software employing models derived from the corresponding crystallographic MASP-2 compound co-structures, such interactions include all contacts that are computed using non-bonded contact parameters between hydrophobic to any contacts for interactions with a maximum contact distance of 3.90 Å.

The term "π-π interaction" or "π-π stacking" interaction includes attractive, non-covalent interactions between aromatic rings that are oriented either roughly parallel or roughly perpendicular (such as in "edge-face" interactions) to each other, since they contain π-bonds.

Typically, the active site of serine proteases such as MASP-2 is shaped as a cleft where the polypeptide substrate or inhibitor binds. Schechter and Berger labeled amino acid residues from the N to C terminus of the polypeptide substrate as follows: Pi, . . . , P3, P2, P1, P1', P2', P3', . . . , Pj) and their respective binding sub-sites Si, . . . , S3, S2, S1, S1', S2', S3', . . . , Sj. The cleavage is catalyzed between P1 and P1' (Schechter, I. & Berger, A. On the size of the active site in proteases. I. Papain. Biochem. Biophys. Res. Commun. 27 (1967)).

The term "binding site" is an area on the protein wherein a small molecule can interact with, such as a region on the surface of MASP-2. The binding site or region may not or only partially overlap with the active site, but nevertheless render the MASP-2 molecule less active or inactive.

The term "or" refers to an alternative and should in general be construed non-exclusively. For example, a claim to "a composition comprising A or B" would typically present an aspect with a composition comprising both A and B. "Or" should, however, be construed to exclude those aspects presented that cannot be combined without contradiction (e.g., a composition pH that is between 9 and 10 or between 7 and 8).

The group "A or B" is equivalent to the group "selected from the group consisting of A and B."

The linking term "comprising" or "comprise" is not closed. For example, "a composition comprising A" must include at least the component A, but it may also include one or more other components (e.g., B; B and C; B, C, and D; and the like). The term "comprising" therefore should in general be construed as not excluding additional ingredients. For example, a claim to "a composition comprising A" would cover compositions that include A and B; A, B, and C; A, B, C, and D; A, B, C, D, and E; and the like.

The term "hypertonic" refers to a formulation with an osmotic pressure above that of human (i.e., greater than 350 mOsm/KglHhO).

The term "agent" refers to a compound or mixture of compounds that, when added to a composition, tend to produce an effect on the composition's properties. For example, a composition comprising a thickening agent is likely to be more viscous than an otherwise identical comparative composition that lacks the thickening agent.

A "synthetic" compound means a compound that is not naturally occurring and that has been synthesized by humans. Reference to a compound herein may be understood to include reference to synthetic compounds, unless the context indicates otherwise.

The expressions, "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

At various places in the present specification, certain features of the compounds are disclosed in groups or in ranges. It is specifically intended that such a disclosure include each and every individual sub-combination of the members of such groups and ranges. For example, the terms "$C_{1-6}$ alkyl" and "$C_1$-$C_6$ alkyl" are specifically intended to individually disclose (without limitation) methyl, ethyl, $C_3$ alkyl, $C_4$ alkyl, $C_5$ alkyl, and $C_6$ alkyl.

The term "substituted" means that an atom or group of atoms formally replaces hydrogen as a "substituent" attached to another group. The term "substituted", unless otherwise indicated, refers to any level of substitution, e.g., mono-, di-, tri-, tetra-, penta-, or higher substitution, where such substitution is permitted (e.g., results in a stable compound). The substituents are independently selected, and substitution may be at any chemically accessible position. It is to be understood that substitution at a given atom is limited by valency. The phrase "optionally substituted" means substituted or unsubstituted. The term "substituted" means that at least hydrogen atom is replaced with a substituent. A single divalent substituent, e.g., oxo, can replace two hydrogen atoms.

The terms "$C_{n-m}$" and "$C_n$-$C_m$" where n and m are integers indicates a group that contains from n to m carbon atoms. Examples include $C_{1-4}$, $C_{1-6}$, and the like. The term is intended to expressly disclose every member in the range, i.e., $C_n$, $C_{n+1}$, $C_{n+2}$ ... $C_{m-2}$, $C_{m-1}$, $C_m$. For example, $C_{1-6}$ is intended to disclose $C_1$, $C_2$, $C_3$, $C_4$, $C_5$, and $C_6$. As used herein, "$C_{n-m}$" means the same as $C_n$-$C_m$.

The term "n-membered," where n is an integer (e.g., 6-membered), typically describes the number of ring-forming atoms in a moiety where the number of ring-forming atoms is n. The term "n-m membered" wherein n and m are integers (e.g., 6-10 membered) describes a range where the number of ring forming atoms is from n to m. For example, piperidinyl is an example of a 6-membered heterocyclyl ring, pyrazolyl is an example of a 5-membered heteroaryl ring, pyridyl or pyridinyl is an example of a 6-membered heteroaryl ring and 1,2,3,4-tetrahydro-naphthalene is an example of a 10-membered cycloalkyl group.

"Alkyl" refers to a straight or branched hydrocarbon chain radical consisting solely of carbon and hydrogen atoms, containing no unsaturation, having from one to twelve carbon atoms, preferably one to eight carbon atoms, more preferably one to six carbon atoms, which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. In certain specific embodiments, an alkyl group may be optionally substituted by one of the following groups: alkyl, alkenyl, halo, haloalkenyl, cyano, nitro, aryl, cycloalkyl, heterocyclyl, heteroaryl, oxo, trimethylsilanyl, —$OR^{100}$, —$OC(O)R^{100}$, —$N(R^{100})_2$, —$C(O)R^{100}$, —$C(O)OR^{100}$, —$C(O)N(R^{100})_2$, —$N(R^{20})C(O)OR^{102}$, —$N(R^{100})C(O)R^{102}$, —$N(R^{102})S(O)_pR^{102}$ (where p is 1 to 2), —$S(O)_pOR^{102}$ (where p is 1 to 2), —$S(O)_tR^{102}$ (where t is 0 to 2), and —$S(O)_pN(R^{100})_2$ (where p is 1 to 2) where each $R^{100}$ is independently hydrogen, alkyl, haloalkyl, cycloalkyl, cycloalkylalkyl, aryl, arylalkyl, heterocyclyl, heterocyclylalkyl, heteroaryl or heteroarylalkyl; and each $R^{102}$ is alkyl, haloalkyl, cycloalkyl, cycloalkylalkyl, aryl, arylalkyl, heterocyclyl, heterocyclylalkyl, heteroaryl, or heteroarylalkyl.

"Alkenyl" refers to a straight or branched hydrocarbon chain radical group consisting solely of carbon and hydrogen atoms, containing at least one double bond, having from two to twelve carbon atoms, preferably two to eight carbon atoms and which is attached to the rest of the molecule by a single bond, e.g., ethenyl, prop-1-enyl, but-1-enyl, pent-1-enyl, penta-1,4-dienyl, and the like. In certain embodiments, an alkyl group may be optionally substituted by one of the following groups: alkyl, alkenyl, halo, haloalkenyl, cyano, nitro, aryl, cycloalkyl, heterocyclyl, heteroaryl, oxo, trimethylsilanyl, —$OR^{100}$, —$OC(O)R^{100}$, —$N(R^{100})_2$, —$C(O)R^{100}$, —$C(O)OR^{100}$, —$C(O)N(R^{100})_2$, —$N(R^{20})C(O)OR^{102}$, —$N(R^{100})C(O)R^{102}$, —$N(R^{102})S(O)_pR^{102}$ (where p is 1 to 2), —$S(O)_pOR^{102}$ (where p is 1 to 2), —$S(O)_tR^{102}$ (where t is 0 to 2), and —$S(O)_pN(R^{100})_2$ (where p is 1 to 2) where each $R^{100}$ is independently hydrogen, alkyl, haloalkyl, cycloalkyl, cycloalkylalkyl, aryl, arylalkyl, heterocyclyl, heterocyclylalkyl, heteroaryl or heteroarylalkyl; and each $R^{102}$ is alkyl, haloalkyl, cycloalkyl, cycloalkylalkyl, aryl, arylalkyl, heterocyclyl, heterocyclylalkyl, heteroaryl, or heteroarylalkyl.

"Alkynyl" refers to a straight-chain or branched hydrocarbon group corresponding to an alkyl group as defined above having one or more triple carbon-carbon bonds. An alkynyl group formally corresponds to an alkyne with one C—H bond replaced by the point of attachment of the alkyl group to the remainder of the compound. The term "$C_{n-m}$ alkynyl" and "$C_n$-$C_m$ alkynyl" refer to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms. Unless indicated otherwise, alkynyl groups are optionally substituted.

"Alkylene" or "alkylene chain" refers to a straight or branched divalent hydrocarbon chain linking the rest of the molecule to a radical group or linking two parts of the molecule, consisting solely of carbon and hydrogen, containing no unsaturation and having from one to twelve carbon atoms, e.g., methylene, ethylene, propylene, n-butylene, and the like. The alkylene chain may optionally contain one or more heteroatoms wherein a carbon in the alkylene chain is replaced with a heteroatom selected from oxygen, nitrogen or sulfur. The alkylene chain is attached to the rest of the molecule through a single bond and to the radical group through a single bond or is attached to two parts of the molecule through a single bond at each point of attachment. In some embodiments, an alkyl group may be optionally substituted by one of the following groups: alkyl, alkenyl, halo, haloalkenyl, cyano, nitro, aryl, cycloalkyl, heterocyclyl, heteroaryl, oxo, trimethylsilanyl, —OR$^{100}$, —OC(O)R$^{100}$, —N(R$^{100}$)$_2$, —C(O)R$^{100}$, —C(O)OR$^{100}$, —C(O)N(R$^{100}$)$_2$, —N(R$^{20}$)C(O)OR$^{102}$, —N(R$^{100}$)C(O)R$^{102}$, —N(R$^{102}$)S(O)$_p$R$^{102}$ (where p is 1 to 2), —S(O)$_p$OR$^{102}$ (where p is 1 to 2), —S(O)$_t$R$^{102}$ (where t is 0 to 2), and —S(O)$_p$N(R$^{100}$)$_2$ (where p is 1 to 2) where each R$^{100}$ is independently hydrogen, alkyl, haloalkyl, cycloalkyl, cycloalkylalkyl, aryl, arylalkyl, heterocyclyl, heterocyclylalkyl, heteroaryl or heteroarylalkyl; and each R$^{102}$ is alkyl, haloalkyl, cycloalkyl, cycloalkylalkyl, aryl, arylalkyl, heterocyclyl, heterocyclylalkyl, heteroaryl, or heteroarylalkyl.

The term "hydroxyalkyl" refers to an alkyl group as defined above in which one or more of the hydrogen atoms has been replaced by a hydroxy group (i.e., —OH). The term "C$_{n-m}$ hydroxyalkyl" refers to a C$_{n-m}$ alkyl group having n to m carbon atoms and from at least one hydroxy group. In some embodiments, the hydroxyalkyl group comprises one hydroxy group. In certain aspects, the hydroxyalkyl group comprises two or more hydroxy groups (e.g., a "dihydroxyalkyl"), each on the same or a different carbon atom(s). In certain aspects, the hydroxyalkyl group has 1, 2, 3, 4, 5, 6, or more hydroxy groups. Examples may include, but are not limited to, hydroxymethyl, 2-hydroxy ethyl, and 1-hydroxy ethyl.

"Aminylalkyl" refers to an alkyl group as defined above in which one or more hydrogen atoms have been replaced by an aminyl group (i.e., —NR$^{100}$R$^{101}$ wherein R$^{100}$ and R$^{101}$ are each independently hydrogen, alkyl, alkenyl, or alkynyl as defined herein). In some embodiments, the aminylalkyl comprises one aminyl group. In some embodiments, the aminyl group is —NH$_2$.

"Carboxyalkyl" refers to an alkyl group as defined above in which one or more hydrogen atoms have been replaced by a carboxy group (i.e., —C(O)OH). In some embodiments, the carboxyalkyl comprises one carboxy group.

"Phosphonalkyl" refers to an alkyl group as defined above in which one or more hydrogen atoms have been replaced by a phosphonate group (e.g., —P(=O)(OR)$_2$, wherein R is hydrogen, alkyl, aryl, heteroaryl, arylalkyl, or heteroarylalkyl). In some embodiments, a phosphonalkyl group is —(CH$_2$)$_n$P(=O)(OR)$_2$ wherein R is, at each occurrence, independently hydrogen, alkyl, aryl, heteroaryl, arylalkyl, or heteroarylalkyl. In some more specific embodiments, R is, at each occurrence, independently hydrogen or alkyl. In some embodiments, the phosphonalkyl comprises one phosphonate group.

"Aryl" refers to a hydrocarbon ring system radical comprising hydrogen, 6 to 18 carbon atoms and at least one aromatic ring. For purposes of this disclosure, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In some embodiments, an aryl group may be optionally substituted by one or more substituents independently selected from the group consisting of alkyl, alkenyl, halo, haloalkyl, haloalkenyl, cyano, nitro, aryl, arylalkyl, cycloalkyl, cycloalkylalkyl, heterocyclyl, heterocyclylalkyl, heteroaryl, heteroarylalkyl, —R$^{101}$—OR$^{100}$, —R$^{101}$OC(O)R$^{100}$, —R$^{101}$—N(R$^{100}$)$_2$, —R$^{101}$—N(R$^{100}$)—R$^{103}$—OR$^{100}$, —R$^{101}$—C(O)R$^{100}$, —R$^{101}$—C(O)OR$^{100}$, —R$^{101}$—C(O)N(R$^{100}$)$_2$, —R$^{101}$—N(R$^{100}$)C(O)OR$^{102}$, —R$^{101}$—N(R$^{100}$)C(O)R$^{102}$, —R$^{101}$—N(R$^{100}$)S(O)$_p$R$^{102}$ (where p is 1 to 2), —R$^{101}$—N=C(OR$^{100}$)R$^{100}$, —R$^{101}$—S(O)$_p$OR$^{102}$ (where p is 1 to 2), —R$^{101}$—S(O)$_t$R$^{102}$ (where t is 0 to 2), and —R$^{101}$—S(O)$_p$N(R$^{100}$)$_2$ (where p is 1 to 2) where each R$^{100}$ is independently hydrogen, alkyl, haloalkyl, cycloalkyl, cycloalkylalkyl, aryl, arylalkyl, heterocyclyl, heterocyclylalkyl, heteroaryl or heteroarylalkyl; each R$^{101}$ is independently a direct bond or a straight or branched alkylene chain; each R$^{102}$ is alkyl, haloalkyl, cycloalkyl, cycloalkylalkyl, aryl, arylalkyl, heterocyclyl, heterocyclylalkyl, heteroaryl or heteroarylalkyl, and each R$^{103}$ is a direct bond or a straight or branched alkylene chain. In some embodiments an aryl group has the following structure:

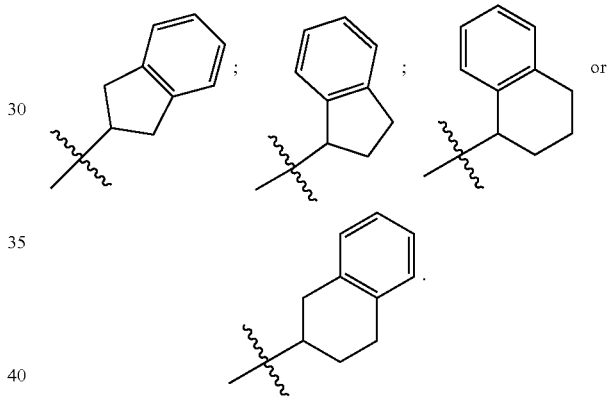

"Arylalkyl" or "aralkyl" refers to a group of formula -alkylene-aryl wherein the alkylene group and aryl groups are as defined herein, respectively. In some embodiments, arylalkyl is C$_{6-10}$ aryl-C$_{1-3}$ alkyl. In some embodiments, arylalkyl is C$_{6-10}$ aryl-C$_{1-4}$ alkyl. In some embodiments, arylalkyl is C$_{6-10}$ aryl-C$_{1-3}$ alkyl. In some embodiments, arylalkyl is phenyl-C$_{1-3}$ alkyl. Examples include, but are not limited to, benzyl, 1-phenylethyl, 4-methylbenzyl, and 1,1-dimethyl-1-phenylmethyl. In some embodiments, arylalkyl is optionally substituted benzyl.

"Aryloxy" refers to a group with the formula —O-aryl wherein aryl is a group as defined above. In some embodiments, the aryloxy group is —O—C$_{6-10}$ aryl. In some embodiments, the aryloxy is a substituted or unsubstituted phenyloxy (i.e., —O—C$_6$ aryl).

"Arylalkoxy" refers to a group with the formula -alkoxy-aryl wherein alkoxy and aryl are groups as defined above, respectively. In some embodiments, arylalkoxy is C$_{6-10}$ aryl-C$_{1-3}$ alkoxy. In some embodiments, arylalkoxy is C$_{6-10}$ aryl-C$_{1-4}$ alkoxy. In some embodiments, arylalkoxy is C$_{6-10}$ aryl-C$_{1-3}$ alkoxy. In some embodiments, arylalkoxy is phenyl-C$_{1-3}$ alkoxy (e.g., methoxy).

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, and the like. In some embodiments, a cycloalkyl group may be optionally substituted by one or more substituents independently selected from the group consisting of alkyl, alkenyl, halo, haloalkyl, haloalkenyl, cyano, nitro, oxo, aryl, arylalkyl, cycloalkyl, cycloalkylalkyl, heterocyclyl, heterocyclylalkyl, heteroaryl, heteroarylalkyl, —$R^{101}$—$OR^{100}$, —$R^{101}$—OC(O)—$R^{100}$, —$R^{101}$—N($R^{100}$)—$R^{103}$—$OR^{100}$, —$R^{101}$—N($R^{100}$)$_2$, —$R^{101}$—C(O)$R^{100}$, —$R^{101}$—C(O)$OR^{100}$, —$R^{101}$—C(O)N($R^{100}$)$_2$, —$R^{101}$—N($R^{100}$)C(O)$OR^{102}$, —$R^{101}$—N($R^{100}$)C(O)$R^{102}$, —$R^{101}$—N($R^{100}$)S(O)$_p$$R^{102}$ (where p is 1 to 2), —$R^{101}$—N=C($OR^{100}$)$R^{100}$, —$R^{101}$—S(O)$_p$$OR^{102}$ (where p is 1 to 2), —$R^{101}$—S(O)$_t$$R^{102}$ (where t is 0 to 2), and —$R^{101}$—S(O)$_p$N($R^{100}$)$_2$ (where p is 1 to 2) where each $R^{100}$ is independently hydrogen, alkyl, haloalkyl, cycloalkyl, cycloalkylalkyl, aryl, arylalkyl, heterocyclyl, heterocyclylalkyl, heteroaryl or heteroarylalkyl; each $R^{101}$ is independently a direct bond or a straight or branched alkylene chain; each $R^{102}$ is alkyl, haloalkyl, cycloalkyl, cycloalkylalkyl, aryl, arylalkyl, heterocyclyl, heterocyclylalkyl, heteroaryl or heteroarylalkyl, and each $R^{103}$ is a direct bond or a straight or branched alkylene chain.

"Cycloalkylalkyl" refers to a radical of the formula —$R^{100}R^{101}$ where $R^{100}$ is an alkylene chain as defined above and $R^{101}$ is a cycloalkyl radical as defined above. When specifically stated in the specification, the alkylene chain and/or the cycloalkyl radical may be optionally substituted as defined above for optionally substituted alkylene chain and optionally substituted cycloalkyl.

"Alkoxy" refers to a radical group having the following formula "—O-alkyl," wherein the alkyl group is as defined herein above. Example alkoxy groups include methoxy, ethoxy, propoxy (e.g., n-propoxy and isopropoxy), t-butoxy, and the like. In some embodiments, the alkyl group has 1 to 6, 1 to 4, or 1 to 3 carbon atoms. Unless indicated otherwise, alkoxy groups are optionally substituted.

"Alkoxyalkyl" refers to a radical having the following formula "-alkylene-O-alkyl," wherein the alkylene and alkyl groups are as defined herein above, respectively. In some embodiments, the alkoxyalkyl group comprises one —O-alkyl group. In some embodiments, the alkoxyalkyl group comprises two or more alkoxy groups. Examples may include, but are not limited to, methoxymethyl, ethoxymethyl, 3-ethoxy ethyl, and 1-m ethoxy ethyl. Unless indicated otherwise, alkoxyalkyl groups are optionally substituted.

"Oxo" refers to a =O group. For example, an oxo connected to a carbon atom forms a carbonyl group (i.e., C=O). Alternatively, when an oxo group is attached to a heteroatom, for example, a sulfoxide, sulfone group, an A-oxide group is formed.

"Sulfido" refers to a =S group.

"Amino" refers to a —NH$_2$ group.

"Carbamyl" refers to a —C(O)NH$_2$ group.

"Carboxy" refers to a —C(O)OH group.

"Carbonyl" refers to a C(=O) group, which also may be written as C(O).

"Cyano" or "nitrile" refers to a —C≡N group, which also may be written as —CN.

"Nitro" refers to a —NO$_2$ group.

"Hydroxy" or "hydroxyl" refers to an —OH group.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

The term "haloalkoxy", employed alone or in combination with other terms, refers to a group of formula —O-haloalkyl, wherein the haloalkyl group is as defined above. Example haloalkoxy groups include trifluoromethoxy, difluoromethoxy, pentafluoroethoxy, and the like.

"Heterocyclyl" refers to a stable 3- to 18-membered non-aromatic ring radical which consists of two to twelve carbon atoms and from one to six heteroatoms selected from the group consisting of nitrogen, oxygen, and sulfur. Unless stated otherwise specifically in the specification, the heterocyclyl radical may be a monocyclic, bicyclic, tricyclic, or tetracyclic ring system, which may include fused, bridged, and spiro ring systems; and the nitrogen, carbon, or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, azetidinyl, 3-azabicyclo[3.1.0]hexan-3-yl, 1-azaspiro[3.3]heptan-1-yl, 5-azaspiro[2.3]hexan-5-yl, 2-oxa-6-azaspiro[3.3]heptan-6-yl, 1-oxa-6-azaspiro[3,4]octan-6-yl, 1-oxa-6-azaspiro[3.3]heptan-6-yl, 6-oxa-1-azaspiro[3.3]heptan-1-yl, 6-azaspiro[3.4]octan-6-yl, 7-oxa-2-azaspiro[3.5]nonan-2-yl, 2,6-diazaspiro[3.3]heptan-2-yl, dioxolanyl, dioxinyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, 1,2,4-thiadiazol-5(4H)-ylidene, tetrahydrofuryl, trioxanyl, trithianyl, triazinanyl, tetrahydropyranyl, thiomorpholinyl, thiamorpholinyl, 1-oxo-thiomorpholinyl, and 1,1-dioxo-thiomorpholinyl. In certain embodiments, a heterocyclyl group may be optionally substituted by one or more substituents selected from the group consisting of alkyl, alkenyl, halo, haloalkyl, haloalkenyl, cyano, oxo, thioxo, nitro, aryl, arylalkyl, cycloalkyl, cycloalkylalkyl, heterocyclyl, heterocyclylalkyl, heteroaryl, heteroaryl alkyl, —$R^{101}$—$OR^{100}$, —$R^{101}$—OC(O)—$R^{100}$, —$R^{101}$—N($R^{100}$)—$R^{103}$—$OR^{100}$, —$R^{101}$—N($R^{100}$)$_2$, —$R^{101}$—C(O)$R^{100}$, —$R^{101}$—C(O)$OR^{100}$, —$R^{101}$—C(O)N($R^{100}$)$_2$, —$R^{101}$—N($R^{100}$)C(O)$OR^{102}$, —$R^{101}$—N($R^{100}$)C(O)$R^{102}$, —$R^{101}$—N($R^{100}$)S(O)$_p$$R^{102}$ (where p is 1 to 2), —$R^{101}$—N=C($OR^{100}$)$R^{102}$, —$R^{101}$—S(O)$_p$$OR^{102}$ (where p is 1 to 2), —$R^{101}$—S(O)$_t$$R^{102}$ (where t is 0 to 2), and —$R^{101}$—S(O)$_p$N($R^{100}$)$_2$ (where p is 1 to 2) where each $R^{100}$ is independently hydrogen, alkyl, alkenyl, haloalkyl, cycloalkyl, cycloalkylalkyl, aryl, arylalkyl, heterocyclyl, heterocyclylalkyl, heteroaryl or heteroarylalkyl; each $R^{101}$ is independently a direct bond or a straight or branched alkylene chain; each $R^{102}$ is alkyl, alkenyl, haloalkyl, cycloalkyl, cycloalkylalkyl, aryl, arylalkyl, heterocyclyl, heterocyclylalkyl, heteroaryl or heteroarylalkyl, and each $R^{103}$ is a direct bond or a straight or branched alkylene chain.

"Heterocyclylalkyl" refers to a radical of the formula —$R^{100}R^{101}$ where $R^{100}$ is an alkylene chain as defined above and $R^{101}$ is a heterocyclyl radical as defined above, and if the heterocyclyl is a nitrogen-containing heterocyclyl, the heterocyclyl may be attached to the alkyl radical at the nitrogen atom. In some embodiments, the alkylene chain of the heterocyclylalkyl radical may be optionally substituted as defined above for an optionally substituted alkylene chain. In some embodiments, the heterocyclyl part of the heterocyclylalkyl radical may be optionally substituted as defined above for an optionally substituted heterocyclyl group.

"Heteroaryl" refers to a 4- to 14-membered ring system radical comprising hydrogen atoms, one to thirteen carbon atoms, one to six heteroatoms selected from the group consisting of nitrogen, oxygen, and sulfur, and at least one aromatic ring. For purposes of this disclosure, the heteroaryl radical may be a monocyclic, bicyclic, tricyclic, or tetracyclic ring system, which may include fused or bridged ring systems; and the nitrogen, carbon, or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1, 4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, benzoxazolinonyl, benzimidazolthionyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrrolyl, pyrido[2,3-d]pyrimidinonyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e. thienyl). In certain embodiments, a heteroaryl group may be optionally substituted by one or more substituents selected from the group consisting of alkyl, alkenyl, halo, haloalkyl, haloalkenyl, cyano, oxo, thioxo, nitro, thioxo, aryl, arylalkyl, cycloalkyl, cycloalkylalkyl, heterocyclyl, heterocyclylalkyl, heteroaryl, heteroarylalkyl, —$R^{101}$—$OR^{100}$, —$R^{101}$—OC(O)—$R^{100}$, —$R^{101}$—N($R^{100}$)—$R^{103}$—$OR^{100}$, —$R^{101}$—N($R^{100}$)$_2$, —$R^{101}$—C(O)$R^{100}$, —$R^{101}$—C(O)$OR^{100}$, —$R^{101}$—C(O)N($R^{100}$)$_2$, —$R^{101}$—N($R^{100}$)C(O)$OR^{102}$, —$R^{101}$—N($R^{100}$)C(O)$R^{100}$)C(O)$R^{102}$, —$R^{101}$—N($R^{100}$)S(O)$_p R^{102}$ (where p is 1 to 2), —$R^{101}$—N═C($OR^{100}$)$R^{100}$, —$R^{101}$—S(O)$_p OR^{102}$ (where p is 1 to 2), —$R^{101}$—S(O)$_t R^{102}$ (where t is 0 to 2), and —$R^{101}$—S(O)$_p N(R^{100})_2$ (where p is 1 to 2) where each $R^{100}$ is independently hydrogen, alkyl, alkenyl, haloalkyl, cycloalkyl, cycloalkylalkyl, aryl, arylalkyl, heterocyclyl, heterocyclylalkyl, heteroaryl or heteroarylalkyl; each $R^{101}$ is independently a direct bond or a straight or branched alkylene chain; each $R^{102}$ is alkyl, alkenyl, haloalkyl, cycloalkyl, cycloalkylalkyl, aryl, arylalkyl, heterocyclyl, heterocyclylalkyl, heteroaryl, or heteroarylalkyl, and each $R^{103}$ is a direct bond or a straight or branched alkylene chain. Preferably, the optional substituents on an optionally substituted bicyclic heteroaryl group for $R^1$ herein are halo. Preferably, the optional substituents on an optionally substituted monocyclic heteroaryl group for $R^1$ herein are alkyl. The term "heteroaryl" includes, e.g., the following structures:

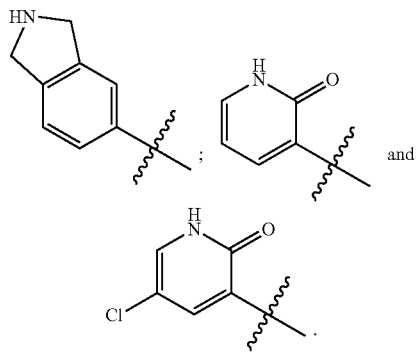

"N-heteroaryl" refers to a heteroaryl radical as defined above containing at least one nitrogen. The point of attachment of the N-heteroaryl to the rest of the molecule can be through a nitrogen atom or a carbon atom in the N-heteroaryl. When specifically stated in the specification, an N-heteroaryl radical may be optionally substituted as described above for an optionally substituted heteroaryl radical.

"Heteroarylalkyl" refers to a radical of the formula —$R^{100}R^{101}$ where $R^{100}$ is an alkylene chain as defined above and $R^{101}$ is a heteroaryl radical as defined above. When specifically stated in the specification, the heteroaryl part of the heteroarylalkyl radical may be optionally substituted as defined above for an optionally substituted heteroaryl group. In some specific embodiments, the alkylene chain part of the heteroarylalkyl radical may be optionally substituted as defined above for an optionally substituted alkylene chain.

The compounds and methods of the present disclosure are also meant to encompass all pharmaceutically acceptable compounds of Structures (I), (II), and (III) being isotopically-labelled by having one or more atoms replaced by an atom having a different atomic mass or mass number.

Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radio-labelled compounds could be useful to help determine or measure the effectiveness of the compounds, by characterizing, for example, the site or mode of action or binding affinity. Certain isotopically-labelled compounds of Structures (I), (II), or (III), for example, those incorporating a radioactive isotope, are useful in drug and/or substrate tissue distribution studies. The radioactive isotopes tritium, i.e., $^3H$, and carbon-14, i.e., $^{14}C$, are particularly useful for this purpose in view of their ease of incorporation and ready means of detection.

Substitution with heavier isotopes such as deuterium, i.e., $^2H$, may afford certain therapeutic advantages resulting from greater metabolic stability, for example, increased in vivo half-life or reduced dosage requirements, and hence may be preferred in some circumstances. In one embodiment, the compounds of Structures (I), (II), or (III) are enriched with deuterium. Such deuterated compounds can be achieved by methods known to one skilled in the art, such as exchanging protons with deuterium or by synthesizing the molecule with enriched starting materials.

Substitution with positron emitting isotopes, such as $^{11}C$, $^{18}F$, $^{15}O$, and $^{13}N$, can be useful in Positron Emission Topography (PET) studies for examining substrate receptor occupancy. Isotopically-labeled compounds of Structures (I), (II), or (III) can generally be prepared by conventional techniques known to those skilled in the art or by processes analogous to those described in the Examples and Preparations as set out below using an appropriate isotopically-labeled reagent in place of the non-labeled reagent previously employed.

This disclosure is also meant to encompass the in vivo metabolic products of the disclosed compounds. Such products may result from, for example, the oxidation, reduction, hydrolysis, amidation, esterification, and the like of an administered compound, primarily due to enzymatic processes. Accordingly, this disclosure includes compounds produced by a process comprising contacting a compound of this disclosure with a mammal for a period of time sufficient to yield a metabolic product thereof. Such products are typically are identified by administering a radio-labelled compound in a detectable dose to an animal, such as rat, mouse, guinea pig, monkey, or to human, allowing sufficient time for metabolism to occur, and isolating its conversion products from the urine, blood, or other biological samples.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution ("unsubstituted"). When a functional group is described as "optionally substituted," and in turn, substituents on the functional group are also "optionally substituted" and so on, for the purposes of this disclosure, such iterations are limited to five, preferably such iterations are limited to two.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts, and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline, and caffeine.

Often crystallizations produce a solvate of the compound of the disclosure (e.g., a compound of Structure (I), (II), or (III)). As used herein, the term "solvate" refers to an aggregate that comprises one or more molecules of a compound of the disclosure with one or more molecules of solvent. The solvent may be water, in which case the solvate may be a hydrate. Alternatively, the solvent may be an organic solvent. Thus, the compounds of the present disclosure may exist as a hydrate, including a monohydrate, dihydrate, hemihydrate, sesquihydrate, trihydrate, tetrahydrate, and the like, as well as the corresponding solvated forms. The compound of the disclosure may be true solvates, while in other cases, the compound of the disclosure may merely retain adventitious water or be a mixture of water plus some adventitious solvent.

A "pharmaceutical composition" refers to a formulation of a compound of the disclosure and a medium generally accepted in the art for the delivery of the biologically active compound to mammals, e.g., humans. Such a medium includes all pharmaceutically acceptable carriers, diluents, or excipients therefor.

"Treating" or "treatment" as used herein covers the treatment of the disease or condition of interest in a mammal, preferably a human, having the disease or condition of interest, and includes:

(a) preventing the disease or condition from occurring in a mammal, in particular, when such mammal is predisposed to the condition but has not yet been diagnosed as having it;

(b) inhibiting the disease or condition, i.e., arresting the disease or condition's development;

(c) relieving (or ameliorating) the disease or condition, i.e., causing regression of the disease or condition; or (d) relieving (or ameliorating) the symptoms resulting from the disease or condition, e.g., without addressing the underlying disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the disclosure, or their pharmaceutically acceptable salts may contain one or more stereocenter and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high-pressure liquid chromatography (HPLC). When the compounds described herein contain olefinic double bonds or other centres giving rise to geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present disclosure contemplates various stereoisomers and mixtures thereof and includes enantiomers, which refers to two stereoisomers whose molecules are non-superimposable mirror images of one another. See, e.g., Smith, M. B. and J. March, March's Advanced Organic Chemistry: Reactions, Mechanisms, and Structure, 6th edition (Wiley, 2007), for a detailed description of the structure and properties of enantiomers and stereoisomers.

A "tautomer" refers to a proton shift from one atom of a molecule to another atom of the same molecule. The present disclosure includes tautomers of any said compounds.

The use of parentheses and brackets in substituent groups is used herein to conserve space. Accordingly, the use of parenthesis in a substituent group indicates that the group enclosed within the parentheses is attached directly to the atom preceding the parenthesis. The use of brackets in a substituent group indicates that the group enclosed within the brackets is also attached directly to the atom preceding the parenthesis.

The chemical naming protocol and structure diagrams used herein are a modified form of the I.U.P.A.C. nomenclature system, using ChemBioDraw Ultra Version 14.0 software program. For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms, which are assumed to be bonded to sufficient hydrogen atoms to complete the valency.

At certain places, the definitions or embodiments may refer to specific rings (e.g., an azetidine ring, a pyridine ring, etc.). Unless otherwise indicated, these rings can be attached to any ring member provided that the valency of the atom is not exceeded.

When any two groups or two instances of the same substituent group are "independently selected" from a list of alternatives, the groups may be the same or different. For example, if $R^a$ and $R^b$ are independently selected from the group consisting of alkyl, fluoro, amino, and hydroxyalkyl, then a molecule with two $R^a$ groups and two $R^b$ groups could have all groups be alkyl group (e.g., four different alkyl groups). Alternatively, the first $R^a$ could be alkyl, the second $R^a$ could be fluoro, the first $R^b$ could be hydroxyalkyl, and the second $R^b$ could be amino (or any other substituents taken from the group). Alternatively, both $R^a$ and the first $R^b$ could be fluoro, while the second $R^b$ could be alkyl (i.e., some pairs of substituent groups may be the same, while other pairs may be different). Unless otherwise indicated, if two or more groups having the same definition are present, but the definition provides for alternatives, it should be understood that each occurrence of the same group is independently selected from the possible alternatives. For example, if two or more $R^a$ groups are present in a compound, and the definition of $R^a$ provides that $R^a$ can be A, B, or C, then it should be understood that each $R^a$ group present in the compound is independently chosen from A, B, and C, so that the $R^a$ groups present in the compound can be the same or different.

Compounds, and salts thereof, including pharmaceutically acceptable salts, can be found together with other substances such as water and solvents (e.g., hydrates and solvates) or can be isolated. When in the solid state, the compounds described herein, and salts thereof may occur in various forms and may, e.g., take the form of solvates, including hydrates. The compounds may be in any solid-state form, such as a polymorph or solvate, so unless clearly indicated otherwise, reference to compounds and salts thereof should be understood as encompassing any solid-state form of the compound.

In some embodiments, the compounds described herein or salts thereof, are substantially isolated. "Substantially isolated" means the compound is at least partially or substantially separated from the environment in which it was formed or detected. Partial separation can include, e.g., a composition enriched in the compounds of the disclosure. Substantial separation can include compositions containing at least about 50%, at least about 60%, at least about 70%, at least about 80%, at least about 90%, at least about 95%, at least about 97%, or at least about 99% by weight of the compounds of the disclosure, or salt thereof.

The following abbreviations may be used herein and, unless otherwise noted, have the meanings indicated below:

μ (micro); ° C. (degrees Celsius); Ac (acetyl); ACN (acetonitrile); anhyd (anhydrous); aq (aqueous); atm (atmosphere(s)); Bn (benzyl); Boc (tert-butoxycarbonyl); Bu (butyl); calcd (calculated); Cbz (benzyloxycarbonyl); chrom. (chromatography); CPME (cyclopentyl methyl ether); $CH_2Cl_2$ (dichloromethane); coned (concentrated); conc (concentration); DCC (N,N'-dicyclohexylcarbodiimide); DIAD (Diisopropyl azodicarboxylate); DIEA (N',N'-diisopropyl ethyl amine); DMAP (4-(N',N-dimethylamino) pyridine); DMF (dimethylformamide); DMSO (dimethylsulfoxide); EDC (N'-(3-dimethylaminopropyl)-N'-ethylcarbodiimide hydrochloride); equiv (equivalent); ES (electrospray); Et (ethyl); $Et_2O$ (diethyl ether); g (gram(s)); h (hour(s)); HATU (N'-[(Dimethylamino)-1H-1,2,3-triazolo-[4,5-b]pyridin-1-ylmethylene]-N-methylmethanaminium hexafluorophosphate N'-oxide); HBTE1 (O-(Benzotriazol-1-yl)-N,N,N',N'-tetramethyl-O-(1H-benzotriazol-1-yl)uronium hexafluorophosphate); HPLC (high-performance liquid chromatography); HOBt (1-hydroxybenzotriazole hydrate); L (liter(s)); m (milli); m-(meta); M (molar); MeCN (acetonitrile); min (minute(s)); mL (milliliter); mol (mole; molecular (as in mol wt)); Ms (methanesulfonyl); MS (mass spectrometry); MW (molecular weight); NBS (A-bromosuccinimide); NCS (A-chlorosuccinimide); NIS (A-iodosuccinimide); NHS (N-hydroxysuccinimide); NMM (4-methylmorpholine); NMR (nuclear magnetic resonance); o-(ortho); obsd (observed); p-(para); Ph (phenyl); Phth (Phthalimide); ppt (precipitate); Pr (propyl); psi (pounds per square inch); temp (temperature); TFA (trifluoroacetic acid); THF (tetrahydrofuran); TPP (triphenylphosphine); and Tr (trityl). Other abbreviations may also be used and have the meanings that would be understood by the person having skill in the art.

II. Compounds

In certain aspects, the present disclosure provides a compound of Structure (I):

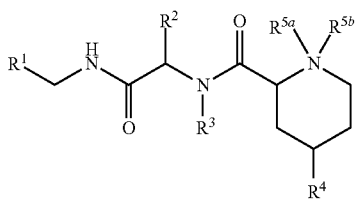

or a stereoisomer, tautomer, or pharmaceutically acceptable salt thereof, wherein:

$R^1$ is a substituted or unsubstituted aryl, substituted or unsubstituted heteroaryl, substituted or unsubstituted cycloalkyl, or a substituted or unsubstituted heterocyclyl;

$R^2$ is hydrogen, alkyl, alkoxy, haloalkyl, haloalkoxy, or cycloalkyl;

$R^3$ is hydrogen, alkyl, haloalkyl, or cycloalkyl;

or $R^2$ and $R^3$, together with the carbon and nitrogen to which they are attached, respectively, form an optionally substituted 4-7 membered heterocyclyl;

$R^4$ is a substituted or unsubstituted aryl, substituted or unsubstituted heteroaryl, substituted or unsubstituted cycloalkyl, or a substituted or unsubstituted heterocyclyl;

$R^{5a}$ is hydrogen, alkyl, haloalkyl, cycloalkyl, phosphonalkyl, $(CH_2)_nC(=O)OR^6$, $C(=O)R^6$, $C(=O)OR^6$, or $C(=O)NR^6R^7$;

$R^{5b}$ is an electron pair or alkyl;

$R^6$ and $R^7$ are, at each occurrence, independently hydrogen, alkyl, haloalkyl, cycloalkyl, or arylalkyl;

$R^8$ is alkyl, haloalkyl, aminylalkyl, substituted or unsubstituted arylalkyl; and n is 1, 2, 3, 4, 5, 6, 7, or 8, provided that A) $R^{5a}$ is alkyl, haloalkyl, cycloalkyl, phosphonalkyl, $(CH_2)_nC(=O)OR^6$, $C(=O)R^6$, $C(=O)OR^6$, or $C(=O)NR^6R^7$ or $R^1$ is substituted with one or more substituents selected from the group consisting of a substituted heteroaryl, $C(=NH)NHC(=O)OR^8$, $C(=NOC(=O)R^8)NH_2$, $C(=NOC(=O)OR^8)NH_2$, and $C(=NOH)NH_2$; and B) when $R^{5a}$ is alkyl or $(CH_2)_nC(=O)OR^6$, $R^1$ does not have the following structure:

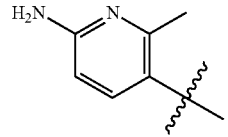 [SMILES: *c1ccc(N)nc1C]

unless $R^2$ and $R^3$, together with the carbon and nitrogen to which they are attached, respectively, form an optionally substituted 4-7 membered heterocyclyl.

In some embodiments, $R^1$ is a substituted or unsubstituted aryl. In certain embodiments, $R^1$ is a substituted or unsubstituted $C_6$-$C_{10}$ aryl. In some more specific embodiments, $R^1$ is a substituted or unsubstituted phenyl. In certain more specific embodiments, $R^1$ is a substituted phenyl.

In some embodiments, $R^1$ is phenyl substituted with one or more of $R^{1a}$, $R^{1b}$, $R^{1c}$, $R^{1d}$, and $R^{1e}$ wherein $R^{1a}$, $R^{1b}$, $R^{1c}$, $R^{1d}$, and $R^{1e}$ are each independently selected from the group consisting of $C(=NH)NHC(=O)OR^8$, $C(=NOC(=O)R^8)NH_2$, $C(=NOC(=O)OR^8)NH_2$, $C(=NOH)NH_2$, $C_{1-6}$ alkyl, $C_{2-6}$ alkenyl, $C_{2-6}$ alkynyl, halo, $C_{1-6}$ haloalkyl, aminylalkyl, hydroxy alkyl, cyano, nitro, $OR^9$, $SR^9$, $C(O)R^9$, $C(O)NR^9R^{10}$, $C(O)OR^9$, $OC(O)R^9$, $OC(O)OR^9$, $OC(O)NR^9R^{10}$, $NR^9R^{10}$, $N(R^9)C(O)R^{10}$, $N(R^9)C(O)NR^{10}R^{11}$, $N(R^9)C(O)OR^{10}$, $C(=NR^9)NR^{10}R^{11}$, $C(=NOR^9)NR^{10}R^{11}$, $C(=NOC(O)R^9)NR^{10}R^{11}$, $C(=NR^9)N(R^{10})C(O)OR^{11}$, $N(R^9)C(=NR^{10})NR^{11}R^{12}$, $S(O)R^9$, $S(O)NR^9R^{10}$, $S(O)_2R^9$, $N(R^9)S(O)_2R^{10}$, $S(O)_2NR^9R^{10}$, OXO, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^9$, $R^{10}$, $R^{11}$, and $R^{12}$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In certain embodiments, $R^{1a}$, $R^{1b}$, $R^{1c}$, $R^{1d}$, or $R^{1e}$ is optionally substituted with one or more substituents selected from the group consisting of halo, CN, $OR^{13}$, $SR^{13}$, $C(O)R^{13}$, $C(O)NR^{13}R^{14}$, $C(O)OR^{13}$, $OC(O)R^{13}$, $OC(O)NR^{13}R^{14}$, $NR^{13}R^{14}$, $NR^{13}C(O)R^{14}$, $NR^{13}C(O)NR^{14}R^{15}$, $NR^{13}C(O)OR^{14}$, $C(=NR^{13})NR^{14}R^{15}$, $NR^{13}C(=NR^{14})NR^{15}R^{16}$, $S(O)R^{13}$, $S(O)NR^{13}R^{14}$, $S(O)_2R^{13}$, $NR^{13}S(O)_2R^{14}$, $S(O)_2NR^{13}R^{14}$ and oxo when $R^{1a}$, $R^{1b}$, $R^{1c}$, $R^{1d}$, or $R^{1e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, wherein $R^{13}$, $R^{14}$, $R^{15}$, and $R^{16}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In some embodiments, $R^1$ is phenyl substituted with at least one substituent selected from the group consisting of $OR^9$, $C(=NR^9)NR^{10}R^{11}$, $C(=NOR^9)NR^{10}R^{11}$, $C(=NOC(O)R^9)NR^{10}R^{11}$, and $C(=NR^9)NR^{10}C(O)OR^{11}$. In certain embodiments, $R^1$ is substituted with at least one substituent selected from the group consisting of $C(=NR^9)NR^{10}R^{11}$, $C(=NOR^9)NR^{10}R^{11}$, $C(=NOC(O)R^9)NR^{10}R^{11}$, and $C(=NR^9)NR^{10}C(O)OR^{11}$. In some more specific embodiments, $R^1$ is substituted with at least one $C(=NR^9)NR^{10}R^{11}$. In some more specific embodiments, $R^1$ is substituted with at least one —$C(=NH)NH_2$.
In some embodiments, $R^1$ has one of the following structures:
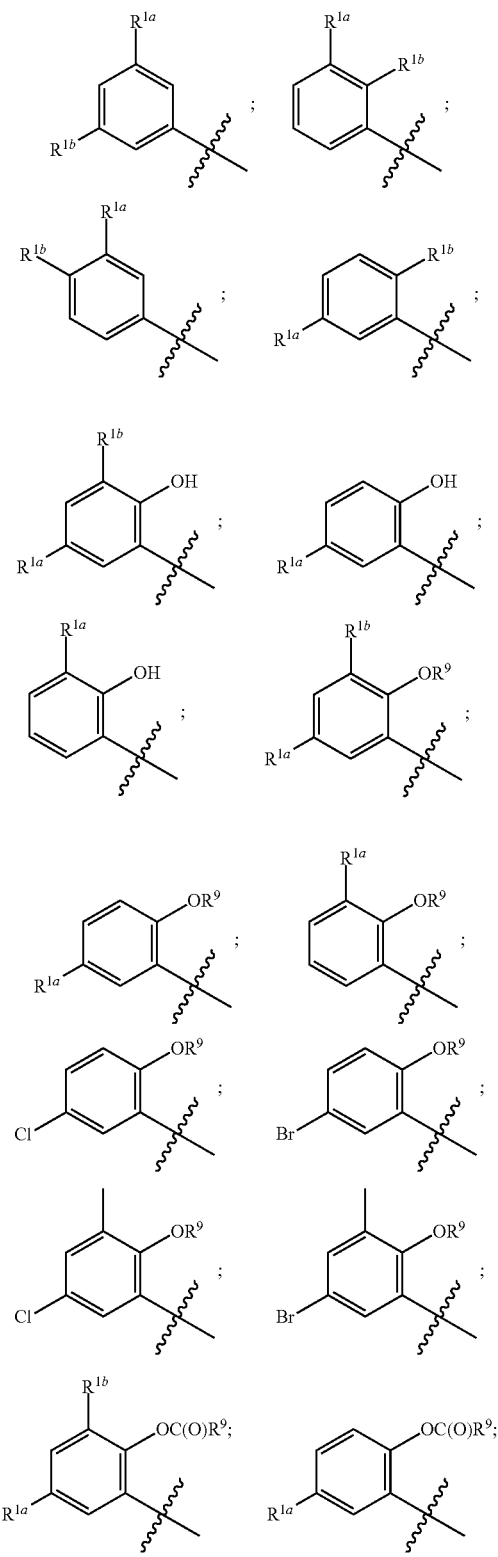
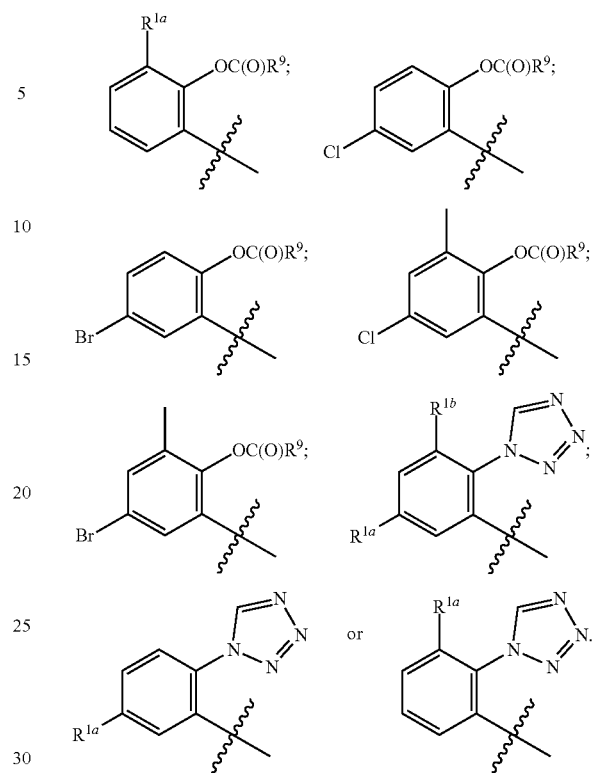
In certain embodiments, $R^1$ has one of the following structures:
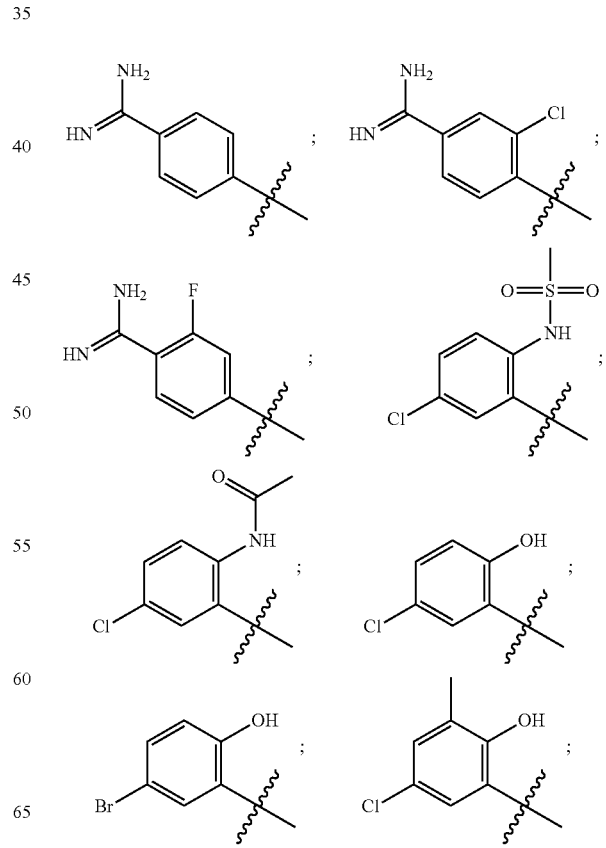

-continued

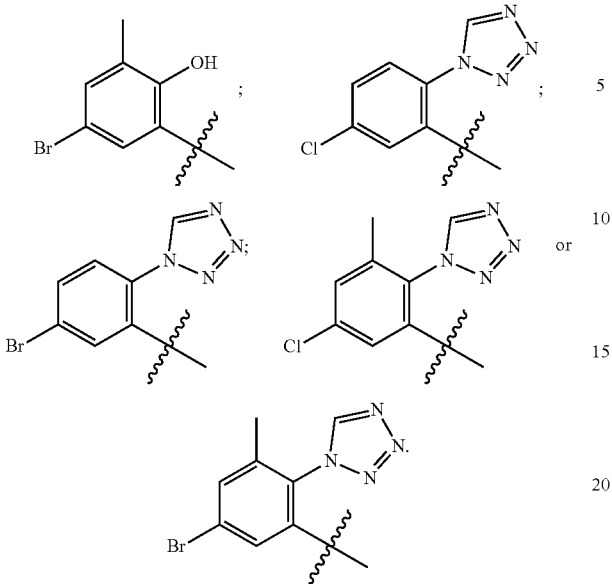

In some more specific embodiments, R has one of the following structures:

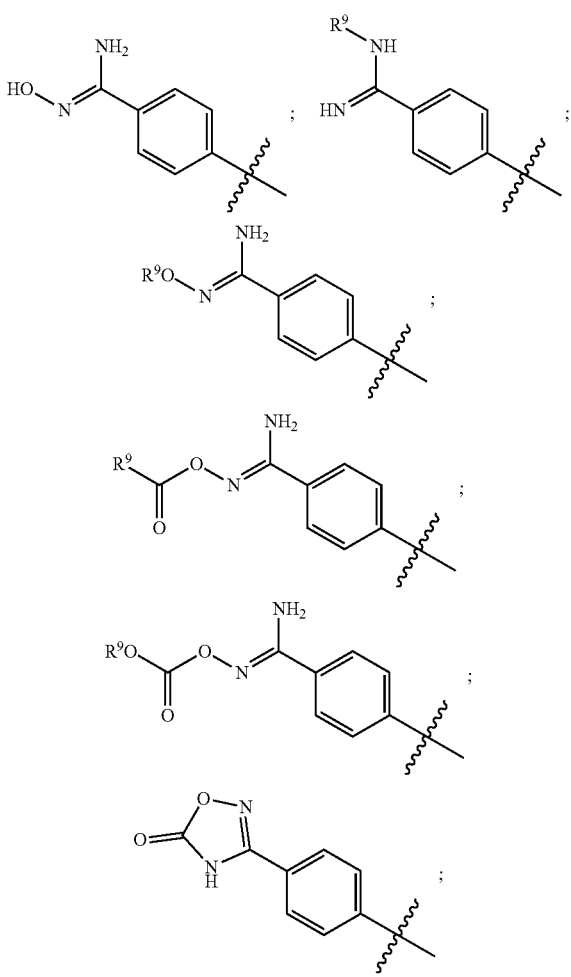

-continued

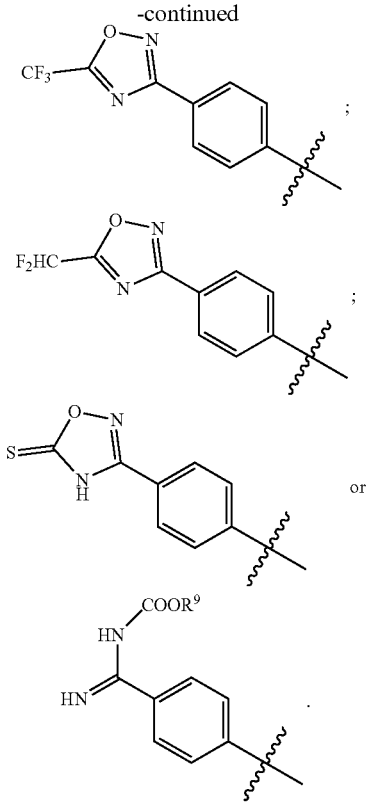

In some of the foregoing embodiments, $R^9$ is $C_{1-6}$ alkyl or $C_{1-6}$ haloalkyl. In certain more specific embodiments, $R^9$ is methyl. In some specific embodiments, $R^9$ is trifluoromethyl.

In certain embodiments, $R^1$ is an unsubstituted phenyl.

In certain other embodiments, $R^1$ is a substituted or unsubstituted heteroaryl. In some embodiments, $R^1$ is a substituted or unsubstituted 5-10 membered heteroaryl. In certain embodiments, $R^1$ is a substituted or unsubstituted pyridinyl, pyrrolopyridinyl, thiophenyl, or benzoimidazolyl. In some more specific embodiments, $R^1$ is a substituted or unsubstituted pyridin-3-yl, 1H-pyrrolo[2,3-b]pyridine-5-yl, thiophen-2-yl, or 1H-benzo[d]imidazol-6-yl.

In certain embodiments, $R^1$ is pyridin-3-yl, 1H-pyrrolo[2,3-b]pyridine-5-yl, thiophen-2-yl, or 1H-benzo[d]imidazol-6-yl substituted with one or more of $R^{1a}$, $R^{1b}$, $R^{1c}$, $R^{1d}$, or $R^{1e}$ wherein $R^{1a}$, $R^{1b}$, $R^{1c}$, $R^{1d}$, and $R^{1e}$ are each independently selected from the group consisting of $C_{1-6}$ alkyl, C2-6 alkenyl, C2-6 alkynyl, halo, $C_{1-6}$ haloalkyl, aminylalkyl, hydroxyalkyl, cyano, nitro, $OR^9$, $SR^9$, $C(O)R^9$, $C(O)NR^9R^{10}$, $C(O)OR^9$, $OC(O)R^9$, $OC(O)OR^9$, $OC(O)NR^9R^{10}$, $NR^9R^{10}$, $N(R^9)C(O)R^{10}$, $N(R^9)C(O)NR^{10}R^{11}$, $N(R^9)C(O)OR^{10}$, $C(=NR^9)NR^{10}R^{11}$, $C(=NOR^9)NR^{10}R^{11}$, $C(=NOC(O)R^9)NR^{10}R^{11}$, $C(=NR^9)N(R^{10})C(O)OR^{11}$, $N(R^9)C(=NR^{10})NR^{11}R^{12}$, $S(O)R^9$, $S(O)NR^9R^{10}$, $S(O)_2R^9$, $N(R^9)S(O)_2R^{10}$, $S(O)_2NR^9R^{10}$, OXO, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^9$, $R^{10}$, $R^{11}$, and $R^{12}$, are, at each occurrence, independently selected from the group consisting of hydrogen, $C_{1-6}$ alkyl, C2-6 alkenyl, C2-6 alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In some embodiments, $R^{1a}$, $R^{1b}$, $R^{1c}$, $R^{1d}$, or $R^{1e}$ is optionally substituted with one or more substituents selected from the group consisting of halo, CN, $OR^{13}$, $SR^{13}$, $C(O)R^{13}$, $C(O)NR^{13}R^{14}$, $C(O)OR^{13}$, $OC(O)R^{13}$, $OC(O)NR^{13}R^{14}$, $NR^{13}R^{14}$, $NR^{13}C(O)R^{14}$, $NR^{13}C(O)NR^{14}R^{15}$, $NR^{13}C(O)OR^{14}$, $C(=NR^{13})NR^{14}R^{15}$, $NR^{13}C(=NR^{14})NR^{15}R^{16}$, $S(O)R^{13}$, $S(O)NR^{13}R^{14}$, $S(O)_2R^{13}$, $NR^{13}S(O)_2R^{14}$, $S(O)_2NR^{13}R^{14}$ and oxo when $R^{1a}$, $R^{1b}$, $R^{1c}$, $R^{1d}$, or $R^{1e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, wherein $R^{13}$, $R^{14}$, $R^{15}$, and $R^{16}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In some embodiments, $R^1$ has one of the following structures:

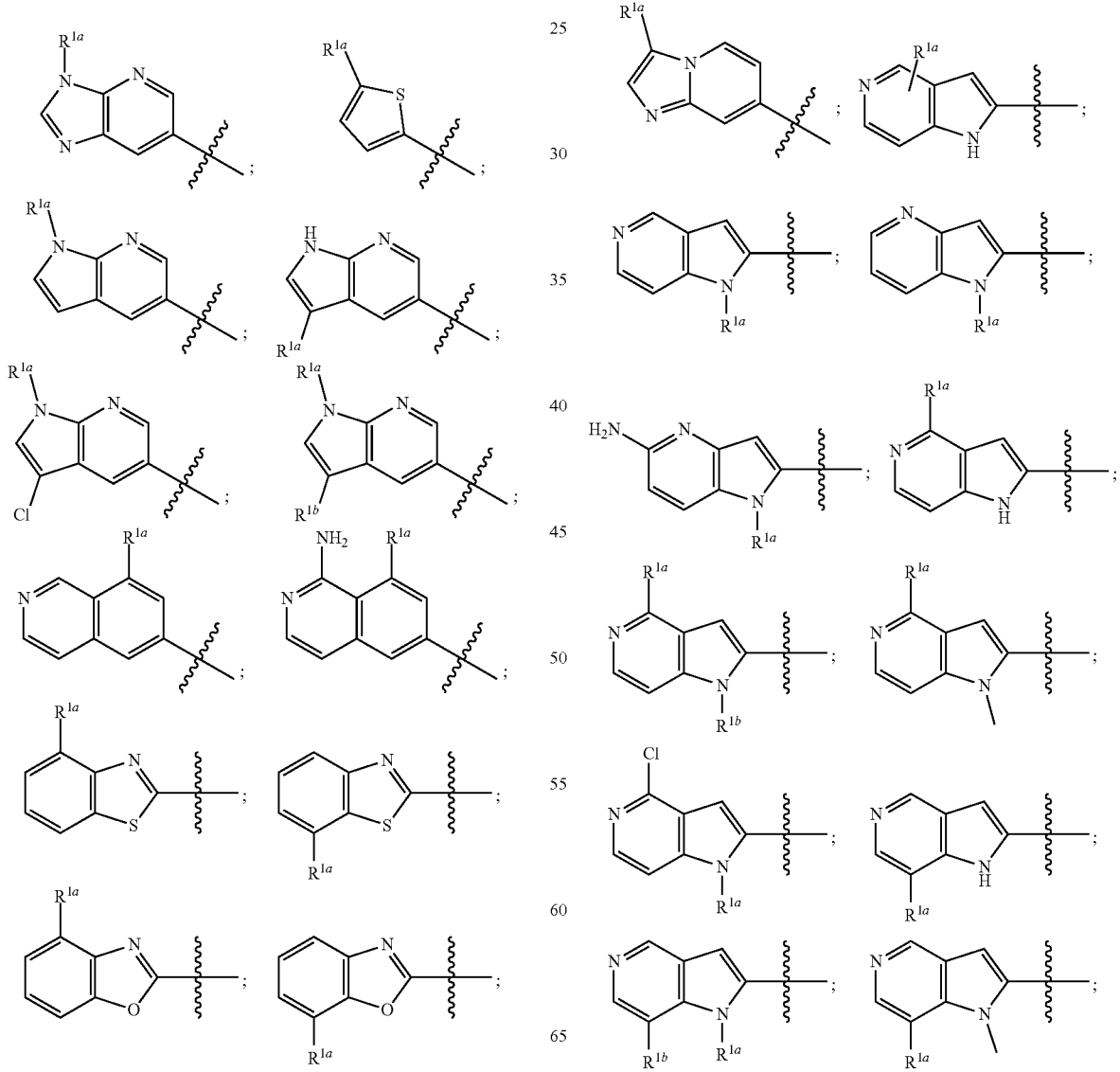

-continued
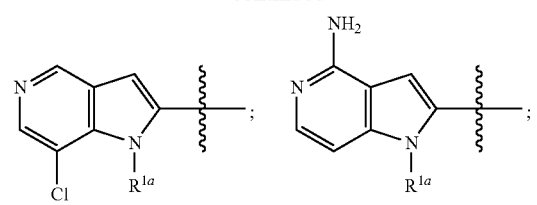
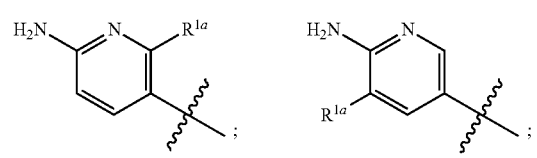
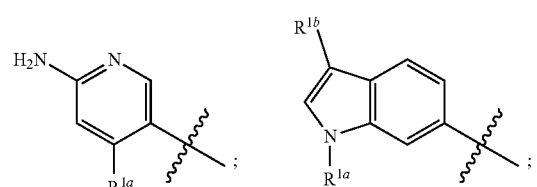
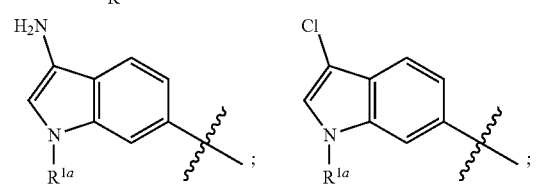
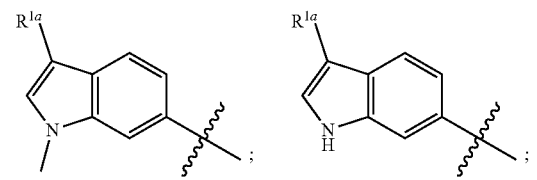
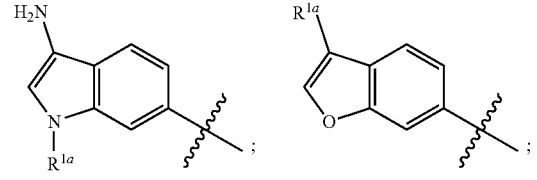
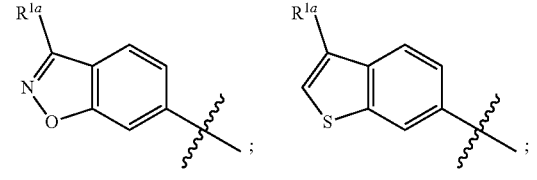
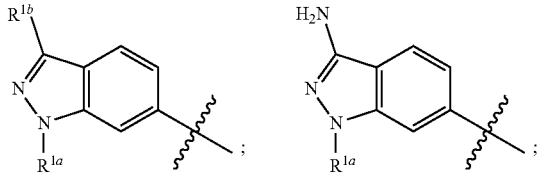
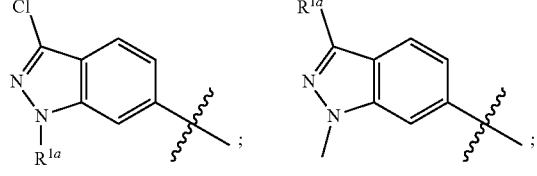
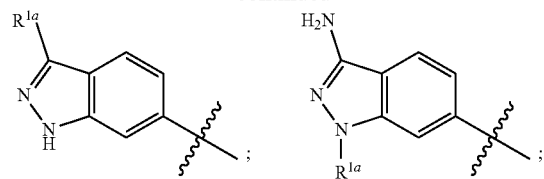
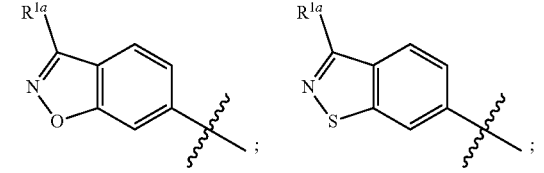
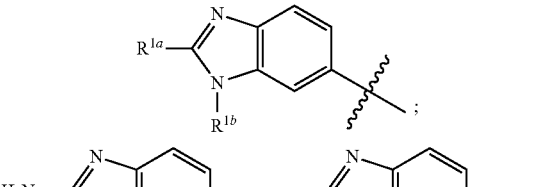
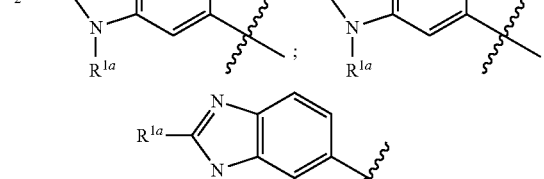
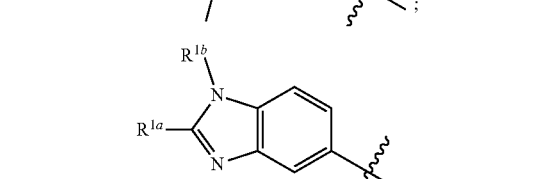
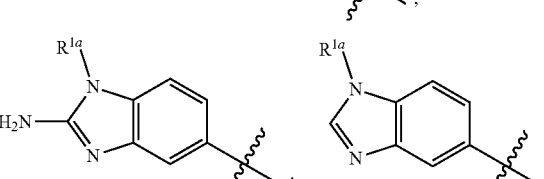
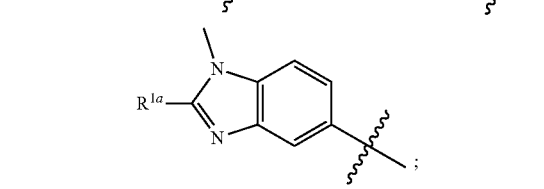
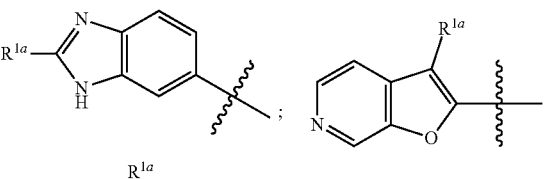
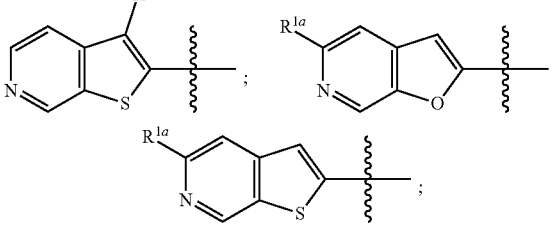

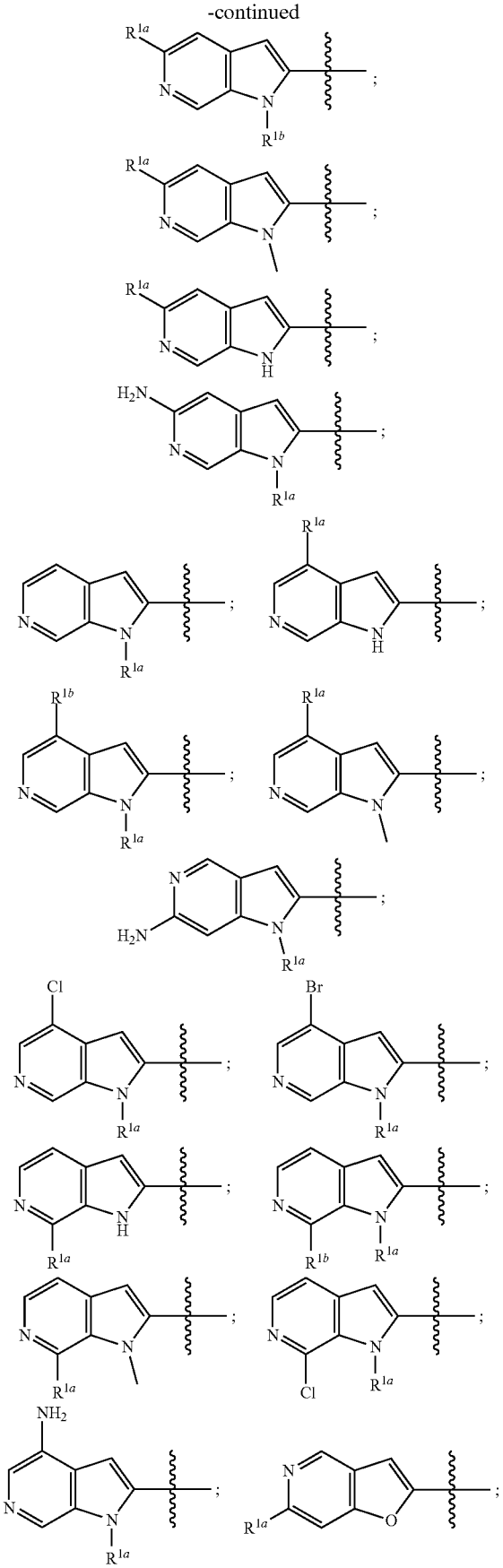
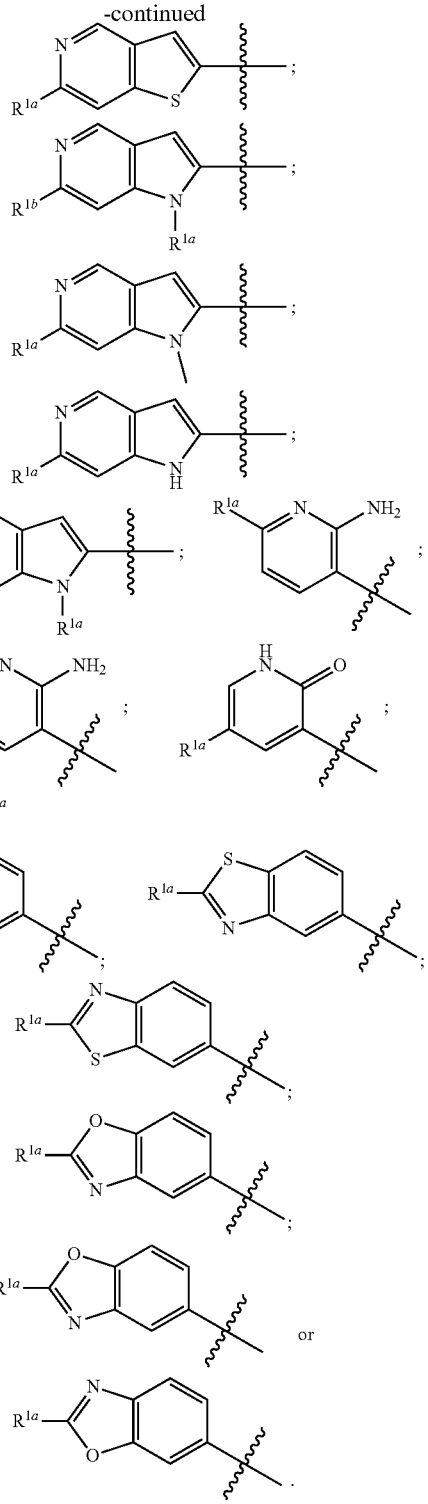

In some embodiments, R or $R^D$ is independently $C_{1-6}$ alkyl, amino, or halo. In certain embodiments, $R^{1a}$ or $R^{1b}$ is methyl or ethyl. In some more specific embodiments, $R^{1a}$ or $R^{1b}$ is F, Cl, or Br. In some embodiments, each $R^{1a}$ or $R^{1b}$ attached to nitrogen is $C_{1-6}$ alkyl. In some more specific embodiments, $R^{1a}$ or $R^{1b}$ is methyl or ethyl. In certain more specific embodiments, $R^1$ has one of the following structures:

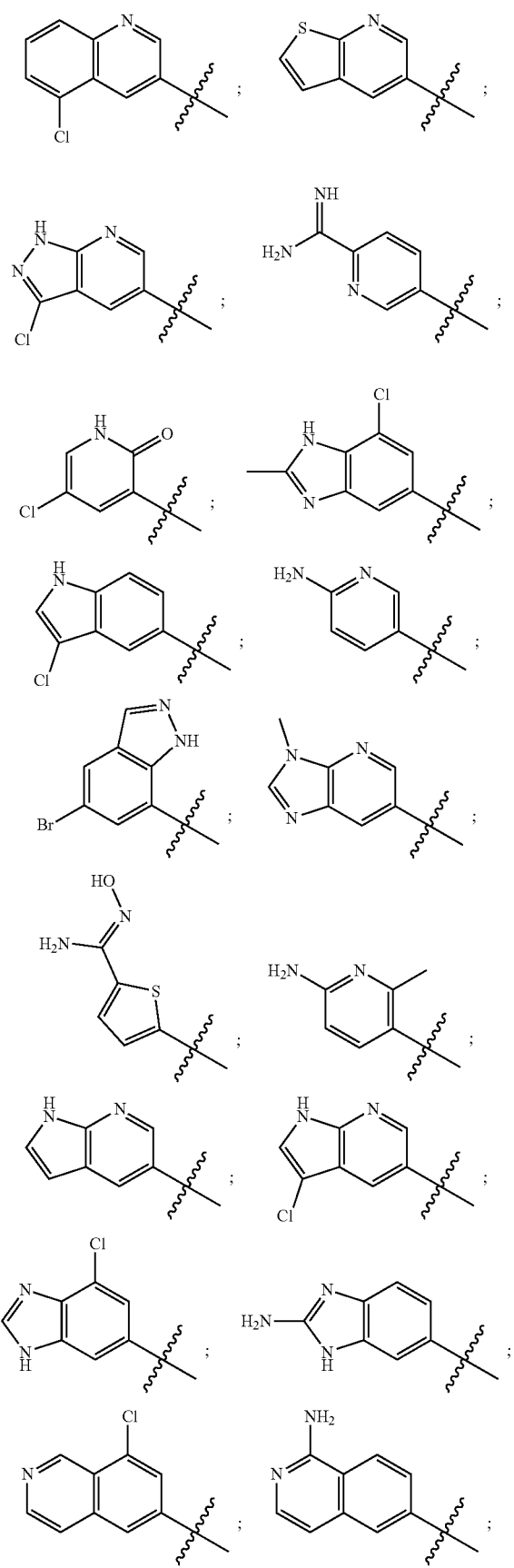
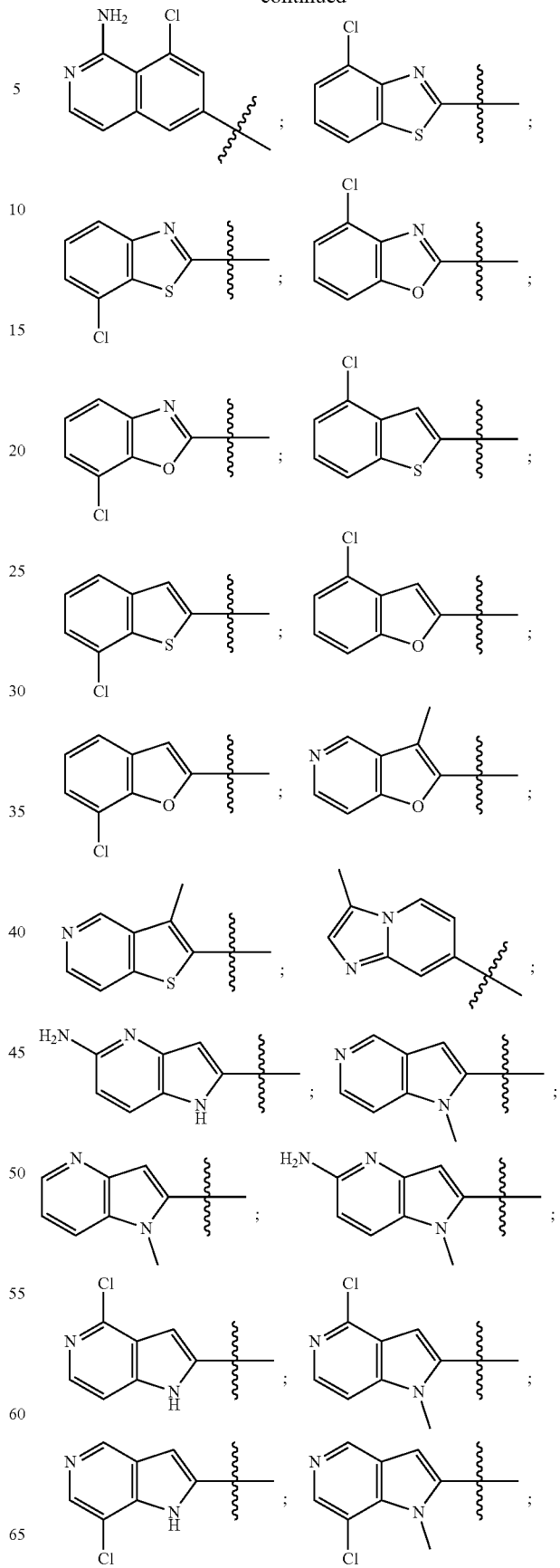

-continued
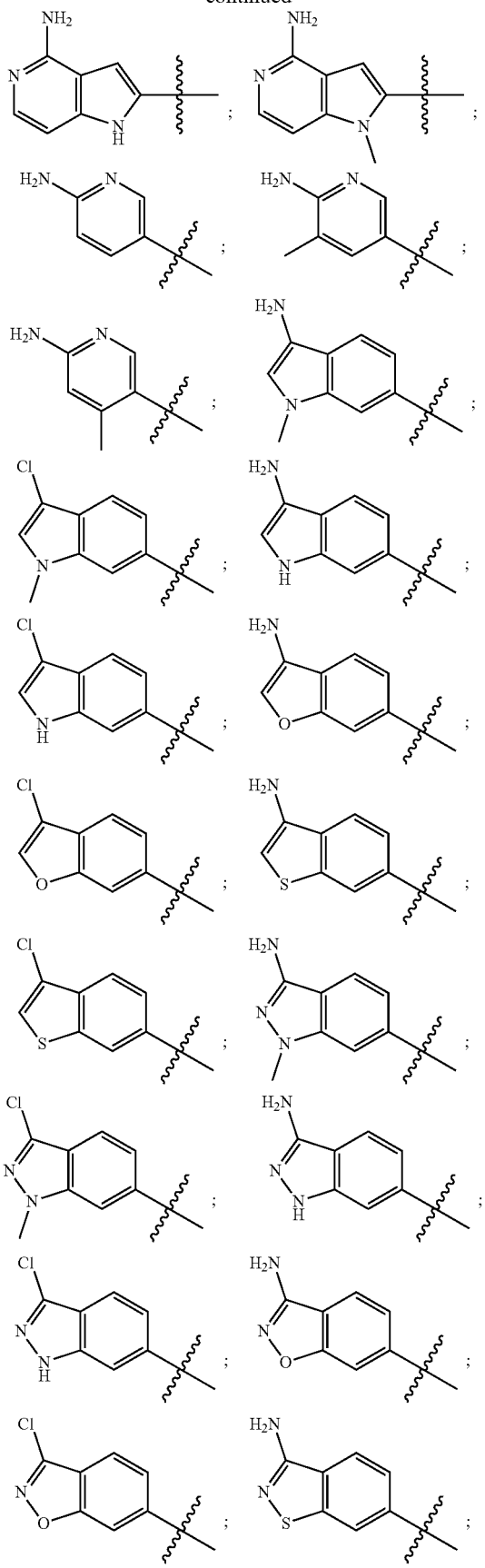
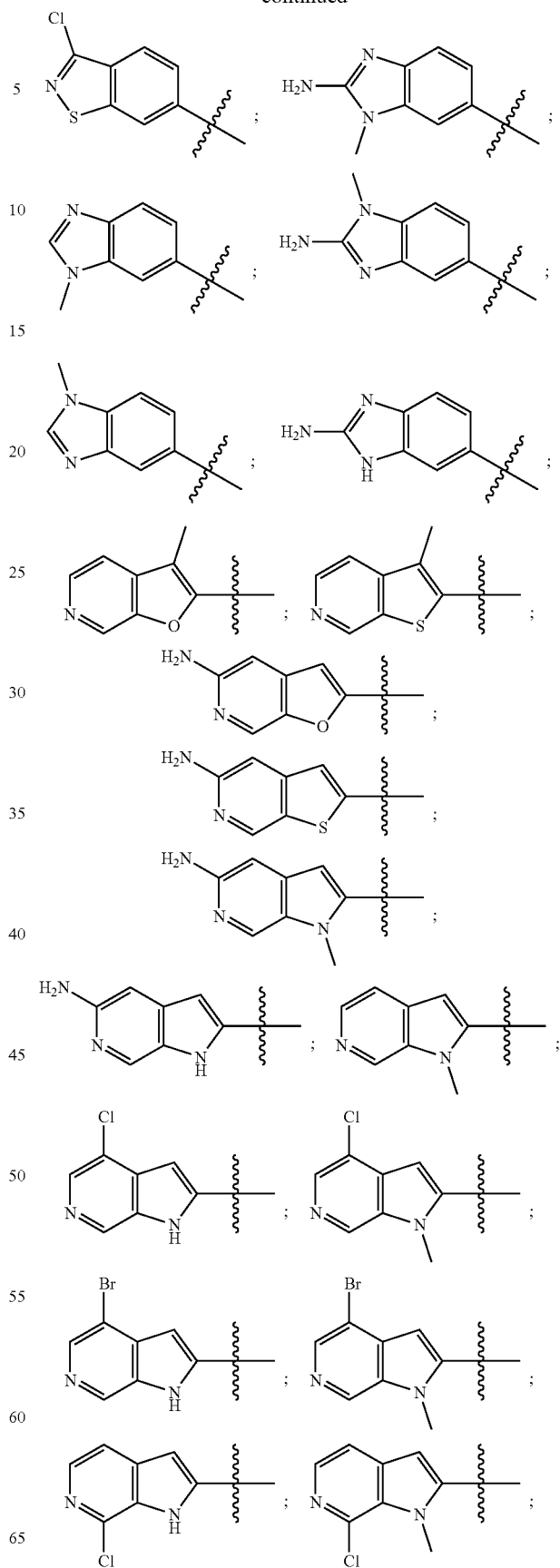

-continued

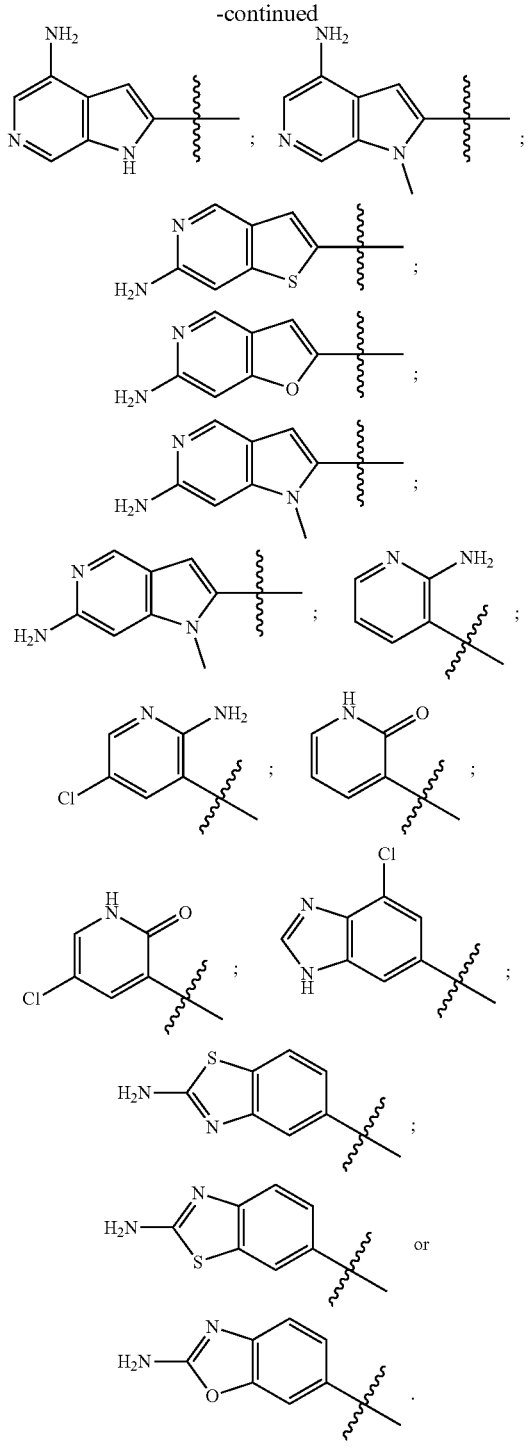
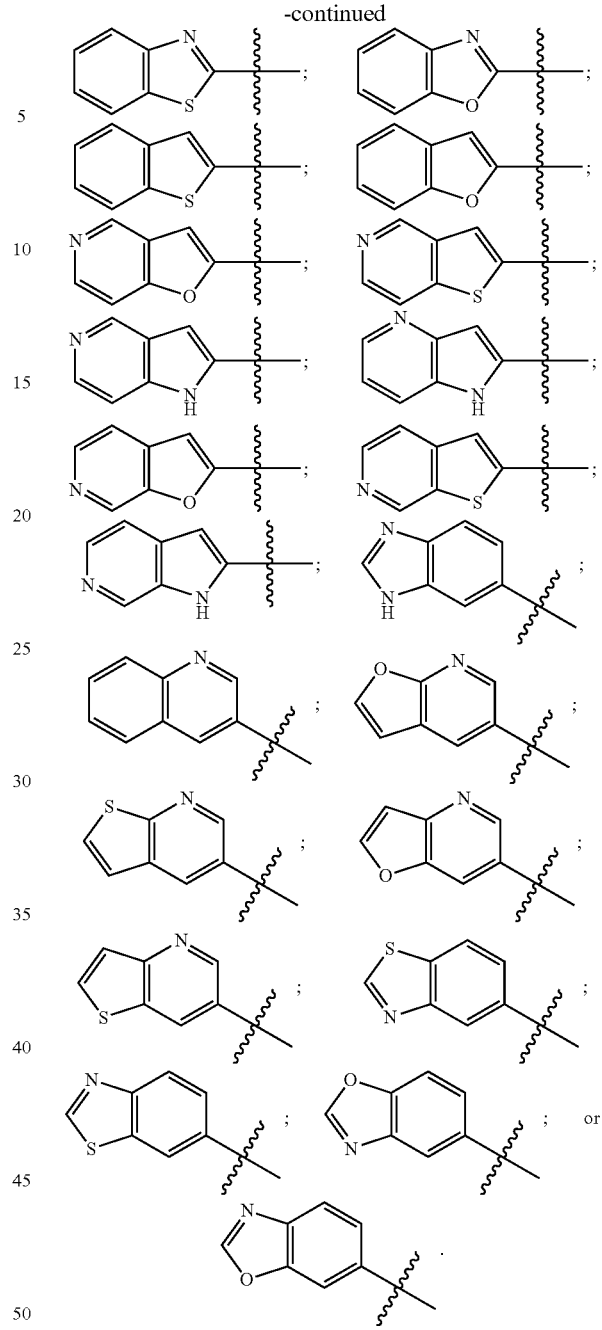

In some embodiments, R¹ has one of the following structures:

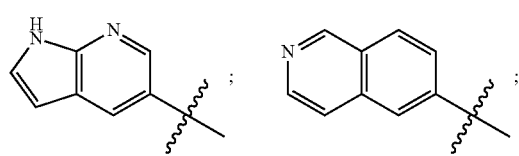

In certain embodiments, R¹ is a substituted or unsubstituted cycloalkyl. In certain embodiments, R¹ is a substituted or unsubstituted $C_3$-$C_6$ cycloalkyl. In some more specific embodiments, R¹ is a substituted $C_3$-$C_6$ cycloalkyl.

In some more specific embodiments, R¹ is a $C_3$-$C_6$ cycloalkyl substituted with one or more of $R^{1a}$, $R^{1b}$, $R^{1c}$, $R^{1d}$, and $R^{1e}$ wherein $R^{1a}$, $R^{1b}$, $R^{1c}$, $R^{1d}$, and $R^{1e}$ are each independently selected from the group consisting of $C_{1-6}$ alkyl, $C_{2-6}$ alkenyl, $C_{2-6}$ alkynyl, $C_{1-6}$ haloalkyl, aminylalkyl, hydroxyalkyl, nitro, $OR^9$, $SR^9$, $C(O)R^9$, $C(O)NR^9R^{10}$, $C(O)OR^9$, $OC(O)R^9$, $OC(O)OR^9$, $OC(O)NR^9R^{10}$, $NR^9R^{10}$, $N(R^9)C(O)R^{10}$, $N(R^9)C(O)NR^{10}R^{11}$, $N(R^9)C(O)OR^{10}$, $C(=NR^9)NR^{10}R^{11}$, $C(=NOR^9)NR^{10}R^{11}$, $C(=NOC(O)R^9)NR^{10}R^{11}$, $C(=NR^9)N(R^{10})C(O)OR^{11}$, $N(R^9)C(=NR^{10})NR^{11}R^{12}$, $S(O)R^9$, $S(O)NR^9R^{10}$, $S(O)_2R^9$, $N(R^9)S(O)_2R^{10}$, S(O)₂NR⁹R¹⁰, OXO, substituted or unsubstituted C₆₋₁₀ aryl, substituted or unsubstituted C₆₋₁₀ arylalkyl, substituted or unsubstituted C₆₋₁₀ aryloxy, substituted or unsubstituted C₆₋₁₀ arylalkoxy, substituted or unsubstituted 5-10 membered heteroaryl, substituted or unsubstituted C₃₋₁₀ cycloalkyl, and substituted or unsubstituted 4-10 membered heterocyclyl, wherein R⁹, R¹⁰, R¹¹, and R¹², are, at each occurrence, independently selected from the group consisting of hydrogen, C₁₋₆ alkyl, C₂₋₆ alkenyl, C₂₋₆ alkynyl, hydroxyl, C₁₋₆ alkoxy, aryl, arylalkyl, C₁₋₆ haloalkyl, C₁₋₆ haloalkoxy, C₁₋₆ hydroxyalkyl, cycloalkyl, heterocyclyl, and heteroaryl.

In some embodiments, R¹ᵃ, R¹ᵇ, R¹ᶜ, R¹ᵈ, or R¹ᵉ is optionally substituted with one or more substituents selected from the group consisting of OR¹³, SR¹³, C(O)R¹³, C(O)NR¹³R¹⁴, C(O)OR¹³, OC(O)R¹³, OC(O)NR¹³R¹⁴, NR¹³R¹⁴, NR¹³C(O)R¹⁴, NR¹³C(O)NR¹⁴R¹⁵, NR¹³C(O)OR¹⁴, C(=NR¹³)NR¹⁴R¹⁵, NR¹³C(=NR¹⁴)NR¹⁵R¹⁶, S(O)R¹³, S(O)NR¹³R¹⁴, S(O)₂R¹³, NR¹³S(O)₂R¹⁴, S(O)₂NR¹³R¹⁴ and oxo when R¹ᵃ, R¹ᵇ, R¹ᶜ, R¹ᵈ, or R¹ᵉ is a substituted C₆₋₁₀ aryl, a substituted C₆₋₁₀ arylalkyl, a substituted C₆₋₁₀ aryloxy, a substituted C₆₋₁₀ arylalkoxy, a substituted 5-10 membered heteroaryl, a substituted C₆₋₁₀ cycloalkyl, and a substituted 4-10 membered heterocyclyl, wherein R¹³, R¹⁴, R¹⁵, and R¹⁶ are, at each occurrence, independently selected from the group consisting of hydrogen, C₁₋₆ alkyl, C₂₋₆ alkenyl, C₂₋₆ alkynyl, hydroxyl, C₁₋₆ alkoxy, aryl, arylalkyl, C₁₋₆ haloalkyl, C₁₋₆ haloalkoxy, C₁₋₆ hydroxyalkyl, cycloalkyl, heterocyclyl, and heteroaryl.

In some embodiments, R¹ is an unsubstituted a C₃-C₆ cycloalkyl.

In certain embodiments, R¹ is a substituted or unsubstituted heterocyclyl. In some more specific embodiments, R¹ is a substituted or unsubstituted 4-10 membered heterocyclyl. In certain more specific embodiments, R¹ is a substituted 4-10 membered heterocyclyl.

In some embodiments, R¹ is a 4-10 membered heterocyclyl substituted with one or more of R¹ᵃ, R¹ᵇ, R¹ᶜ, R¹ᵈ, and R¹ᵉ wherein R¹ᵃ, R¹ᵇ, R¹ᶜ, R¹ᵈ, and R¹ᵉ are each independently selected from the group consisting of C₁₋₆ alkyl, C₂₋₆ alkenyl, C₂₋₆ alkynyl, halo, C₁₋₆ haloalkyl, aminylalkyl, hydroxyalkyl, cyano, nitro, OR⁹, SR⁹, C(O)R⁹, C(O)NR⁹R¹⁰, C(O)OR⁹, OC(O)R⁹, OC(O)OR⁹, OC(O)NR⁹R¹⁰, NR⁹R¹⁰, N(R⁹)C(O)R¹⁰, N(R⁹)C(O)NR¹⁰R¹¹, N(R⁹)C(O)OR¹⁰, C(=NR⁹)NR¹⁰R¹¹, C(=NOR⁹)NR¹⁰R¹¹, C(=NOC(O)R⁹)NR¹⁰R¹¹, C(=NR⁹)N(R¹⁰)C(O)OR¹¹, N(R⁹)C(=NR¹⁰)NR¹¹R¹², S(O)R⁹, S(O)NR⁹R¹⁰, S(O)₂R⁹, N(R⁹)S(O)₂R¹⁰, S(O)₂NR⁹R¹⁰, OXO, substituted or unsubstituted C₆₋₁₀ aryl, substituted or unsubstituted C₆₋₁₀ arylalkyl, substituted or unsubstituted C₆₋₁₀ aryloxy, substituted or unsubstituted C₆₋₁₀ arylalkoxy, substituted or unsubstituted 5-10 membered heteroaryl, substituted or unsubstituted C₃₋₁₀ cycloalkyl, and substituted or unsubstituted 4-10 membered heterocyclyl, wherein R⁹, R¹⁰, R¹¹, and R¹², are, at each occurrence, independently selected from the group consisting of hydrogen, C₁₋₆ alkyl, C₂₋₆ alkenyl, C₂₋₆ alkynyl, hydroxyl, C₁₋₆ alkoxy, aryl, arylalkyl, C₁₋₆ haloalkyl, C₁₋₆ haloalkoxy, C₁₋₆ hydroxyalkyl, cycloalkyl, heterocyclyl, and heteroaryl.

In certain embodiments, R¹ᵃ, R¹ᵇ, R¹ᶜ, R¹ᵈ, or R¹ᵉ is optionally substituted with one or more substituents selected from the group consisting of OR¹³, SR¹³, C(O)R¹³, C(O)NR¹³R¹⁴, C(O)OR¹³, OC(O)R¹³, OC(O)NR¹³R¹⁴, NR¹³R¹⁴, NR¹³C(O)R¹⁴, NR¹³C(O)NR¹⁴R¹⁵, NR¹³C(O)OR¹⁴, C(=NR¹³)NR¹⁴R¹⁵, NR¹³C(=NR¹⁴)NR¹⁵R¹⁶, S(O)R¹³, S(O)NR¹³R¹⁴, S(O)₂R¹³, NR¹³S(O)₂R¹⁴, S(O)₂NR¹³R¹⁴ and oxo when R¹ᵃ, R¹ᵇ, R¹ᶜ, R¹ᵈ, or R¹ᵉ is a substituted C₆₋₁₀ aryl, a substituted C₆₋₁₀ arylalkyl, a substituted C₆₋₁₀ aryloxy, a substituted C₆₋₁₀ arylalkoxy, a substituted 5-10 membered heteroaryl, a substituted C₆₋₁₀ cycloalkyl, and a substituted 4-10 membered heterocyclyl, wherein R¹³, R¹⁴, R¹⁵, and R¹⁶ are, at each occurrence, independently selected from the group consisting of hydrogen, C₁₋₆ alkyl, C₂₋₆ alkenyl, C₂₋₆ alkynyl, hydroxyl, C₁₋₆ alkoxy, aryl, arylalkyl, C₁₋₆ haloalkyl, C₁₋₆ haloalkoxy, C₁₋₆ hydroxyalkyl, cycloalkyl, heterocyclyl, and heteroaryl.

In some embodiments, R¹ is an unsubstituted 4-10 membered heterocyclyl. In certain embodiments, R¹ is substituted with one or more substituents selected from the group consisting of a substituted heteroaryl, C(=NH)NHC(=O)OR⁸, C(=NOC(=O)R⁸)NH₂, C(=NOC(=O)OR⁸)NH₂, and C(=NOH)NH₂. In some more specific embodiments, R¹ is substituted with a substituted heteroaryl having one of the following structures:

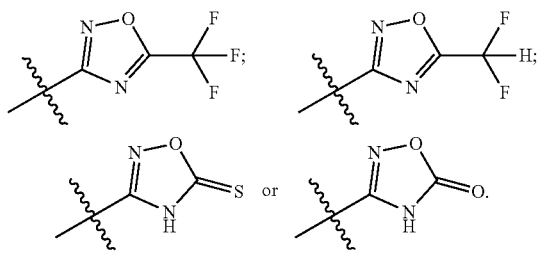

In some embodiments, R¹ is substituted with C(=NH)NHC(=O)OR⁸ and R⁸ is a substituted or unsubstituted arylalkyl. In certain embodiments, R¹ is substituted with C(=NH)NHC(=O)OR⁸ and R⁸ has one of the following structures:

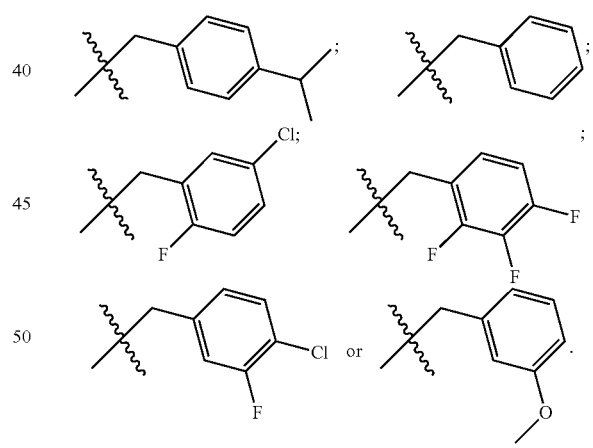

In some embodiments, R¹ is substituted with C(=NOC(=O)R⁸)NH₂ and R⁸ is an aminylalkyl. In certain more specific embodiments, R¹ is substituted with C(=NOC(=O)R⁸)NH₂ and R⁸ has the following structure:

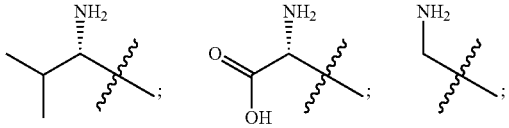

-continued

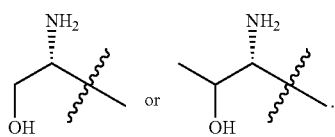 or 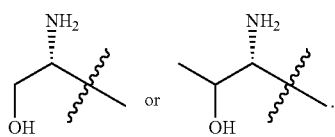

In certain embodiments, $R^1$ is substituted with $C(=NOC(=O)OR^8)NH_2$ and $R^8$ is an alkyl, a haloalkyl, or a substituted or unsubstituted arylalkyl. In some embodiments, $R^1$ is substituted with $C(=NOC(=O)OR^8)NH_2$ and $R^8$ has one of the following structures:

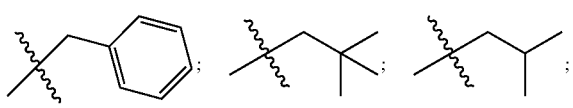

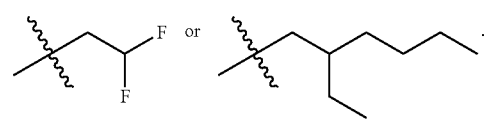

In some more specific embodiments, $R^1$ is substituted with $C(=NOH)NH_2$. In some embodiments, $R^1$ has one of the following structures:

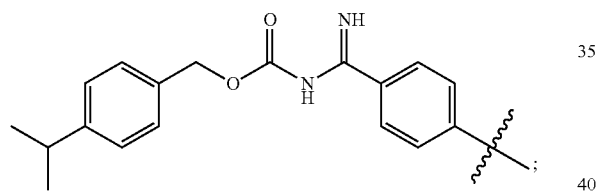

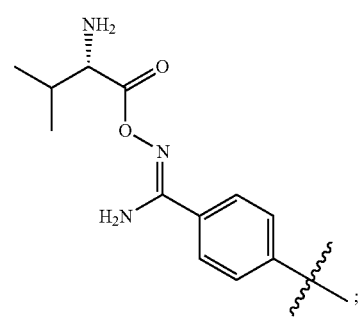

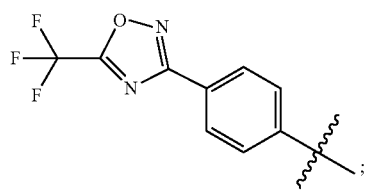

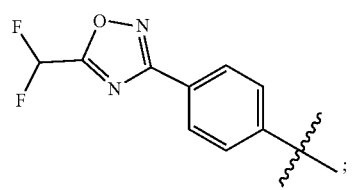

-continued

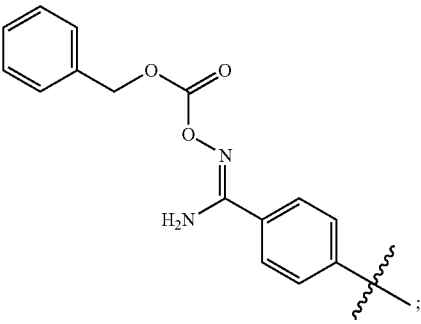

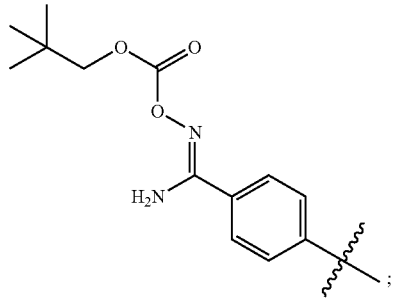

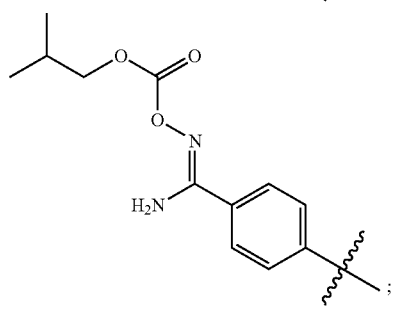

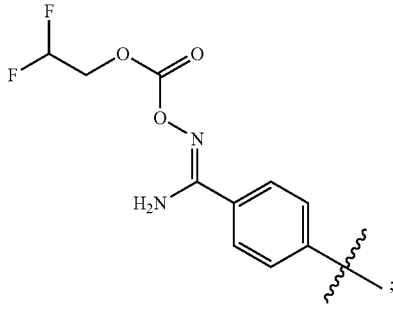

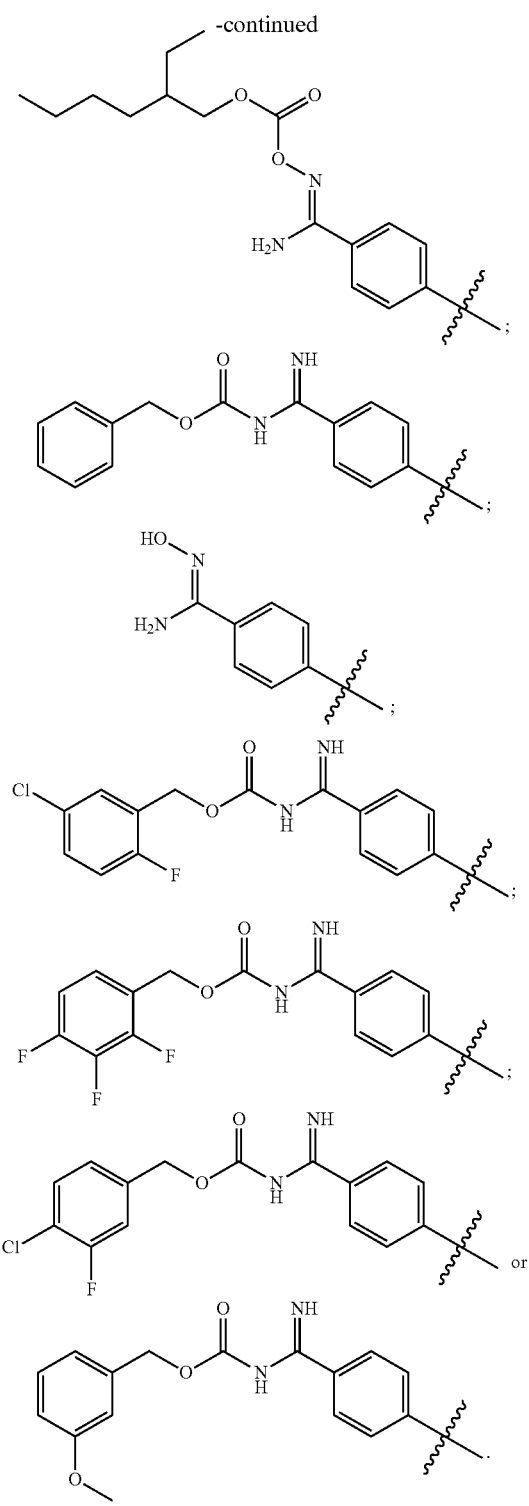

In some embodiments, R² is hydrogen or $C_1$-$C_6$ alkyl. In certain embodiments, R² is $C_1$-$C_6$ alkyl. In some more specific embodiments, R² is —$CH_3$.

In some embodiments, R² and R³, together with the carbon and nitrogen to which they are attached, respectively, form an optionally substituted 4-7 membered heterocyclyl. In certain embodiments, R² and R³, together with the carbon and nitrogen to which they are attached, respectively, form an optionally substituted 4, 5, or 6 membered heterocyclyl.

In some more specific embodiments, R² and R³, together with the carbon and nitrogen to which they are attached, respectively, form an optionally substituted 4-membered heterocyclyl.

In some embodiments, the compound has one of the following Structures (IA1), (IB1), (IC1), (ID1), (IE1), (IF1), (IG1), or (IH1):

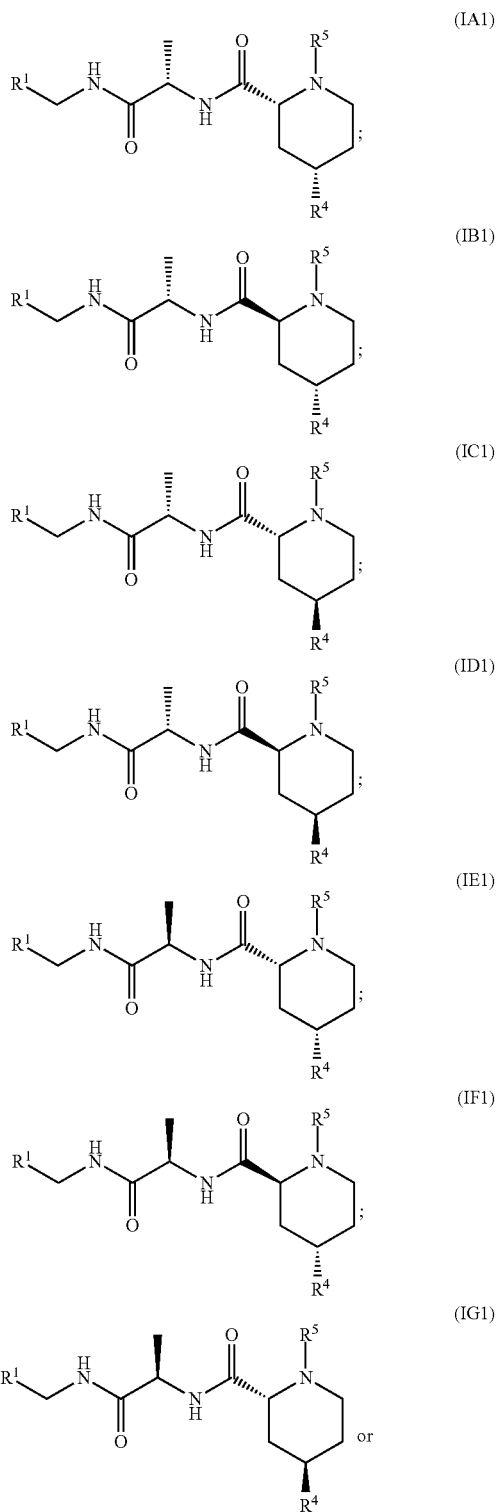

-continued (IH1)
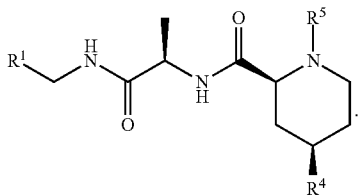

In some embodiments, the compound has one of the following Structures (IA2), (IB2), (IC2), (ID2), (IE2), (IF2), (IG2), or (IH2):

(IA2)
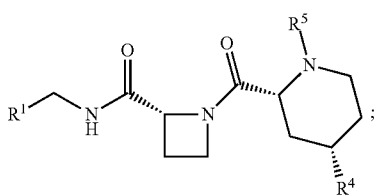

(IB2)
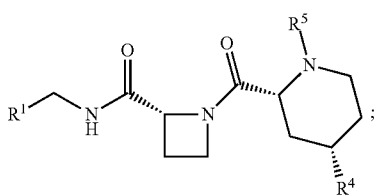

(IC2)
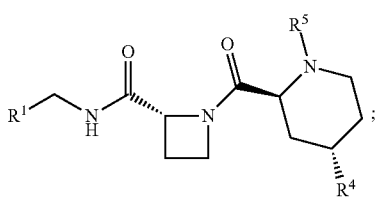

(ID2)
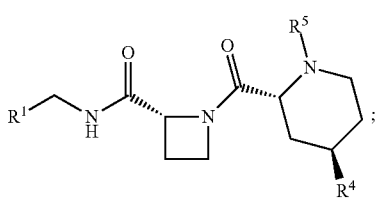

(IE2)
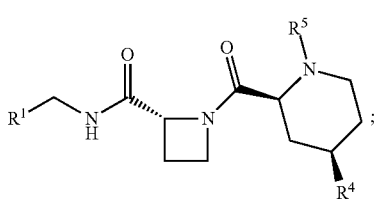

(IF2)
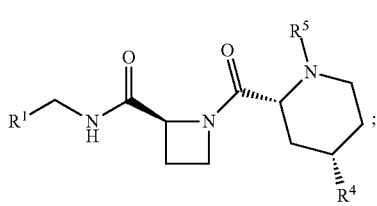

(IG2)
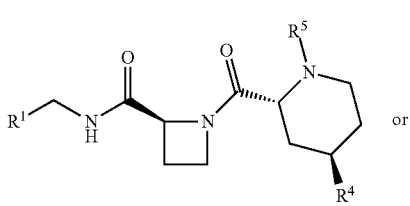

or (IH2)
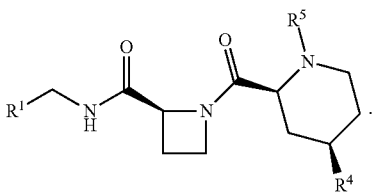

In some embodiments, $R^4$ is a substituted or unsubstituted aryl. In certain embodiments, $R^4$ is a substituted or unsubstituted $C_6$-$C_{10}$ aryl. In some more specific embodiments, $R^4$ is a substituted or unsubstituted phenyl. In certain embodiments, $R^4$ is an unsubstituted phenyl.

In some more specific embodiments, $R^4$ is phenyl substituted with one or more of $R^{4a}$, $R^{4b}$, $R^{4c}$, $R^{4d}$, or $R^{4e}$ wherein $R^{4a}$, $R^{4b}$, $R^{4c}$, $R^{4d}$, and $R^{4e}$ are each independently selected from the group consisting of $C_{1-6}$ alkyl, $C_{2-6}$ alkenyl, $C_{2-6}$ alkynyl, halo, $C_{1-6}$ haloalkyl, aminylalkyl, hydroxy alkyl, cyano, nitro, $OR^{17}$, $SR^{17}$, $C(O)R^{17}$, $C(O)NR^{17}R^{18}$, $C(O)OR^{17}$, $OC(O)R^{17}$, $OC(O)OR^{17}$, $OC(O)NR^{17}R^{18}$, $NR^{17}R^{18}$, $N(R^{17})C(O)R^{18}$, $N(R^{17})C(O)NR^{18}R^{19}$, $N(R^{17})C(O)OR^{18}$, $C(=NR^{17})NR^{18}R^{19}$, $C(=NOR^{17})NR^{18}R^{19}$, $C(=NOC(O)R^{17})NR^{18}R^{19}$, $C(=NR^{17})N(R^{18})C(O)OR^{19}$, $N(R^{17})C(=NR^{18})NR^{19}R^{20}$, $S(O)R^{17}$, $S(O)NR^{17}R^{18}$, $S(O)_2R^{17}$, $N(R^{17})S(O)_2R^{18}$, $S(O)_2NR^{17}R^{18}$, OXO, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^{17}$, $R^{18}$, $R^{19}$, and $R^{20}$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In certain more specific embodiments, $R^{4a}$, $R^{4b}$, $R^{4c}$, $R^{4d}$, or $R^{4e}$ is optionally substituted with one or more substituents selected from the group consisting of halo, CN, $OR^{21}$, $SR^{21}$, $C(O)R^{21}$, $C(O)NR^{21}R^{22}$, $C(O)OR^{21}$, $OC(O)R^{21}$, $OC(O)NR^{21}R^{22}$, $NR^{21}R^{22}$, $NR^{21}C(O)R^{22}$, $NR^{21}C(O)NR^{22}R^{23}$, $NR^{21}C(O)OR^{22}$, $C(=NR^{21})NR^{22}R^{23}$, $NR^{21}C(=NR^{22})NR^{23}R^{24}$, $S(O)R^{21}$, $S(O)NR^{21}R^{22}$, $S(O)_2R^{21}$, $NR^{21}S(O)_2R^{22}$, $S(O)_2NR^{21}R^{22}$ and oxo when $R^{4a}$, $R^{4b}$, $R^{4c}$, $R^{4d}$, or $R^{4e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, wherein $R^{21}$, $R^{22}$, $R^{23}$, and $R^{24}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In some embodiments, R⁴ has one of the following structures:

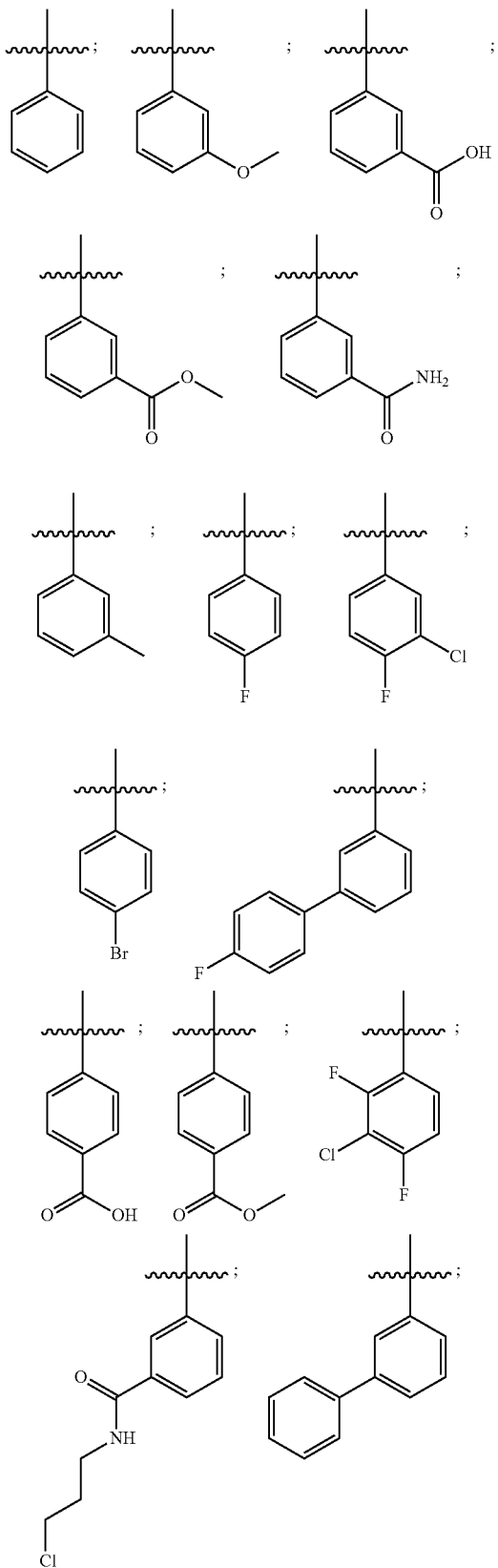

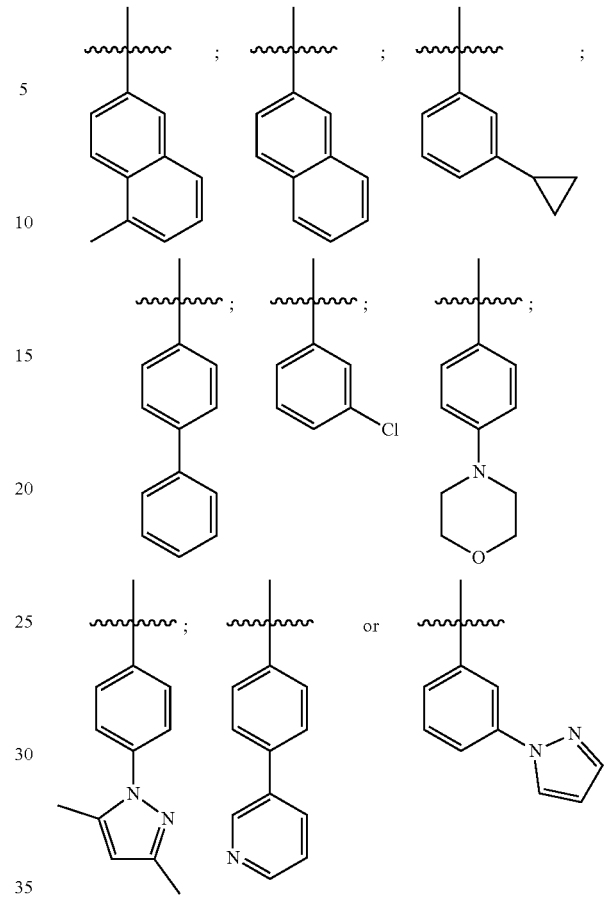

In some embodiments, R has one of the following structures:

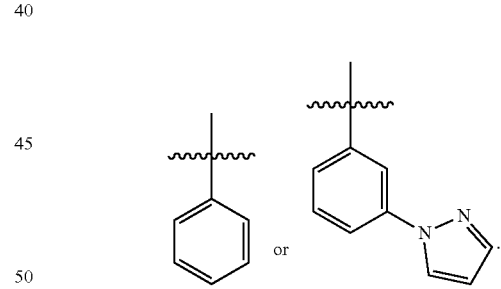

In some embodiments, $R^{5a}$ is alkyl, C(=O)OR⁶, phosphonalkyl, or $(CH_2)_nC(=O)OR^6$. In certain embodiments, $R^{5a}$ is alkyl. In some specific embodiments, $R^{5a}$ is methyl. In certain more specific embodiments, $R^{5a}$ is ethyl. In some embodiments, $R^{5a}$ is C(=O)OR⁶. In some more specific embodiments, $R^{5a}$ has one of the following structures:

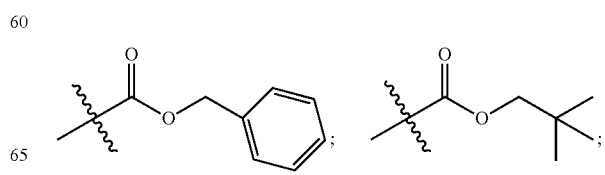

-continued

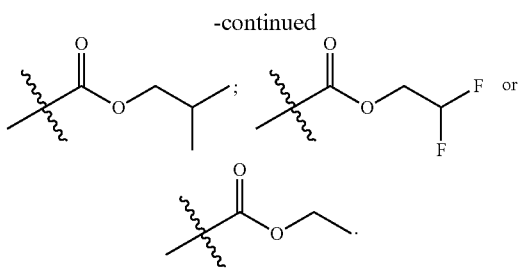

In certain embodiments, $R^{5a}$ is phosphonalkyl. In some specific embodiments, $R^{5a}$ has one of the following structures:

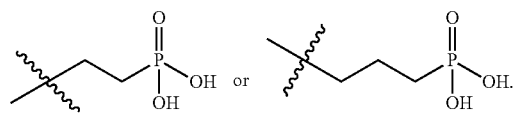 [SMILES: *CCP(=O)(O)O ; "or" ; *CCCP(=O)(O)O]

In certain embodiments, $R^{5a}$ is $(CH_2)_nC(=O)OR^6$. In some more specific embodiments, $R^{5a}$ has one of the following structures:

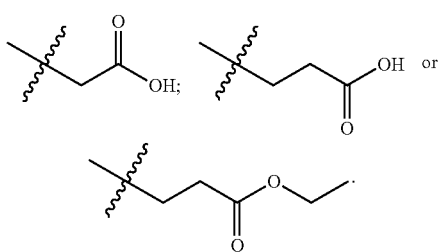

In certain specific embodiments, $R^{5b}$ is an electron pair. In other embodiments, $R^{5b}$ is alkyl (e.g., $C_1$-$C_6$ alkyl). In some embodiments, $R^{5b}$ is methyl.

An additional embodiment provides a compound having the following Structure (II):

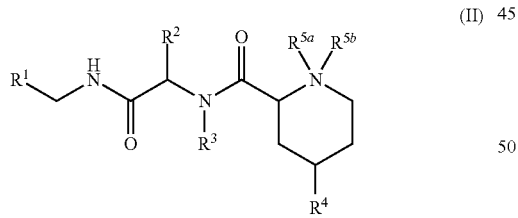

or a stereoisomer, tautomer, or pharmaceutically acceptable salt thereof, wherein:

$R^1$ is a substituted or unsubstituted aryl, substituted or unsubstituted heteroaryl, substituted or unsubstituted cycloalkyl, or a substituted or unsubstituted heterocyclyl;

$R^2$ is hydrogen, alkyl, alkoxy, haloalkyl, haloalkoxy, or cycloalkyl;

$R^3$ is hydrogen, alkyl, haloalkyl, or cycloalkyl;

or $R^2$ and $R^3$, together with the carbon and nitrogen to which they are attached, respectively, form an optionally substituted 4-7 membered heterocyclyl;

$R^4$ is a substituted or unsubstituted aryl, substituted or unsubstituted heteroaryl, substituted or unsubstituted cycloalkyl, or a substituted or unsubstituted heterocyclyl;

$R^{5a}$ is hydrogen, alkyl, haloalkyl, cycloalkyl, phosphonalkyl, $(CH_2)_nC(=O)OR^6$, $C(=O)R^6$, $C(=O)OR^6$, or $C(=O)NR^6R^7$;

$R^{5b}$ is an electron pair or alkyl;

$R^6$ and $R^7$ are, at each occurrence, independently hydrogen, alkyl, haloalkyl, cycloalkyl, or arylalkyl;

$R^8$ is alkyl, haloalkyl, aminylalkyl, substituted or unsubstituted arylalkyl; and n is 1, 2, 3, 4, 5, 6, 7, or 8, provided that A) $R^{5a}$ is alkyl, haloalkyl, cycloalkyl, phosphonalkyl, $(CH_2)_nC(=O)OR^6$, $C(=O)R^6$, $C(=O)OR^6$, or $C(=O)NR^6R^7$ or $R^1$ is substituted with one or more substituents selected from the group consisting of a substituted heteroaryl, $C(=NH)NHC(=O)OR^8$, $C(=NOC(=O)R^8)NH_2$, $C(=NOC(=O)OR^8)NH_2$, and $C(=NOH)NH_2$; and B) the compound of Structure (I) does not have one of the following structures:

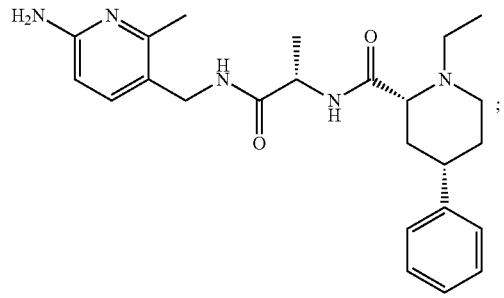

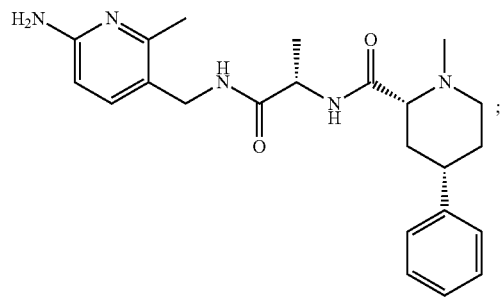

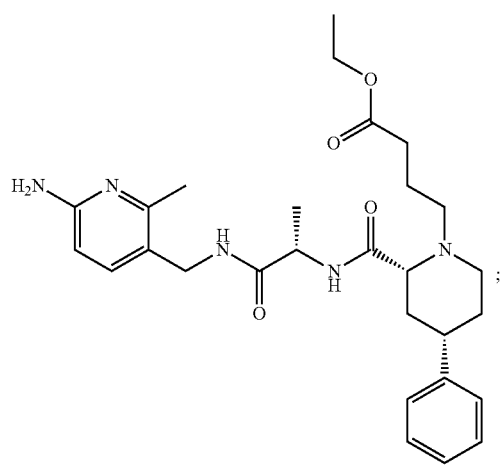

-continued

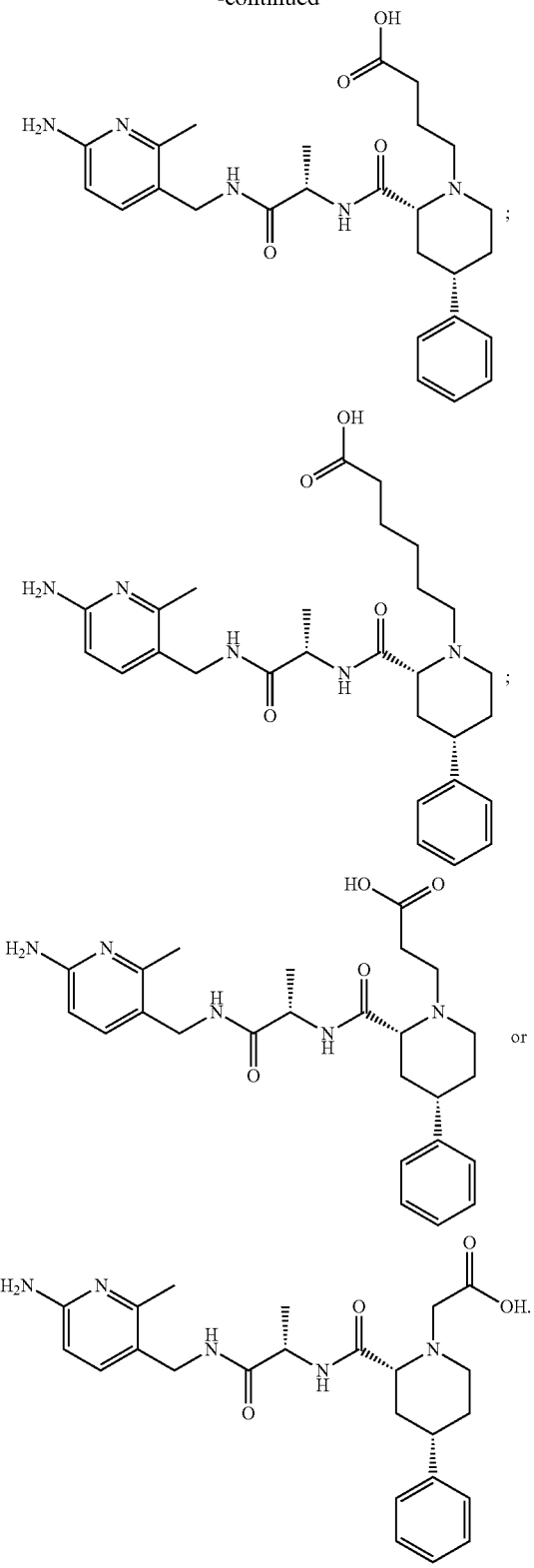

In some embodiments, R is a substituted or unsubstituted aryl. In certain embodiments, $R^1$ is a substituted or unsubstituted $C_6$-$C_{10}$ aryl. In some more specific embodiments, $R^1$ is a substituted or unsubstituted phenyl. In certain more specific embodiments, $R^1$ is a substituted phenyl.

In some embodiments, $R^1$ is phenyl substituted with one or more of $R^{1a}$, $R^{1b}$, $R^{1c}$, $R^{1d}$, and $R^{1e}$ wherein $R^{1a}$, $R^{1b}$, $R^{1c}$, $R^{1d}$, and $R^{1e}$ are each independently selected from the group consisting of C(=NH)NHC(=O)$OR^8$, C(=NOC(=O)$R^8$)$NH_2$, C(=NOC(=O)$OR^8$)$NH_2$, C(=NOH)$NH_2$, $C_{1-6}$ alkyl, $C_{2-6}$ alkenyl, $C_{2-6}$ alkynyl, halo, $C_{1-6}$ haloalkyl, aminylalkyl, hydroxy alkyl, cyano, nitro, $OR^9$, $SR^9$, C(O)$R^9$, C(O)$NR^9R^{10}$, C(O)$OR^9$, OC(O)$R^9$, OC(O)$OR^9$, OC(O)$NR^9R^{10}$, $NR^9R^{10}$, N($R^9$)C(O)$R^{10}$, N($R^9$)C(O)$NR^{10}R^{11}$, N($R^9$)C(O)$OR^{10}$, C(=$NR^9$)$NR^{10}R^{11}$, C(=$NOR^9$)$NR^{10}R^{11}$, C(=NOC(O)$R^9$)$NR^{10}R^{11}$, C(=$NR^9$)N($R^{10}$)C(O)$OR^{11}$, N($R^9$)C(=$NR^{10}$)$NR^{11}R^{12}$, S(O)$R^9$, S(O)$NR^9R^{10}$, S(O)$_2R^9$, N($R^9$)S(O)$_2R^{10}$, S(O)$_2NR^9R^{10}$, OXO, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^9$, $R^{10}$, $R^{11}$, and $R^{12}$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In certain embodiments, $R^{1a}$, $R^{1b}$, $R^{1c}$, $R^{1d}$, or $R^{1e}$ is optionally substituted with one or more substituents selected from the group consisting of halo, CN, $OR^{13}$, $SR^{13}$, C(O)$R^{13}$, C(O)$NR^{13}R^{14}$, C(O)$OR^{13}$, OC(O)$R^{13}$, OC(O)$NR^{13}R^{14}$, $NR^{13}R^{14}$, $NR^{13}$C(O)$R^{14}$, $NR^{13}$C(O)$NR^{14}R^{15}$, $NR^{13}$C(O)$OR^{14}$, C(=$NR^{13}$)$NR^{14}R^{15}$, $NR^{13}$C(=$NR^{14}$)$NR^{15}R^{16}$, S(O)$R^{13}$, S(O)$NR^{13}R^{14}$, S(O)$_2R^{13}$, $NR^{13}$S(O)$_2R^{14}$, S(O)$_2NR^{13}R^{14}$ and oxo when $R^{1a}$, $R^{1b}$, $R^{1c}$, $R^{1d}$, or $R^{1e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, wherein $R^{13}$, $R^{14}$, $R^{15}$, and $R^{16}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In some embodiments, $R^1$ is phenyl substituted with at least one substituent selected from the group consisting of $OR^9$, C(=$NR^9$)$NR^{10}R^{11}$, C(=$NOR^9$)$NR^{10}R^{11}$, C(=NOC(O)$R^9$)$NR^{10}R^{11}$, and C(=$NR^9$)$NR^{10}$C(O)$OR^{11}$. In certain embodiments, $R^1$ is substituted with at least one substituent selected from the group consisting of C(=$NR^9$)$NR^{10}R^{11}$, C(=$NOR^9$)$NR^{10}R^{11}$, C(=NOC(O)$R^9$)$NR^{10}R^{11}$, and C(=$NR^9$)$NR^{10}$C(O)$OR^{11}$. In some more specific embodiments, $R^1$ is substituted with at least one C(=$NR^9$)$NR^{10}R^{11}$. In some more specific embodiments, $R^1$ is substituted with at least one —C(=NH)$NH_2$.

In some embodiments, $R^1$ has one of the following structures:

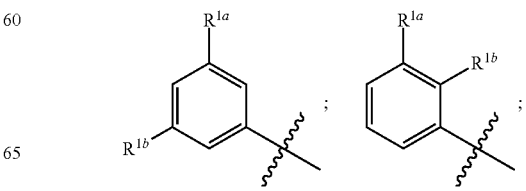

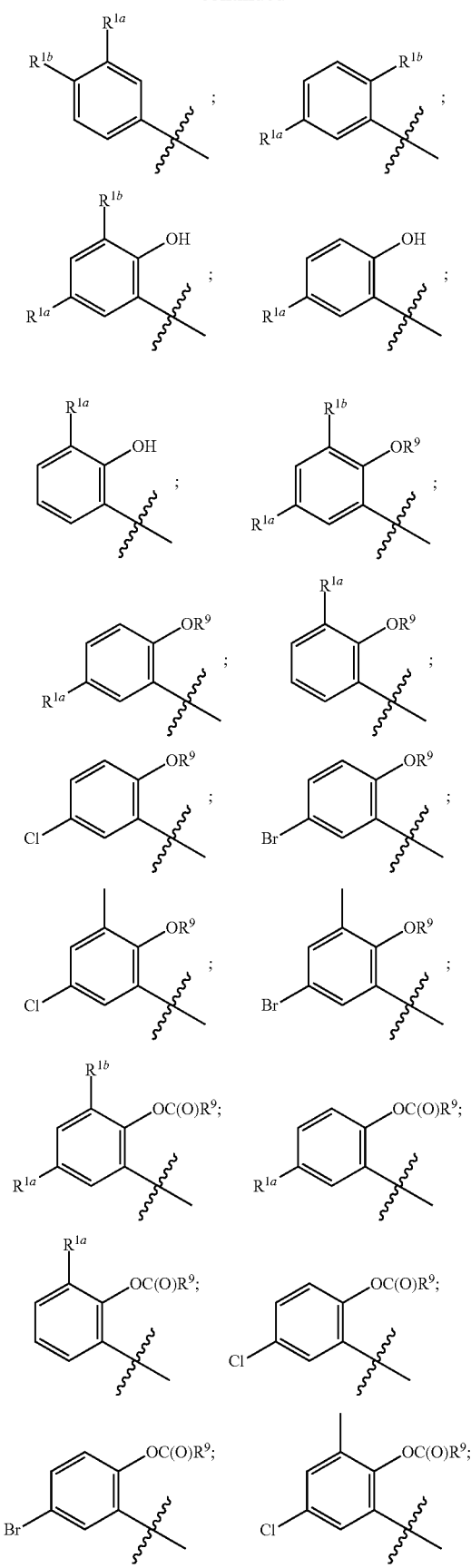
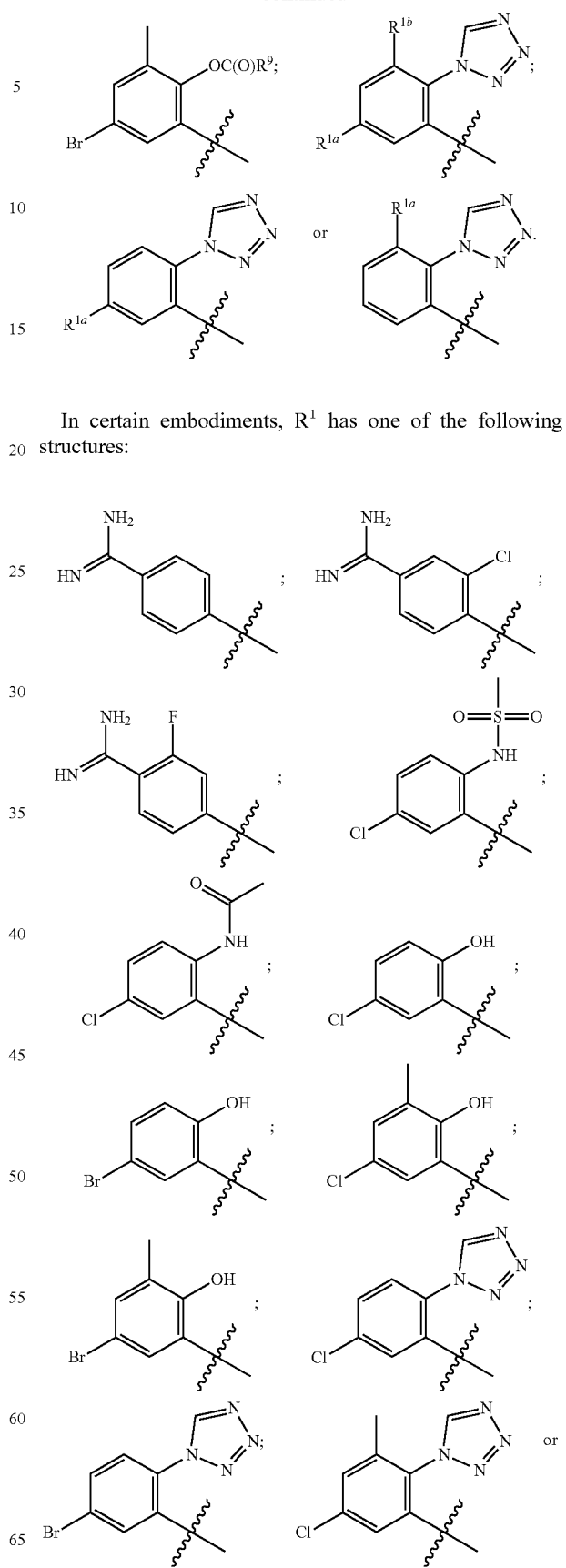
In certain embodiments, $R^1$ has one of the following structures:

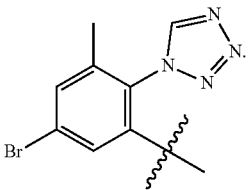

In some more specific embodiments. R¹ has one of the following structures:

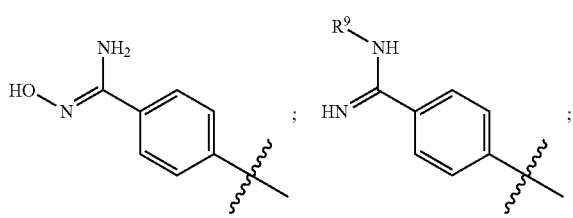

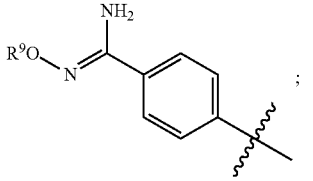

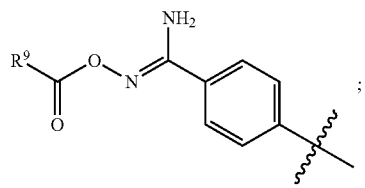

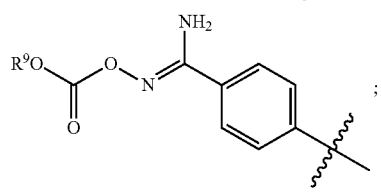

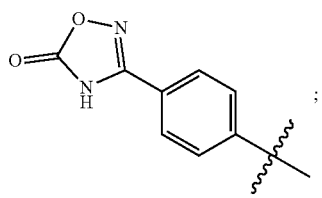

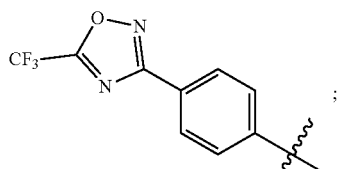

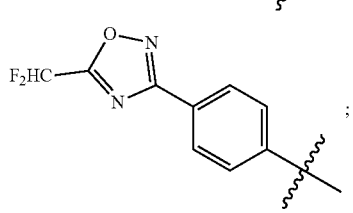

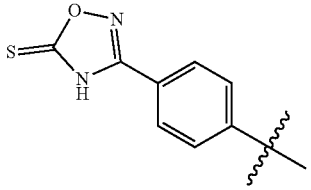

or

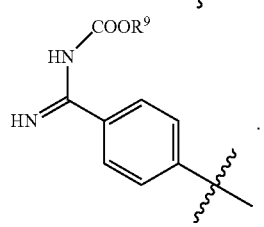

In some of the foregoing embodiments, $R^9$ is $C_{1-6}$ alkyl or $C_{1-6}$ haloalkyl. In certain more specific embodiments, $R^9$ is methyl. In some specific embodiments, $R^9$ is trifluoromethyl.

In certain embodiments, $R^1$ is an unsubstituted phenyl.

In certain other embodiments, $R^1$ is a substituted or unsubstituted heteroaryl. In some embodiments, $R^1$ is a substituted or unsubstituted 5-10 membered heteroaryl. In certain embodiments, $R^1$ is a substituted or unsubstituted pyridinyl, pyrrolopyridinyl, thiophenyl, or benzoimidazolyl. In some more specific embodiments, $R^1$ is a substituted or unsubstituted pyridin-3-yl, 1H-pyrrolo[2,3-b]pyridine-5-yl, thiophen-2-yl, or 1H-benzo[d]imidazol-6-yl.

In certain embodiments, $R^1$ is pyridin-3-yl, 1H-pyrrolo[2,3-b]pyridine-5-yl, thiophen-2-yl, or 1H-benzo[d]imidazol-6-yl substituted with one or more of $R^{1a}$, $R^{1b}$, $R^{1c}$, $R^{1d}$, and $R^{1e}$ wherein $R^{1a}$, $R^{1b}$, $R^{1c}$, $R^{1d}$, and $R^{1e}$ are each independently selected from the group consisting of $C_{1-6}$ alkyl, $C_{2-6}$ alkenyl, $C_{2-6}$ alkynyl, halo, $C_{1-6}$ haloalkyl, aminylalkyl, hydroxyalkyl, cyano, nitro, $OR^9$, $SR^9$, $C(O)R^9$, $C(O)NR^9R^{10}$, $C(O)OR^9$, $OC(O)R^9$, $OC(O)OR^9$, $OC(O)NR^9R^{12}$, $NR^9R^{10}$, $N(R^9)C(O)R^{10}$, $N(R^9)C(O)NR^{10}R^{11}$, $N(R^9)C(O)OR^{10}$, $C(=NR^9)NR^{10}R^{11}$, $C(=NOR^9)NR^{10}R^{11}$, $C(=NOC(O)R^9)NR^{10}R^{11}$, $C(=NR^9)N(R^{10})C(O)OR^{11}$, $N(R^9)C(=NR^{10})NR^{11}R^{12}$, $S(O)R^9$, $S(O)NR^9R^{10}$, $S(O)_2R^9$, $N(R^9)S(O)_2R^{10}$, $S(O)_2NR^9R^{10}$, OXO, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^9$, $R^{10}$, $R^{11}$, and $R^{12}$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In some embodiments, $R^{1a}$, $R^{1b}$, $R^{1c}$, $R^{1d}$, or $R^{1e}$ is optionally substituted with one or more substituents selected from the group consisting of halo, CN, $OR^{13}$, $SR^{13}$, $C(O)R^{13}$, $C(O)NR^{13}R^{14}$, $C(O)OR^{13}$, $OC(O)R^{13}$, $OC(O)NR^{13}R^{14}$, $NR^{13}R^{14}$, $NR^{13}C(O)R^{14}$, $NR^{13}C(O)NR^{14}R^{15}$, $NR^{13}C(O)OR^{14}$, $C(=NR^{13})NR^{14}R^{15}$, $NR^{13}C(=NR^{14})NR^{15}R^{16}$, $S(O)R^{13}$, $S(O)NR^{13}R^{14}$, $S(O)_2R^{13}$, $NR^{13}S(O)_2R^{14}$, $S(O)_2NR^{13}R^{14}$ and oxo when $R^{1a}$, $R^{1b}$, $R^{1c}$, $R^{1d}$, or $R^{1e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, wherein $R^{13}$, $R^{14}$, $R^{15}$, and $R^{16}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.
In some embodiments, $R^1$ has one of the following structures:
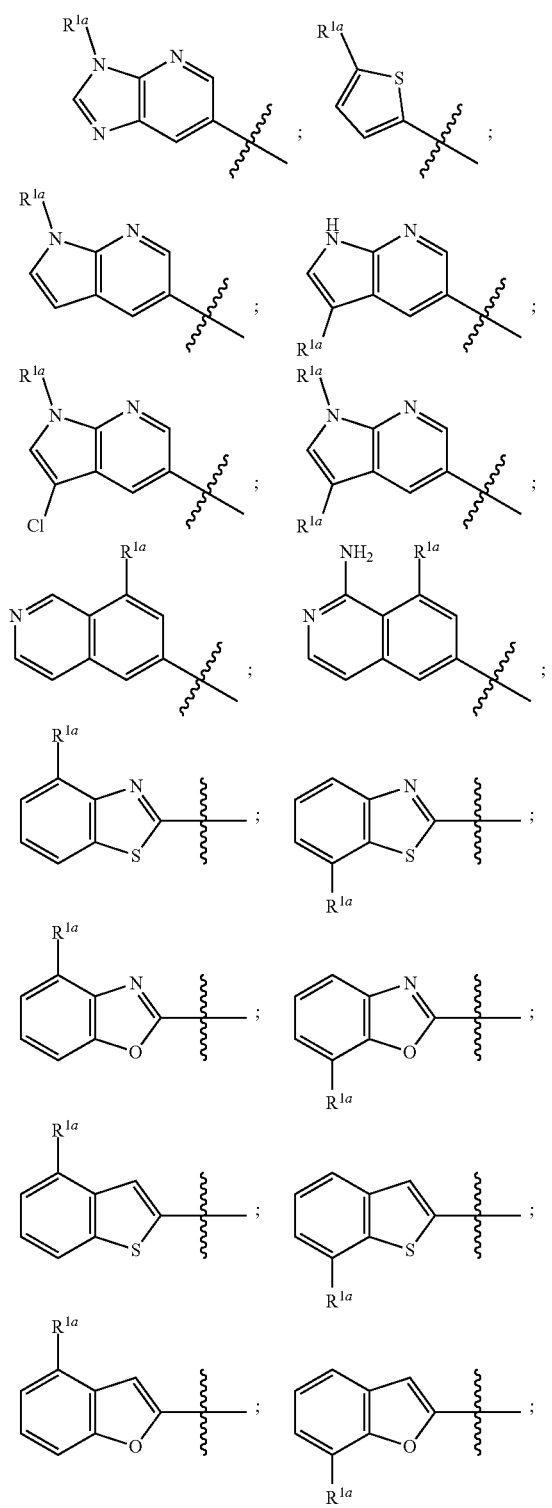
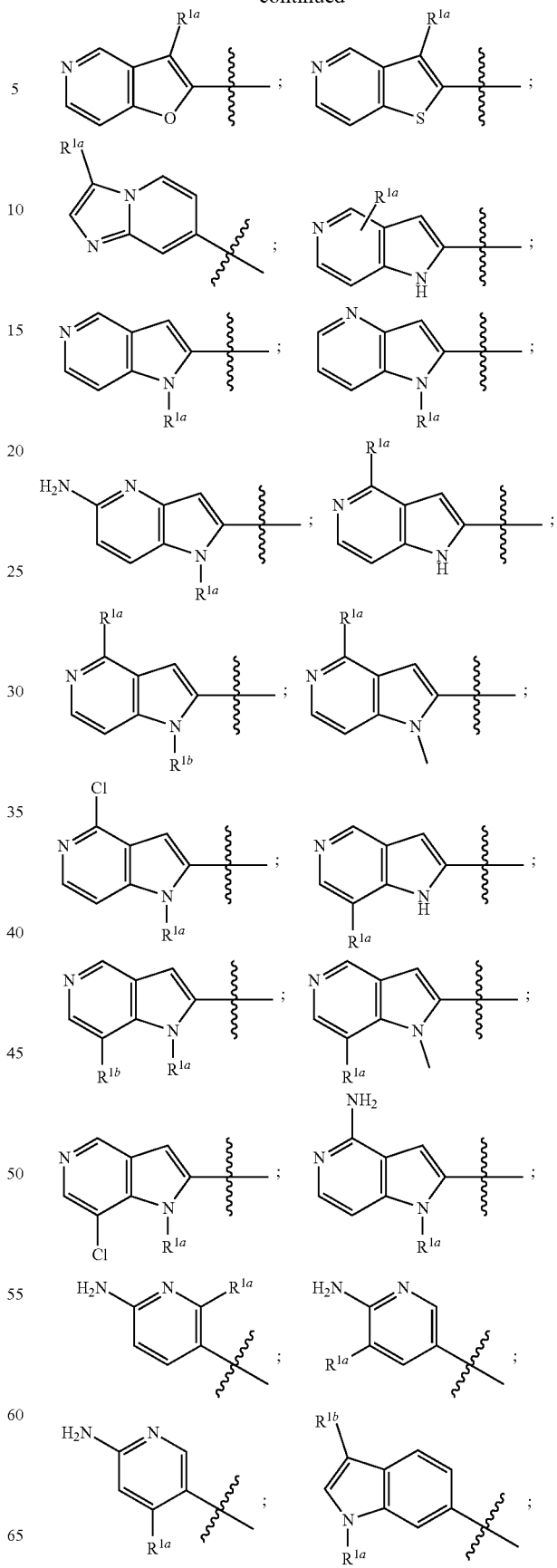

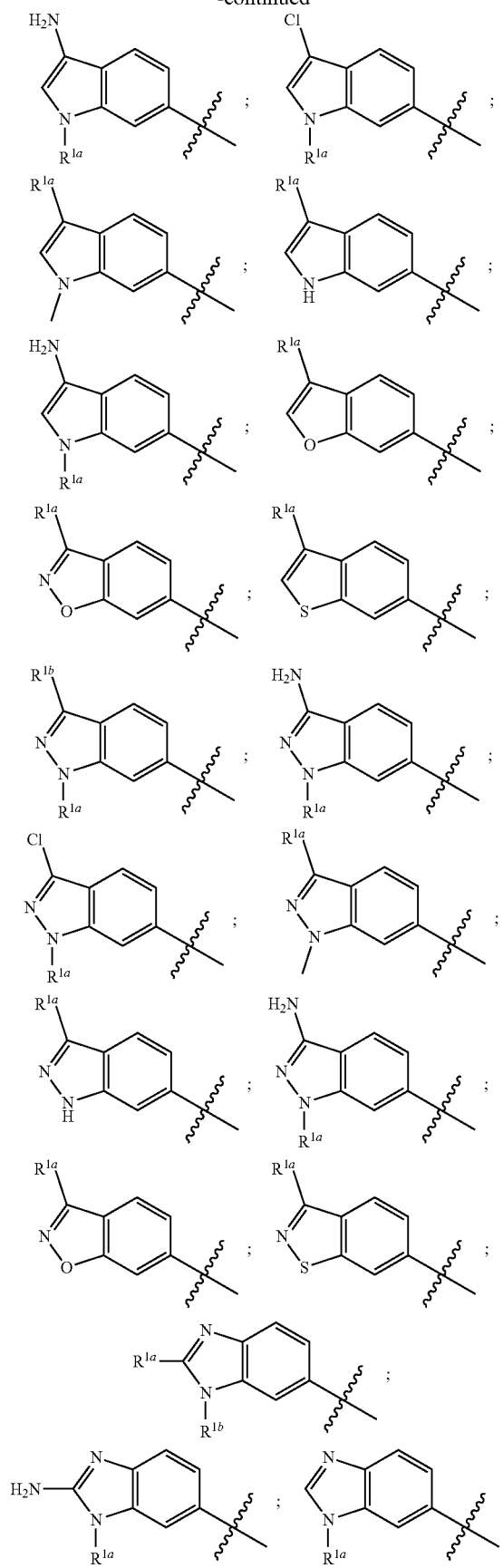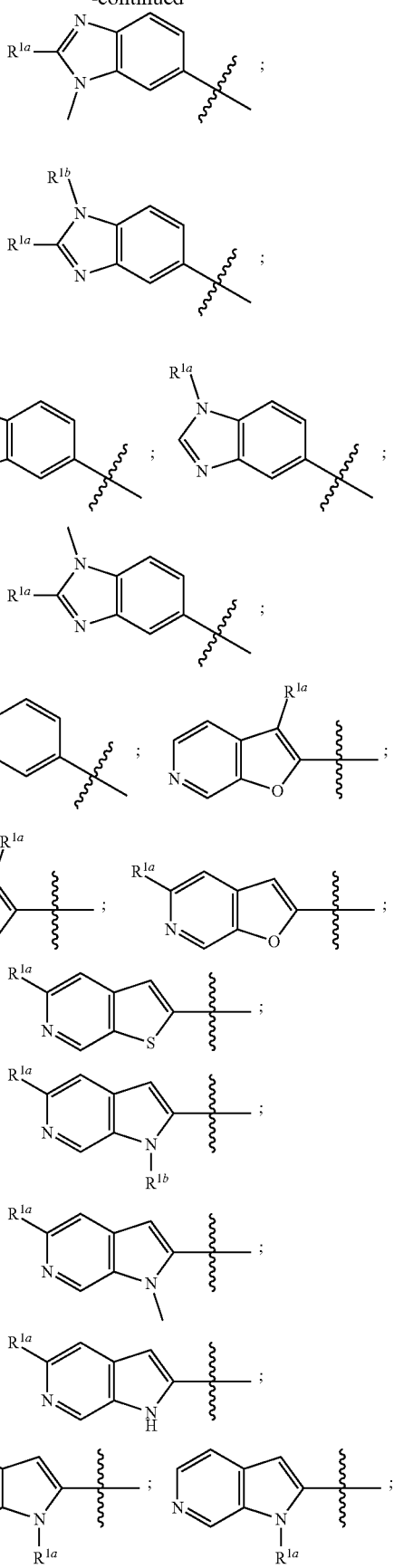

-continued

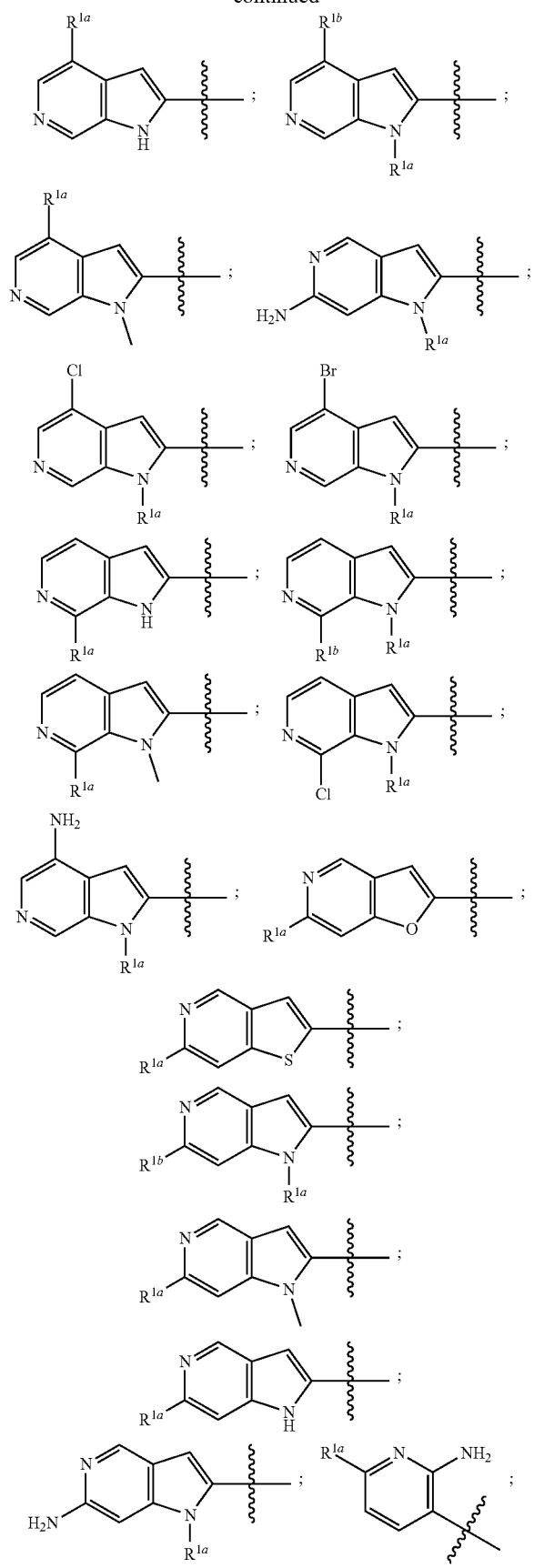

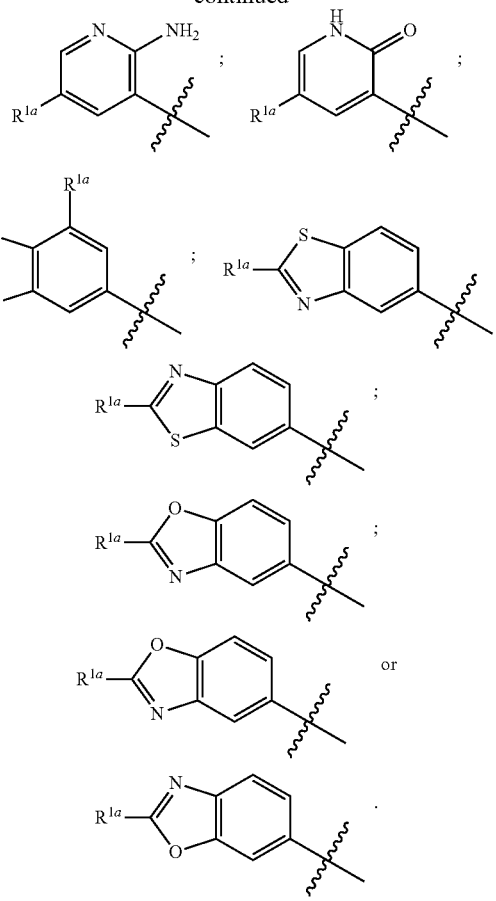

In some embodiments, R or $R^D$ is independently $C_{1-6}$ alkyl, amino, or halo. In certain embodiments, $R^{1a}$ or $R^{1b}$ is methyl or ethyl. In some more specific embodiments, $R^{1a}$ or $R^{1b}$ is F, Cl, or Br. In some embodiments, each $R^{1a}$ or $R^{1b}$ attached to nitrogen is $C_{1-6}$ alkyl. In some more specific embodiments, $R^{1a}$ or $R^{1b}$ is methyl or ethyl. In certain more specific embodiments, $R^1$ has one of the following structures:

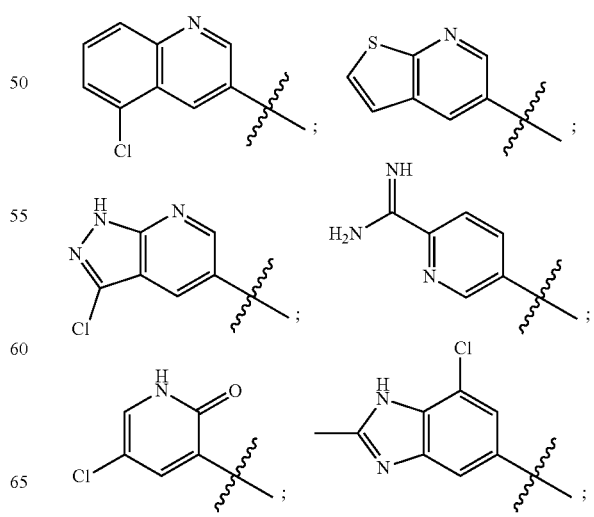

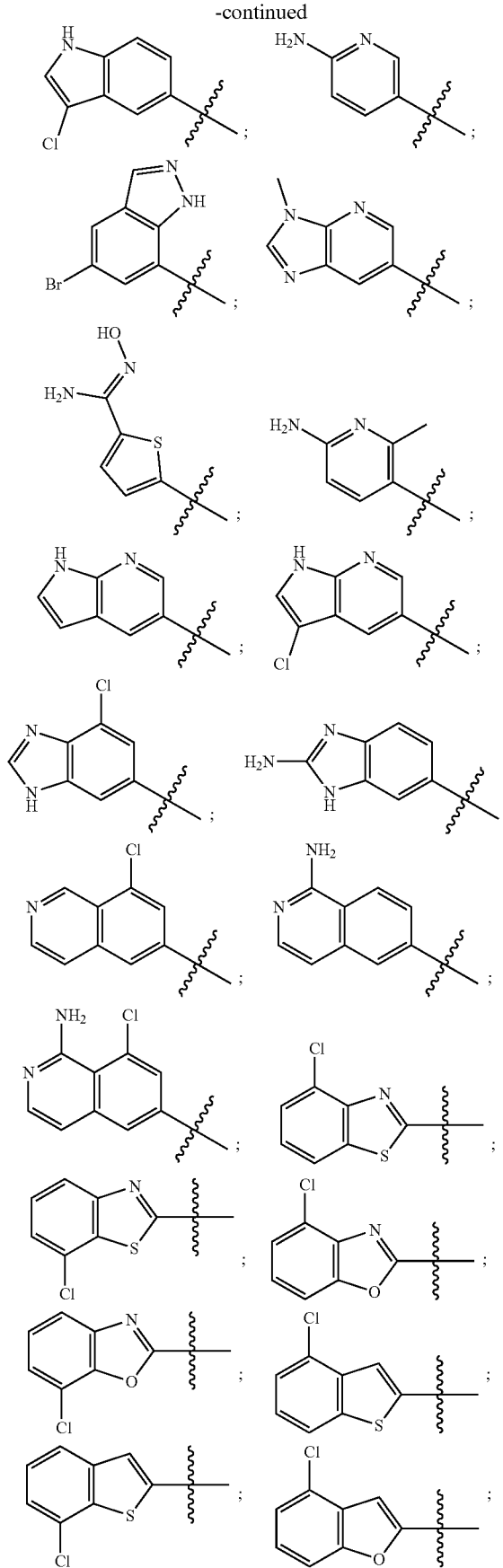
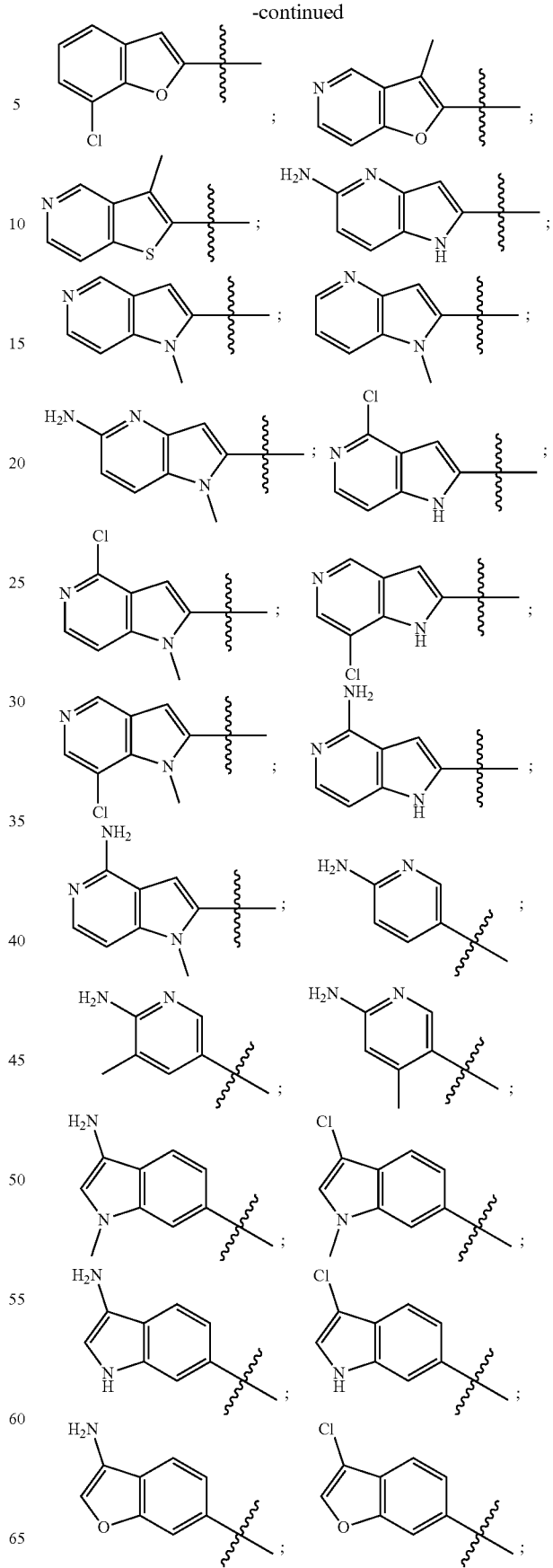

-continued
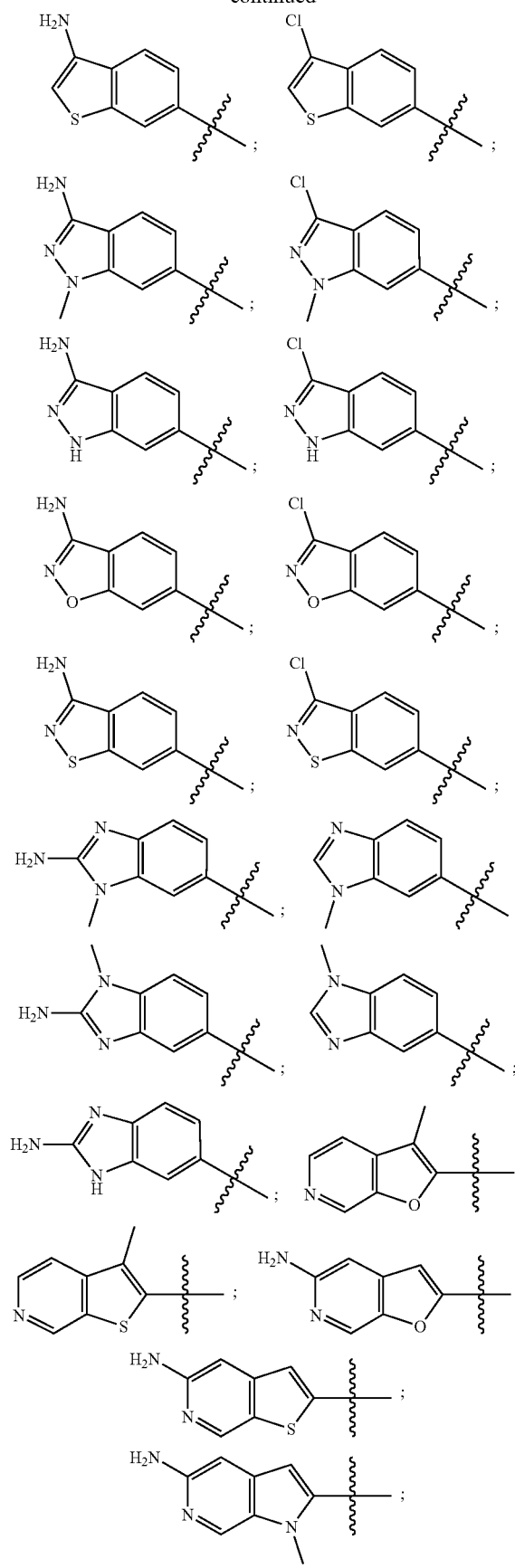
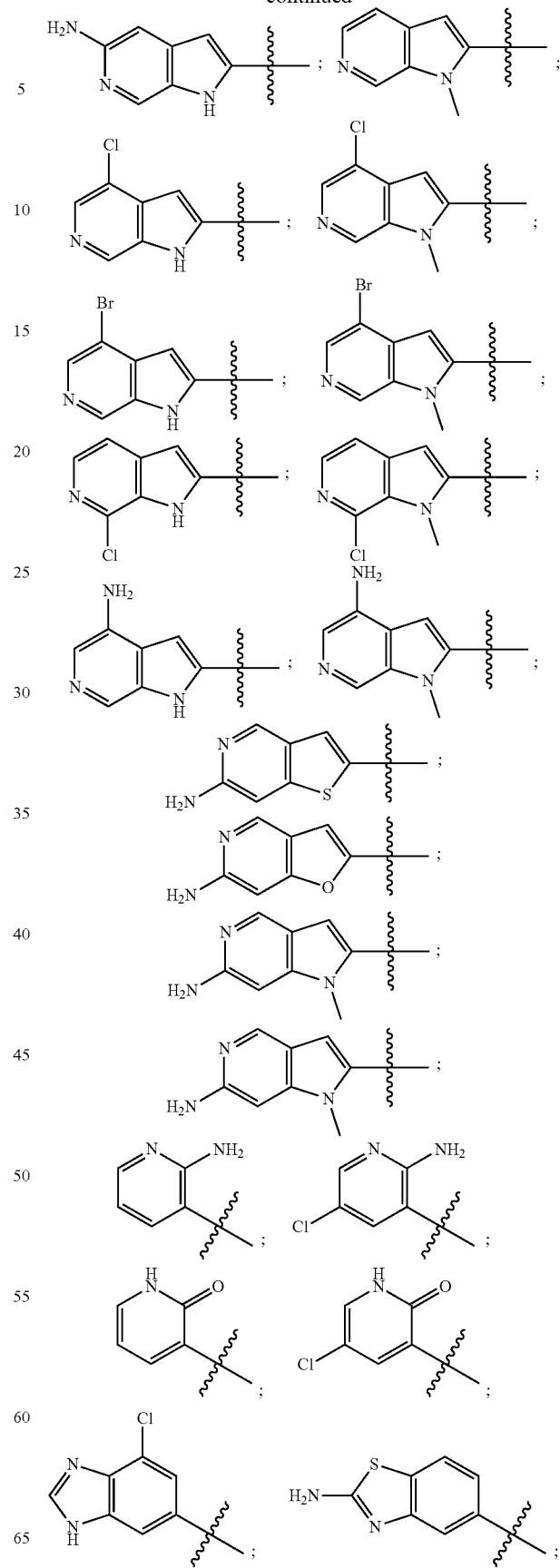

-continued

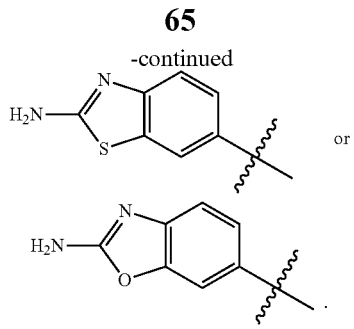
or

In some embodiments, R¹ has one of the following structures:

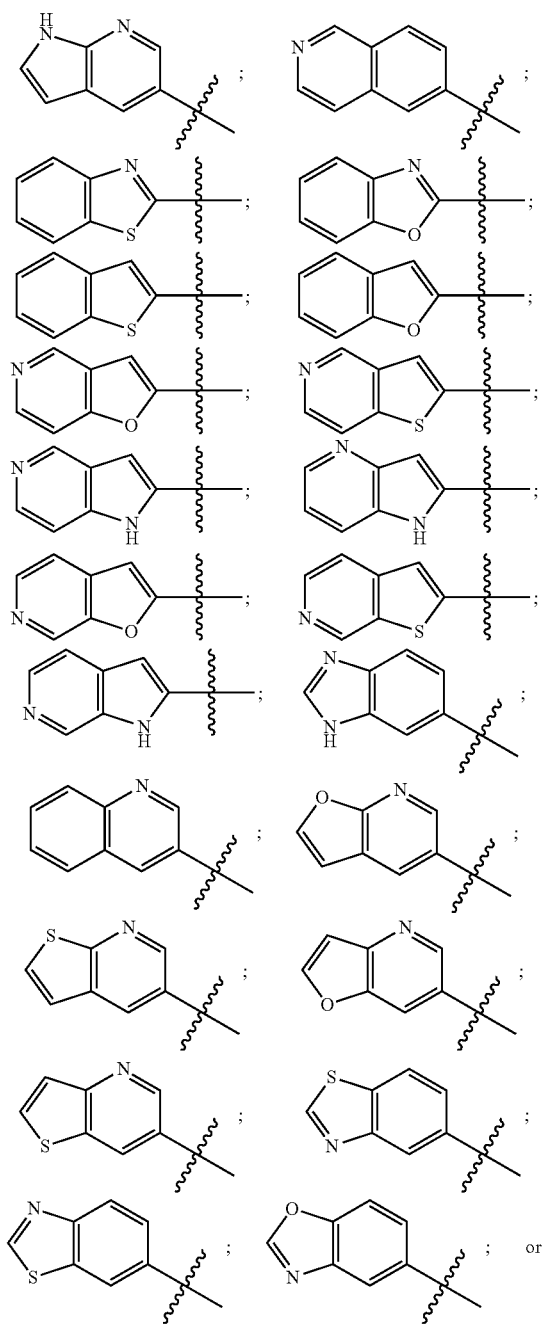

-continued

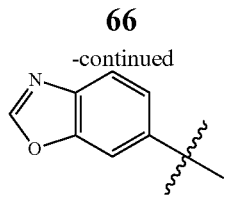

In certain embodiments, R is a substituted or unsubstituted cycloalkyl. In certain embodiments, R¹ is a substituted or unsubstituted $C_3$-$C_6$ cycloalkyl. In some more specific embodiments, R¹ is a substituted $C_3$-$C_6$ cycloalkyl.

In some more specific embodiments, R¹ is a $C_3$-$C_6$ cycloalkyl substituted with one or more of $R^{1a}$, $R^{1b}$, $R^{1c}$, $R^{1d}$, and $R^{1e}$ wherein $R^{1a}$, $R^{1b}$, $R^{1c}$, $R^{1d}$, and $R^{1e}$ are each independently selected from the group consisting of $C_{1-6}$ alkyl, $C_{2-6}$ alkenyl, $C_{2-6}$ alkynyl, $C_{1-6}$ haloalkyl, aminylalkyl, hydroxyalkyl, nitro, $OR^9$, $SR^9$, $C(O)R^9$, $C(O)NR^9R^{10}$, $C(O)OR^9$, $OC(O)R^9$, $OC(O)OR^9$, $OC(O)NR^9R^{10}$, $NR^9R^{10}$, $N(R^9)C(O)R^{10}$, $N(R^9)C(O)NR^{10}R^{11}$, $N(R^9)C(O)OR^{10}$, $C(=NR^9)NR^{10}R^{11}$, $C(=NOR^9)NR^{10}R^{11}$, $C(=NOC(O)R^9)NR^{10}R^{11}$, $C(=NR^9)N(R^{10})C(O)OR^{11}$, $N(R^9)C(=NR^{10})NR^{11}R^{12}$, $S(O)R^9$, $S(O)NR^9R^{10}$, $S(O)_2R^9$, $N(R^9)S(O)_2R^{10}$, $S(O)_2NR^9R^{10}$, OXO, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted CG-IO cycloalkyl, and substituted or unsubstituted 4-10 membered heterocyclyl, wherein $R^9$, $R^{10}$, $R^{11}$, and $R^{12}$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In some embodiments, $R^{1a}$, $R^{1b}$, $R^{1c}$, $R^{1d}$, or $R^{1e}$ is optionally substituted with one or more substituents selected from the group consisting of halo, CN, $OR^{13}$, $SR^{13}$, $C(O)R^{13}$, $C(O)NR^{13}R^{14}$, $C(O)OR^{13}$, $OC(O)R^{13}$, $OC(O)NR^{13}R^{14}$, $NR^{13}R^{14}$, $NR^{13}C(O)R^{14}$, $NR^{13}C(O)NR^{14}R^{15}$, $NR^{13}C(O)OR^{14}$, $C(=NR^{13})NR^{14}R^{15}$, $NR^{13}C(=NR^{14})NR^{15}R^{16}$, $S(O)R^{13}$, $S(O)NR^{13}R^{14}$, $S(O)_2R^{13}$, $NR^{13}S(O)_2R^{14}$, $S(O)_2NR^{13}R^{14}$ and oxo when $R^{1a}$, $R^{1b}$, $R^{1c}$, $R^{1d}$, or $R^{1e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, wherein $R^{13}$, $R^{14}$, $R^{15}$, and $R^{16}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In some embodiments, R¹ is an unsubstituted a $C_3$-$C_6$ cycloalkyl.

In certain embodiments, R¹ is a substituted or unsubstituted heterocyclyl. In some more specific embodiments, R¹ is a substituted or unsubstituted 4-10 membered heterocyclyl. In certain more specific embodiments, R¹ is a substituted 4-10 membered heterocyclyl.

In some embodiments, R¹ is a 4-10 membered heterocyclyl substituted with one or more of $R^{1a}$, $R^{1b}$, $R^{1c}$, $R^{1d}$, and $R^{1e}$ wherein $R^{1a}$, $R^{1b}$, $R^{1c}$, $R^{1d}$, and $R^{1e}$ are each independently selected from the group consisting of $C_{1-6}$ alkyl, $C_{2-6}$ alkenyl, $C_{2-6}$ alkynyl, halo, $C_{1-6}$ haloalkyl, aminylalkyl, hydroxyalkyl, cyano, nitro, $OR^9$, $SR^9$, $C(O)R^9$, $C(O)NR^9R^{10}$, $C(O)OR^9$, $OC(O)R^9$, $OC(O)OR^9$, $OC(O)NR^9R^{10}$, $NR^9R^{10}$, $N(R^9)C(O)R^{10}$, $N(R^9)C(O)NR^{10}R^{11}$, $N(R^9)C(O)$ OR$^{10}$, C(=NR$^9$)NR$^{10}$R$^{11}$, C(=NOR$^9$)NR$^{10}$R$^{11}$, C(=NOC(O)R$^9$)NR$^{10}$R$^{11}$, C(=NR$^9$)N(R$^{10}$)C(O)OR$^{11}$, N(R$^9$)C(=NR$^{10}$)NR$^{11}$R$^{12}$, S(O)R$^9$, S(O)NR$^9$R$^{10}$, S(O)$_2$R$^9$, N(R$^9$)S(O)$_2$R$^{10}$, S(O)$_2$NR$^9$R$^{10}$, OXO, substituted or unsubstituted C$_{6-10}$ aryl, substituted or unsubstituted C$_{6-10}$ arylalkyl, substituted or unsubstituted C$_{6-10}$ aryloxy, substituted or unsubstituted C$_{6-10}$ arylalkoxy, substituted or unsubstituted 5-10 membered heteroaryl, substituted or unsubstituted C$_{3-10}$ cycloalkyl, and substituted or unsubstituted 4-10 membered heterocyclyl, wherein R$^9$, R$^{10}$, R$^{11}$, and R$^{12}$, are, at each occurrence, independently selected from the group consisting of hydrogen, C$_{1-6}$ alkyl, C$_{2-6}$ alkenyl, C$_{2-6}$ alkynyl, hydroxyl, C$_{1-6}$ alkoxy, aryl, arylalkyl, C$_{1-6}$ haloalkyl, C$_{1-6}$ haloalkoxy, C$_{1-6}$ hydroxyalkyl, cycloalkyl, heterocyclyl, and heteroaryl.

In certain embodiments, R$^{1a}$, R$^{1b}$, R$^{1c}$, R$^{1d}$, or R$^{1e}$ is optionally substituted with one or more substituents selected from the group consisting of OR$^{13}$, SR$^{13}$, C(O)R$^{13}$, C(O)NR$^{13}$R$^{14}$, C(O)OR$^{13}$, OC(O)R$^{13}$, OC(O)NR$^{13}$R$^{14}$, NR$^{13}$R$^{14}$, NR$^{13}$C(O)R$^{14}$, NR$^{13}$C(O)NR$^{14}$R$^{15}$, NR$^{13}$C(O)OR$^{14}$, C(=NR$^{13}$)NR$^{14}$R$^{15}$, NR$^{13}$C(=NR$^{14}$)NR$^{15}$R$^{16}$, S(O)R$^{13}$, S(O)NR$^{13}$R$^{14}$, S(O)$_2$R$^{13}$, NR$^{13}$S(O)$_2$R$^{14}$, S(O)$_2$NR$^{13}$R$^{14}$ and oxo when R$^{1a}$, R$^{1b}$, R$^{1c}$, R$^{1d}$, or R$^{1e}$ is a substituted C$_{6-10}$ aryl, a substituted C$_{6-10}$ arylalkyl, a substituted C$_{6-10}$ aryloxy, a substituted C$_{6-10}$ arylalkoxy, a substituted 5-10 membered heteroaryl, a substituted C$_{3-10}$ cycloalkyl, and a substituted 4-10 membered heterocyclyl, wherein R$^{13}$, R$^{14}$, R$^{15}$, and R$^{16}$ are, at each occurrence, independently selected from the group consisting of hydrogen, C$_{1-6}$ alkyl, C$_{2-6}$ alkenyl, C$_{2-6}$ alkynyl, hydroxyl, C$_{1-6}$ alkoxy, aryl, arylalkyl, C$_{1-6}$ haloalkyl, C$_{1-6}$ haloalkoxy, C$_{1-6}$ hydroxyalkyl, cycloalkyl, heterocyclyl, and heteroaryl.

In some embodiments, R$^1$ is an unsubstituted 4-10 membered heterocyclyl. In certain embodiments, R$^1$ is substituted with one or more substituents selected from the group consisting of a substituted heteroaryl, C(=NH)NHC(=O)OR$^8$, C(=NOC(=O)R$^8$)NH$_2$, C(=NOC(=O)OR$^8$)NH$_2$, and C(=NOH)NH$_2$. In some more specific embodiments, R$^1$ is substituted with a substituted heteroaryl having one of the following structures:

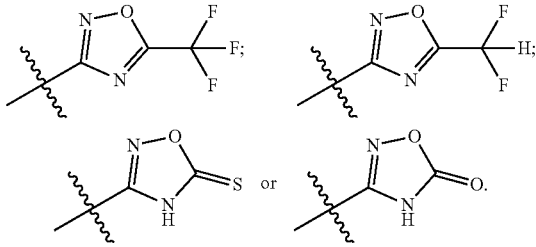

In some embodiments, R$^1$ is substituted with C(=NH)NHC(=O)OR$^8$ and R$^8$ is a substituted or unsubstituted arylalkyl. In certain embodiments, R$^1$ is substituted with C(=NH)NHC(=O)OR$^8$ and R$^8$ has one of the following structures:

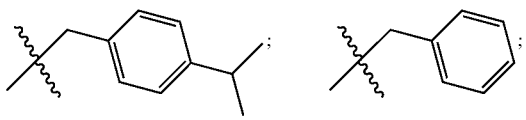

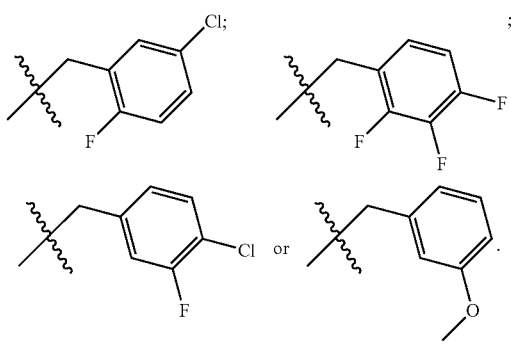

In some embodiments, R$^1$ is substituted with C(=NOC(=O)R$^8$)NH$_2$ and R$^8$ is an aminylalkyl. In certain more specific embodiments, R$^1$ is substituted with C(=NOC(=O)R$^8$)NH$_2$ and R$^8$ has the following structure:

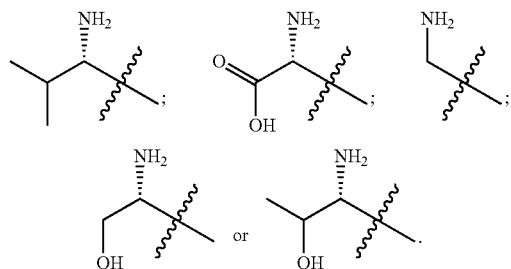

In certain embodiments, R$^1$ is substituted with C(=NOC(=O)OR$^8$)NH$_2$ and R$^8$ is an alkyl, a haloalkyl, or a substituted or unsubstituted arylalkyl. In some embodiments, R$^1$ is substituted with C(=NOC(=O)OR$^8$)NH$_2$ and R$^8$ has one of the following structures:

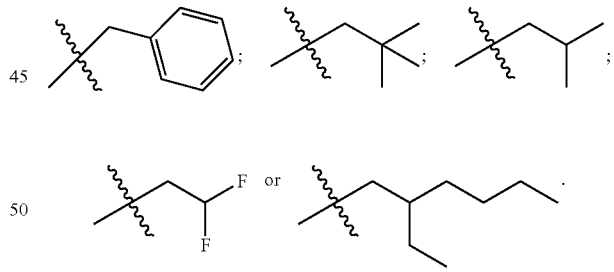

In some more specific embodiments, R$^1$ is substituted with C(=NOH)NH$_2$. In some embodiments, R$^1$ has one of the following structures:

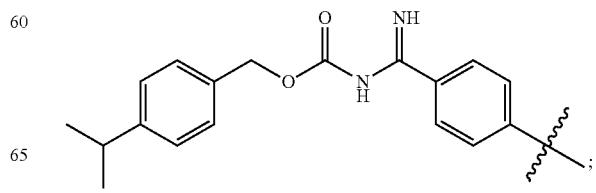

69
-continued
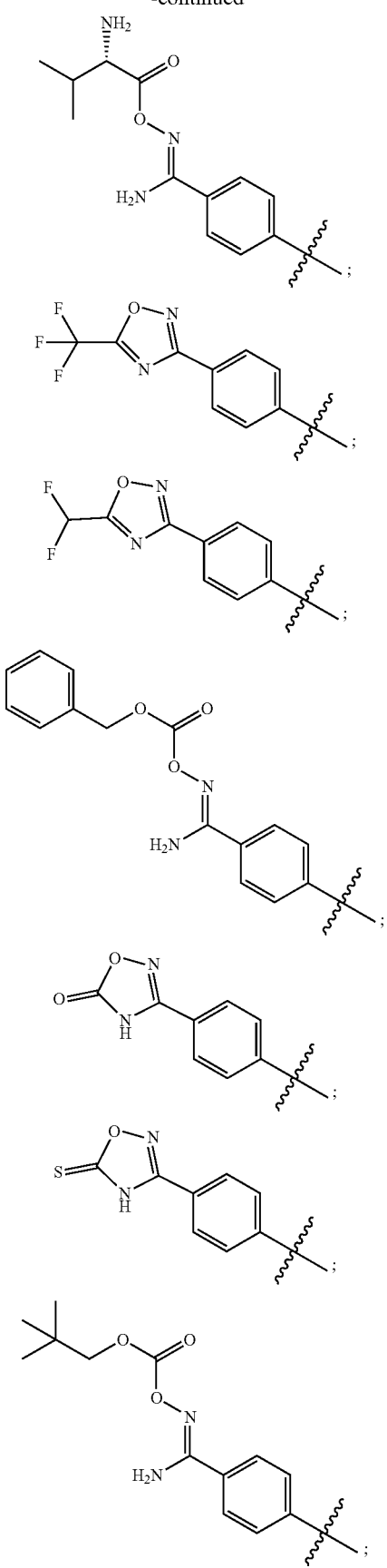
70
-continued
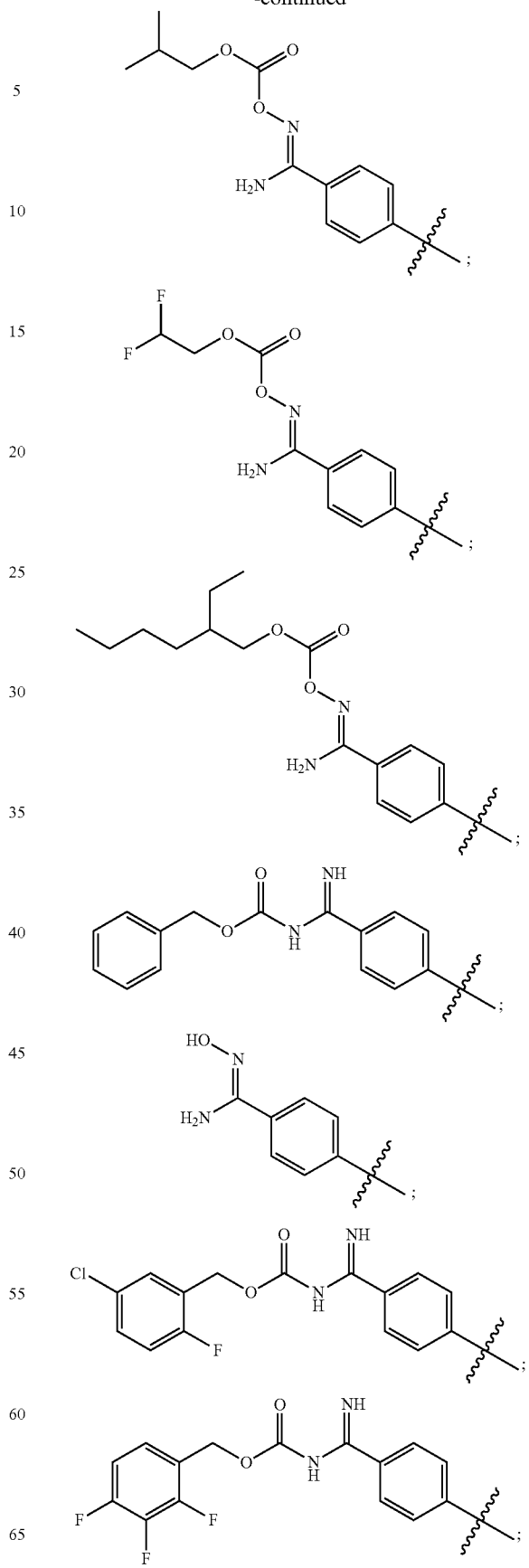

-continued

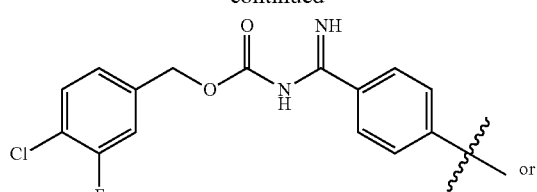
or

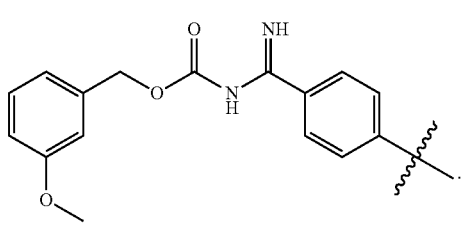
.

In some embodiments, R² is hydrogen or C₁-C₆ alkyl. In certain embodiments, R² is C₁-C₆ alkyl. In some more specific embodiments, R² is —CH₃.

In some embodiments, R² and R³, together with the carbon and nitrogen to which they are attached, respectively, form an optionally substituted 4-7 membered heterocyclyl. In certain embodiments, R² and R³, together with the carbon and nitrogen to which they are attached, respectively, form an optionally substituted 4, 5, or 6 membered heterocyclyl. In some more specific embodiments, R² and R³, together with the carbon and nitrogen to which they are attached, respectively, form an optionally substituted 4-membered heterocyclyl.

In some embodiments, the compound has one of the following Structures (IA1), (IB1), (IC1), (ID1), (IE1), (IF1), (IG1), or (IH1):

(IA1)
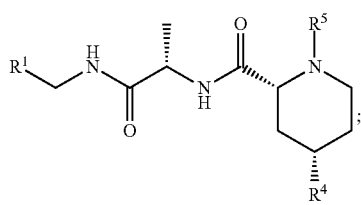

(IB1)
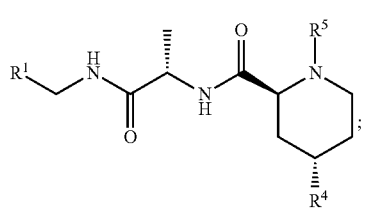

(IC1)
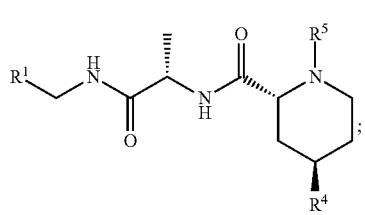

(ID1)
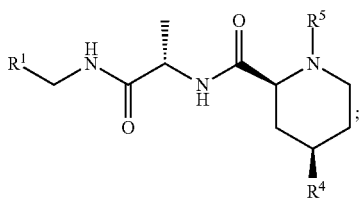

(IE1)
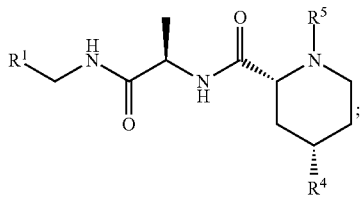

(IF1)
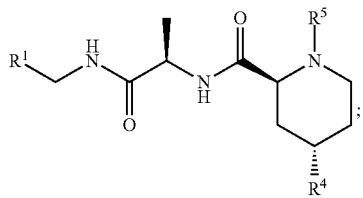

(IG1)
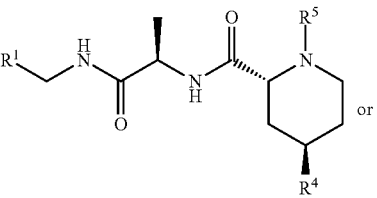
or (IH1)
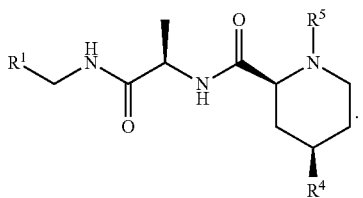
.

In some embodiments, the compound has one of the following Structures (IA2), (IB2), (IC2), (ID2), (IE2), (IF2), (IG2), or (IH2):

(IA2)
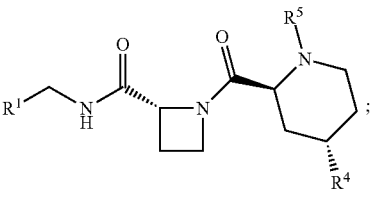

(IB2)
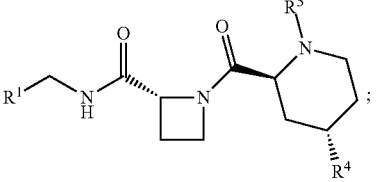

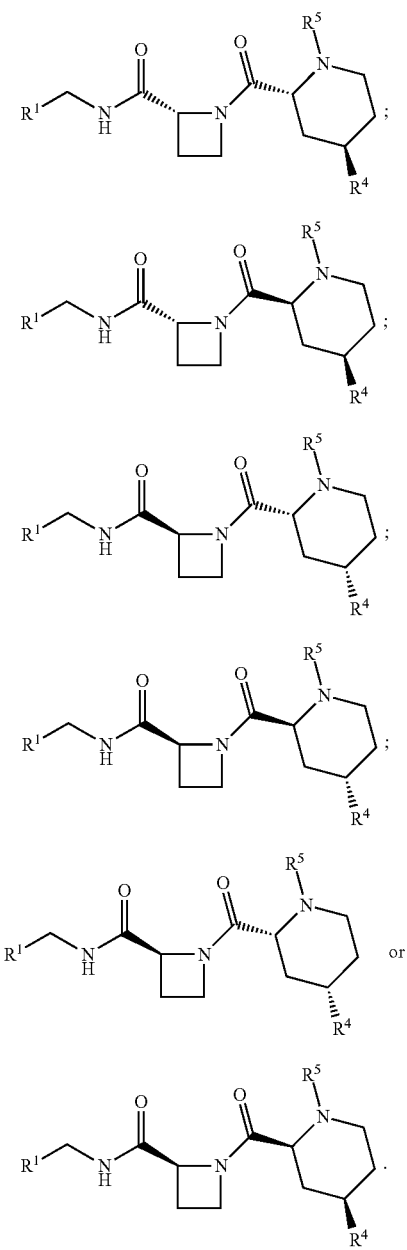

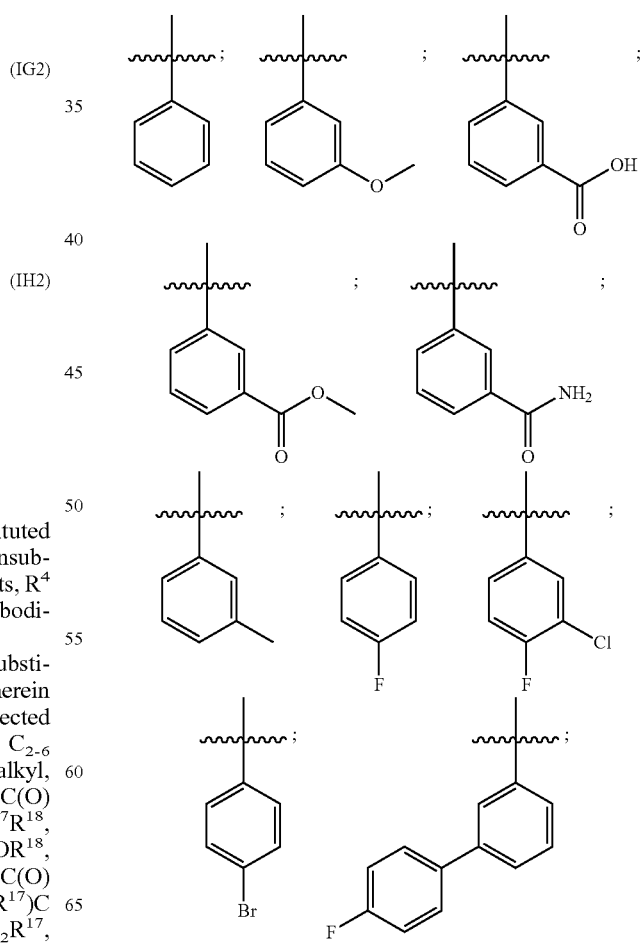

unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^{17}$, $R^{18}$, $R^{19}$, and $R^{20}$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In certain more specific embodiments, $R^{4a}$, $R^{4b}$, $R^{4c}$, $R^{4d}$, or $R^{4e}$ is optionally substituted with one or more substituents selected from the group consisting of $OR^{21}$, $SR^{21}$, $C(O)R^{21}$, $C(O)NR^{21}R^{22}$, $C(O)OR^{21}$, $OC(O)R^{21}$, $OC(O)NR^{21}R^{22}$, $NR^{21}R^{22}$, $NR^{21}C(O)R^{22}$, $NR^{21}C(O)NR^{22}R^{23}$, $NR^{21}C(O)OR^{22}$, $C(=NR^{21})NR^{22}R^{23}$, $NR^{21}C(=NR^{22})NR^{23}R^{24}$, $S(O)R^{21}$, $S(O)NR^{21}R^{22}$, $S(O)_2R^{21}$, $NR^{21}S(O)_2R^{22}$, $S(O)_2NR^{21}R^{22}$ and oxo when $R^{4a}$, $R^{4b}$, $R^{4c}$, $R^{4d}$, or $R^{4e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, wherein $R^{21}$, $R^{22}$, $R^{23}$, and $R^{24}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In some embodiments, $R^4$ has one of the following structures:

In some embodiments, R is a substituted or unsubstituted aryl. In certain embodiments, $R^4$ is a substituted or unsubstituted $C_6$-$C_{10}$ aryl. In some more specific embodiments, $R^4$ is a substituted or unsubstituted phenyl. In certain embodiments, $R^4$ is an unsubstituted phenyl.

In some more specific embodiments, $R^4$ is phenyl substituted with one or more of $R^{4a}$, $R^{4b}$, $R^{4c}$, $R^{4d}$, or $R^{4e}$ wherein $R^{4a}$, $R^{4b}$, $R^{4c}$, $R^{4d}$, and $R^{4e}$ are each independently selected from the group consisting of $C_{1-6}$ alkyl, $C_{2-6}$ alkenyl, $C_{2-6}$ alkynyl, halo, $C_{1-6}$ haloalkyl, aminylalkyl, hydroxy alkyl, cyano, nitro, $OR^{17}$, $SR^{17}$, $C(O)R^{17}$, $C(O)NR^{17}R^{18}$, $C(O)OR^{17}$, $OC(O)R^{17}$, $OC(O)OR^{17}$, $OC(O)NR^{17}R^{18}$, $NR^{17}R^{18}$, $N(R^{17})C(O)R^{18}$, $N(R^{17})C(O)NR^{18}R^{19}$, $N(R^{17})C(O)OR^{18}$, $C(=NR^{17})NR^{18}R^{19}$, $C(=NOR^{17})NR^{18}R^{19}$, $C(=NOC(O)R^{17})NR^{18}R^{19}$, $C(=NR^{17})N(R^{18})C(O)OR^{19}$, $N(R^{17})C(=NR^{18})NR^{19}R^{20}$, $S(O)R^{17}$, $S(O)NR^{17}R^{18}$, $S(O)_2R^{17}$, $N(R^{17})S(O)_2R^{18}$, $S(O)_2NR^{17}R^{18}$, OXO, substituted or -continued

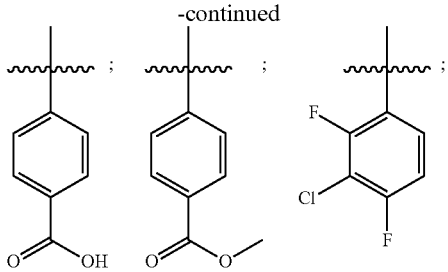

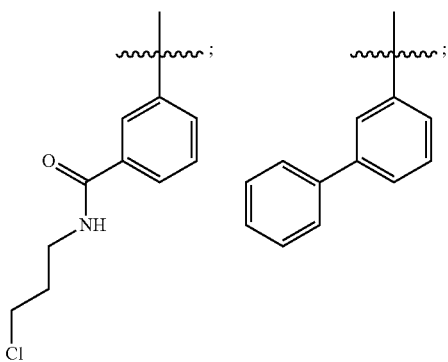

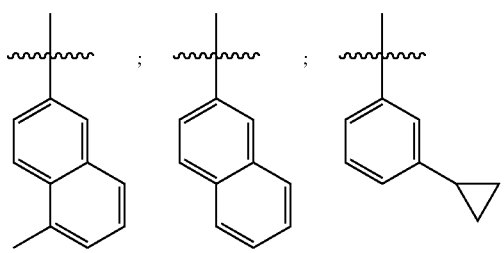

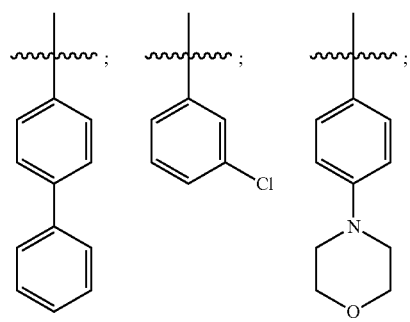

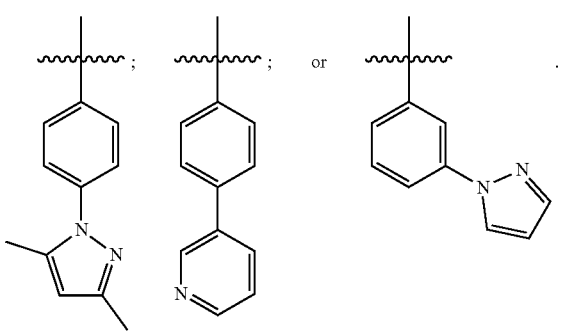

In some embodiments, $R^4$ has one of the following structures:

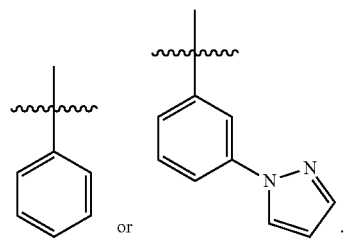 [SMILES: *c1ccccc1 ; *c1cccc(-n2cccn2)c1]

In some embodiments, $R^{5a}$ is alkyl, $C(=O)OR^6$, phosphonalkyl, or $(CH_2)_nC(=O)OR^6$. In certain embodiments, $R^{5a}$ is alkyl. In some specific embodiments, $R^{5a}$ is methyl. In certain more specific embodiments, $R^{5a}$ is ethyl. In some embodiments, $R^{5a}$ is $C(=O)OR^6$. In some more specific embodiments, $R^{5a}$ has one of the following structures:

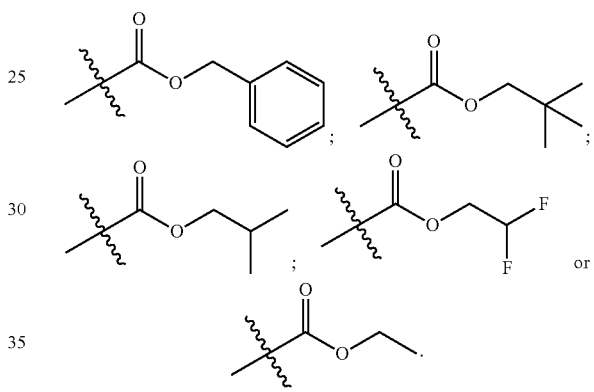

In certain embodiments, $R^{5a}$ is phosphonalkyl. In some specific embodiments, $R^{5a}$ has one of the following structures:

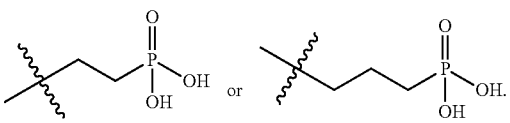 [SMILES: *CCP(=O)(O)O ; *CCCP(=O)(O)O]

In certain embodiments, $R^{5a}$ is $(CH_2)_nC(=O)OR^6$. In some more specific embodiments, $R^{5a}$ has one of the following structures:

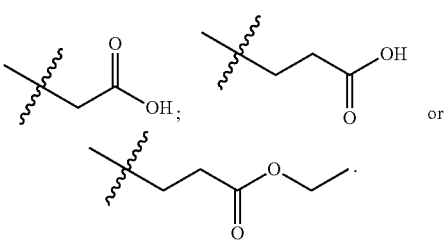

In certain specific embodiments, $R^{5b}$ is an electron pair. In other embodiments, $R^{5b}$ is alkyl (e.g., $C_1$-$C_6$ alkyl). In some embodiments, $R^{5b}$ is methyl.

Still another embodiment provides a compound having the following Structure (III):

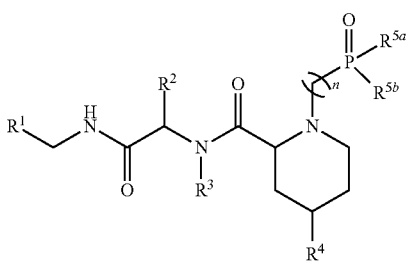

or a stereoisomer, tautomer, or pharmaceutically acceptable salt thereof, wherein:

$R^1$ is a substituted or unsubstituted aryl, substituted or unsubstituted heteroaryl, substituted or unsubstituted cycloalkyl, or a substituted or unsubstituted heterocyclyl;

$R^2$ is hydrogen, alkyl, alkoxy, haloalkyl, haloalkoxy, or cycloalkyl;

$R^3$ is hydrogen, alkyl, haloalkyl, or cycloalkyl;

or $R^2$ and $R^3$, together with the carbon and nitrogen to which they are attached, respectively, form an optionally substituted 4-7 membered heterocyclyl;

$R^4$ is a substituted or unsubstituted aryl, substituted or unsubstituted heteroaryl, substituted or unsubstituted cycloalkyl, or a substituted or unsubstituted heterocyclyl;

$R^{5a}$ and $R^{5b}$ at each occurrence, independently have one of the following structures:

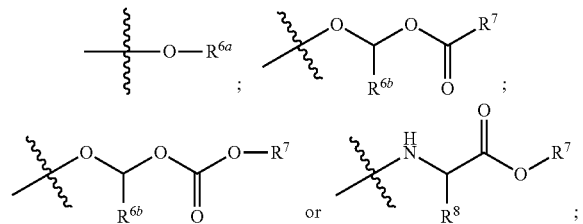

or $R^{5a}$ and $R^{5b}$, together with the phosphorus atom to which they are attached form an optionally substituted 4-7 membered heterocyclyl;

$R^{6a}$ is alkyl, haloalkyl, aryl, heteroaryl, cycloalkyl, or heterocyclyl;

$R^{6b}$ is, at each occurrence, independently hydrogen or alkyl;

$R^7$ is, at each occurrence, independently alkyl, haloalkyl, heteroaryl, cycloalkyl, heterocyclyl, arylalkyl, heteroarylalkyl, cycloalkylalkyl, or heterocyclylalkyl;

$R^8$ is an amino acid side chain; and n is 1, 2, 3, 4, 5, 6, 7, or 8.

In some embodiments, $R^1$ is a substituted or unsubstituted aryl. In certain embodiments, $R^1$ is a substituted or unsubstituted $C_6$-$C_{10}$ aryl. In some more specific embodiments, $R^1$ is a substituted or unsubstituted phenyl. In certain more specific embodiments, $R^1$ is a substituted phenyl.

In some embodiments, $R^1$ is phenyl substituted with one or more of $R^{1a}$, $R^{1b}$, $R^{1c}$, $R^{1d}$, and $R^{1e}$ wherein $R^{1a}$, $R^{1b}$, $R^{1c}$, $R^{1d}$, and $R^{1e}$ are each independently selected from the group consisting of $C(=NH)NHC(=O)OR^8$, $C(=NOC(=O)R^8)NH_2$, $C(=NOC(=O)OR^8)NH_2$, $C(=NOH)NH_2$, $C_{1-6}$ alkyl, $C_{2-6}$ alkenyl, $C_{2-6}$ alkynyl, halo, $C_{1-6}$ haloalkyl, aminylalkyl, hydroxy alkyl, cyano, nitro, $OR^9$, $SR^9$, $C(O)R^9$, $C(O)NR^9R^{10}$, $C(O)OR^9$, $OC(O)R^9$, $OC(O)OR^9$, $OC(O)NR^9R^{10}$, $NR^9R^{10}$, $N(R^9)C(O)R^{10}$, $N(R^9)C(O)NR^{10}R^{11}$, $N(R^9)C(O)OR^{10}$, $C(=NR^9)NR^{10}R^{11}$, $C(=NOR^9)NR^{10}R^{11}$, $C(=NOC(O)R^9)NR^{10}R^{11}$, $C(=NR^9)N(R^{10})C(O)OR^{11}$, $N(R^9)C(=NR^{10})NR^{11}R^{12}$, $S(O)R^9$, $S(O)NR^9R^{10}$, $S(O)_2R^9$, $N(R^9)S(O)_2R^{10}$, $S(O)_2NR^9R^{10}$, OXO, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{6-10}$ cycloalkyl, and substituted or unsubstituted 4-10 membered heterocyclyl, wherein $R^9$, $R^{10}$, $R^{11}$, and $R^{12}$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In certain embodiments, $R^{1a}$, $R^{1b}$, $R^{1c}$, $R^{1d}$, or $R^{1e}$ is optionally substituted with one or more substituents selected from the group consisting of halo, CN, $OR^{13}$, $SR^{13}$, $C(O)R^{13}$, $C(O)NR^{13}R^{14}$, $C(O)OR^{13}$, $OC(O)R^{13}$, $OC(O)NR^{13}R^{14}$, $NR^{13}R^{14}$, $NR^{13}C(O)R^{14}$, $NR^{13}C(O)NR^{14}R^{15}$, $NR^{13}C(O)OR^{14}$, $C(=NR^{13})NR^{14}R^{15}$, $NR^{13}C(=NR^{14})NR^{15}R^{16}$, $S(O)R^{13}$, $S(O)NR^{13}R^{14}$, $S(O)_2R^{13}$, $NR^{13}S(O)_2R^{14}$, $S(O)_2NR^{13}R^{14}$ and oxo when $R^{1a}$, $R^{1b}$, $R^{1c}$, $R^{1d}$, or $R^{1e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, wherein $R^{13}$, $R^{14}$, $R^{15}$, and $R^{16}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In some embodiments, $R^1$ is phenyl substituted with at least one substituent selected from the group consisting of $OR^9$, $C(=NR^9)NR^{10}R^{11}$, $C(=NOR^9)NR^{10}R^{11}$, $C(=NOC(O)R^9)NR^{10}R^{11}$, and $C(=NR^9)NR^{10}C(O)OR^{11}$. In certain embodiments, $R^1$ is substituted with at least one substituent selected from the group consisting of $C(=NR^9)NR^{10}R^{11}$, $C(=NOR^9)NR^{10}R^{11}$, $C(=NOC(O)R^9)NR^{10}R^{11}$, and $C(=NR^9)NR^{10}C(O)OR^{11}$. In some more specific embodiments, $R^1$ is substituted with at least one $C(=NR^9)NR^{10}R^{11}$. In some more specific embodiments, $R^1$ is substituted with at least one —$C(=NH)NH_2$.

In some embodiments, $R^1$ has one of the following structures:

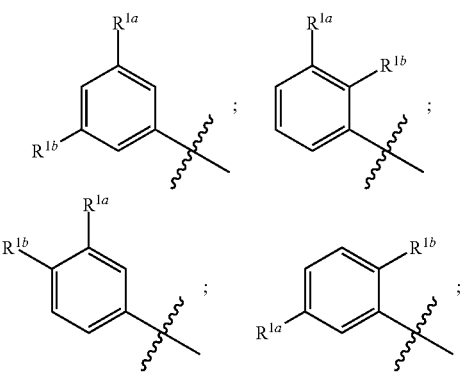

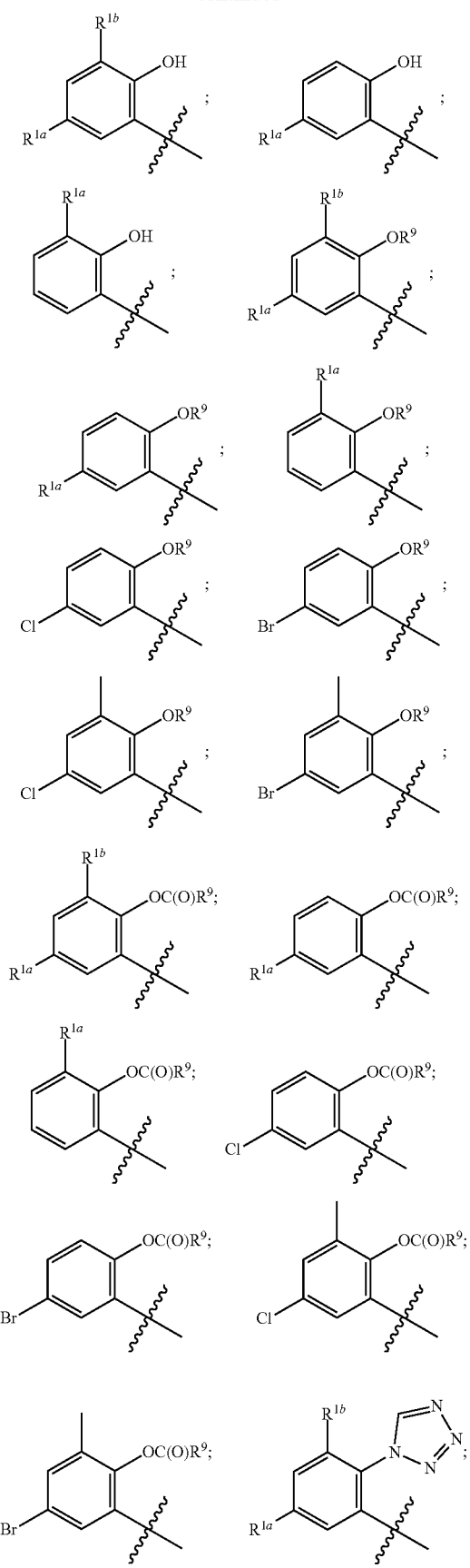
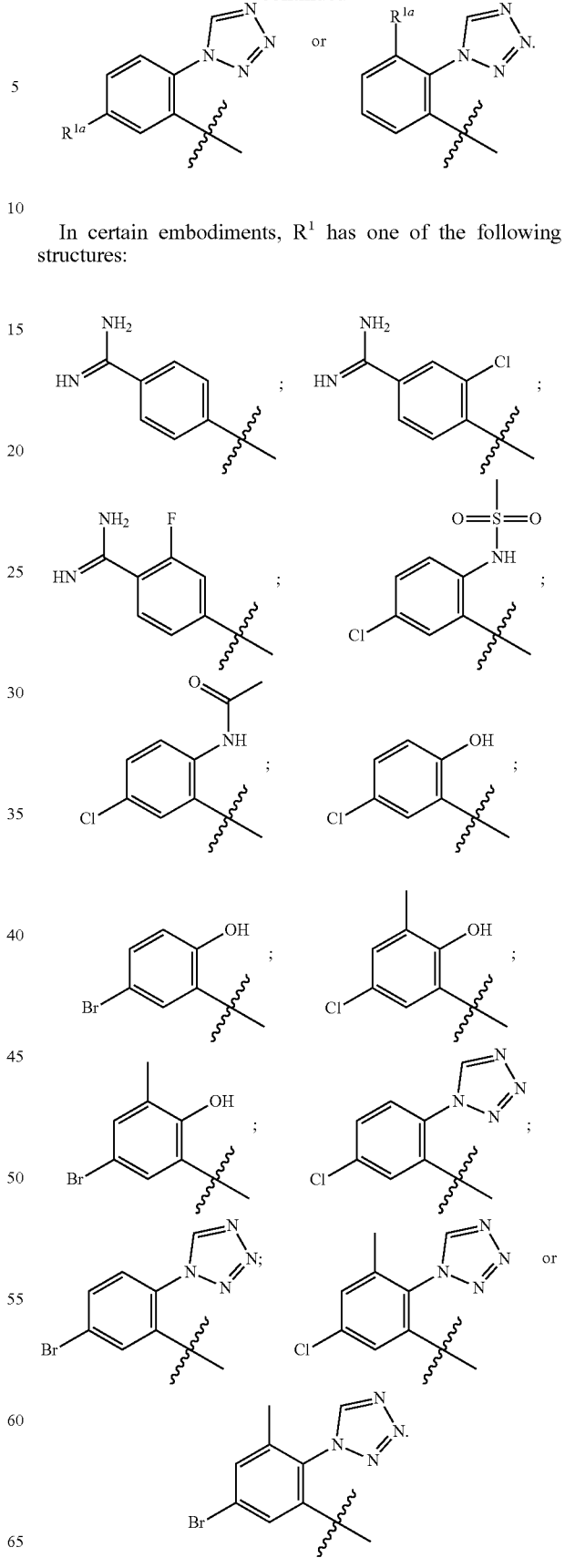
In certain embodiments, $R^1$ has one of the following structures:

In some more specific embodiments, $R^1$ has one of the following structures:

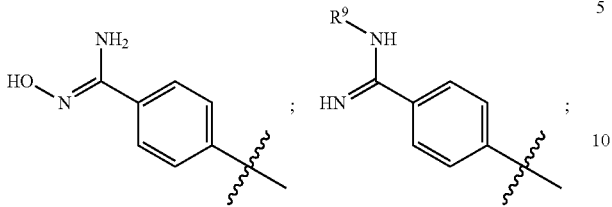

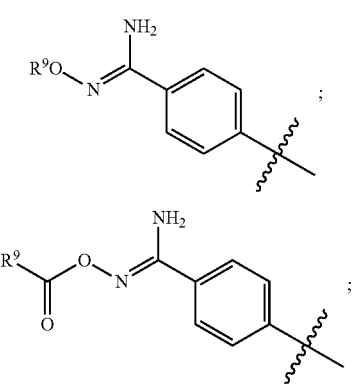

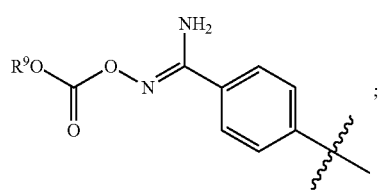

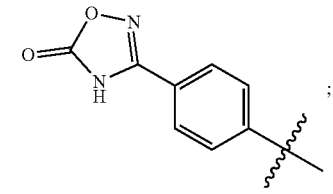

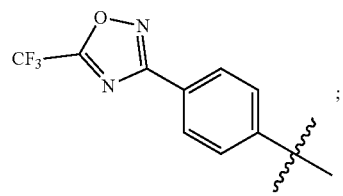

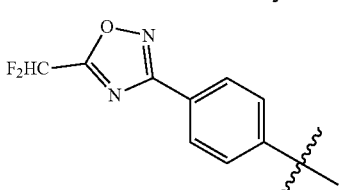

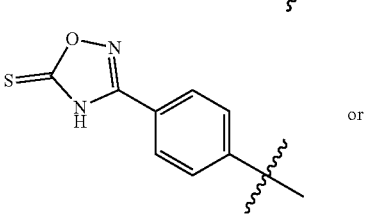

or

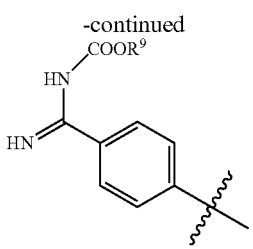

In some of the foregoing embodiments, $R^9$ is $C_{1-6}$ alkyl or $C_{1-6}$ haloalkyl. In certain more specific embodiments, $R^9$ is methyl. In some specific embodiments, $R^9$ is trifluoromethyl.

In certain embodiments, $R^1$ is an unsubstituted phenyl.

In certain other embodiments, $R^1$ is a substituted or unsubstituted heteroaryl. In some embodiments, $R^1$ is a substituted or unsubstituted 5-10 membered heteroaryl. In certain embodiments, $R^1$ is a substituted or unsubstituted pyridinyl, pyrrolopyridinyl, thiophenyl, or benzoimidazolyl. In some more specific embodiments, $R^1$ is a substituted or unsubstituted pyridin-3-yl, 1H-pyrrolo[2,3-b]pyridine-5-yl, thiophen-2-yl, or 1H-benzo[d]imidazol-6-yl.

In certain embodiments, $R^1$ is pyridin-3-yl, 1H-pyrrolo[2,3-b]pyridine-5-yl, thiophen-2-yl, or 1H-benzo[d]imidazol-6-yl substituted with one or more of $R^{1a}$, $R^{1b}$, $R^{1c}$, $R^{1d}$, and $R^{1e}$ wherein $R^{1a}$, $R^{1b}$, $R^{1c}$, $R^{1d}$, and $R^{1e}$ are each independently selected from the group consisting of $C_{1-6}$ alkyl, $C_{2-6}$ alkenyl, $C_{2-6}$ alkynyl, halo, $C_{1-6}$ haloalkyl, aminylalkyl, hydroxyalkyl, cyano, nitro, $OR^9$, $SR^9$, $C(O)R^9$, $C(O)NR^9R^{10}$, $C(O)OR^9$, $OC(O)R^9$, $OC(O)OR^9$, $OC(O)NR^9R^{10}$, $NR^9R^{10}$, $N(R^9)C(O)R^{10}$, $N(R^9)C(O)NR^{10}R^{11}$, $N(R^9)C(O)OR^{10}$, $C(=NR^9)NR^{10}R^{11}$, $C(=NOR^9)NR^{10}R^{11}$, $C(=NOC(O)R^9)NR^{10}R^{11}$, $C(=NR^9)N(R^{10})C(O)OR^{11}$, $N(R^9)C(=NR^{10})NR^{11}R^{12}$, $S(O)R^9$, $S(O)NR^9R^{10}$, $S(O)_2R^9$, $N(R^9)S(O)_2R^{10}$, $S(O)_2NR^9R^{10}$, OXO, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^9$, $R^{10}$, $R^{11}$, and $R^{12}$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In some embodiments, $R^{1a}$, $R^{1b}$, $R^{1c}$, $R^{1d}$, or $R^{1e}$ is optionally substituted with one or more substituents selected from the group consisting of halo, CN, $OR^{13}$, $SR^{13}$, $C(O)R^{13}$, $C(O)NR^{13}R^{14}$, $C(O)OR^{13}$, $OC(O)R^{13}$, $OC(O)NR^{13}R^{14}$, $NR^{13}R^{14}$, $NR^{13}C(O)R^{14}$, $NR^{13}C(O)NR^{14}R^{15}$, $NR^{13}C(O)OR^{14}$, $C(=NR^{13})NR^{14}R^{15}$, $NR^{13}C(=NR^{14})NR^{15}R^{16}$, $S(O)R^{13}$, $S(O)NR^{13}R^{14}$, $S(O)_2R^{13}$, $NR^{13}S(O)_2R^{14}$, $S(O)_2NR^{13}R^{14}$ and oxo when $R^{1a}$, $R^{1b}$, $R^{1c}$, $R^{1d}$, or $R^{1e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, wherein $R^{13}$, $R^{14}$, $R^{15}$, and $R^{16}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In some embodiments, R¹ has one of the following structures:
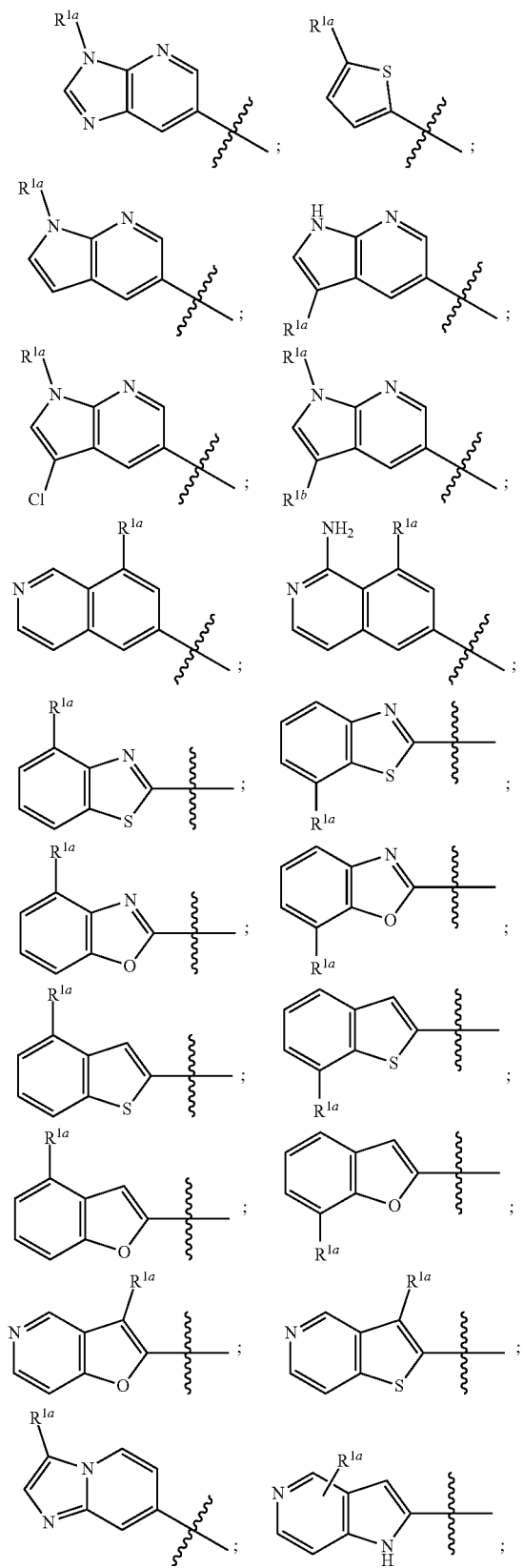
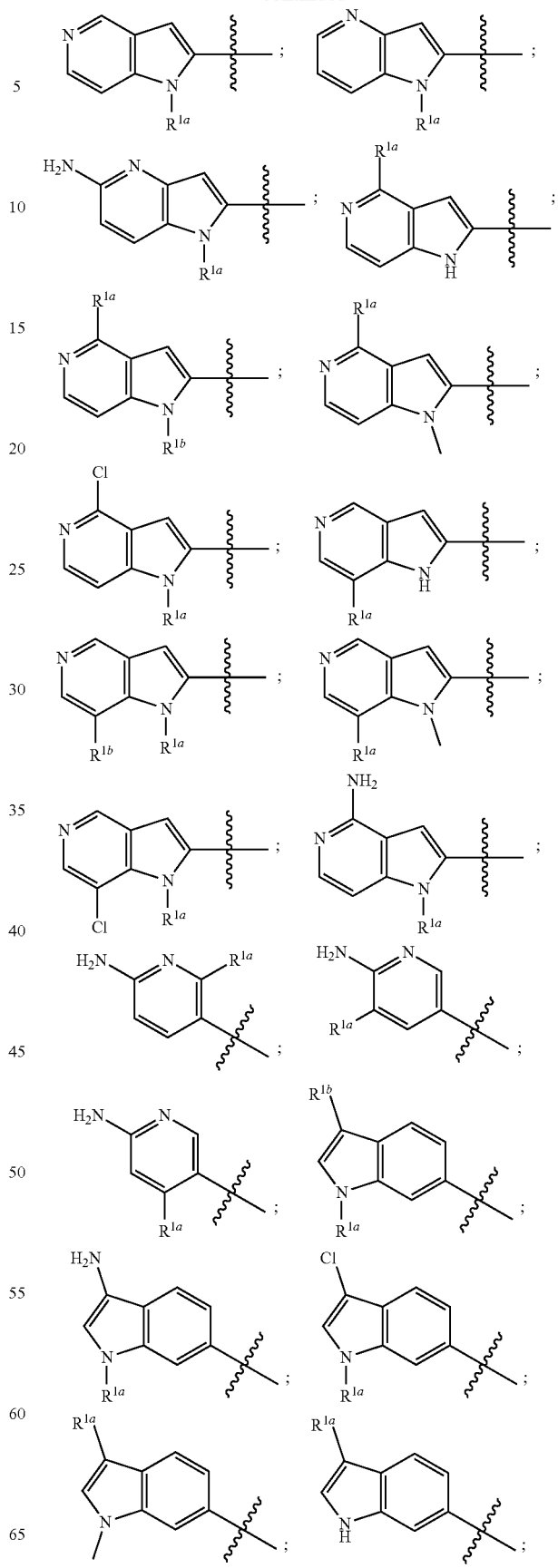

-continued
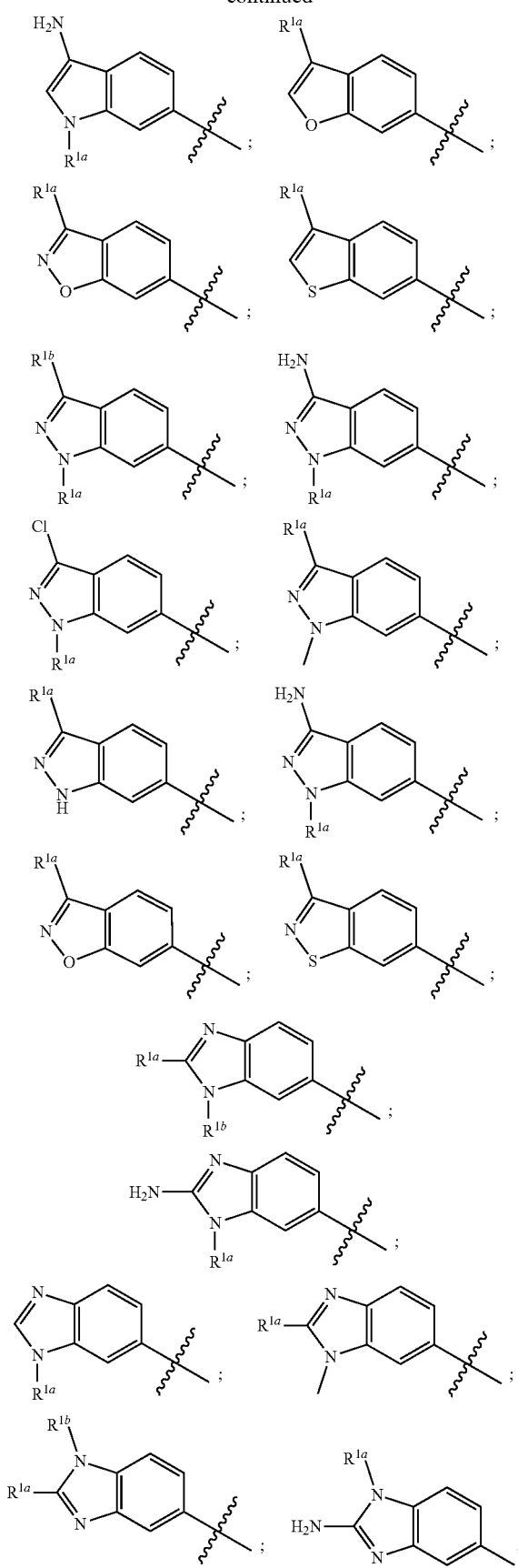
-continued
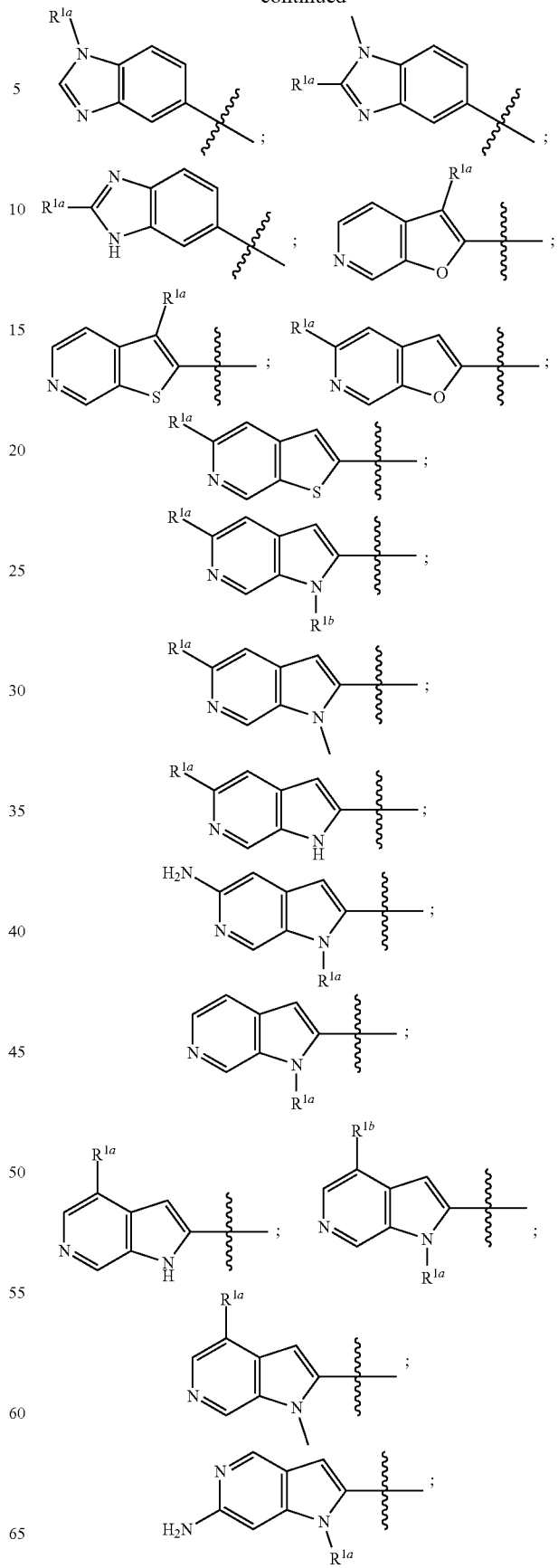

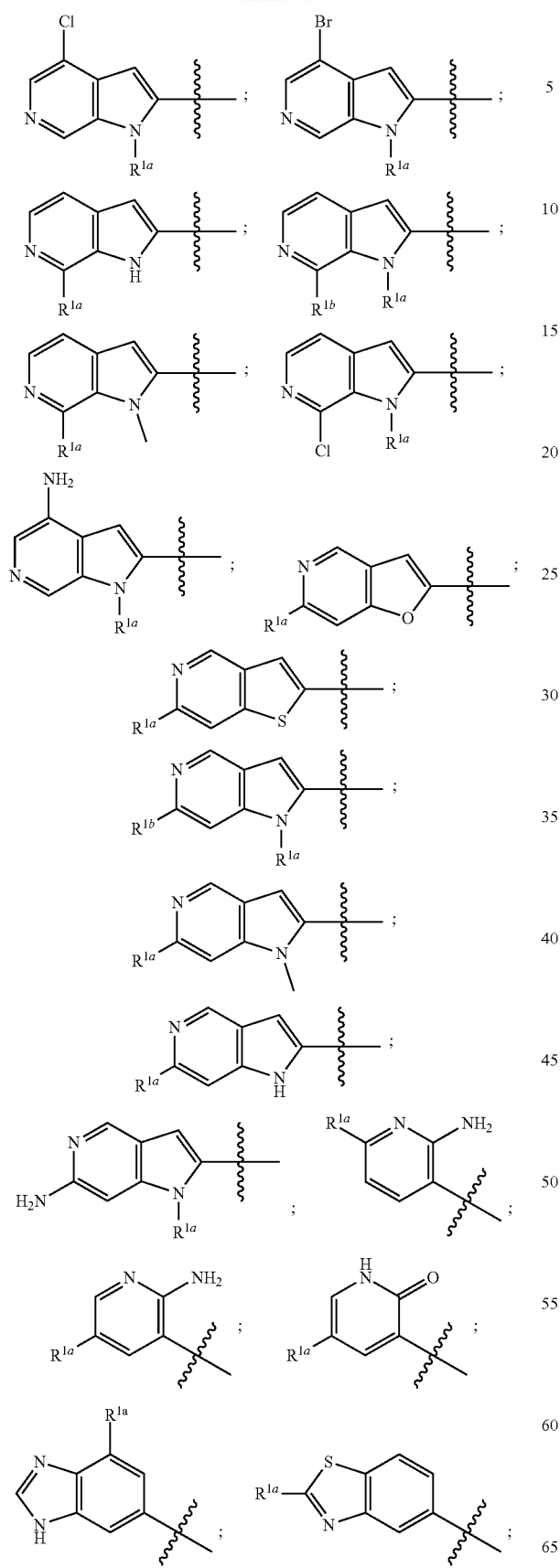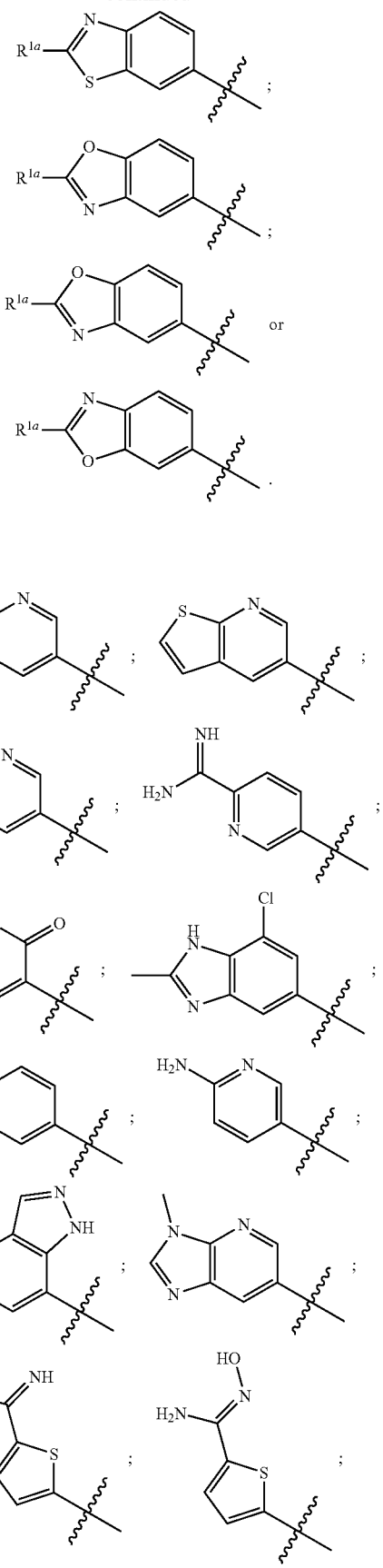

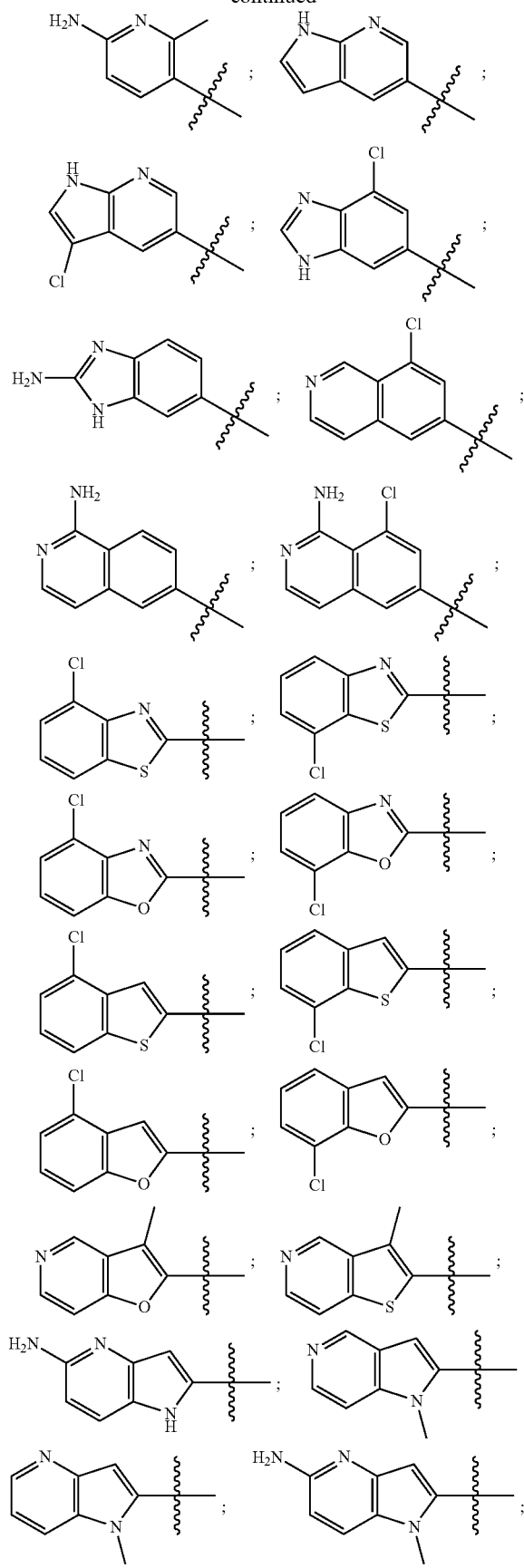
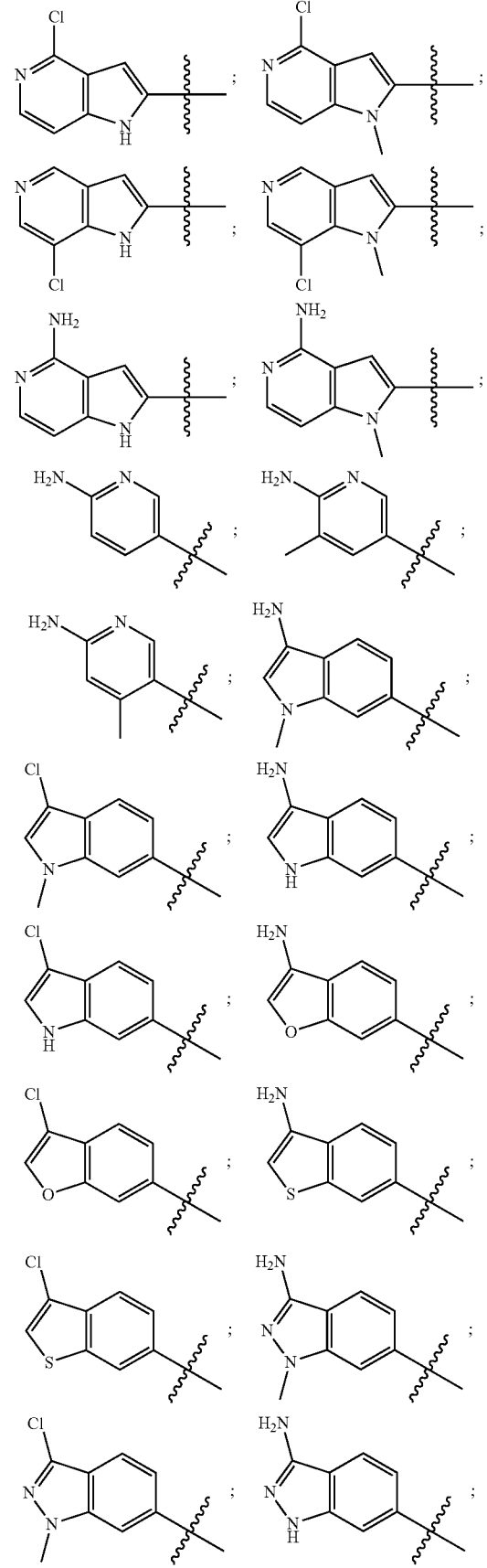

-continued
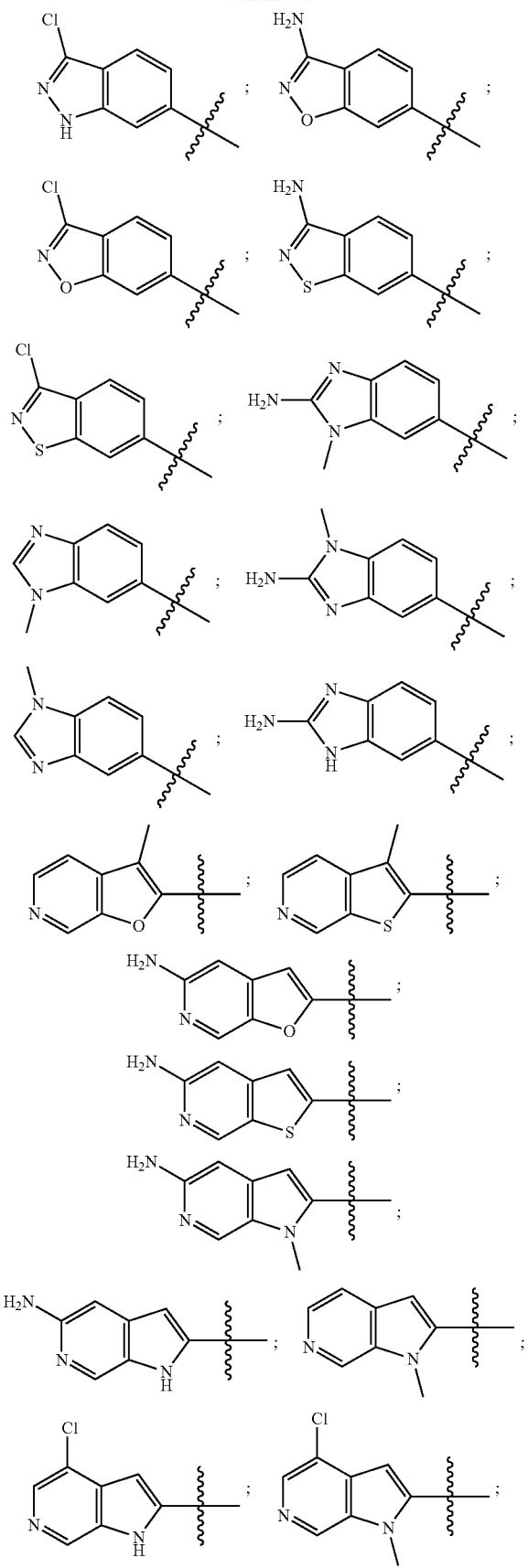
-continued
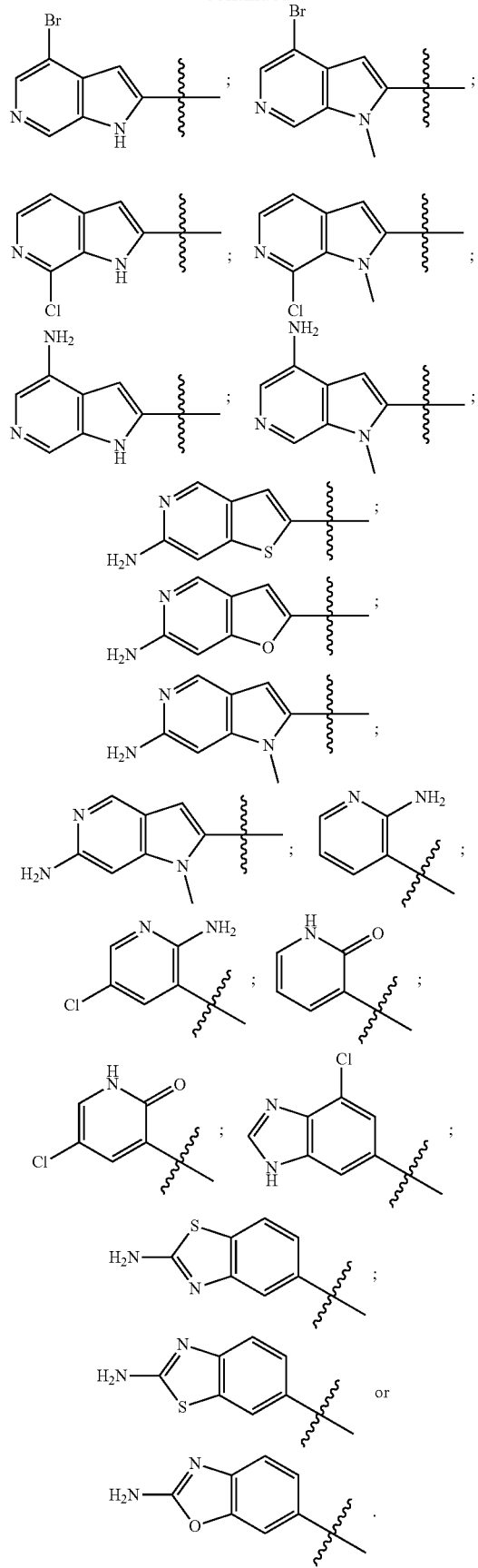

In some embodiments. R¹ has one of the following structures:

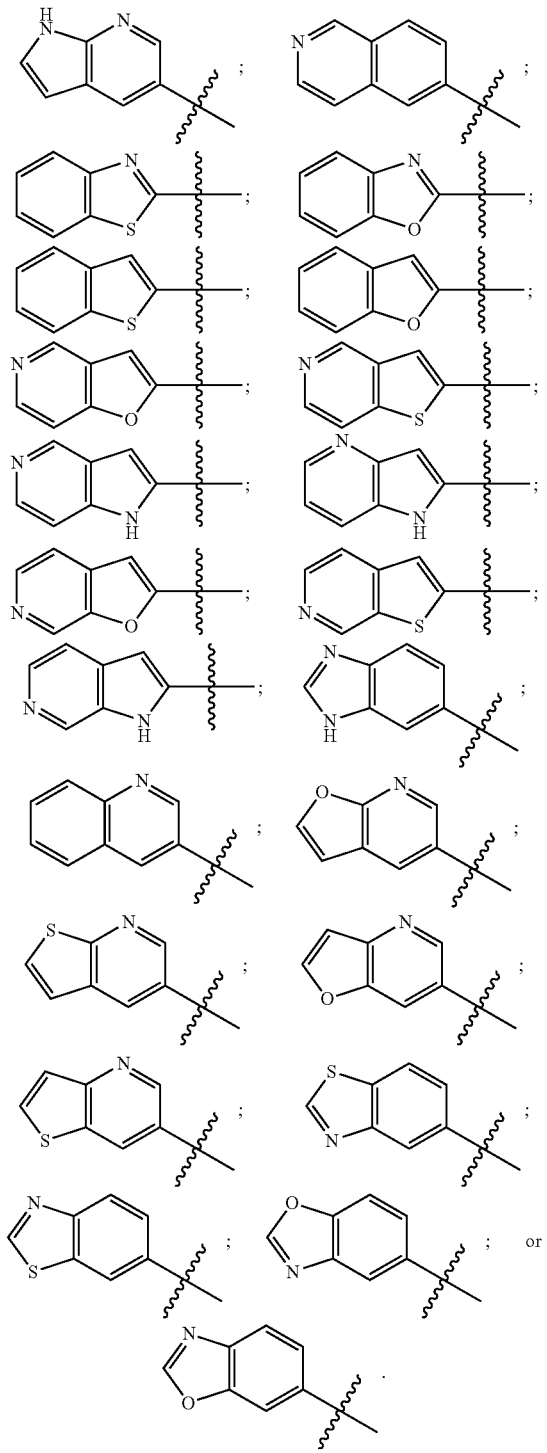

In certain embodiments, R¹ is a substituted or unsubstituted cycloalkyl. In certain embodiments, R¹ is a substituted or unsubstituted $C_3$-$C_6$ cycloalkyl. In some more specific embodiments, R¹ is a substituted $C_3$-$C_6$ cycloalkyl.

In some more specific embodiments, R¹ is a $C_3$-$C_6$ cycloalkyl substituted with one or more of $R^{1a}$, $R^{1b}$, $R^{1c}$, $R^{1d}$, and $R^{1e}$ wherein $R^{1a}$, $R^{1b}$, $R^{1c}$, $R^{1d}$, and $R^{1e}$ are each independently selected from the group consisting of $C_{1-6}$ alkyl, $C_{2-6}$ alkenyl, $C_{2-6}$ alkynyl, $C_{1-6}$ haloalkyl, aminylalkyl, hydroxyalkyl, nitro, $OR^9$, $SR^9$, $C(O)R^9$, $C(O)NR^9R^{10}$, $C(O)OR^9$, $OC(O)R^9$, $OC(O)OR^9$, $OC(O)NR^9R^{10}$, $NR^9R^{10}$, $N(R^9)C(O)R^{10}$, $N(R^9)C(O)NR^{10}R^{11}$, $N(R^9)C(O)OR^{10}$, $C(=NR^9)NR^{10}R^{11}$, $C(=NOR^9)NR^{10}R^{11}$, $C(=NOC(O)R^9)NR^{10}R^{11}$, $C(=NR^9)N(R^{10})C(O)OR^{11}$, $N(R^9)C(=NR^{10})NR^{11}R^{12}$, $S(O)R^9$, $S(O)NR^9R^{10}$, $S(O)_2R^9$, $N(R^9)S(O)_2R^{10}$, $S(O)_2NR^9R^{10}$, OXO, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^9$, $R^{10}$, $R^{11}$, and $R^{12}$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In some embodiments, $R^{1a}$, $R^{1b}$, $R^{1c}$, $R^{1d}$, or $R^{1e}$ is optionally substituted with one or more substituents selected from the group consisting of halo, CN, $OR^{13}$, $SR^{13}$, $C(O)R^{13}$, $C(O)NR^{13}R^{14}$, $C(O)OR^{13}$, $OC(O)R^{13}$, $OC(O)NR^{13}R^{14}$, $NR^{13}R^{14}$, $NR^{13}C(O)R^{14}$, $NR^{13}C(O)NR^{14}R^{15}$, $NR^{13}C(O)OR^{14}$, $C(=NR^{13})NR^{14}R^{15}$, $NR^{13}C(=NR^{14})NR^{15}R^{16}$, $S(O)R^{13}$, $S(O)NR^{13}R^{14}$, $S(O)_2R^{13}$, $NR^{13}S(O)_2R^{14}$, $S(O)_2NR^{13}R^{14}$ and oxo when $R^{1a}$, $R^{1b}$, $R^{1c}$, $R^{1d}$, or $R^{1e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, wherein $R^{13}$, $R^{14}$, $R^{15}$, and $R^{16}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In some embodiments, R¹ is an unsubstituted a $C_3$-$C_6$ cycloalkyl.

In certain embodiments, R¹ is a substituted or unsubstituted heterocyclyl. In some more specific embodiments, R¹ is a substituted or unsubstituted 4-10 membered heterocyclyl. In certain more specific embodiments, R¹ is a substituted 4-10 membered heterocyclyl.

In some embodiments, R¹ is a 4-10 membered heterocyclyl substituted with one or more of $R^{1a}$, $R^{1b}$, $R^{1c}$, $R^{1d}$, and $R^{1e}$ wherein $R^{1a}$, $R^{1b}$, $R^{1c}$, $R^{1d}$, and $R^{1e}$ are each independently selected from the group consisting of $C_{1-6}$ alkyl, $C_{2-6}$ alkenyl, $C_{2-6}$ alkynyl, halo, $C_{1-6}$ haloalkyl, aminylalkyl, hydroxyalkyl, cyano, nitro, $OR^9$, $SR^9$, $C(O)R^9$, $C(O)NR^9R^{10}$, $C(O)OR^9$, $OC(O)R^9$, $OC(O)OR^9$, $OC(O)NR^9R^{10}$, $NR^9R^{10}$, $N(R^9)C(O)R^{10}$, $N(R^9)C(O)NR^{10}R^{11}$, $N(R^9)C(O)OR^{10}$, $C(=NR^9)NR^{10}R^{11}$, $C(=NOR^9)NR^{10}R^{11}$, $C(=NOC(O)R^9)NR^{10}R^{11}$, $C(=NR^9)N(R^{10})C(O)OR^{11}$, $N(R^9)C(=NR^{10})NR^{11}R^{12}$, $S(O)R^9$, $S(O)NR^9R^{10}$, $S(O)_2R^9$, $N(R^9)S(O)_2R^{10}$, $S(O)_2NR^9R^{10}$, OXO, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^9$, $R^{10}$, $R^{11}$, and $R^{12}$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In certain embodiments, $R^{1a}$, $R^{1b}$, $R^{1c}$, $R^{1d}$, or $R^{1e}$ is optionally substituted with one or more substituents selected from the group consisting of $OR^{13}$, $SR^{13}$, $C(O)R^{13}$, $C(O)NR^{13}R^{14}$, $C(O)OR^{13}$, $OC(O)R^{13}$, $OC(O)NR^{13}R^{14}$, $NR^{13}R^{14}$, $NR^{13}C(O)R^{14}$, $NR^{13}C(O)NR^{14}R^{15}$, $NR^{13}C(O)OR^{14}$, $C(=NR^{13})NR^{14}R^{15}$, $NR^{13}C(=NR^{14})NR^{15}R^{16}$, $S(O)R^{13}$, $S(O)NR^{13}R^{14}$, $S(O)_2R^{13}$, $NR^{13}S(O)_2R^{14}$, $S(O)_2NR^{13}R^{14}$ and oxo when $R^{1a}$, $R^{1b}$, $R^{1c}$, $R^{1d}$, or $R^{1e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{6-10}$ cycloalkyl, and a substituted 4-10 membered heterocyclyl, wherein $R^{13}$, $R^{14}$, $R^{15}$, and $R^{16}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In some embodiments, $R^1$ is an unsubstituted 4-10 membered heterocyclyl. In certain embodiments, $R^1$ is substituted with one or more substituents selected from the group consisting of a substituted heteroaryl, $C(=NH)NHC(=O)OR^8$, $C(=NOC(=O)R^8)NH_2$, $C(=NOC(=O)OR^8)NH_2$, and $C(=NOH)NH_2$. In some more specific embodiments, $R^1$ is substituted with a substituted heteroaryl having one of the following structures:

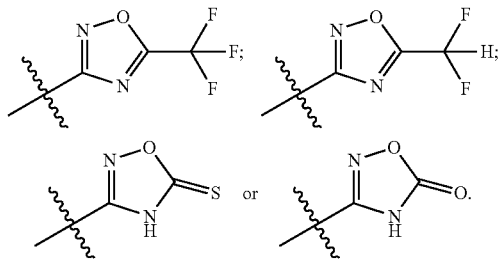

In some embodiments, $R^1$ is substituted with $C(=NH)NHC(=O)OR^8$ and $R^8$ is a substituted or unsubstituted arylalkyl. In certain embodiments, $R^1$ is substituted with $C(=NH)NHC(=O)OR^8$ and $R^8$ has one of the following structures:

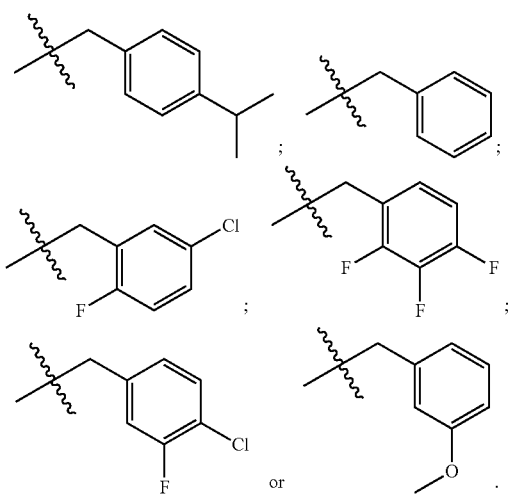

In some embodiments, $R^1$ is substituted with $C(=NOC(=O)R^8)NH_2$ and $R^8$ is an aminylalkyl. In certain more specific embodiments, $R^1$ is substituted with $C(=NOC(=O)R^8)NH_2$ and $R^8$ has the following structure:

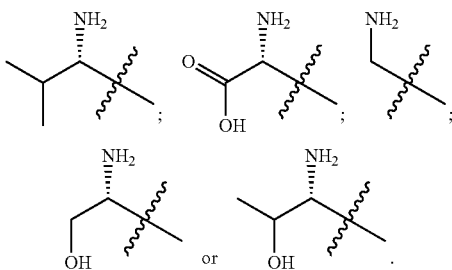

In certain embodiments, $R^1$ is substituted with $C(=NOC(=O)OR^8)NH_2$ and $R^8$ is an alkyl, a haloalkyl, or a substituted or unsubstituted arylalkyl. In some embodiments, $R^1$ is substituted with $C(=NOC(=O)OR^8)NH_2$ and $R^8$ has one of the following structures:

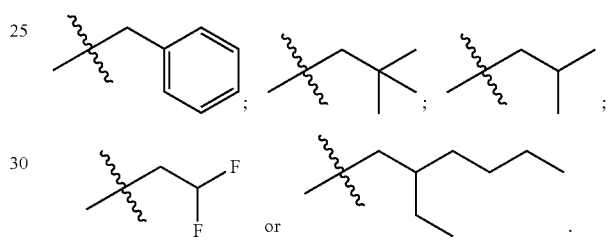

In some more specific embodiments, $R^1$ is substituted with $C(=NOH)NH_2$. In some embodiments, $R^1$ has one of the following structures:

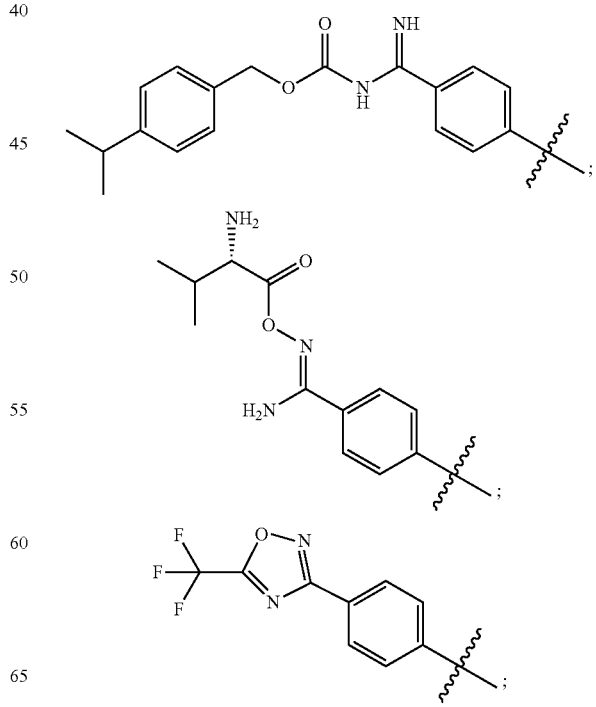

97
-continued
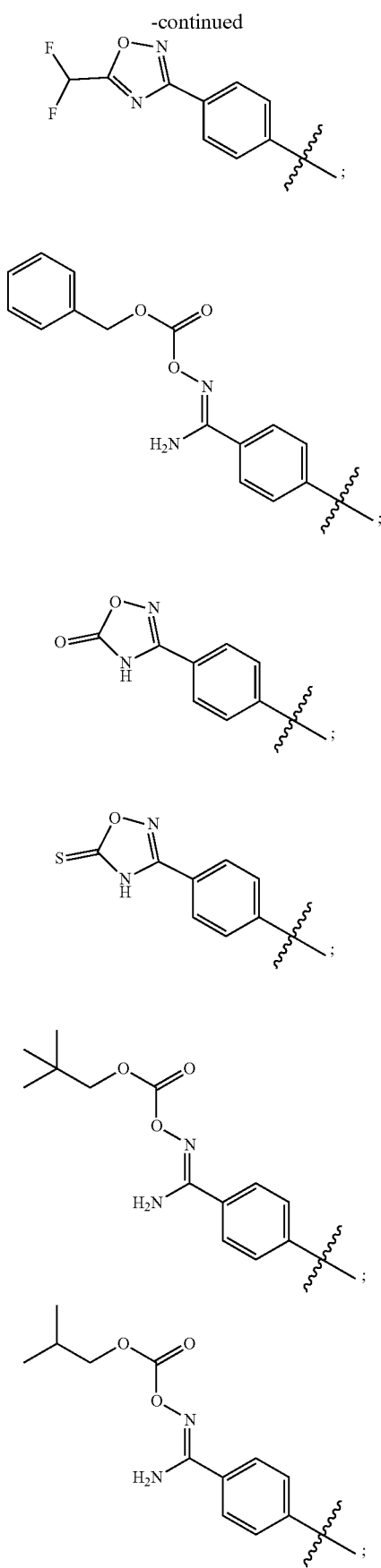
98
-continued
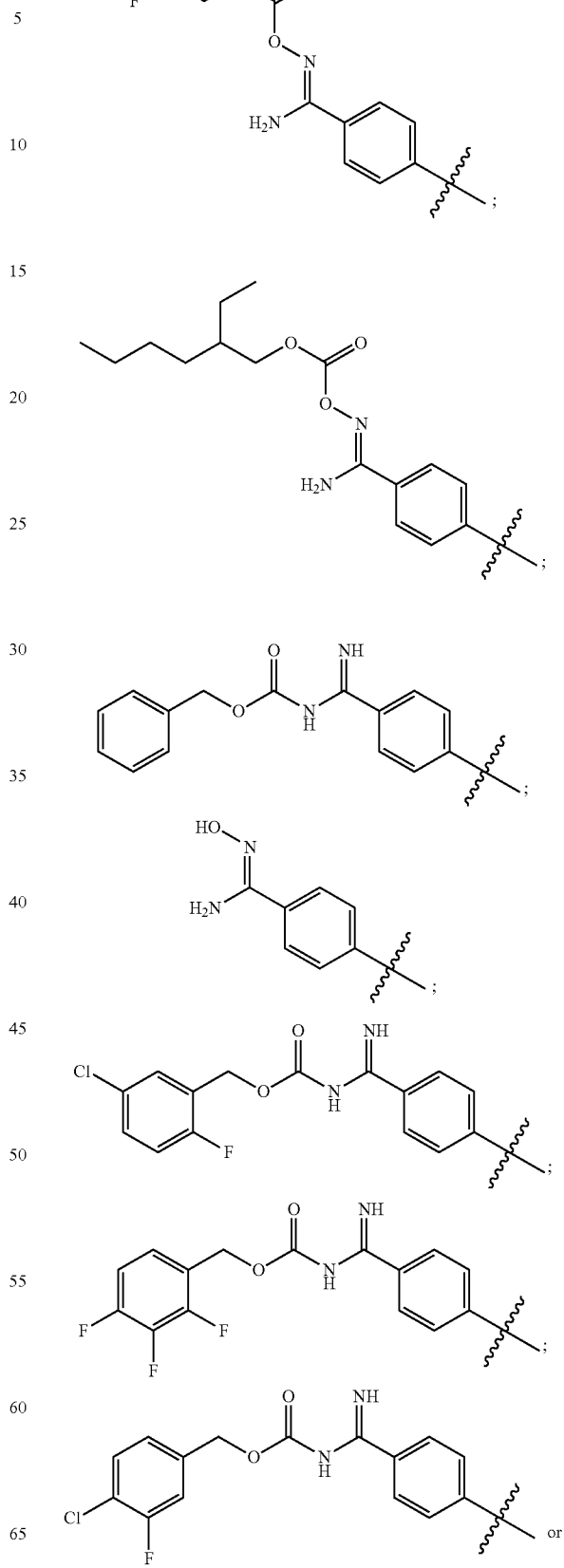

-continued

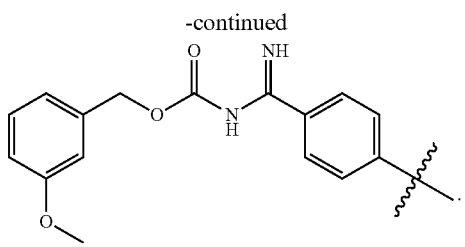

In some embodiments, R² is hydrogen or $C_1$-$C_6$ alkyl. In certain embodiments, R² is $C_1$-$C_6$ alkyl. In some more specific embodiments, R² is —$CH_3$.

In some embodiments, R² and R³, together with the carbon and nitrogen to which they are attached, respectively, form an optionally substituted 4-7 membered heterocyclyl. In certain embodiments, R² and R³, together with the carbon and nitrogen to which they are attached, respectively, form an optionally substituted 4, 5, or 6 membered heterocyclyl. In some more specific embodiments, R² and R³, together with the carbon and nitrogen to which they are attached, respectively, form an optionally substituted 4-membered heterocyclyl.

In some embodiments, the compound has one of the following Structures (IIIA1), (IIIB1), (IIIC1), (IIID1), (IIIE1), (IIIF1), (IIIG1), or (IIIH1):

(IIIA1)

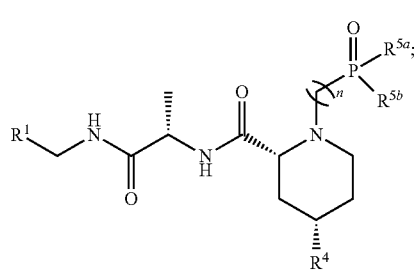

(IIIB1)

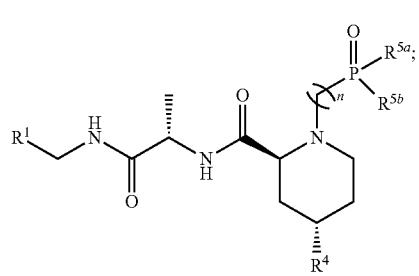

(IIIC1)

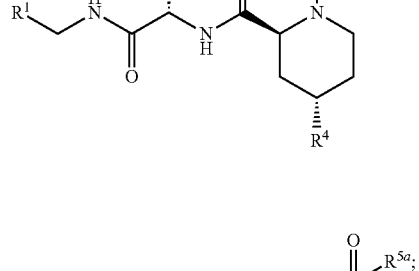

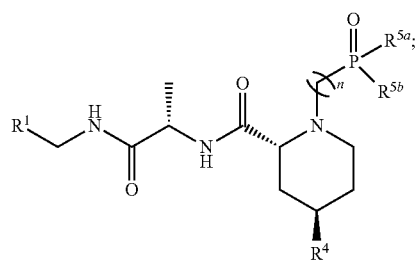

-continued (IIID1)

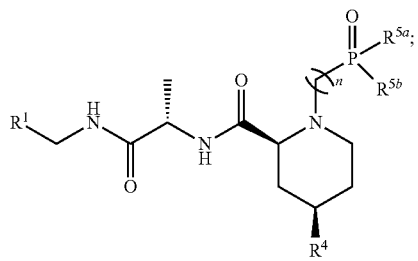

(IIIE1)

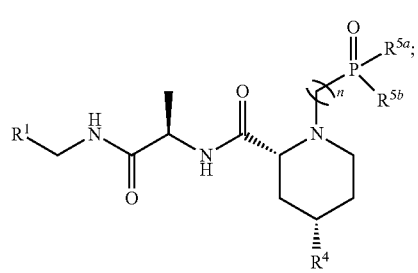

(IIIF1)

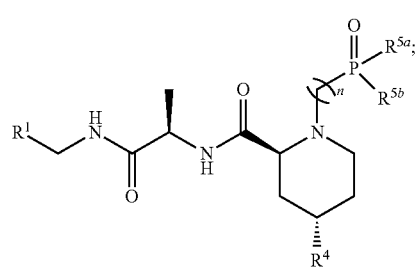

(IIIG1)

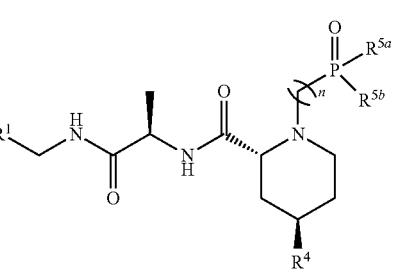

or (IIIH1)

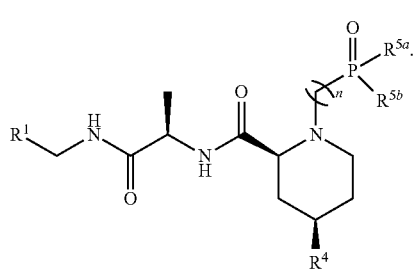

In certain specific embodiments, the compound has one of the following Structures (IIIA2), (IIIB2), (IIIC2), (IIID2), (IIIE2), (IIIF2), (IIIG2), or (IIIH2):

(IIIA2)

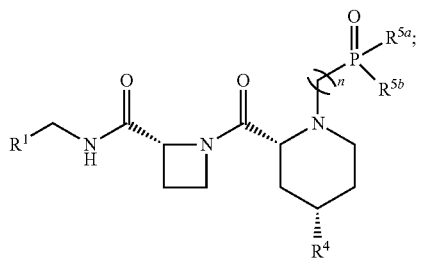

(IIIB2)

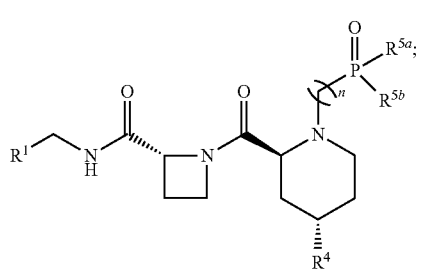

(IIIC2)

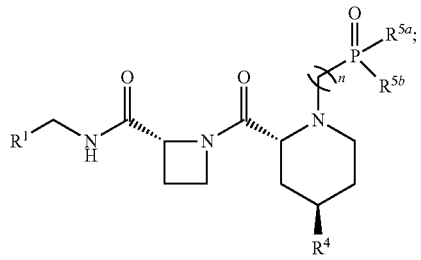

(IIID2)

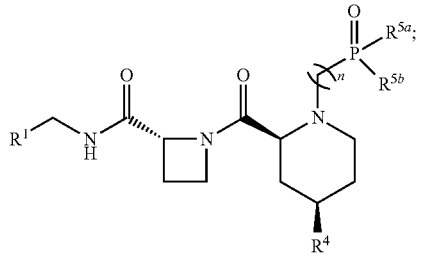

(IIIE2)

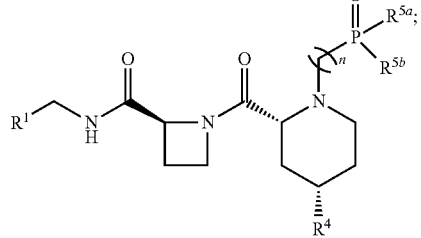

(IIIF2)

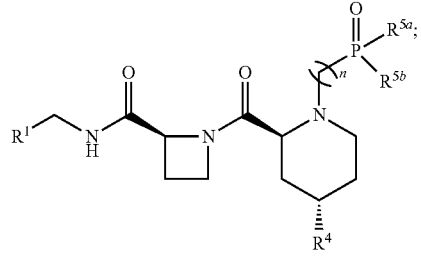

-continued

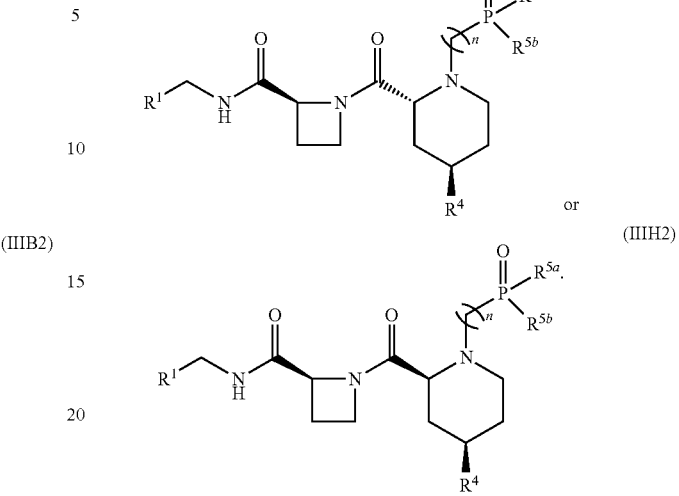

In some embodiments, R is a substituted or unsubstituted aryl. In certain embodiments, $R^4$ is a substituted or unsubstituted $C_6$-$C_{10}$ aryl. In some more specific embodiments, $R^4$ is a substituted or unsubstituted phenyl. In some embodiments, $R^4$ is an unsubstituted phenyl.

In some more specific embodiments, $R^4$ is phenyl substituted with one or more of $R^{4a}$, $R^{4b}$, $R^{4c}$, $R^{4d}$, or $R^{4e}$ wherein $R^{4a}$, $R^{4b}$, $R^{4c}$, $R^{4d}$, and $R^{4e}$ are each independently selected from the group consisting of $C_{1-6}$ alkyl, $C_{2-6}$ alkenyl, $C_{2-6}$ alkynyl, halo, $C_{1-6}$ haloalkyl, aminylalkyl, hydroxy alkyl, cyano, nitro, $OR^{17}$, $SR^{17}$, $C(O)R^{17}$, $C(O)NR^{17}R^{18}$, $C(O)OR^{17}$, $OC(O)R^{17}$, $OC(O)OR^{17}$, $OC(O)NR^{17}R^{18}$, $NR^{17}R^{18}$, $N(R^{17})C(O)R^{18}$, $N(R^{17})C(O)NR^{18}R^{19}$, $N(R^{17})C(O)OR^{18}$, $C(=NR^{17})NR^{18}R^{19}$, $C(=NOR^{17})NR^{18}R^{19}$, $C(=NOC(O)R^{17})NR^{18}R^{19}$, $C(=NR^{17})N(R^{18})C(O)OR^{19}$, $N(R^{17})C(=NR^{18})NR^{19}R^{20}$, $S(O)R^{17}$, $S(O)NR^{17}R^{18}$, $S(O)_2R^{17}$, $N(R^{17})S(O)_2R^{18}$, $S(O)_2NR^{17}R^{18}$, OXO, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^{17}$, $R^{18}$, $R^{19}$, and $R^{20}$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In certain more specific embodiments, $R^{4a}$, $R^{4b}$, $R^{4c}$, $R^{4d}$, or $R^{4e}$ is optionally substituted with one or more substituents selected from the group consisting of halo, CN, $OR^{21}$, $SR^{21}$, $C(O)R^{21}$, $C(O)NR^{21}R^{22}$, $C(O)OR^{21}$, $OC(O)R^{21}$, $OC(O)NR^{21}R^{22}$, $NR^{21}R^{22}$, $NR^{21}C(O)R^{22}$, $NR^{21}C(O)NR^{22}R^{23}$, $NR^{21}C(O)OR^{22}$, $C(=NR^{21})NR^{22}R^{23}$, $NR^{21}C(=NR^{22})NR^{23}R^{24}$, $S(O)R^{21}$, $S(O)NR^{21}R^{22}$, $S(O)_2R^{21}$, $NR^{21}S(O)_2R^{22}$, $S(O)_2NR^{21}R^{22}$ and oxo when $R^{4a}$, $R^{4b}$, $R^{4c}$, $R^{4d}$, or $R^{4e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, wherein $R^{21}$, $R^{22}$, $R^{23}$, and $R^{24}$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In some embodiments, $R^4$ has one of the following structures:

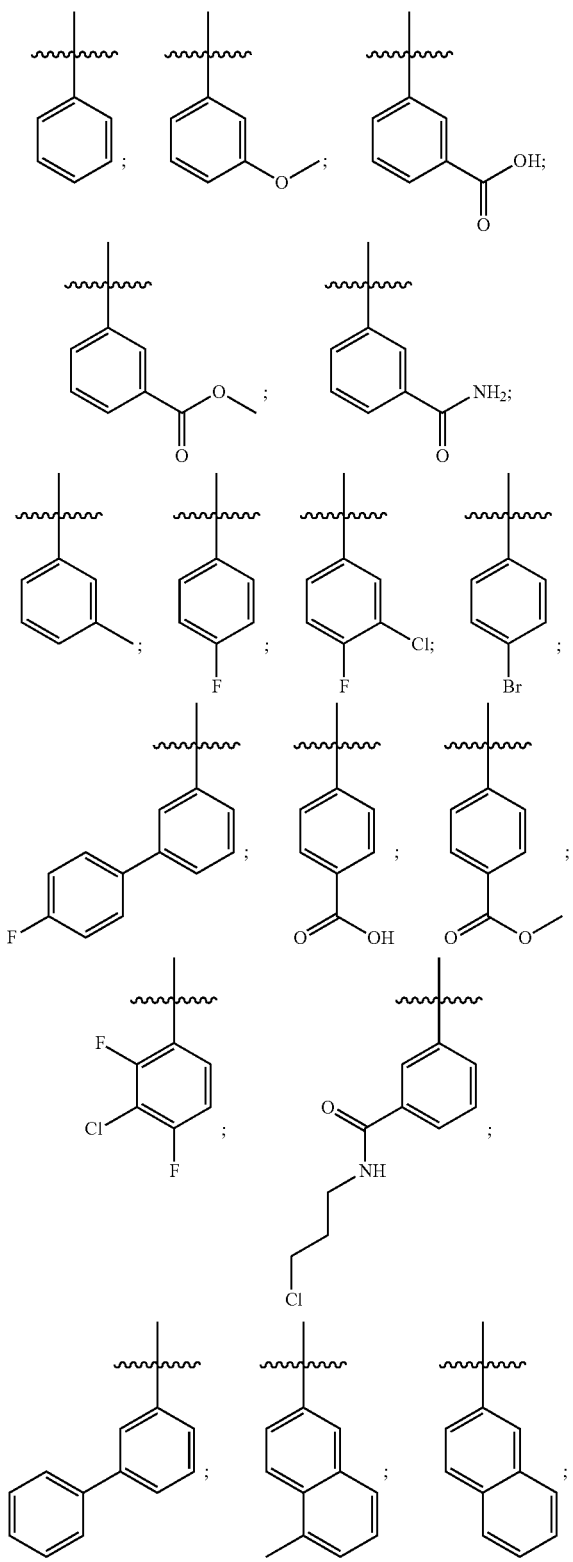

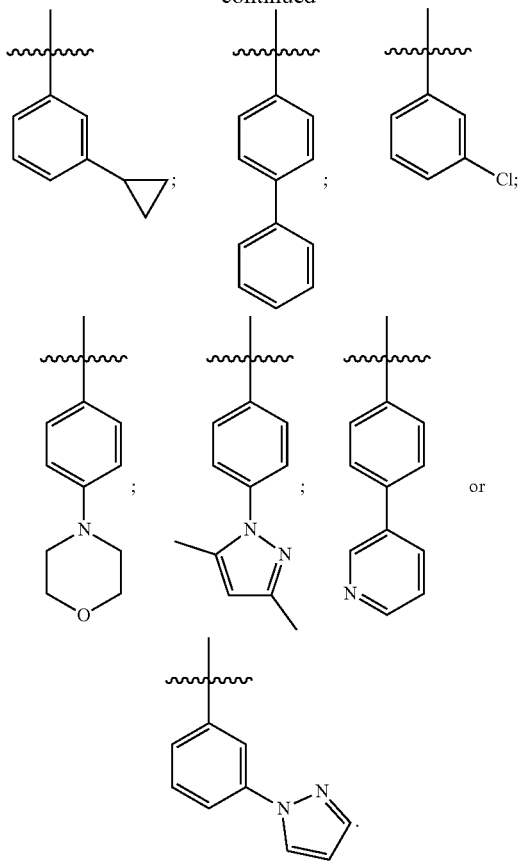

In some specific embodiments. R has one of the following structures:

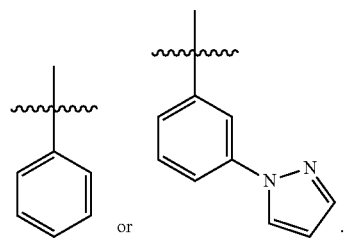 [SMILES: *c1ccccc1 ; *c1cccc(-n2cccn2)c1]

In certain specific embodiments, the compound has the Following structure (IIIa):

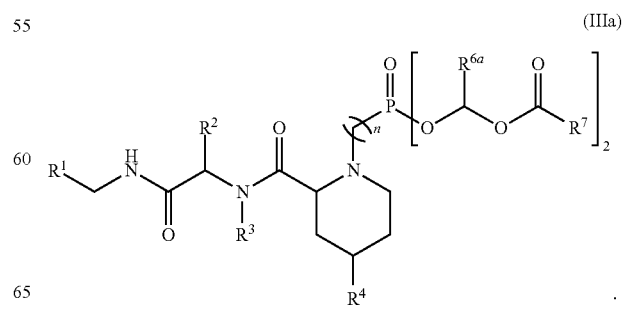

(IIIa)

In other embodiments, the compound has the following structure (IIIb):

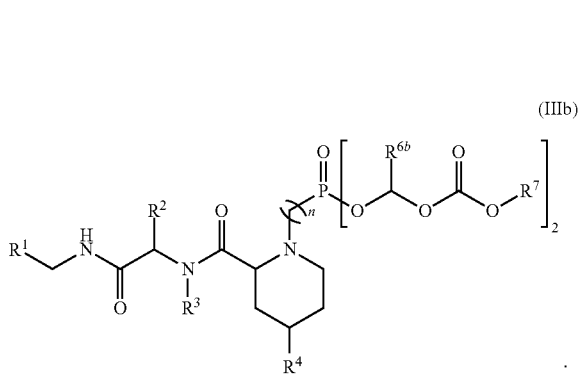

In still other embodiments, the compound has the following structure (IIIc):

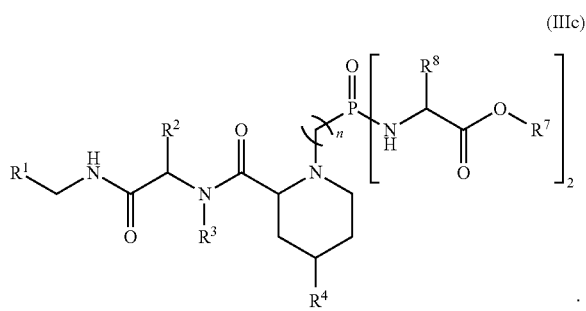

In some embodiments, the compound has the following structure (IIId):

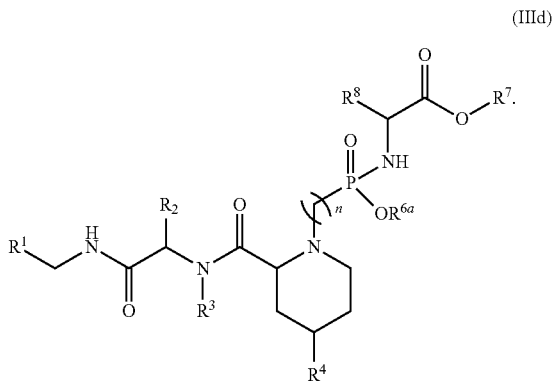

In certain embodiments, the compound has the following structure (IIIe):

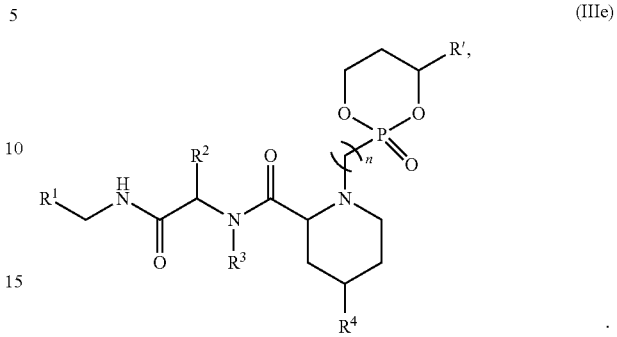

wherein:

R' is a substituted or unsubstituted aryl or a substituted or unsubstituted heteroaryl.

In some of the foregoing embodiments, $R^{6a}$ is aryl, heteroaryl, cycloalkyl, or heterocyclyl.

In some embodiments, the compounds of Structure (I), (II) or (III), and embodiments thereof, can be in the form of a salt such as a pharmaceutically acceptable salt.

The compounds of Structure (I), (II) or (III), and embodiments thereof, are useful as inhibitors of MASP-2 and for therapeutic use. The compounds of Structure (I), (II), or (III), and embodiments thereof, are useful in the treatment of MASP-2-associated diseases and disorders, and in the manufacture of medicaments for treating MASP-2-associated diseases and disorders. The present disclosure also provides methods of treating a MASP-2-associated disease and disorder comprising administering to a patient a therapeutically effective amount of a compound of Structure (I), (II), or (III), or an embodiment thereof, optionally in the form of a salt.

In some embodiments the compound Structure (I), (II), or (III) or an embodiment thereof is provided in the form of a pharmaceutical composition comprising the compound or a salt thereof, such as a pharmaceutically acceptable salt, and at least one pharmaceutically acceptable carrier or excipient.

In certain aspects, the compound is one or more selected from the compounds of Structure (I), (II), or (III) set forth in the Examples, including the compounds listed in Table 1, (e.g., compounds with selectivity for MASP-2 over thrombin). In certain aspects, one or more of the variables defining the compounds of Structure (I), (II), or (III) is selected from the corresponding substituents in the compounds of Structure (I), (II), or (III) in the Examples including the compounds listed in Table 1, preferably, those of the compounds with selectivity for MASP-2 over thrombin.

In certain aspects, the disclosure sets forth a stereochemically pure enantiomer or diastereomer (e.g., an optically active compound with one or more stereocenter(s)). Unless specifically indicated otherwise, for any compound with one or more stereocenters is intended to include and to describe both the pure (+) and (−) enantiomers, any other diastereomers, mixtures that are enriched in an enantiomer or diastereomer (e.g., 10%, 20%, 30%, 40%, 50%, 60%, 70% 75%, 80%, 85, 90%, or 95% enantiomeric or diastereomeric excess), and a racemic mixture of enantiomers or diastereomers.

Certain embodiments provide a pharmaceutically acceptable salt of the indicated chemical structure (e.g., a hydrohalide, such as a hydrochloride or dihydrochloride). Examples of pharmaceutically acceptable salts are set forth in, e.g., Burge, S. M. et al., J. Pharm. Sci 1977, 66, 1-19.

They include chlorides, bromides, iodides, formates, acetates, propionates, oxalates, malonates, succinates, fumarates, maleates, tartrates, citrates, benzoates, phthalates, sulfonates, aryl sulfonates, alkylsulfonates, salts of fatty acids, and the like. Salts can be prepared by a variety of methods known to the skilled artisan, including a precipitation with the conjugate acid or base (e.g., treatment with gaseous HCl or an HCl solution).

In certain embodiments provide a prodrug. A prodrug is a compound that is converted to a biologically active form under physiological conditions, often by hydrolysis, oxidation, or reduction (e.g., ester to acid form; carbamate to amino or hydroxy group; hydroxyamidine to amidine) Exemplary prodrugs are set forth in, e.g., Tilley, J. W., "Prodrugs of Benzamide," *Prodrugs* 2007, 191-222; Peterlin-Masic et al. *Curr. Pharma. Design* 2006, 12, 73-91. Prodrugs for the amidine group include amidoximes, O-alkylamidoximes, acylamidines, carbamates, 1,2,4-oxadiazolin-4-ones, and the like.

In certain aspects, the compound is useful for selectively inhibiting MASP-2 over thrombin, the method comprising administering the compound as described herein. In certain aspects, the selectivity ratio of MASP-2 Thrombin is at least 1.1:1, 1.25:1, 1.5:1, 1.75:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, or 30:1.

III. Synthesis

Compounds described herein, including salts thereof, can be prepared using known organic synthesis techniques and can be synthesized according to any of numerous possible synthetic routes, such as those illustrated in the Examples below.

The reactions for preparing compounds described herein can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the disclosure can involve the protection and deprotection of various chemical groups. The need for protection and deprotection, and the selection of appropriate protecting groups, can be readily determined by one skilled in the art. The chemistry of protecting groups is described, e.g., in Kocienski, Protecting Groups, (Thieme, 2007); Robertson, Protecting Group Chemistry, (Oxford University Press, 2000); Smith et al., March's Advanced Organic Chemistry: Reactions, Mechanisms, and Structure, 6th Ed. (Wiley, 2007); Peturssion et al., "Protecting Groups in Carbohydrate Chemistry," *J. Chem. Educ.,* 1997, 77(11), 1297; and Wuts et al, Protective Groups in Organic Synthesis, 4th Ed., (Wiley, 2006).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high-performance liquid chromatography (HPLC) or thin layer chromatography (TLC).

The particular synthetic methods used in the Examples provide general guidance in connection with preparing the compounds of the disclosure. One skilled in the art would understand that the preparations can be modified or optimized using general knowledge of organic chemistry to prepare various compounds within the scope of the present disclosure.

Starting materials, reagents and intermediates whose synthesis is not described herein are either commercially available, known in the literature, or may be prepared by methods known to one skilled in the art.

It will be appreciated by one skilled in the art that the processes described are not the exclusive means by which compounds of the disclosure may be synthesized and that a broad repertoire of synthetic organic reactions is available to be potentially employed in synthesizing compounds of the disclosure. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry, Vols.* 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, 2nd Edition, 2004); Katritzky et al. (Ed.), *Comprehensive Heterocyclic Chemistry* (Pergamon Press, 1984); Katritzky et al., *Comprehensive Heterocyclic Chemistry II* (Pergamon Press, 1996); Smith et al., *March's Advanced Organic Chemistry; Reactions, Mechanisms, and Structure,* 6th Ed. (Wiley, 2007); Trost et al. (Ed.), *Comprehensive Organic Synthesis* (Pergamon Press, 1991).

IV. Methods of Treatment

In another aspect, the present disclosure provides a method of treating a patient suffering from, or at risk for developing a MASP-2-associated disease or disorder such as a MASP-2-dependent complement-associated disease or disorder comprising administering a small molecule inhibitor of MASP-2.

The compound can be any small molecule inhibitor of MASP-2. In some embodiments, the compound can be a small molecule inhibitor of MASP-2 that binds to the serine protease domain of MASP-2. In some embodiments, the compound can be a small molecule inhibitor such as a synthetic small molecule inhibitor of MASP-2. In some embodiments, the compound can be a small molecule inhibitor of MASP-2 that binds to the catalytic, substrate-binding region of MASP-2. In some embodiments, the compound selectively inhibits MASP-2 relative to thrombin. For example, in some embodiments, the compound is a compound of Structure (I), (II), or (III) as described in any of the foregoing embodiments.

As described in U.S. Pat. Nos. 7,919,094; 8,840,893; 8,652,477; 8,951,522, 9,011,860, 9,475,885, 9,644,035, U.S. Patent Application Publication Nos. US 2013/0344073, US 2013/0266560, US 2015/0166675, US 2017/0137537, US 2017/0166660, US 2017/0189525,US 2017/0267781, US 2017/0283508, US 2017/0253667, US 2018/0105604, and PCT Publication Nos. WO 2018/045054, WO 2019/036460 and co-pending U.S. Patent Application Ser. No.

62/688,611 (each of which is assigned to Omeros Corporation, the assignee of the instant application, each of which is hereby incorporated by reference), MASP-2-dependent complement activation has been implicated as contributing to the pathogenesis of numerous acute and chronic disease states. For example, as described in U.S. Pat. No. 8,951,522, the primary function of the complement system, a part of the innate immune system, is to protect the host against infectious agents, however, inappropriate or over-activation of the complement system can lead to serious disease, such as thrombotic microangiopathies (TMAs, including aHUS, TTP and HUS) in which endothelial damage as well as fibrin and platelet-rich thrombi in the microvasculature lead to organ damage. The lectin pathway plays a dominant role in activating complement in settings of endothelial cell stress or injury and preventing the activation of MASP-2 and the lectin pathway halts the sequence of enzymatic reactions that lead to the formation of the membrane attack complex, platelet activation and leukocyte recruitment. As described in U.S. Pat. No. 8,652,477, in addition to initiation of the lectin pathway, MASP-2 can also activate the coagulation system and is capable of cleaving prothrombin to thrombin.

Accordingly, in some embodiments, the method comprises administering to a patient suffering from or at risk for developing a MASP-2-dependent complement-associated disease or disorder an amount of a compound of the disclosure in an amount sufficient to inhibit MASP-2 dependent complement activation in the mammalian subject to thereby treat the disease or disorder. In some embodiments, the method can further comprise, prior to administering a compound of the disclosure to the patient, determining that the patient is afflicted with the lectin complement-associated disease or disorder.

In some embodiments, the MASP-2-dependent complement-associated disease or disorder is selected from the group consisting of a thrombotic microangiopathy (TMA), a renal condition, an inflammatory reaction resulting from tissue or organ transplantation, an ischemia reperfusion injury, a complication associated with diabetes, a cardiovascular disease or disorder, an inflammatory gastrointestinal disorder, a pulmonary disorder, an ophthalmic disease or disorder, disseminated intravascular coagulation, graft-versus-host disease, veno-occlusive disease, diffuse alveolar hemorrhage, or similar, as well as combinations thereof.

In some embodiments, the MASP-2-dependent complement-associated disease or disorder is a thrombotic microangiopathy (TMA) including thrombotic thrombocytopenic purpura (TTP), refractory TTP, Upshaw-Schulman Syndrome (USS), hemolytic uremic syndrome (HUS), atypical hemolytic syndrome (aHUS), non-Factor H-dependent atypical hemolytic syndrome, aHUS secondary to an infection, plasma therapy-resistant aHUS, a TMA secondary to cancer, a TMA secondary to chemotherapy, a TMA secondary to transplantation, or a TMA associated with hematopoietic stem cell transplant.

In some embodiments, the method comprises administering to a patient suffering from or at risk for developing graft-versus-host disease (GVHD), including acute GVHD, chronic GVHD or steroid-resistant GVHD an amount of a compound of the disclosure in an amount sufficient to inhibit MASP-2 dependent complement activation in the mammalian subject to thereby treat the disease or disorder. In some embodiments, the subject suffering from or at risk for developing GVHD has previously undergone, is undergoing, or will undergo a hematopoietic stem cell transplant.

In some embodiments, the method comprises administering to a patient suffering from, or at risk for developing diffuse alveolar hemorrhage (DAH) an amount of a compound of the disclosure in an amount sufficient to inhibit MASP-2 dependent complement activation in the mammalian subject to thereby treat the disease or disorder. In some embodiments, the subject suffering from, or at risk for developing DAH has previously undergone, is undergoing, or will undergo a hematopoietic stem cell transplant.

In some embodiments, the method comprises administering to a patient suffering from, or at risk for developing veno-occlusive disease (VOD) an amount of a compound of the disclosure in an amount sufficient to inhibit MASP-2 dependent complement activation in the mammalian subject to thereby treat the disease or disorder. In some embodiments, the subject suffering from, or at risk for developing VOD has previously undergone, is undergoing, or will undergo a hematopoietic stem cell transplant.

In some embodiments, the method comprises administering to a patient suffering from, or at risk for developing idiopathic pneumonia syndrome (IPS) an amount of a compound of the disclosure in an amount sufficient to inhibit MASP-2 dependent complement activation in the mammalian subject to thereby treat the disease or disorder. In some embodiments, the subject suffering from, or at risk for developing IPS has previously undergone, is undergoing, or will undergo a hematopoietic stem cell transplant.

In some embodiments, the method comprises administering to a patient suffering from, or at risk for developing capillary leak syndrome (CLS) an amount of a compound of the disclosure in an amount sufficient to inhibit MASP-2 dependent complement activation in the mammalian subject to thereby treat the disease or disorder. In some embodiments, the subject suffering from, or at risk for developing CLS has previously undergone, is undergoing, or will undergo a hematopoietic stem cell transplant.

In some embodiments, the method comprises administering to a patient suffering from, or at risk for developing engraftment syndrome (ES) an amount of a compound of the disclosure in an amount sufficient to inhibit MASP-2 dependent complement activation in the mammalian subject to thereby treat the disease or disorder. In some embodiments, the subject suffering from, or at risk for developing ES has previously undergone, is undergoing, or will undergo a hematopoietic stem cell transplant.

In some embodiments, the method comprises administering to a patient suffering from, or at risk for developing fluid overload (FO) an amount of a compound of the disclosure in an amount sufficient to inhibit MASP-2 dependent complement activation in the mammalian subject to thereby treat the disease or disorder. In some embodiments, the subject suffering from, or at risk for developing FO has previously undergone, is undergoing, or will undergo a hematopoietic stem cell transplant.

In some embodiments, the method comprises administering to a patient suffering from any of the above-referenced diseases or conditions an amount of a compound as disclosed in PCT Application No. PCT/US19/34225, which is hereby incorporated in its entirety.

In some embodiments, the MASP-2-dependent complement-associated disease or disorder is a renal condition including mesangioproliferative glomerulonephritis, membranous glomerulonephritis, membranoproliferative glomerulonephritis (mesangiocapillary glomerulonephritis), acute post infectious glomerulonephritis (poststreptococcal glomerulonephritis), C3 glomerulopathy, cryoglobulinemic glomerulonephritis, pauci-immune necrotizing crescentic glomerulonephritis, lupus nephritis, Henoch-Schonlein purpura nephritis, IgA nephropathy, and the like, as well as combinations thereof.

In some embodiments, the MASP-2-dependent complement-associated disease or disorder is renal fibrosis (e.g., tubulointerstitial fibrosis) and/or proteinuria in a subject suffering from or at risk for developing chronic kidney disease, chronic renal failure, glomerular disease (e.g., focal segmental glomerulosclerosis), an immune complex disorder (e.g., IgA nephropathy, membranous nephropathy), lupus nephritis, nephrotic syndrome, diabetic nephropathy, tubulointerstitial damage and glomerulonepthritis (e.g., C3 glomerulopathy), or a disease or condition associated with proteinuria, including, but not limited to, nephrotic syndrome, pre-eclampsia, eclampsia, toxic lesions of kidneys, amyloidosis, collagen vascular diseases (e.g., systemic lupus erythematosus), dehydration, glomerular diseases (e.g., membranous glomerulonephritis, focal segmental glomerulonephritis, C3 glomerulopathy, minimal change disease, lipoid nephrosis), strenuous exercise, stress, benign orthostatis (postural) proteinuria, focal segmental glomerulosclerosis, IgA nephropathy (i.e., Berger's disease), IgM nephropathy, membranoproliferative glomerulonephritis, membranous nephropathy, minimal change disease, sarcoidosis, Alport's syndrome, diabetes mellitus (diabetic nephropathy), drug-induced toxicity (e.g., NSAIDS, nicotine, penicillamine, lithium carbonate, gold and other heavy metals, ACE inhibitors, antibiotics (e.g., adriamycin), opiates (e.g., heroin), or other nephrotoxins); Fabry's disease, infections (e.g., HIV, syphilis, hepatitis A, B or C, poststreptococcal infection, urinary schistosomiasis); aminoaciduria, Fanconi syndrome, hypertensive nephrosclerosis, interstitial nephritis, sickle cell disease, hemoglobinuria, multiple myeloma, myoglobinuria, organ rejection (e.g., kidney transplant rejection), ebola hemorrhagic fever, Nail patella syndrome, familial Mediterranean fever, HELLP syndrome, systemic lupus erythematosus, Wegener's granulomatosis, Rheumatoid arthritis, Glycogen storage disease type 1, Goodpasture's syndrome, Henoch-Schonlein purpura, urinary tract infection which has spread to the kidneys, Sjogren's syndrome and post-infections glomerulonepthritis.

In some embodiments, the MASP-2-dependent complement-associated disease or disorder is an inflammatory reaction resulting from tissue or solid organ transplantation, including allotransplantation or xenotransplantation of whole organs (e.g., kidney, heart, liver, pancreas, lung, cornea, and the like) or tissue grafts (e.g., valves, tendons, bone marrow, and the like).

In some embodiments, the MASP-2-dependent complement-associated disorder is an ischemia reperfusion injury (I/R), including myocardial I/R, gastrointestinal I/R, renal I/R, and I/R following an aortic aneurism repair, I/R associated with cardiopulmonary bypass, cerebral I/R, stroke, organ transplant or reattachment of severed or traumatized limbs or digits; revascularization to transplants and/or replants, and hemodynamic resuscitation following shock, surgical procedures, or similar, as well as combinations thereof.

In some embodiments, the MASP-2-dependent complement-associated disease or disorder is a complication associated with non-obese diabetes (Type-1 diabetes or Insulin-dependent diabetes mellitus) and/or complications associated with Type-1 or Type-2 (adult onset) diabetes including diabetic angiopathy, diabetic neuropathy, diabetic retinopathy, diabetic macular edema, and the like, as well as combinations thereof.

In some embodiments, the MASP-2-dependent complement-associated disease or disorder is a cardiovascular disease or disorder, including Henoch-Schonlein purpura nephritis, systemic lupus erythematosus-associated vasculitis, vasculitis associated with rheumatoid arthritis (also called malignant rheumatoid arthritis), immune complex vasculitis, and Takayasu's disease; dilated cardiomyopathy; diabetic angiopathy; Kawasaki's disease (arteritis); venous gas embolus (VGE); and inhibition of restenosis following stent placement, rotational atherectomy, percutaneous transluminal coronary angioplasty (PTCA), and the like as well as combinations thereof.

In some embodiments, the MASP-2-dependent complement-associated disease or disorder is an inflammatory gastrointestinal disorder, including pancreatitis, diverticulitis and bowel disorders including Crohn's disease, ulcerative colitis, irritable bowel syndrome, inflammatory bowel disease (IBD), or similar, as well as combinations thereof.

In some embodiments, the MASP-2-dependent complement-associated disease or disorder is a pulmonary disorder, including acute respiratory distress syndrome, transfusion-related acute lung injury, ischemia/reperfusion acute lung injury, chronic obstructive pulmonary disease, asthma, Wegener's granulomatosis, antiglomerular basement membrane disease (Goodpasture's disease), meconium aspiration syndrome, aspiration pneumonia, bronchiolitis obliterans syndrome, idiopathic pulmonary fibrosis, acute lung injury secondary to burn, non-cardiogenic pulmonary edema, transfusion-related respiratory depression, emphysema, and the like, as well as combinations thereof.

In some embodiments, the MASP-2-dependent complement-associated disease or disorder is an extracorporeal exposure-triggered inflammatory reaction and the method comprises treating a subject undergoing an extracorporeal circulation procedure. In some embodiments, the extracorporeal circulation procedure includes hemodialysis, plasmapheresis, leukopheresis, extracorporeal membrane oxygenation (ECMO), heparin-induced extracorporeal membrane oxygenation LDL precipitation (HELP), cardiopulmonary bypass (CPB), and the like.

In some embodiments, the MASP-2-dependent complement-associated disease or disorder is selected from inflammatory or non-inflammatory arthritides and other musculoskeletal disorders, e.g., osteoarthritis, rheumatoid arthritis, juvenile rheumatoid arthritis, gout, neuropathic arthropathy, psoriatic arthritis, ankylosing spondylitis or other spondyloarthropathies and crystalline arthropathies, muscular dystrophy, systemic lupus erythematosus (SLE), or similar, as well as combinations thereof.

In some embodiments, the MASP-2-dependent complement-associated disease or disorder is a skin disorder; for example, psoriasis, autoimmune bullous dermatoses, eosinophilic spongiosis, bullous pemphigoid, epidermolysis bullosa acquisita, atopic dermatitis, herpes gestationis, and other skin disorders. In some embodiments, the MASP-2-dependent complement-associated disease or disorder is a thermal burn, chemical burn, or combinations thereof, including capillary leakage caused thereby.

In some embodiments, the MASP-2-dependent complement-associated disease or disorder is a peripheral nervous system (PNS) and/or central nervous system (CNS) disorder or injury including multiple sclerosis (MS), myasthenia gravis (MG), Huntington's disease (HD), amyotrophic lateral sclerosis (ALS), Guillain Barre syndrome, reperfusion following stroke, degenerative discs, cerebral trauma, Parkinson's disease (PD), Alzheimer's disease (AD), Miller-Fisher syndrome, cerebral trauma and/or hemorrhage, traumatic brain injury, demyelination, meningitis, or similar, as well as combinations thereof.

In some embodiments, the MASP-2-dependent complement-associated disease or disorder is sepsis or a condition resulting from sepsis including severe sepsis, septic shock, acute respiratory distress syndrome resulting from sepsis, hemolytic anemia, systemic inflammatory response syndrome, hemorrhagic shock, or the like, as well as combinations thereof.

In some embodiments, the MASP-2-dependent complement-associated disease or disorder is a urogenital disorder including painful bladder disease, sensory bladder disease, chronic abacterial cystitis and interstitial cystitis, male and female infertility, placental dysfunction and miscarriage, pre-eclampsia, or similar, as well as combinations thereof.

In some embodiments, the MASP-2-dependent complement-associated disease or disorder is an inflammatory reaction in a subject being treated with chemotherapeutics and/or radiation therapy, including for the treatment of cancerous conditions.

In some embodiments, the MASP-2-dependent complement-associated disease or disorder is an angiogenesis-dependent cancer, including a solid tumor(s), blood borne tumor(s), high-risk carcinoid tumors, tumor metastases, and the like, including combinations thereof.

In some embodiments, the MASP-2-dependent complement-associated disease or disorder is an angiogenesis-dependent benign tumor, including hemangiomas, acoustic neuromas, neurofibromas, trachomas, carcinoid tumors, pyogenic granulomas, or similar, as well as combinations thereof.

In some embodiments, the MASP-2-dependent complement-associated disease or disorder is an endocrine disorder including Hashimoto's thyroiditis, stress, anxiety, other potential hormonal disorders involving regulated release of prolactin, growth or insulin-like growth factor, adrenocorticotropin from the pituitary, or similar, as well as combinations thereof.

In some embodiments, the MASP-2-dependent complement-associated disease or disorder is an ophthalmic disease or disorder including age-related macular degeneration, glaucoma, endophthalmitis, and the like, as well as combinations thereof.

In some embodiments, the MASP-2-dependent complement-associated disease or disorder is an ocular angiogenic disease or condition including age-related macular degeneration, uveitis, ocular melanoma, corneal neovascularization, primary pterygium, HSV stromal keratitis, HSV-1-induced corneal lymphangiogenesis, proliferative diabetic retinopathy, diabetic macular edema, retinopathy of prematurity, retinal vein occlusion, corneal graft rejection, neovascular glaucoma, vitreous hemorrhage secondary to proliferative diabetic retinopathy, neuromyelitis optica, rubeosis, or similar, as well as combinations thereof.

In some embodiments, the MASP-2-dependent complement-associated disease or disorder is disseminated intravascular coagulation (DIC) or other complement mediated coagulation disorder, including DIC secondary to sepsis, severe trauma, including neurological trauma (e.g., acute head injury; see Kumura et al, *Acta Neurochirurgica* 55:23-28 (1987), infection (e.g., bacterial, viral, fungal, parasitic), cancer, obstetrical complications, liver disease, severe toxic reaction (e.g., snake bite, insect bite, transfusion reaction), shock, heat stroke, transplant rejection, vascular aneurysm, hepatic failure, cancer treatment by chemotherapy or radiation therapy, burn, or accidental radiation exposure.

In some embodiments, the MASP-2-dependent complement-associated disease or disorder is selected from the group consisting of acute radiation syndrome, dense deposit disease, Degos Disease, Catastrophic Antiphospholipid Syndrome (CAPS), Behcet's disease, cryoglobulinemia, paroxysmal nocturnal hemoglobinuria (PNH), cold agglutinin disease, and combinations thereof.

In some embodiments, the MASP-2-dependent complement-associated disease or disorder is selected from the group consisting of aHUS, HSCT-TMA, IgAN, Lupus Nephritis (LN), and combinations thereof.

In some embodiments, the method comprises administering to a patient suffering from, or at risk for developing a disease, disorder or condition associated with fibrin-induced activation of the complement system and the associated activation of the coagulation and/or contact systems an amount of a compound according to any one of the foregoing embodiments (e.g., a compound of Structure (I), (II), or (III)) in an amount sufficient to inhibit MASP-2 dependent complement activation in the mammalian subject to thereby treat the disease or disorder. In some embodiments, the subject is suffering from, or at risk of developing, a disease, disorder or condition associated with complement-related inflammation, excessive coagulation or contact system activation initiated by fibrin or activated platelets. In some embodiments, the subject is suffering from a disease or disorder selected from the group consisting of arterial thrombosis, venous thrombosis, deep vein thrombosis, post-surgical thrombosis, restenosis following coronary artery bypass graft and/or an interventional cardiovascular procedure (e.g., angioplasty or stent placement), atherosclerosis, plaque rupture, plaque instability, restenosis, hypotension, acute respiratory distress syndrome (ARDS), systemic inflammatory response syndrome (SIRS), disseminated intravascular coagulation (DIC), veno-occlusive disease (VOD), thrombotic microangiopathy, lupus nephritis, superficial thrombophlebitis, Factor V Leiden mutation, ischemic/reperfusion injury, human immunodeficiency virus (HIV) infection, undergoing hormone-replacement therapy (HRT), Alzheimer's disease and/or suffering from a hypercoagulable state.

In some embodiments, the subject is suffering from, or at risk for developing an acquired hypercoagulable state due to at least one or more of the following: undergoing therapy with a drug selected from the group consisting of 5-FU, GM-CSF, cisplatin, heparin, COX-2 inhibitor, contrast media, corticosteroids and antipsychotics; venous stasis (immobilization, surgery, etc.), antiphospholipid syndrome, cancer (promyelocytic leukemia, lung, breast, prostate, pancreas, stomach and colon tumors), tissue injury due to trauma or surgery, presence of a catheter in a central vein, acquired deficiency of a protein involved in clot formation (e.g., protein C), paroxysmal nocturnal hemoglobinuria (PNH), elevated levels of homocysteine, heart failure, presence of a mechanical valve, pulmonary hypertension with in situ thrombosis, atrial fibrillation, heparin-induced thrombocytopenia (HIT), heparin-induced thrombocytopenia and thrombosis (HITT), Kawasaki disease with in situ thrombus, Takayasu arteritis with in situ thrombus, thrombophilia of metastatic cancer, elevated Factor VIII levels, pregnancy, inflammatory bowel disease (IBD), or due to a genetic defect that causes or increases the risk of developing, a hypercoagulable state, such as a genetic defect selected from the group consisting of a Prothrombin 20210 gene mutation, an MTHFR mutation, a deficiency of protein C, a deficiency of protein S, a deficiency of protein A, a deficiency of protein Z, an antithrombin deficiency, and a genetic disorder producing thrombophilia.

In some embodiments, the subject is suffering from, or at risk for developing, a disease or disorder that is amenable to treatment with a kallikrein inhibitor. In some embodiments, the subject is suffering from, or at risk for developing a disease or disorder amenable to treatment with a kallikrein inhibitor is selected from the group consisting of hereditary angioedema, diabetic macular edema and bleeding during cardiopulmonary bypass. In some embodiments, the subject is suffering from, or at risk for developing, a disease or disorder that is amenable to treatment with a thrombin inhibitor, such as arterial thrombosis, venous thrombosis, pulmonary embolism, atrial fibrillation, heparin-induced thrombocytopenia, conversion from one anticoagulant to another, or off-label use for extracorporeal circuit patency of continuous renal replacement therapy (CRRT) in critically ill patients with HIT (maintenance).

In some embodiments, the subject has previously experienced, is currently suffering from, or is at risk for developing atrial fibrillation and the MASP-2 inhibitory compound (e.g., a compound of Structure (I), (II), or (III)) is administered in an amount sufficient to reduce the risk of stroke in said subject. In some embodiments, the subject is suffering from, or at risk for developing, a disease or disorder that is amenable to treatment with a factor XII inhibitor, such as deep vein thrombosis (both primary prophylaxis and extended therapy), pulmonary embolism, nonvalvular atrial fibrillation, prevention of recurrent ischemia after acute coronary syndrome in subjects with or without atrial fibrillation, end-stage renal disease, cerebral ischemia, angina, or to reduce or prevent clotting associated with medical devices (e.g., valves, small caliber grafts, etc.) and/or extracorporeal circuits.

In some embodiments, the subject has previously experienced, is currently suffering from, or is at risk for developing nonvalvular atrial fibrillation and the MASP-2 inhibitory compound (e.g., a compound of Structure (I), (II), or (III)) is administered in an amount sufficient to reduce the risk of stroke and/or embolism in said subject. In some embodiments, the subject has an acquired disease or disorder that increases the propensity for thromboembolism, such as a disease or disorder selected from the group consisting of atherosclerosis, antiphospholipid antibodies, cancer (e.g., promyelocytic leukemia, lung, breast, prostate, pancreatic, stomach and colon), hyperhomocysteinemia, infection, tissue injury, venous stasis (such as due to surgery, orthopedic or paralytic immobilization, heart failure, pregnancy, or obesity) and a subject taking oral contraceptives that contain estrogen.

In some embodiments, the subject is in need of anticoagulant therapy and the MASP-2 inhibitory compound (e.g., a compound of Structure (I), (II), or (III)) is used as a replacement for standard anticoagulant therapy (e.g, Warfarin). In some embodiments, the subject has a condition that normally prohibits standard anticoagulant therapy, such as CNS amyloid angiopathy. In some embodiments of the method, the MASP-2 inhibitory compound is administered as a bridging agent perioperatively in a subject otherwise on standard anti coagulation therapy. In some embodiments, the subject has sickle cell disease which is a vaso-occlusive disorder involving activation of platelets.

Atypical hemolytic uremic syndrome (aHUS) is part of a group of conditions termed "Thrombotic microangiopathies." In the atypical form of HUS (aHUS), the disease is associated with defective complement regulation and can be either sporadic or familial. Familial cases of aHUS are associated with mutations in genes coding for complement activation or complement regulatory proteins, including complement factor H, factor I, factor B, membrane cofactor CD46 as well as complement factor H-related protein 1 (CFHR1) and complement factor H-related protein 3 (CFHR3). (Zipfel, P. F., et al., PloS Genetics 3(3):e41 (2007)). The unifying feature of this diverse array of genetic mutations associated with aHUS is a predisposition to enhanced complement activation on cellular or tissue surfaces. A subject is a risk for developing aHUS upon the onset of at least one or more symptoms indicative of aHUS (e.g, the presence of anemia, thrombocytopenia and/or renal insufficiency) and/or the presence of thrombotic microangiopathy in a biopsy obtained from the subject. The determination of whether a subject is at risk for developing aHUS comprises determining whether the subject has a genetic predisposition to developing aHUS, which may be carried out by assessing genetic information (e.g. from a database containing the genotype of the subject), or performing at least one genetic screening test on the subject to determine the presence or absence of a genetic marker associated with aHUS (i.e., determining the presence or absence of a genetic mutation associated with aHUS in the genes encoding complement factor H (CFH), factor I (CFI), factor B (CFB), membrane cofactor CD46, C3, complement factor H-related protein 1 (CFHR1), or THBD (encoding the anticoagulant protein thrombodulin) or complement factor H-related protein 3 (CFHR3), or complement factor H-related protein 4 (CFHR4)) either via genome sequencing or gene-specific analysis (e.g, PCR analysis), and/or determining whether the subject has a family history of aHUS. Methods of genetic screening for the presence or absence of a genetic mutation associated with aHUS are well established, for example, see Noris M et al. "Atypical Hemolytic-Uremic Syndrome," 2007 Nov. 16 [Updated 2011 Mar. 10], In: Pagon R A, Bird T D, Dolan C R, et al., editors. GeneReviews™, Seattle (Wash.): University of Washington, Seattle.

Hematopoietic stem cell transplant-associated TMA (HSCT-TMA) is a life-threatening complication that is triggered by endothelial injury. The kidney is the most commonly affected organ, though HSCT-TMA can be a multisystem disease that also involves the lung, bowel, heart, and brain. The occurrence of even mild TMA is associated with long-term renal impairment. Development of post-allogeneic HSCT-associated TMA differs in frequency based on varying diagnostic criteria and conditioning and graft-versus-host disease prophylaxis regimens, with calcineurin inhibitors being the most frequent drugs implicated (Ho V T et al., Biol Blood Marrow Transplant, 11(8):571-5, 2005).

Immunoglobulin A nephropathy (IgAN) is an autoimmune kidney disease resulting in intrarenal inflammation and kidney injury. IgAN is the most common primary glomerular disease globally. With an annual incidence of approximately 2.5 per 100,000, it is estimated that 1 in 1400 persons in the U.S. will develop IgAN. As many as 40% of patients with IgAN will develop end-stage renal disease (ESRD). Patients typically present with microscopic hematuria with mild to moderate proteinuria and variable levels of renal insufficiency (Wyatt R. J., et al., NEnglJMed 36S(25): 2402-4, 2013). Clinical markers such as impaired kidney function, sustained hypertension, and heavy proteinuria (over 1 g per day) are associated with poor prognosis (Goto M et al., Nephrol Dial Transplant 24(10):3068-74, 2009; Berthoux F. et al., J Am Soc Nephrol 22(4):752-61, 2011). Proteinuria is the strongest prognostic factor independent of other risk factors in multiple large observational studies and prospective trials (Coppo R. et al., J Nephrol 18(5):503-12, 2005; Reich H. N., et al., J Am Soc Nephrol 18(12):3177-83, 2007). It is estimated that 15-20% of patients reach ESRD within 10 years of disease onset if left untreated (D'Amico G., Am J Kidney Dis 36(2):227-37, 2000). The diagnostic hallmark of IgAN is the predominance of IgA deposits, alone or with IgG, IgM, or both, in the glomerular mesangium.

A main complication of systemic lupus erythematosus (SLE) is nephritis, also known as lupus nephritis, which is classified as a secondary form of glomerulonephritis. Up to 60% of adults with SLE have some form of kidney involvement later in the course of the disease (Koda-Kimble et al., Koda-Kimble and Young's Applied Therapeutics: the clinical use of drugs, 10th Ed, Lippincott Williams & Wilkins: pages 792-9, 2012) with a prevalence of 20-70 per 100,000 people in the U.S. Lupus nephritis often presents in patients with other symptoms of active SLE, including fatigue, fever, rash, arthritis, serositis, or central nervous system disease (Pisetsky D.S. et al., Med Clin North Am 81(1): 113-28, 1997). Some patients have asymptomatic lupus nephritis; however, during regular follow-up, laboratory abnormalities such as elevated serum creatinine levels, low albumin levels, or urinary protein or sediment suggest active lupus nephritis.

V. Compositions, Dosage, and Administration

The compounds as described herein (e.g., a compound of Structure (I), (II), or (III)) can be administered in a manner compatible with the dosage formulation, and in such amount as will be effective or suitable for treatment. The quantity to be administered depends on a variety of factors including, e.g., the age, body weight, physical activity, and diet of the individual, and the desired effect. In certain embodiments, the size of the dose may also be determined by the existence, nature, and extent of any adverse side effects that accompany the administration of the compound in a particular individual.

It will be understood, however, that the specific dose level and frequency of dosage for any particular patient may be varied by a physician and will depend upon a variety of factors including the activity of the specific compound employed, the metabolic stability and length of action of that compound, the age, body weight, hereditary characteristics, general health, sex, diet, mode and time of administration, rate of excretion, drug combination, the severity of the particular condition, and the host undergoing therapy.

In certain embodiments, the dose may take the form of solid, semi-solid, or liquid forms, preferably in unit dosage forms suitable for simple administration of precise dosages.

As used herein, the term "unit dosage form" refers to physically discrete units suitable as unitary dosages for humans and other mammals, each unit containing a predetermined quantity of an active agent calculated to produce the desired onset, tolerability, and/or efficacious effects, in association with a suitable pharmaceutical excipient (e.g., an ampoule). In addition, more concentrated dosage forms may be prepared, from which the more dilute unit dosage forms may then be produced.

The compounds described herein (e.g., a compound of Structure (I), (II), or (III)) can be administered to a subject in need of treatment using methods known in the art, such as by oral administration or by injection. The injection can be, e.g., subcutaneous, intravenous, intraperitoneal, or intramuscular. As described herein, parenteral formulations can be prepared in dosage unit form for ease of administration and uniformity of dosage. As used herein the term "unit dosage form" refers to physically discrete units suited as unitary dosages for the subject to be treated; each unit containing a predetermined quantity of active compound calculated to produce the desired therapeutic effect.

The pharmaceutical compositions of the present application comprise a therapeutically effective amount of a compound of the present disclosure ((e.g., a compound of Structure (I), (II), or (III)) formulated together with one or more pharmaceutically acceptable carriers or excipient. As used herein, the term "pharmaceutically acceptable carrier" means a nontoxic, inert solid, semi-solid or liquid filler, diluent, encapsulating material or formulation auxiliary of any type. The pharmaceutical compositions of this application can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations include, for example, sterile injectable aqueous or oleaginous suspensions formulated according to the known art using suitable dispersing or wetting agents and suspending agents. The sterile injectable preparation may also be a sterile injectable solution, suspension or emulsion in a nontoxic parenterally acceptable diluent or solvent. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished using a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Solid compositions of a similar type may also be employed as fillers in soft and hard filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose, or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents.

Dosage forms for topical or transdermal administration of a compound as disclosed in the foregoing embodiments (e.g., a compound of Structure (I), (II), or (III)) include ointments, pastes, creams, lotions, gels, powders, solutions, sprays, inhalants, or patches. For example, the active component may be ad-mixed under sterile conditions with a pharmaceutically acceptable carrier or excipient and any needed preservatives or buffers as may be required.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present disclosure, disorders are treated or prevented in a subject, such as a human or other animal, by administering to the subject a therapeutically effective amount of a compound according to any one of the foregoing embodiments, in such amounts and for such time as is necessary to achieve the desired result. As is well understood in the medical arts a therapeutically effective amount of a compound will be at a reasonable benefit/risk ratio applicable to any medical treatment.

In general, compounds (e.g., compounds of Structure (I), (II), or (III)) will be administered in therapeutically effective amounts via any of the usual and acceptable modes known in the art, either singly or in combination with one or more other therapeutic agents. A therapeutically effective amount may vary widely depending on the severity of the disease, the age and relative health of the subject, the potency of the compound used and other factors.

In general, satisfactory results are indicated to be obtained systemically at daily dosages of from about 0.03 to 2.5 mg/kg per body weight. An indicated daily dosage in the larger mammal, e.g., humans, is in the range from about 0.5 mg to about 250 mg, about 5 mg to about 150 mg, about 5 mg to about 100 mg, about 10 mg to about 75 mg, about 10 mg to about 50 mg, such as 10, 20, 30, 40, or about 50 mg, conveniently administered, e.g., in divided doses up to four times a day or in retard form. Suitable unit dosage forms for oral administration comprise from ca. 1 to 60 mg active ingredient.

In certain embodiments, a therapeutic amount or dose of the compound (e.g., compounds of Structure (I), (II), or (III)) may range from about 0.1 mg/kg to about 500 mg/kg, alternatively from about 1 mg/kg to about 50 mg/kg. In general, treatment regimens according to the present application comprise administration to a patient in need of such treatment from about 10 mg to about 1000 mg of the compound(s) per day in single or multiple doses. Therapeutic amounts or doses will also vary depending on route of administration, as well as the possibility of co-usage with other agents.

Upon improvement of a subject's condition, a maintenance dose of a compound, composition or combination of this application may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds (e.g., compounds of Structure (I), (II), or (III)) and compositions thereof will be decided by an attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The application also provides for a pharmaceutical combination, e.g., a kit, comprising:

a) a first agent which is a compound of the application as disclosed herein, in free form or in pharmaceutically acceptable salt form, and b) at least one co-agent. The kit can comprise instructions for its administration.

Methods for preparing such dosage forms are known to those skilled in the art (see, e.g., REMINGTON'S PHARMACEUTICAL SCIENCES, 18th ED., Mack Publishing Co., Easton, Pa. (1990)). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., REMINGTON'S PHARMACEUTICAL SCIENCES, 18th ED., Mack Publishing Co., Easton, Pa. (1990)).

EXAMPLES

The following examples are provided by way of illustration only and not by way of limitation. Those of skill will readily recognize a variety of noncritical parameters which could be changed or modified to yield essentially similar results.

General Methods

The following examples are provided by way of illustration only and not by way of limitation. Those of skill will readily recognize a variety of noncritical parameters which could be changed or modified to yield essentially similar results.

If not otherwise stated, chromatography refers to flash chromatography conducted on silica gel.

Amine column refers to flash chromatography conducted on Redisep Rf Gold high performance amine column.

Another method for HPLC purification was performed on a Waters preparative reverse phase HPLC system with the combination of UV/MS detectors (254 nm and 280 nm) and XBridge Prep (19×50 mm) C18 10 µM OBD column. Eluents were a mixture of water and acetonitrile (with 0.1% trifluoroacetic acid). Flow rate was typically 50 mL/min with a linear gradient of water in acetonitrile from 15-40% or 25-50% or 5-30% in 8 minutes. The injection volume was from 0.2 to 1 mL with maximum 20 mg per load.

Abbreviations

μ micro
° C. degrees Celsius
Ac acetyl
anhyd anhydrous
aq aqueous
atm atmosphere(s)
Bn benzyl
Boc tert-butoxycarbonyl
Bu butyl
calcd calculated
Cbz benzyloxycarbonyl
CPME cyclopentyl methyl ether
concd concentrated
conc concentration
DCC N,N'-dicyclohexylcarbodiimide
DIEA N,N-diisopropylethylamine
DMAP 4-(N,N-dimethylamino)pyridine
DMF dimethylformamide
DMSO dimethylsulfoxide
EDC N-(3-dimethylaminopropyl)-N'-ethylcarbodiimide hydrochloride
equiv equivalent
ES electrospray
Et ethyl
Et$_2$O diethyl ether
g gram(s)
h hour(s)
HATU A-[(Dimethylamino)-1H-1,2,3-triazolo-[4,5-b]pyridin-1-ylmethylene]-A-methylmethanaminium hexafluorophosphate N'-oxide
HBTU N,N,N',N'-Tetramethyl-t)-(1H-benzotriazol-1-yl)uronium hexafluorophosphate, O-(Benzotriazol-1-yl)-
HPLC high-performance liquid chromatography/high-performance liquid chromatography
HOBt 1-hydroxybenzotriazole hydrate
iPrOH iso-propanol
L liter(s)
LiOH lithium hydroxide
m milli
M molar
MeCN acetonitrile
min minute(s)
mL milliliter
mol mole; molecular (as in mol wt)
MS mass spectrometry
MW molecular weight
NBS N-bromosuccinimide
NETS N-hydroxysuccinimide
NMM 4-methylmorpholine
NMR nuclear magnetic resonance
o ortho
obsd observed
p para
Ph phenyl
ppt precipitate
Pr propyl
psi pounds per square inch
temp temperature
TFA trifluoroacetic acid
THF tetrahydrofuran Example 1

Preparation of (2-((2R,4S)-2-(((S)-1-(((1H-pyrrolo[3,2-c]pyridin-2-yl)methyl)amino)-1-oxopropan-2-yl)carbamoyl)-4-phenylpiperidin-1-yl)ethyl)phosphonic acid di-trifluoroacetate salt (Compound I-15

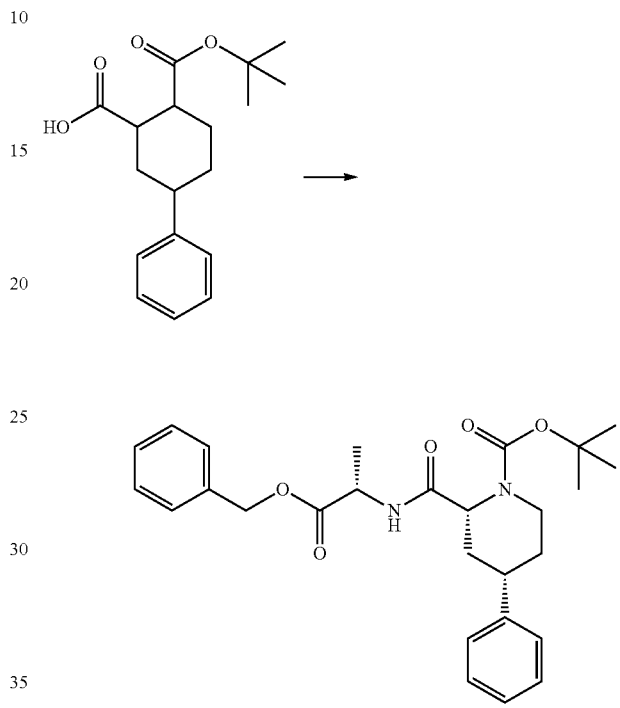

Step 1: To a solution of (2R,4S)-1-(tert-butoxycarbonyl)-4-phenylpiperidine-2-carboxylic acid (4.5 g, 14.7 mmol) in DMF (35 mL) was added HOBt (2.2 g, 16.2 mmol), DIEA (3 mL) and EDC (3.1 g, 16.2 mmol). After stirring for 30 min at RT, benzyl L-alanine hydrochloride (3.5 g mg, 16.2 mmol) was added and stirred for 16 h. The reaction mixture was concentrated in vacuo and the residue partitioned between EtOAc and 10% KHSO$_4$ solution. The organic layer was separated, washed with H$_2$O and saturated aq. NaHCO$_3$., dried over anhyd Na$_2$SO$_4$ then concentrated in vacuo. The residue was purified by chromatography (10% EtOAc-hexanes; the 3$^{rd}$ UV-active material eluting from the column) to give tert-butyl (2R,4S)-2-(((S)-1-(benzyloxy)-1-oxopropan-2-yl)carbamoyl)-4-phenylpiperidine-1-carboxylate (2.59 g, 34% yield).

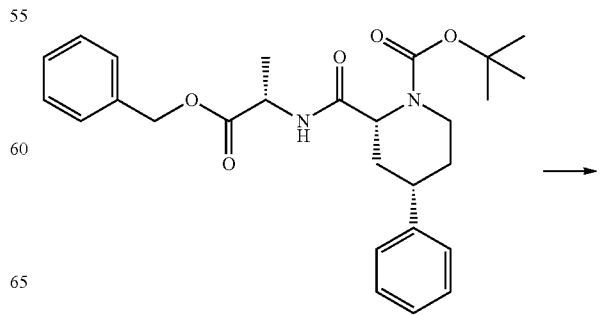

-continued

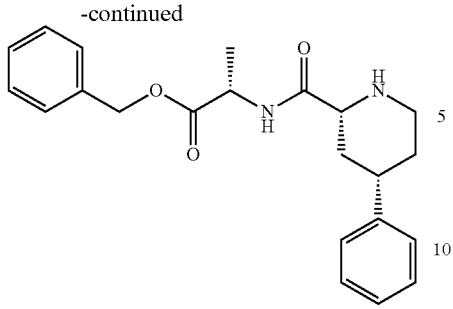

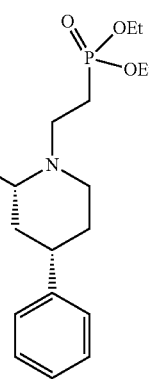

Step 2: To a stirred solution of tert-butyl (2R,4S)-2-(((S)-1-(benzyloxy)-1-oxopropan-2-yl)carbamoyl)-4-phenylpiperidine-1-carboxylate (200 mg, 0.43 mmol) in DCM (2 mL) was added TFA (1 mL). The reaction was stirred at RT for 1 h. then concentrated in vacuo to yield benzyl ((2R,4S)-4-phenylpiperidine-2-carbonyl)-L-alaninate trifluoroacetate salt (201 mg, 100% yield)

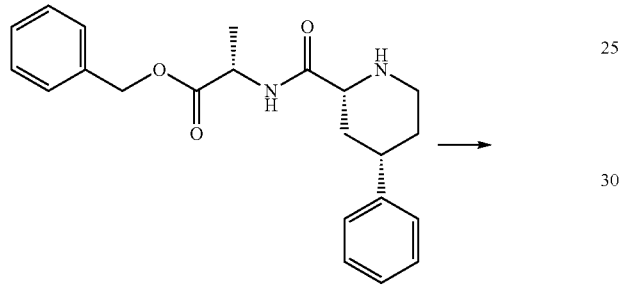

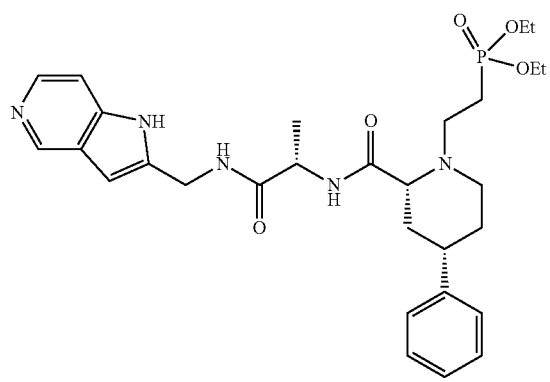

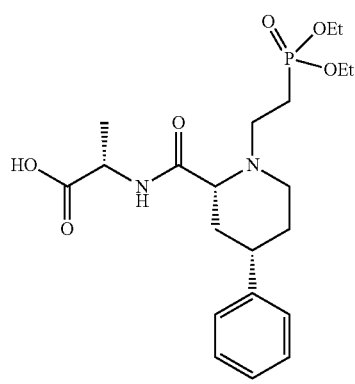

Step 3: To (2R,4S)-4-phenylpiperidine-2-carbonyl)-L-alaninate trifluoroacetate salt (70 mg, 0.15 mmol) dissolved in DMF (2 mL) was added K$_2$CO$_3$ (100 mg, 0.72 mmol) and stirred for 30 min. After adding Diethyl (2-bromoethyl) phosphonate (0.2 mL), the reaction mixture was stirred at 50° C. for 2 h. with the reaction monitored by LCMS. The crude reaction mixture was quenched with water, extracted with EtOAc (2×20 mL) and the crude product dissolved in MeOH. The solution was charged with 10% Pd/C and the reaction mixture stirred under H$_2$ atmosphere for 1 h. The crude reaction mixture was filtered over Celite®, washed with MeOH and concentrated in vacuo to yield ((2R,4S)-1-(2-(diethoxyphosphoryl)ethyl)-4-phenylpiperidine-2-carbonyl)-L-alanine. The crude material was used in the next reaction without further purification.

Step 4: To a stirred solution of (2R,4S)-1-(2-(diethoxyphosphoryl)ethyl)-4-phenylpiperidine-2-carbonyl)-L-alanine (50 mg, 0.11 mmol) in DCM (5 mL) was added NHS (13 mg, 0.11 mmol) with stirring at RT until dissolved. DCC (23 mg, 0.11 mmol) was added and the solution stirred for 1 h before 1H-pyrrolo[3,2-c]pyridin-2-yl)methanamine (32 mg, 0.22 mmol) was added. The resultant mixture was sonicated and left to stirred overnight at RT. After filtering thru a bed of Celite®, the solution was evaporated to dryness and the crude material purified by flash chromatography using an amine column with EtOAc as eluent to afford diethyl (2-((2R,4S)-2-(((S)-1-(((1H-pyrrolo[3,2-c]pyridin-2-yl)methyl)amino)-1-oxopropan-2-yl)carbamoyl)-4-phenylpiperidin-1-yl)ethyl)phosphonate (70 mg, 82% yield over two steps) as a white solid.

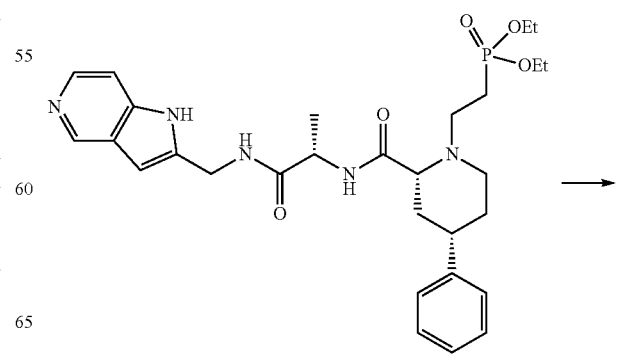

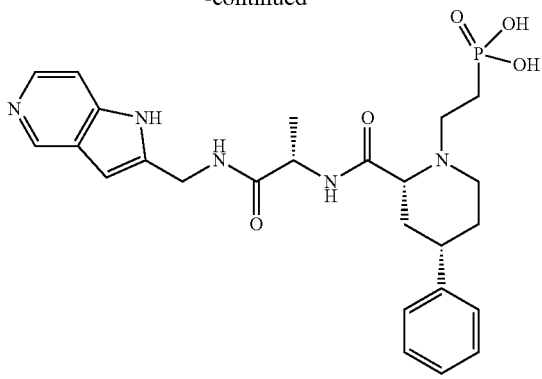

Step 5: To a stirred solution of diethyl (2-((2R,4S)-2-(((S)-1-(((1H-pyrrolo[3,2-c]pyridin-2-yl)methyl)amino)-1-oxopropan-2-yl)carbamoyl)-4-phenylpiperidin-1-yl)ethyl) phosphonate (70 mg, 0.12 mmol) in DCM was added TMSBr (1 mL). The reaction mixture was stirred at 40° C. for 3 h. with the reaction monitored by TLC. Upon completion, the reaction mixture was slowly quenched with MeOH (2 mL) at 0° C. The solvent was evaporated in vacuo and the crude material purified by prep HPLC using to yield (2-((2R,4S)-2-(((S)-1-(((1H-pyrrolo[3,2-c]pyridin-2-yl) methyl)amino)-1-oxopropan-2-yl)carbamoyl)-4-phenylpiperidin-1-yl)ethyl)phosphonic acid di-trifluoroacetate salt (71 mg, 80% yield) as white solid.

Example 2

Preparation of benzyl (imino(4-(((S)-2-((2R,4S)-4-phenylpiperidine-2-carboxamido)propanamido) methyl)phenyl)methyl)carbamate di-trifluoroacetate salt (Compound I-32)

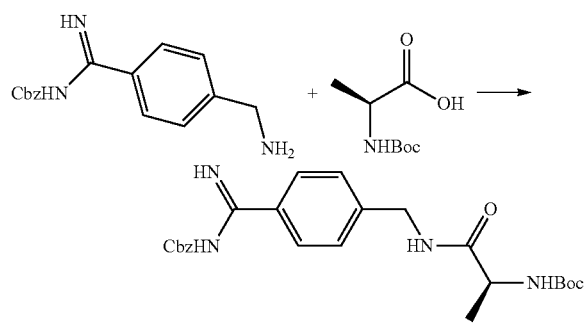

Step 1: To a stirred solution of (tert-butoxycarbonyl)-L-alanine (1.23 g, 6.52 mmol) in DCM (125 mL) was added DCC (1.48 g, 7.17 mmol) and NHS (825 mg, 7.17 mmol). The suspension was stirred for 1 h at RT and then added to a suspension of benzyl ((4-(aminomethyl)phenyl)(imino) methyl)carbamate hydrochloride (2.5 g, 7.82 mmol) in saturated aqueous NaHCO₃(125 mL). After stirring the reaction mixture for 1 h at RT, the aqueous layer was separated, extracted with DCM (2×60 mL) and the organics combined, dried over MgSO₄, filtered and concentrated in vacuo. The crude material was purified via flash chromatography using a 0-100% Hex/EtOAc gradient to afford benzyl (S)-((4-((2-((tert-butoxycarbonyl)amino)propanamido)methyl)phenyl) (imino)methyl)carbamate (2.0, 56% yield).

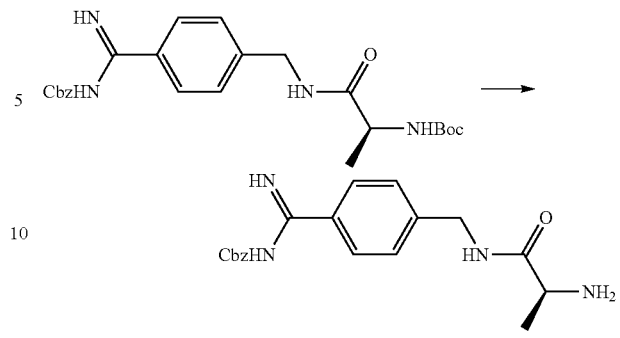

Step 2: To benzyl (S)-((4-((2-((tert-butoxycarbonyl) amino)propanamido)methyl)phenyl) (imino)methyl)carbamate (1.0 g, 2.15 mmol) was added a solution of 6 M HCl in IPA (11 mL). After stirring the solution at RT for 2 h, the reaction was judged complete by TLC. The solution was concentrated in vacuo to afford benzyl (S)-((4-((2-((tert-butoxycarbonyl)amino)propanamido)methyl)phenyl) (imino)methyl)carbamate hydrochloride (540 mg, 64%) as a white solid.

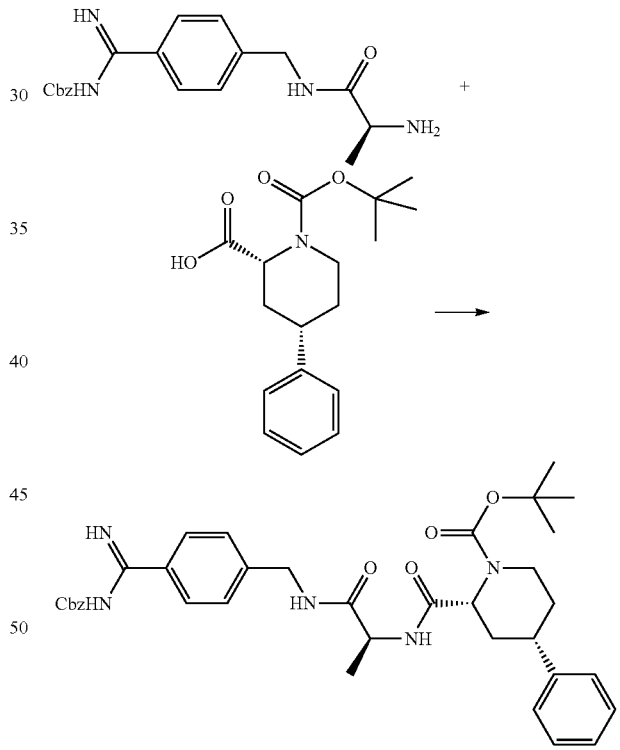

Step 3: To a stirred solution of benzyl (S)-((4-((2-((tert-butoxycarbonyl)amino)propanamido) methyl)phenyl) (imino)methyl)carbamate (1.27 g, 3.24 mmol), (2R,4S)-1-(tert-butoxycarbonyl)-4-phenylpiperidine-2-carboxylic acid (900 mg, 2.95 mmol) in DMF (10 mL) were added EDC (622 mg, 3.29 mmol), HOBt (570 mg, 3.24 mmol) and DIEA (700 μL). The reaction was stirred overnight at RT. The solution was diluted with EtOAc (100 mL), washed with water (4×60 mL) and saturated aqueous NH₄Cl (80 mL). After drying over MgSO₄, the solution was filtered, concentrated in vacuo and the crude material purified via flash chromatography using a 0-100% Hep/EtOAc gradient to afford tert-butyl (2R,4S)-2-(((S)-1-((4-(N-((benzyloxy)carbonyl)carbamimidoyl)benzyl)amino)-1-oxopropan-2-yl)carbamoyl)-4-phenylpiperidine-1-carboxylate (905 mg, 48% yield).

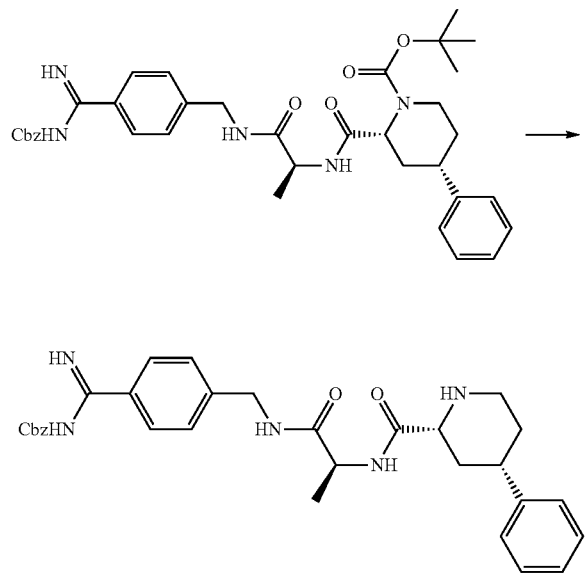

Step 4: To a solution of tert-butyl (2R,4S)-2-(((S)-1-((4-(N-((benzyloxy)carbonyl) carbamimidoyl)benzyl)amino)-1-oxopropan-2-yl)carbamoyl)-4-phenylpiperidine-1-carboxylate (22 mg, 0.035 mmol) in DCM (3 mL) was added TFA (500 uL). After stirring the mixture at RT for 90 min, the solution was concentrated in vacuo. The crude material was purified by reverse-phase HPLC using the 15%-40% gradient to afford benzyl (imino(4-(((S)-2-((2R,4S)-4-phenylpiperidine-2-carboxamido)propanamido)methyl)phenyl)methyl)carbamate di trifluoroacetate salt (10 mg, 44%) as a white solid Example 3

Preparation of ethyl 3-((2R,4S)-2-(((S)-1-((4-(N-((benzyloxy)carbonyl)carbamimidoyl)benzyl)amino)-1-oxopropan-2-yl)carbamoyl)-4-phenylpiperidin-1-yl)propanoate (Compound I-12)

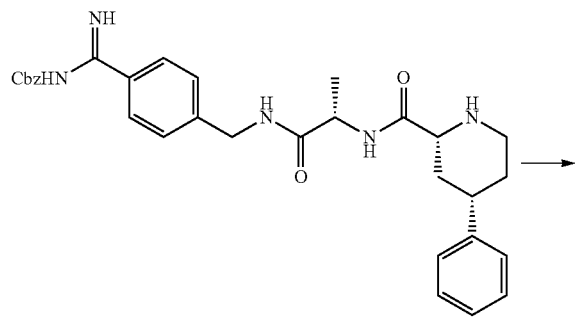

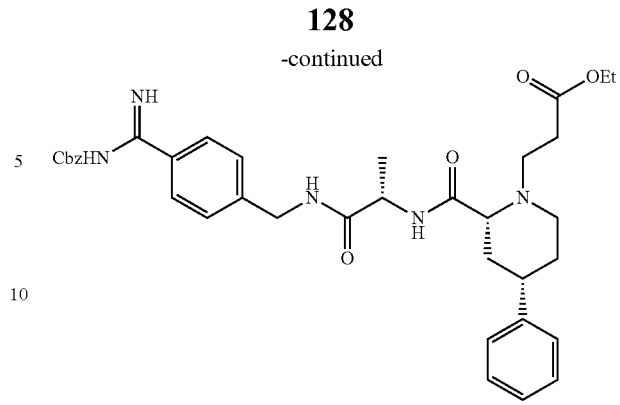

To a stirred solution of benzyl (imino(4-(((S)-2-((2R,4S)-4-phenylpiperidine-2-carboxamido)propanamido)methyl)phenyl)methyl)carbamate (100 mg, 0.14 mmol) in DCM (2 mL) and NEt$_3$ (0.8 mL) was added bromoester (0.2 ml) under an Ar atmosphere. After stirring for 24 h at RT, the reaction mixture was concentrated and purified using an amine column with EtOAc as eluent to afford ethyl 3-((2R,4S)-2-(((S)-1-((4-(N-((benzyloxy)carbonyl)carbamimidoyl)benzyl)amino)-1-oxopropan-2-yl)carbamoyl)-4-phenylpiperidin-1-yl)propanoate (70 mg, 78% yield) as a white solid.

Example 4

Preparation of ethyl 3-((2R,4S)-2-(((S)-1-((4-carbamimidoylbenzyl)amino)-1-oxopropan-2-yl)carbamoyl)-4-phenylpiperidin-1-yl)propanoate (Compound I-13)

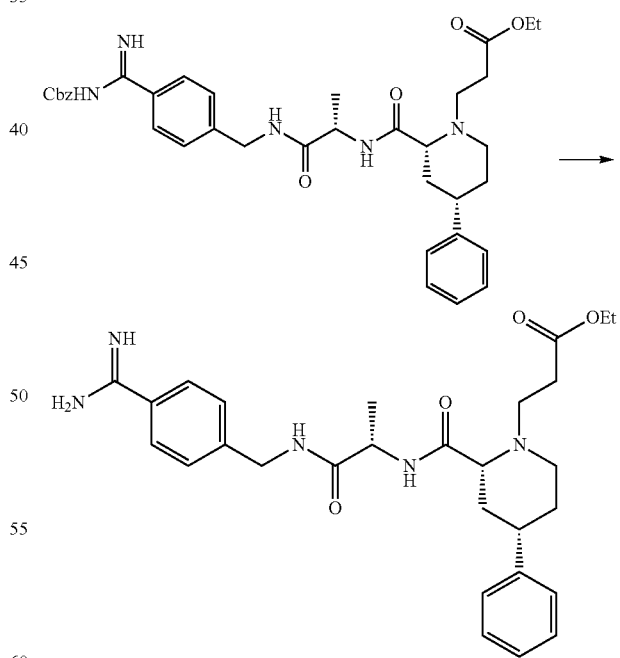

A stirred solution of consisting of ethyl 3-((2R,4S)-2-(((S)-1-((4-(N-((benzyloxy)carbonyl) carbamimidoyl)benzyl)amino)-1-oxopropan-2-yl)carbamoyl)-4-phenylpiperidin-1-yl)propanoate (55 mg, 0.085 mmol) in MeOH (15 mL) and 10% Pd/C was stirred under a H$_2$ atmosphere for 2 h. Upon completion of the reaction, the mixture was filtered

Example 5

Preparation of 3-((2R,4S)-2-(((S)-1-((4-carbamimidoylbenzyl)amino)-1-oxopropan-2-yl)carbamoyl)-4-phenylpiperidin-1-yl)propanoic acid di-trifluoroacetate salt (Compound I-14)

through Celite® and washed with MeOH. The organic residues were concentrated in vacuo to yield ethyl 3-((2R,4S)-2-(((S)-1-((4-carbamimidoylbenzyl)amino)-1-oxopropan-2-yl)carbamoyl)-4-phenylpiperidin-1-yl)propanoate (43 mg, 100% yield) as a white solid.

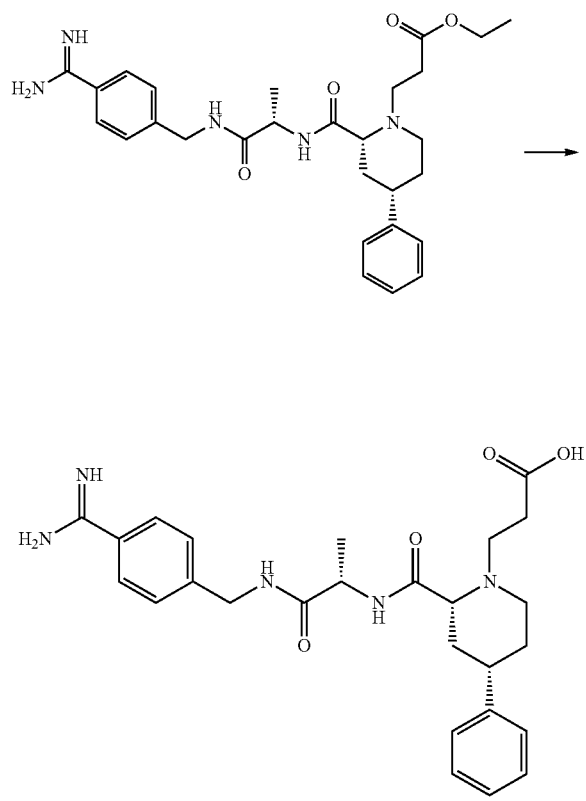

To a stirred solution of ethyl 3-((2R,4S)-2-(((S)-1-((4-carbamimidoylbenzyl)amino)-1-oxopropan-2-yl)carbamoyl)-4-phenylpiperidin-1-yl)propanoate (20 mg, 0.04 mmol) in THF (2 mL), at RT, was added LiOH (15 mg) dissolved in 2 ml of water. After stirring at RT for 18 h, the reaction mixture was acidified with TFA and purified by reverse-phase HPLC to yield 3-((2R,4S)-2-(((S)-1-((4-carbamimidoylbenzyl)amino)-1-oxopropan-2-yl)carbamoyl)-4-phenylpiperidin-1-yl)propanoic acid di-trifluoroacetate salt (15 mg, 53% yield) as a white solid.

Example 6

Preparation of (2R,4S)-2-(((S)-1-((4-carbamimidoylbenzyl)amino)-1-oxopropan-2-yl)carbamoyl)-1,1-dimethyl-4-phenylpiperidin-1-ium 2,2,2-trifluoroacetate trifluoroacetic Acid salt (Compound I-10)

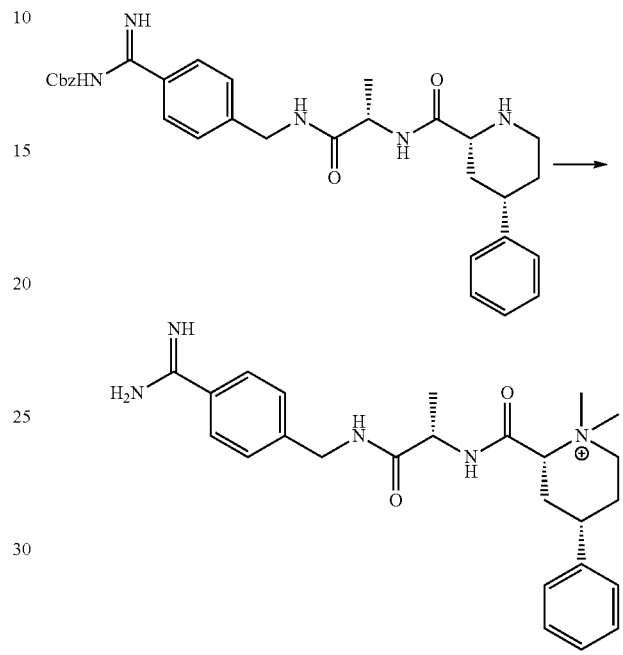

To a stirred solution of benzyl (imino(4-(((S)-2-((2R,4S)-4-phenylpiperidine-2-carboxamido)propanamido)methyl)phenyl)methyl)carbamate trifluoroacetate salt (50 mg, 0.068 mmol) in DCM (2 mL) and NEt$_3$ (0.1 mL) was added methyl iodide (0.048 ml, 0.8 mmol) under an Ar atmosphere. After stirring for 18 h at RT, the reaction mixture was concentrated and filtered through an amine column with EtOAc as eluent. The residue was dissolved in MeOH and the resultant solution charged with 10% Pd/C and stirred under a H$_2$ atmosphere for 30 min. The crude reaction was filtered over Celite, washed with MeOH and the washes concentrated in vacuo and purified on reverse-phase HPLC to yield (2R,4S)-2-(((S)-1-((4-carbamimidoylbenzyl)amino)-1-oxopropan-2-yl)carbamoyl)-1,1-dimethyl-4-phenylpiperidin-1-ium 2,2,2-trifluoroacetate trifluoroacetic acid salt (15 mg, 33% yield over two steps) as a white solid.

Example 7

Preparation of (2R,4S)—N—((S)-1-(((5-((Z)—N-hydroxycarbamimidoyl)thiophen-2-yl)methyl)amino)-1-oxopropan-2-yl)-4-phenylpiperidine-2-carboxamide hydrochloride (Compound I-24)

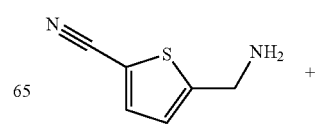

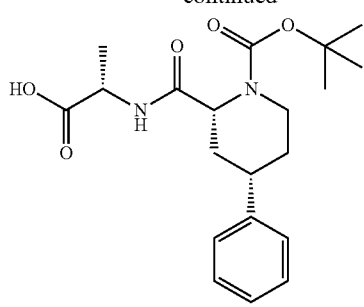

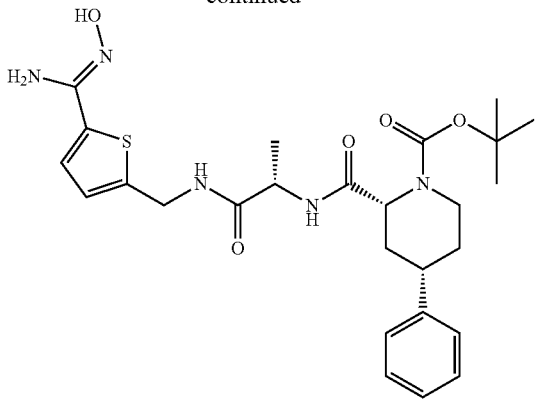

Step 2: To a suspension of tert-butyl (2R,4S)-2-(((S)-1-(((5-cyanothiophen-2-yl)methyl)amino)-1-oxopropan-2-yl)carbamoyl)-4-phenylpiperidine-1-carboxylate (100 mg, 0.2 mmol) and hydroxylamine hydrochloride (56 mg, 0.8 mmol) in methanol (2 mL) was added DIEA (139 μL, 0.8 mmol). The mixture was heated to 69° C. and stirred at this temperature overnight. After the reaction was allowed to cool to RT and concentrated in vacuo, the residue was triturated in water (5 mL) and the solid was collected via filtration. The solid was washed with water (2×5 mL) and dried in vacuo to afford tert-butyl (2R,4S)-2-(((S)-1-(((5-((Z)—N-hydroxycarbamimidoyl)thiophen-2-yl)methyl)amino)-1-oxopropan-2-yl)carbamoyl)-4-phenylpiperidine-1-carboxylate (100 mg, 94%) as an off-white solid.

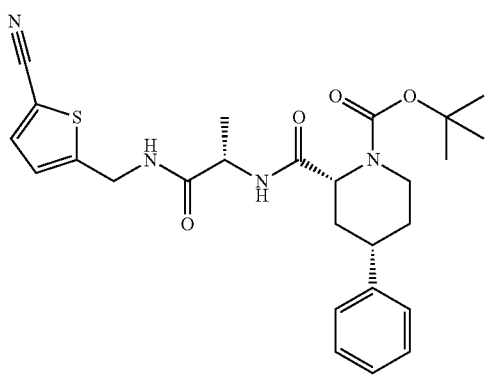

Step 1: A solution of ((2R,4S)-1-(tert-butoxycarbonyl)-4-phenylpiperidine-2-carbonyl)-L-alanine (100 mg, 0.27 mmol) and DCC (60 mg, 0.29 mmol) in DCM (6 mL) was stirred for 1 h at RT. The resultant slurry was then added to a suspension of 5-(aminomethyl)thiophene-2-carbonitrile hydrochloride (60 mg, 0.33 mmol) in saturated aqueous NaHCO₃(6 mL) and the mixture was stirred for 1 h at RT. The mixture was partitioned and the aqueous portion was extracted with DCM (3×40 mL). The organics layers were combined, dried over MgSO₄, filtered and concentrated. The crude material was purified via flash chromatography (SiO₂, 12 g) using a gradient of 0-100% heptane/ethyl acetate to afford tert-butyl (2R,4S)-2-(((S)-1-(((5-cyanothiophen-2-yl)methyl)amino)-1-oxopropan-2-yl)carbamoyl)-4-phenylpiperidine-1-carboxylate (130 mg, 97) as an off-white solid.

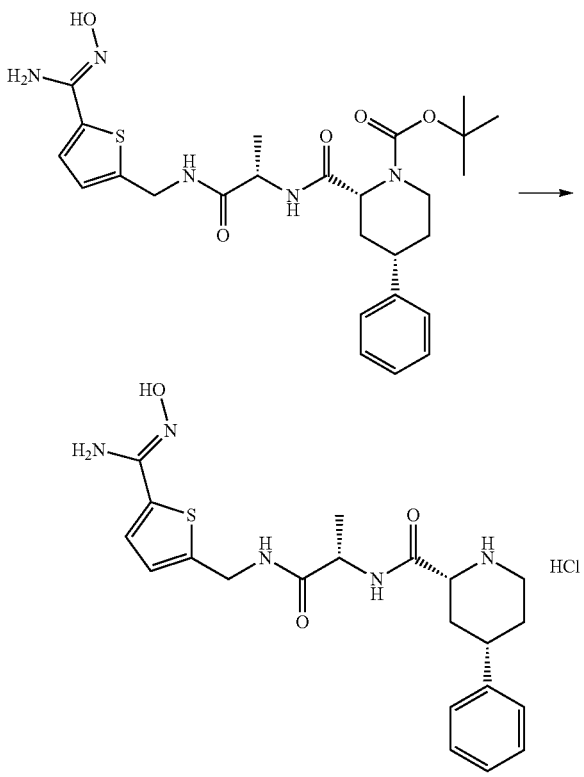 [SMILES: C[C@H](NC(=O)[C@H]1C[C@@H](c2ccccc2)CCN1C(=O)OC(C)(C)C)C(=O)NCc1ccc(/C(N)=N/O)s1 ; C[C@H](NC(=O)[C@H]1C[C@@H](c2ccccc2)CCN1)C(=O)NCc1ccc(/C(N)=N/O)s1 ; Cl]

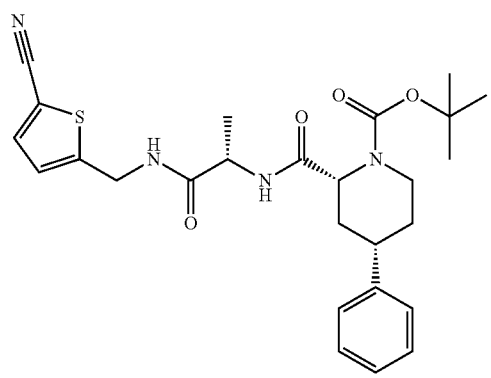

Step 3: Hydrochloric acid (6 M in IPA, 3 mL) was added to tert-butyl (2R,4S)-2-(((S)-1-(((5-((Z)—N-hydroxycarbamimidoyl)thiophen-2-yl)methyl)amino)-1-oxopropan-2- yl)carbamoyl)-4-phenylpiperidine-1-carboxylate (30 mg, 0.057 mmol) and the reaction was stirred overnight at rt. The reaction was concentrated to afford (2R,4S)—N—((S)-1-(((5-((Z)—N-hydroxycarbamimidoyl)thiophen-2-yl)methyl)amino)-1-oxopropan-2-yl)-4-phenylpiperidine-2-carboxamide hydrochloride (18 mg, 68%) as an off-white solid.

Example 8

Preparation of (2R,4S)—N—((S)-1-((4-((Z)—N'-hydroxycarbamimidoyl)benzyl)amino)-1-oxopropan-2-yl)-4-phenylpiperidine-2-carboxamide di-trifluoroacetate salt (Compound I-30)

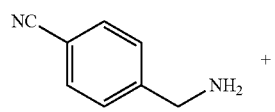

+

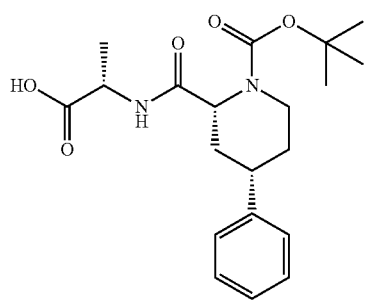

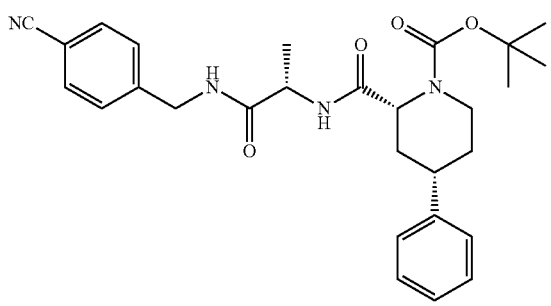

Step 1. A solution of ((2R,4S)-1-(tert-butoxycarbonyl)-4-phenylpiperidine-2-carbonyl)-L-alanine and DCM (6 mL) was stirred for 1 h at RT. The resultant slurry was then added to a suspension of 5-(aminomethyl)phenyl-carbonitrile hydrochloride (60 mg, 0.33 mmol) in saturated aqueous NaHCO$_3$(6 mL) and the mixture was stirred for 1 h at RT. The mixture was partitioned and the aqueous portion was extracted with DCM (3×40 mL). The organics layers were combined, dried over MgSO$_4$, filtered and concentrated. The crude material was purified via flash chromatography (SiO$_2$, 12 g) using a gradient of 0-100% heptane/EtOAc to afford desired product.

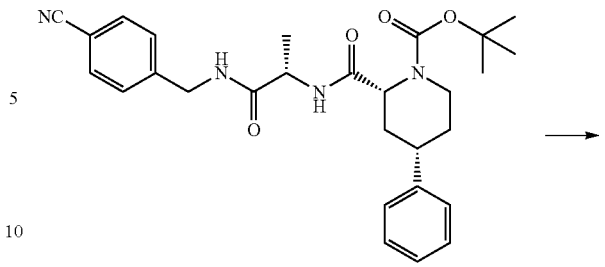

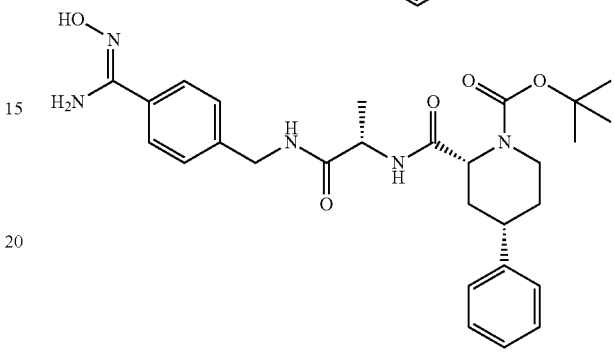

Step 2. A suspension of tert-butyl (2R,4S)-2-(((S)-1-((4-cyanobenzyl)amino)-1-oxopropan-2-yl)carbamoyl)-4-phenylpiperidine-1-carboxylate and hydroxylamine hydrochloride in methanol was added DIEA. The mixture was heated to 69° C. and stirred at this temperature overnight. After the reaction cooled to RT and was concentrated in vacuo, the residue was triturated in water (5 mL) and the solid was collected via filtration. The solid was washed with water (2×5 mL) and dried in vacuo to afford tert-butyl (2R,4S)-2-(((S)-1-((4-((Z)—N'-hydroxycarbamimidoyl)benzyl)amino)-1-oxopropan-2-yl)carbamoyl)-4-phenylpiperidine-1-carboxylate.

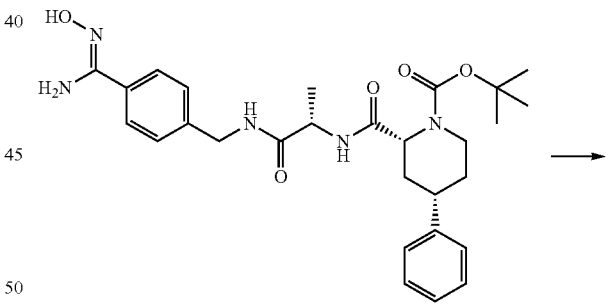

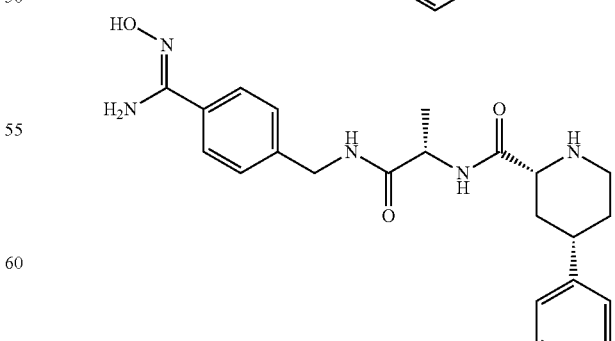

Step 3. A solution of tert-butyl (2R,4S)-2-(((S)-1-((4-((Z)—N'-hydroxycarbamimidoyl)benzyl)amino)-1-oxopropan-2-yl)carbamoyl)-4-phenylpiperidine-1-carboxylate in 6 M HCl/IPA (1 mL) was stirred at RT for 1.5 h. The reaction was concentrated and the residue purified via preparatory HPLC to afford the desired compound.

Example 9

Preparation of (2R,4S)—N-((2S)-1-((4-((Z)—N'-((((2-Ethylhexyl)oxy)carbonyl)oxy)carbamimidoyl)benzyl)amino)-1-oxopropan-2-yl)-4-phenylpiperidine-2-carboxamide di-trifluoroacetate salt (Compound I-1)

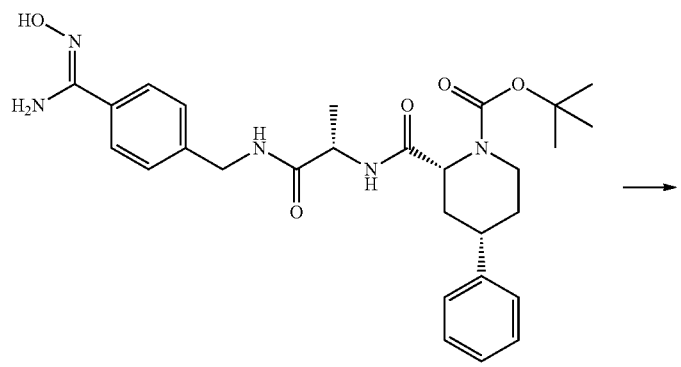

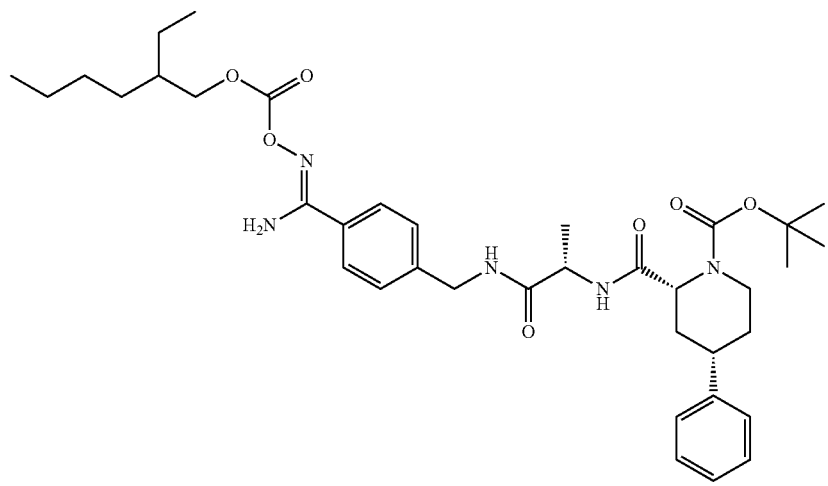

Step 1: To a stirred solution of tert-butyl (2R,4S)-2-(((S)-1-((4-((Z)—N'-hydroxycarbamimidoyl)benzyl)amino)-1-oxopropan-2-yl)carbamoyl)-4-phenylpiperidine-1-carboxylate (see, Example 8 Step 2) (28 mg, 0.053 mmol) in DCM (2.5 mL) was added DIEA (0.2 mL) followed by 2-ethylhexyl chloroformate (0.1 mL) and the resultant solution stirred at RT for 15 min. After the reaction was judged complete by LCMS, the reaction was quenched with MeOH and the solution concentrated to dryness. The residue was purified by chromatography (100% EtOAc eluting from the column) to give tert-butyl (2R,4S)-2-(((2S)-1-((4-((Z)—N'-((((2-ethylhexyl)oxy)carbonyl)oxy)carbamimidoyl)benzyl)amino)-1-oxopropan-2-yl)carbamoyl)-4-phenylpiperidine-1-carboxylate (20 mg, 56% yield) as a white solid.

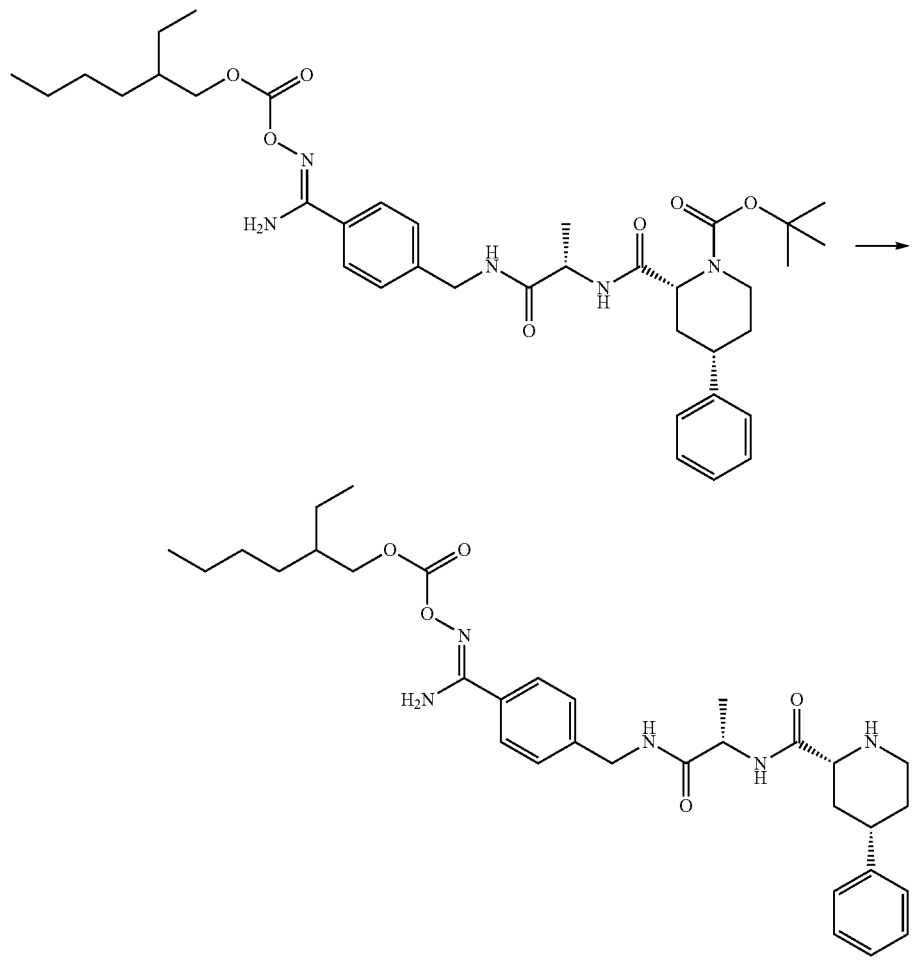

Step 2: To a stirred solution of tert-butyl (2R,4S)-2-(((2S)-1-((4-((Z)—N'-((((2-ethylhexyl)oxy)carbonyl)oxy)carbamimidoyl)benzyl)amino)-1-oxopropan-2-yl)carbamoyl)-4-phenylpiperidine-1-carboxylate (20 mg, 0.029 mmol) in DCM (2 mL) was added TFA (0.4 mL). The resultant solution was stirred at RT until judged complete by LCMS. The crude solution was concentrated and purified by reverse phase HPLC to yield (2R,4S)—N-((2S)-1-((4-((Z)—N'-((((2-ethylhexyl)oxy)carbonyl)oxy)carbamimidoyl)benzyl)amino)-1-oxopropan-2-yl)-4-phenylpiperidine-2-carboxamide di-trifluoroacetate salt (11 mg, 55% yield) as a white solid.

The following compounds were synthesized in a similar fashion using the appropriate chloroformate as described in Example 9, Step 1 followed by de-protection as described for Example 9, Step 2:

| Example No. | Compound Name | Yield (mass, %) |
|---|---|---|
| 10 | (2R,4S)-N-((S)-1-((4-((Z)-N'-(((2,2-difluoroethoxy)carbonyl)oxy)carbamimidoyl)benzyl)amino)-1-oxopropan-2-yl)-4-phenylpiperidine-2-carboxamide Di-Trifluoroacetate salt (Compound I-2) | 16 mg, 66% |
| 11 | (2R,4S)-N-((S)-1-((4-((Z)-N'-((isobutoxycarbonyl)oxy)carbamimidoyl)benzyl)amino)-1-oxopropan-2-yl)-4-phenylpiperidine-2-carboxamide Di-Trifluoroacetate salt (Compound I-3) | 23 mg, 87% yield |
| 12 | (2R,4S)-N-((S)-1-((4-((Z)-N'-(((neopentyloxy)carbonyl)oxy)carbamimidoyl)benzyl)amino)-1-oxopropan-2-yl)-4-phenylpiperidine-2-carboxamide Di-Trifluoroacetate salt (Compound I-4) | 15 mg, 42% yield |
| 13 | (2R,4S)-N-((S)-1-((4-((Z)-N'-(((benzyloxy)carbonyl)oxy)carbamimidoyl)benzyl)amino)-1-oxopropan-2-yl)-4-phenylpiperidine-2-carboxamide Di-Trifluoroacetate salt (Compound I-6) | 22 mg, 74% yield |

Example 14

Preparation of (2R,4S)—N—((S)-1-((4-((Z)—N'-((L-valyl)oxy)carbamimidoyl)benzyl)amino)-1-oxo-propan-2-yl)-4-phenylpiperidine-2-carboxamide dihydrochloride salt (Compound I-7)

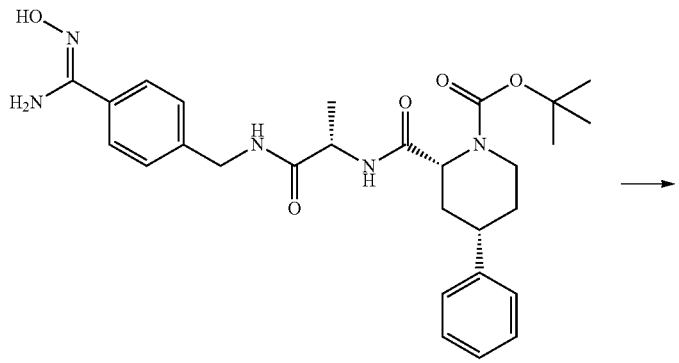

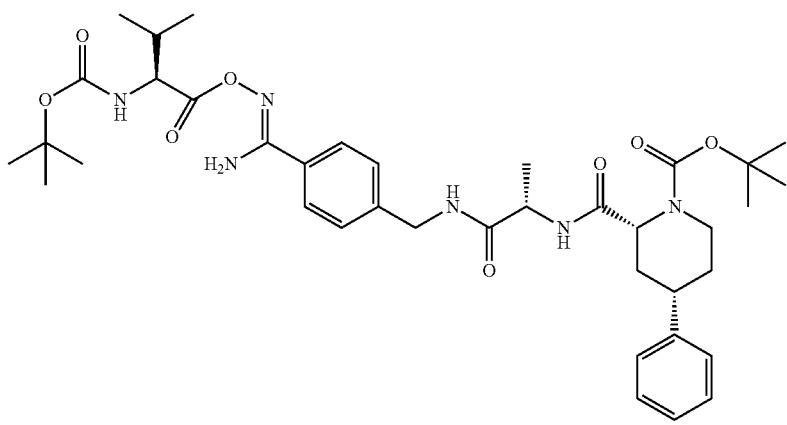

Step 1. Synthesis of tert-butyl (2R,4S)-2-(((S)-1-((4-((Z)—N'-(((tert-butoxycarbonyl)-L-valyl)oxy)carbamimidoyl)benzyl)amino)-1-oxopropan-2-yl)carbamoyl)-4-phenylpiperidine-1-carboxylate was obtained from using according to the procedure described in Example 1, Step 4.

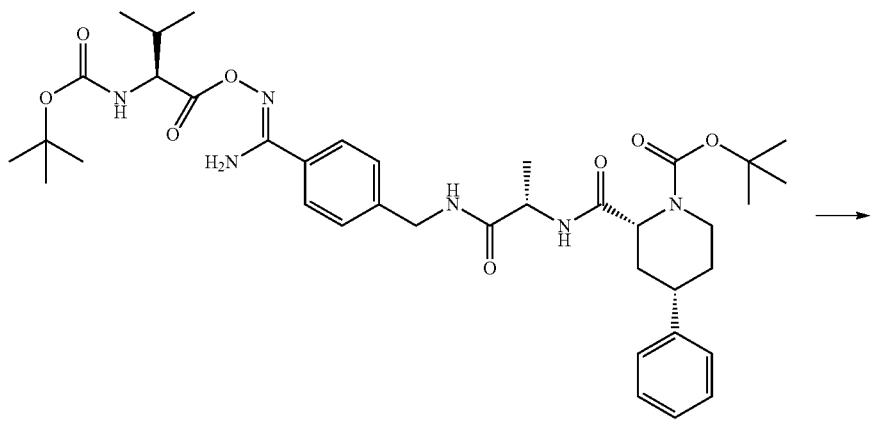

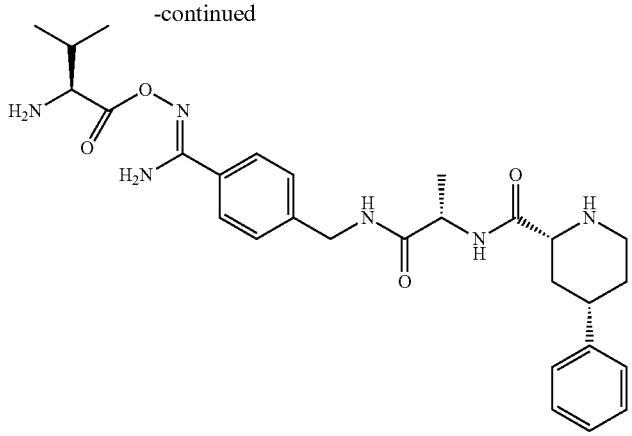

Step 2. (2R,4S)—N—((S)-1-((4-((Z)—N'-((L-valyl)oxy) carbamimidoyl)benzyl)amino)-1-oxopropan-2-yl)-4-phenylpiperidine-2-carboxamide dihydrochloride salt was obtained using a procedure analogous to that used in Example 8 Step 3 except the desired compound was obtained without additional purification by prep HPLC (5 mg, 58% yield) as a white solid.

Example 15

Preparation of (2R,4S)—N—((S)-1-oxo-1-((4-(5-oxo-4,5-dihydro-1,2,4-oxadiazol-3-yl)benzyl)amino)propan-2-yl)-4-phenylpiperidine-2-carboxamide trifluoroacetate salt (Compound I-5)

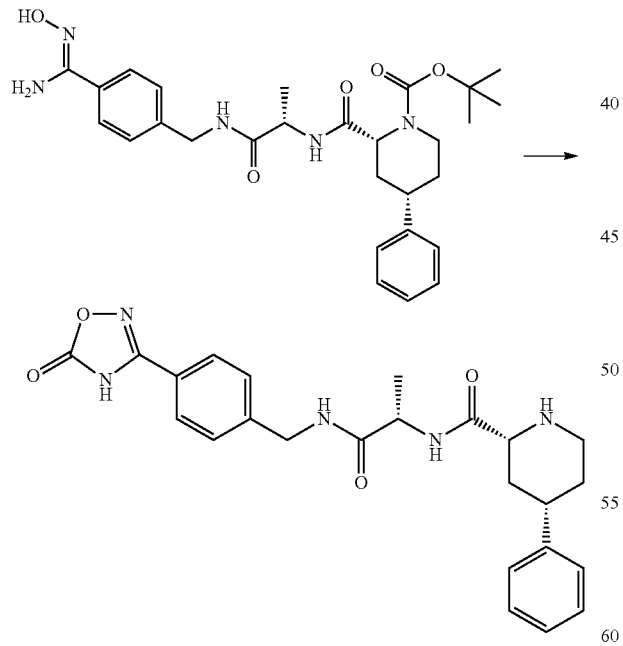

To a stirred solution of tert-butyl (2R,4S)-2-(((S)-1-((4-((Z)—N'-hydroxycarbamimidoyl)benzyl)amino)-1-oxopropan-2-yl)carbamoyl)-4-phenylpiperidine-1-carboxylate (Example 8 Step 2) (30 mg, 0.057) in dioxane (1 mL) was added CDI (46 mg, 0.29 mmol). The reaction mixture was stirred at 100° C. for 30 min. at which time it was judged complete by LCMS. The residue was passed through a plug of silica using EtOAc as eluent. After concentrating in vacuo, the isolated material was treated using the conditions described in Example 2 Step 4 to yield (10 mg, 31% yield over two steps) of the desired product (2R,4S)—N—((S)-1-oxo-1-((4-(5-oxo-4,5-dihydro-1,2,4-oxadiazol-3-yl)benzyl)amino)propan-2-yl)-4-phenylpiperidine-2-carboxamide trifluoroacetate salt.

Example 16

Preparation of (2R,4S)—N—((S)-1-oxo-1-((4-(5-thioxo-4,5-dihydro-1,2,4-oxadiazol-3-yl)benzyl)amino)propan-2-yl)-4-phenylpiperidine-2-carboxamide trifluoroacetate salt (Compound I-11)

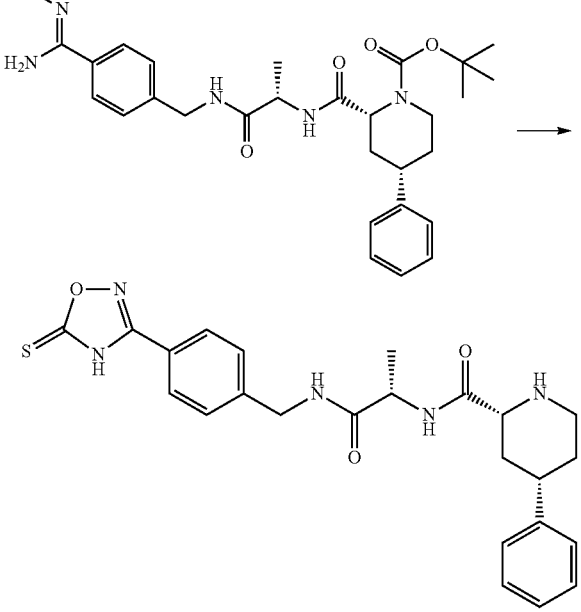

Synthesis of (2R,4S)—N—((S)-1-oxo-1-((4-(5-thioxo-4,5-dihydro-1,2,4-oxadiazol-3-yl)benzyl)amino)propan-2-yl)-4-phenylpiperidine-2-carboxamide trifluoroacetate salt was

Example 17

Preparation of (2R,4S)—N—((S)-1-oxo-1-((4-(5-(trifluoromethyl)-1,2,4-oxadiazol-3-yl)benzyl)amino)propan-2-yl)-4-phenylpiperidine-2-carboxamide trifluoroacetate salt (Compound I-30)

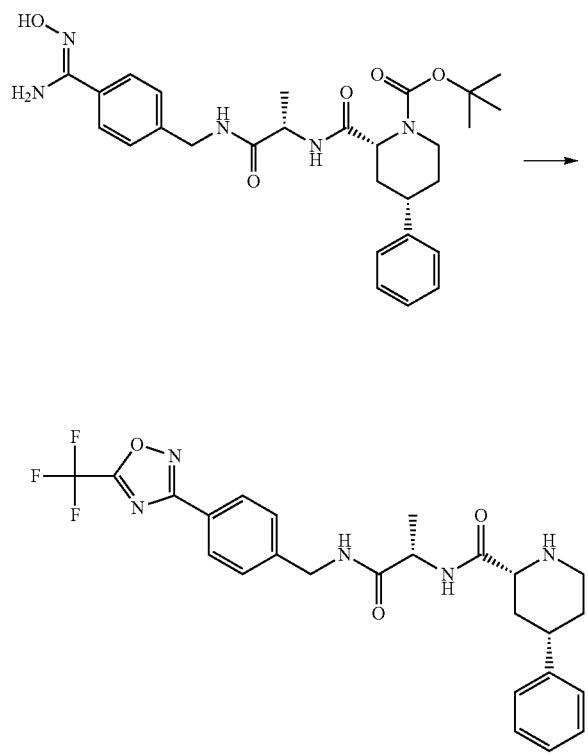

To a solution of tert-butyl (2R,4S)-2-(((S)-1-((4-((Z)-N'-hydroxycarbamimidoyl)benzyl)amino)-1-oxopropan-2-yl)carbamoyl)-4-phenylpiperidine-1-carboxylate (50 mg, 0.095) in anhydrous THE (5 mL), chilled to ice-bath temperature, was added trifluoroacetic anhydride (40 μL, 0.28 mmol). The reaction mixture was allowed to warm to RT over 2 h at which time it was judged complete by TLC. The reaction mixture was further diluted with DCM, washed with cold sat. NaHCO₃ solution, dried over Na₂SO₄ then concentrated in vacuo. The crude material was purified by flash chromatography (SiO₂) using a 0-100% Hep/EtOAc gradient to afford tert-butyl (2R,4S)-2-(((S)-1-oxo-1-((4-(5-(trifluoromethyl)-1,2,4-oxadiazol-3-yl)benzyl)amino)propan-2-yl)carbamoyl)-4-phenylpiperidine-1-carboxylate (34 mg, 60% yield). The isolated intermediate was de-protected using the conditions described in Example 2 Step 4 to give the title compound (19 mg, 55%)

Example 18

Preparation of (2R,4S)-1-ethyl-N—((S)-1-oxo-1-((4-(5-(trifluoromethyl)-1,2,4-oxadiazol-3-yl)benzyl)amino)propan-2-yl)-4-phenylpiperidine-2-carboxamide trifluoroacetate salt (Compound I-8)

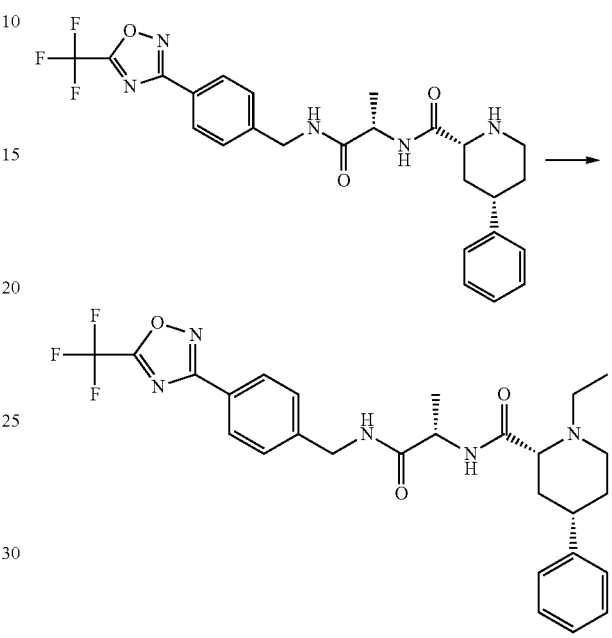

To a stirred solution of (2R,4S)—N—((S)-1-oxo-1-((4-(5-(trifluoromethyl)-1,2,4-oxadiazol-3-yl)benzyl)amino)propan-2-yl)-4-phenylpiperidine-2-carboxamide trifluoroacetate salt Example 17 (60 mg, 0.097 mmol) in DCM (2 mL) and NEt₃ (0.3 mL) was added ethyl bromide (0.3 ml) under an Ar atmosphere. After stirring for 18 h at RT, the reaction mixture was concentrated and purified using reverse phase HPLC to yield (2R,4S)-1-ethyl-N—((S)-1-oxo-1-((4-(5-(trifluoromethyl)-1,2,4-oxadiazol-3-yl)benzyl)amino)propan-2-yl)-4-phenylpiperidine-2-carboxamide trifluoroacetate (16 mg, 26% yield) as a white solid.

Example 19

Preparation of ethyl (2R,4S)-2-(((S)-1-oxo-1-((4-(5-(trifluoromethyl)-1,2,4-oxadiazol-3-yl)benzyl)amino)propan-2-yl)carbamoyl)-4-phenylpiperidine-1-carboxylate (Compound I-25)

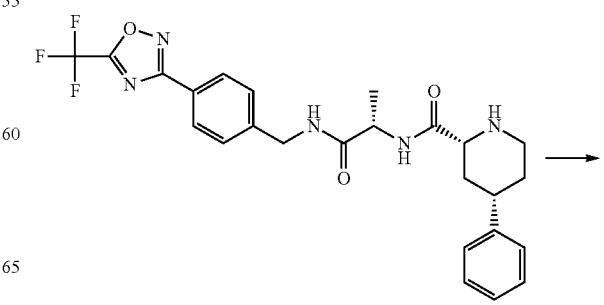

145

-continued

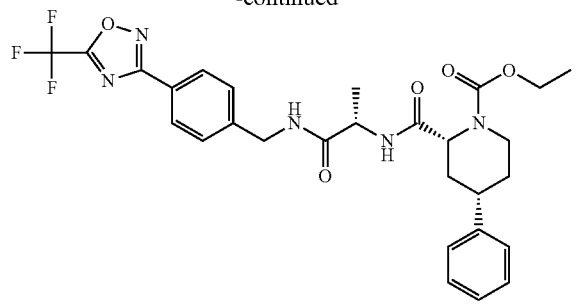

146

-continued

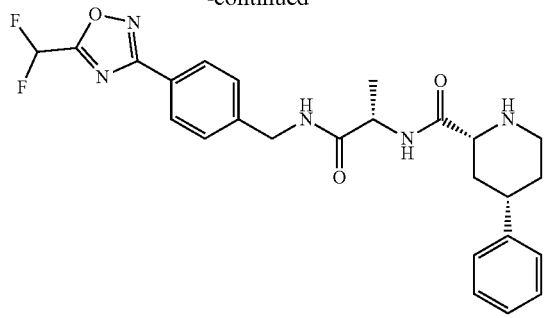

Desired product (11.1 mg, 69%) was obtained using the procedure described for the synthesis of Example 18 with ethyl chloroformate replacing ethyl bromide as the reactant.

The following compounds were synthesized as described in Example 18 in a similar fashion using the appropriate chloroformate The desired compound was obtained using the procedure described for the synthesis of Example 17 with 2,2-difluoroacetic anhydride replacing trifluoroacetic anhydride as the reactant (15 mg, 44% yield).

| Example No. | Compound Name | Yield (mass, %) |
| --- | --- | --- |
| 20 | neopentyl (2R,4S)-2-(((S)-1-oxo-1-((4-(5-(trifluoromethyl)-1,2,4-oxadiazol-3-yl)benzyl)amino)propan-2-yl)carbamoyl)-4-phenylpiperidine-1-carboxylate | 16.8 mg, 74% |
| 21 | 2,2-difluoroethyl (2R,4S)-2-(((S)-1-oxo-1-((4-(5-(trifluoromethyl)-1,2,4-oxadiazol-3-yl)benzyl)amino)propan-2-yl)carbamoyl)-4-phenylpiperidine-1-carboxylate | 13.9 mg, 60% |
| 22 | benzyl (2R,4S)-2-(((S)-1-oxo-1-((4-(5-(trifluoromethyl)-1,2,4-oxadiazol-3-yl)benzyl)amino)propan-2-yl)carbamoyl)-4-phenylpiperidine-1-carboxylate | 10.9 mg, 46% |
| 23 | isobutyl (2R,4S)-2-(((S)-1-oxo-1-((4-(5-(trifluoromethyl)-1,2,4-oxadiazol-3-yl)benzyl)amino)propan-2-yl)carbamoyl)-4-phenylpiperidine-1-carboxylate | 14 mg, 63% |

Example 24

Preparation of (2R,4S)—N—((S)-1-((4-(5-(difluoromethyl)-1,2,4-oxadiazol-3-yl)benzyl)amino)-1-oxopropan-2-yl)-1-ethyl-4-phenylpiperidine-2-carboxamide trifluoroacetate salt (Compound I-9)

Example 25

Preparation of benzyl ((4-(((S)-2-((2R,4S)-1-ethyl-4-phenylpiperidine-2-carboxamido)propanamido)methyl)phenyl)(imino)methyl)carbamate (Compound I-20)

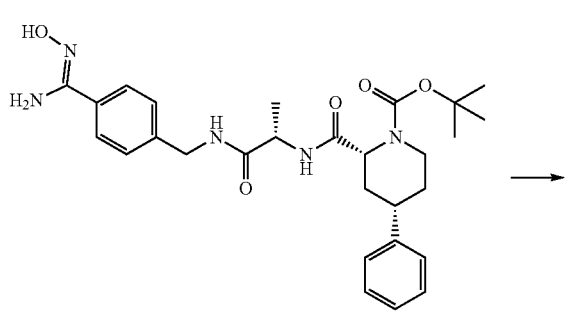

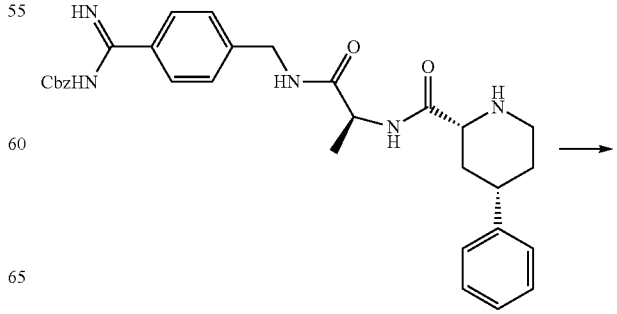

147

-continued

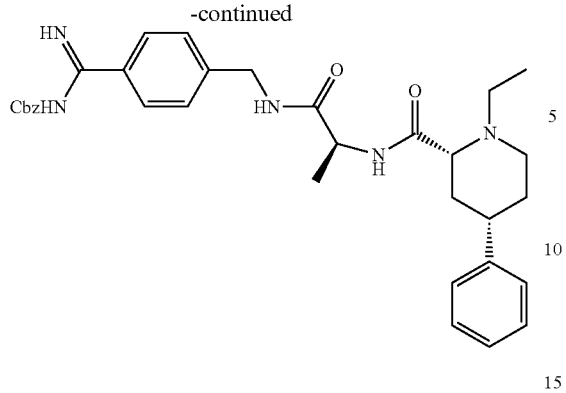

The desired compound was obtained using the procedure described for the synthesis of Example 3 replacing bromoester with ethyl bromide as reactant. (62 mg, 98% yield)

Example 26

Preparation of (2R,4S)—N—((S)-1-((4-carbamimidoylbenzyl)amino)-1-OXOPROPAN-2-yl)-1-ethyl-4-phenylpiperidine-2-carboxamide (Compound I-21)

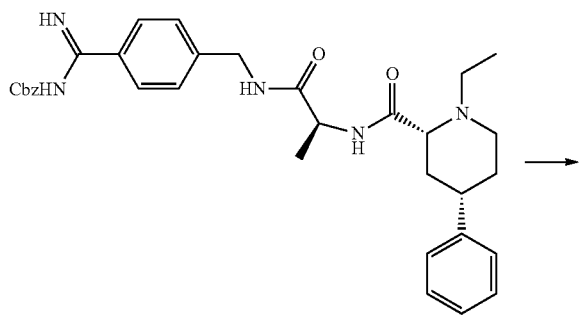

A solution consisting of (2R,4S)—N—((S)-1-((4-carbamimidoylbenzyl)amino)-1 oxopropan-2-yl)-1-ethyl-4-phenylpiperidine-2-carboxamide (31 mg, 0.05 mmol) and 10% Pd/C (15 mg, 50 wt %) in anhydrous MeOH (550 μL, 0.1M) was stirred under an atmosphere of H$_2$ for approximately 30 mins at which time it was judged complete by LCMS. The reaction mixture was filtered thru Celite®, washed with MeOH and the filtrate concentrated in vacuo to afford di-tert-butyl (2R,4R)-4-(4-fluorophenyl)-6-oxopiperidine-1,2-dicarboxylate (12.2 mg, 51% yield) as a white solid powder following lyophilization.

148

Example 27

Preparation of (2R,4S)-4-(3-(1H-pyrazol-1-yl)phenyl)-N—((S)-1-((5-chloro-2-(1H-tetrazol-1-yl)benzyl)amino)-1-oxopropan-2-yl)-1-ethylpiperidine-2-carboxamide (Compound I-22)

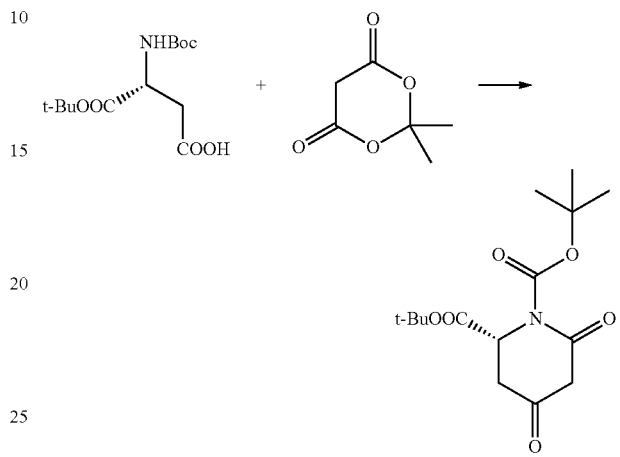

Step 1: To a solution of N-Boc-D-aspartic acid 1-(tert-butyl) ester (10 g, 35 mmol) and Meldrum's acid (5 g, 35 mmol) in anhydrous DCM (140 mL, 0.25M) at 0° C., was added DMAP (6.3 g, 52 mmol) followed by EDC (10 g, 52 mmol). The reaction temperature was maintained at 0° C. for 1 h, then warmed to RT. Upon completion as judged by TLC, the reaction mixture was washed with 1N KHSO$_4$, dried over sodium sulfate, concentrated and rigorously dried in vacuo. The crude mixture was then dissolved in anhydrous toluene (350 mL, 0.1M) and heated to reflux. Upon completion of reaction (monitored by TLC), the reaction mixture was concentrated in vacuo to afford di-tert-butyl (R)-4,6-dioxopiperidine-1,2-dicarboxylate as a pale yellow solid (10.34 g, 95 yield).

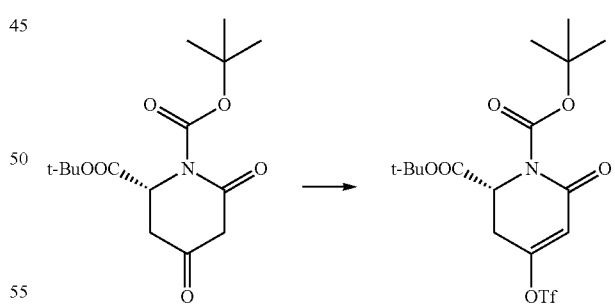

Step 2: To a solution of di-tert-butyl (R)-4,6-dioxopiperidine-1,2-dicarboxylate (10.34 g, 33 mmol) in anhydrous DCM (110 mL) at 0° C., was added N-phenyl-bis(trifluoromethanesulfonimide) (14 g, 40 mmol) followed by DIEA (12 mL, 66 mmol). After stirring at 0° C. for two h, the reaction mixture was concentrated and purified on a silica column using a 5-20% EtOAc/Heptane gradient to afford di-tert-butyl (R)-6-oxo-4-(((trifluoromethyl)sulfonyl)oxy)-3,6-dihydropyridine-1,2(2H)-dicarboxylate as a white solid (11.5 g, 78% yield).

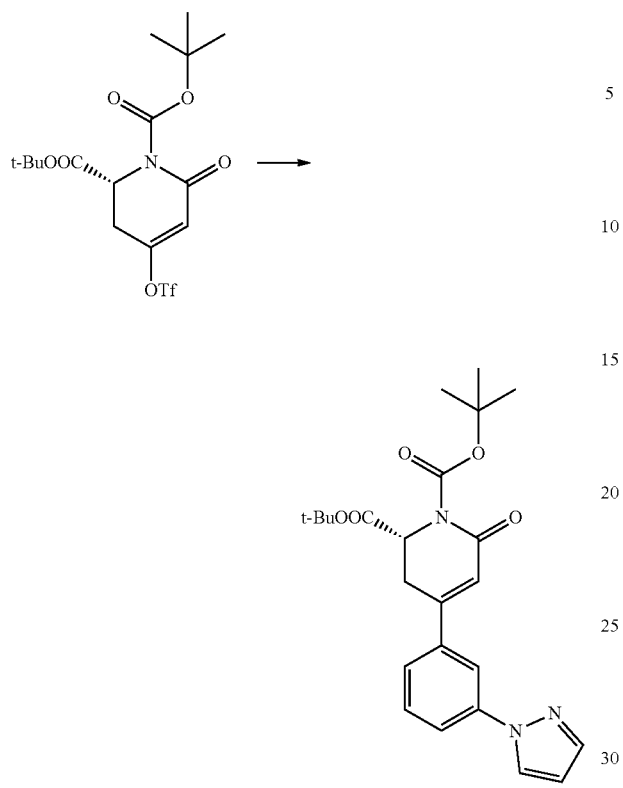

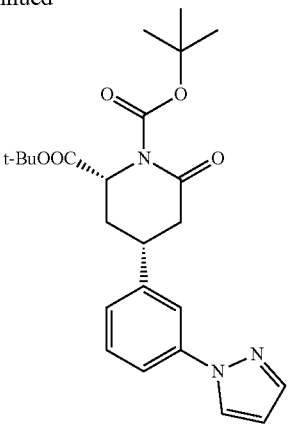

Step 4: A solution consisting of di-tert-butyl (R)-4-(3-(1H-pyrazol-1-yl)phenyl)-6-oxo-3,6-dihydropyridine-1,2(2H)-dicarboxylate (0.67 mmol) and 10% Pd/C (60 mg, 20 wt %) in EtOAc (3.5 mL) and MeOH (1 mL) was stirred overnight at 40° C. under an atmosphere of H₂.

The reaction mixture was filtered through a bed of Celite®, washed thoroughly with MeOH then concentrated in vacuo to afford di-tert-butyl (2R,4R)-4-(3-(1H-pyrazol-1-yl)phenyl)-6-oxopiperidine-1,2-dicarboxylate (245 mg, 82% yield) as a white solid.

Step 3: To a solution of di-tert-butyl (R)-6-oxo-4-(((trifluoromethyl)sulfonyl)oxy)-3,6-dihydropyridine-1,2(2H)-dicarboxylate (300 mg, 0.67 mmol), (3-(1H-pyrazol-1-yl)phenyl)boronic acid (270 mg, 1 mmol) and bis(triphenylphosphine)palladium(II) chloride (24 mg, 0.03 mmol) in THF (17 mL) was added potassium carbonate solution (2N aqueous, 10 mL). The solution was sparged with argon for 10 minutes, then heated to 40° C. Upon completion the reaction mixture was cooled to RT, diluted with EtOAc and partitioned. The organic solvent was dried over sodium sulfate, concentrated and purified on a silica column using a 20-100% EtOAc/Heptane gradient to afford di-tert-butyl (R)-4-(3-(1H-pyrazol-1-yl)phenyl)-6-oxo-3,6-dihydropyridine-1,2(2H)-dicarboxylate as a white solid which was carried forward without further purification.

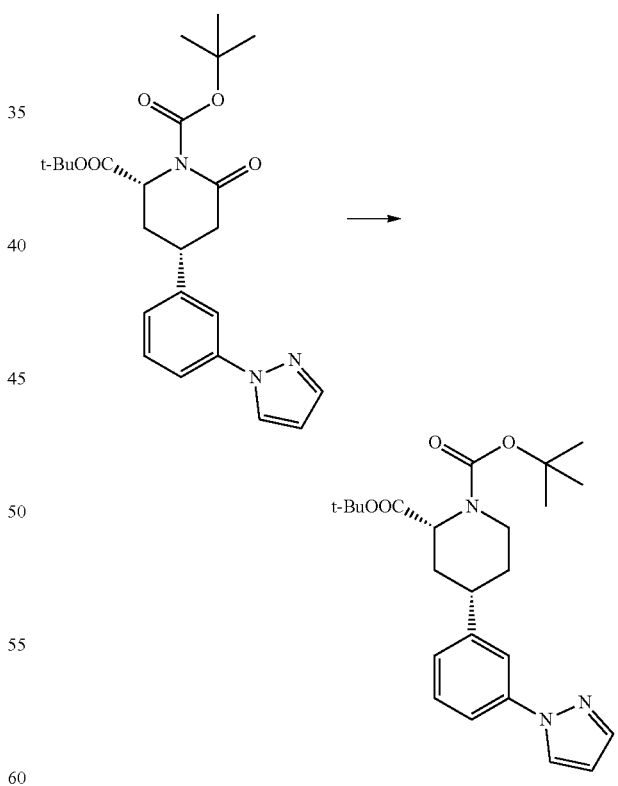

Step 5: To a solution of di-tert-butyl (2R,4R)-4-(4-fluorophenyl)-6-oxopiperidine-1,2-dicarboxylate (245 mg, 0.55 mmol) in anhydrous THF (3.4 mL) at 0° C. was added, dropwise, a solution of borane-dimethylsulfide in THF (2M, 1.4 mL, 2.8 mmol). The reaction mixture was left to warm to RT overnight before cooling to 0° C. After quenching the reaction mixture by addition of MeOH (1 mL) and stirring for 10 minutes, the reaction mixture was concentrated and the crude material purified on a silica column using a 0-40% EtOAc/Heptane gradient to afford di-tert-butyl (2R,4S)-4-(3-(1H-pyrazol-1-yl)phenyl)piperidine-1,2-dicarboxylate (196 mg, 83% yield over two steps) as a white solid

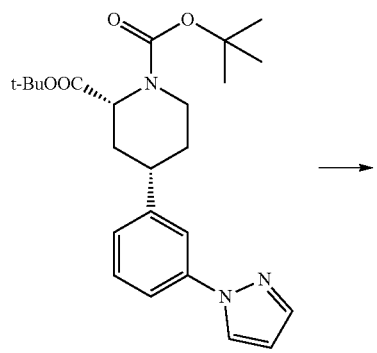

Step 6: To di-tert-butyl (2R,4S)-4-(3-(1H-pyrazol-1-yl)phenyl)piperidine-1,2-dicarboxylate (196 mg, 0.46 mmol) was added a solution of 4M HCl in dioxane (2.3 mL). The reaction mixture was stirred until the reaction was judged complete by LCMS. Upon completion, the reaction mixture was concentrated and the crude material dissolved in a solution of THF (920 µL) and aqueous 1N sodium hydroxide (1.8 mL). After adding Boc anhydride (105 mg, 0.48 mmol) the reaction mixture was left to stir overnight. The reaction mixture was acidified with 1M potassium bisulfate, extracted three times with EtOAc and the organic layer concentrated in vacuo to afford (2R,4S)-4-(3-(1H-pyrazol-1-yl)phenyl)-1-(tert-butoxycarbonyl)piperidine-2-carboxylic acid (168 mg, 98% yield over two steps) as a white solid.

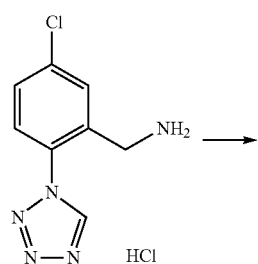

-continued

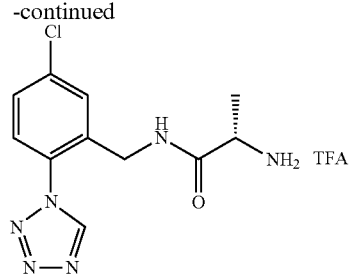

Step 7: tert-Butyl (S)-(1-((5-chloro-2-(1H-tetrazol-1-yl)benzyl)amino)-1-oxopropan-2-yl)carbamate trifluoroacetate was synthesized using the procedures described in Example 2 Steps 1 and 4 (3.54 g, 76% yield over two steps).

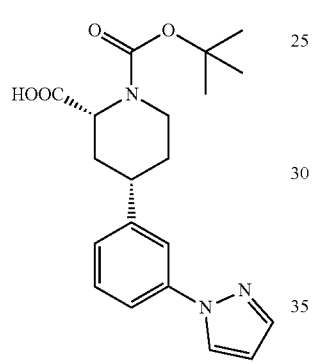

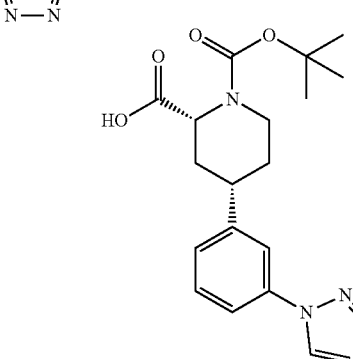

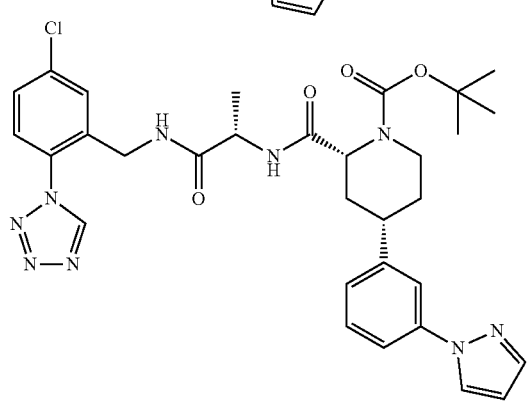

Step 8: To a solution of (2R,4S)-4-(3-(1H-pyrazol-1-yl)phenyl)-1-(tert-butoxycarbonyl)piperidine-2-carboxylic acid (45 mg, 0.12 mmol) and tert-Butyl (S)-(1-((5-chloro-2-(1H-tetrazol-1-yl)benzyl)amino)-1-oxopropan-2-yl)carbamate trifluoroacetate (42 mg, 0.15 mmol) in anhydrous DMF (2.4 mL) were added DIEA (85 µL, 0.5 mmol), HOBT (20 mg, 0.15 mmol) and EDC (28 mg, 0.15 mmol). After stirring overnight at RT, the reaction mixture was diluted with EtOAc then washed with saturated ammonium chloride, followed by saturated sodium bicarbonate, water (2 times), then brine. The organic layer was concentrated in vacuo and the isolated crude purified on a silica column using a 0-30% EtOAc/Heptane gradient to afford tert-butyl (2R,4S)-4-(3-(1H-pyrazol-1-yl)phenyl)-2-(((S)-1-((5-chloro-2-(1H-tetrazol-1-yl)benzyl)amino)-1-oxopropan-2-yl)carbamoyl)piperidine-1-carboxylate (54 mg, 71% yield).

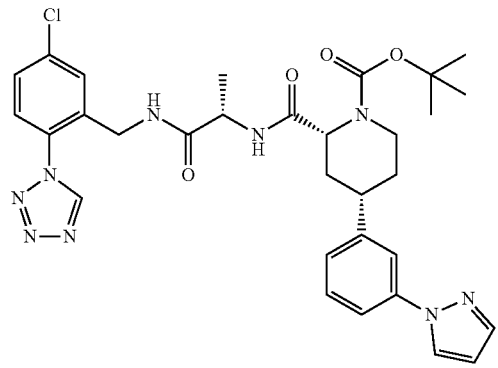

Step 9: To a solution of tert-butyl (2R,4S)-4-(3-(1H-pyrazol-1-yl)phenyl)-2-(((S)-1-((5-chloro-2-(1H-tetrazol-1-yl)benzyl)amino)-1-oxopropan-2-yl)carbamoyl)piperidine-1-carboxylate (54 mg, 0.08 mmol) in anhydrous MeOH (130 µL) was added a solution of 6M HCl in isopropanol (300 µL, 1.7 mmol). The reaction mixture was stirred at RT until judged complete by LCMS before being concentrated to dryness and carried forward without further purification.

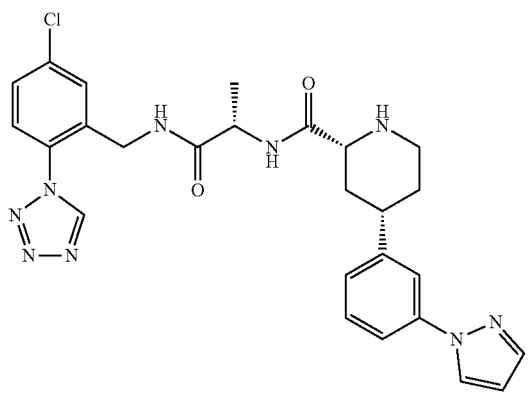

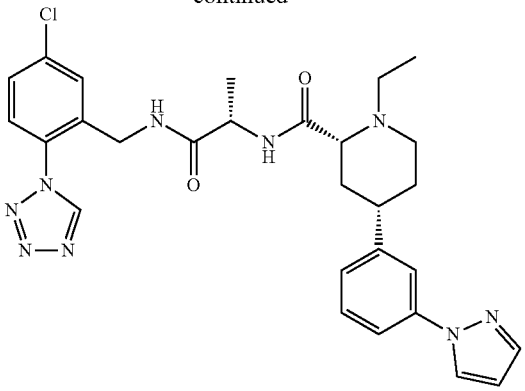

Step 10: (2R,4S)-4-(3-(1H-pyrazol-1-yl)phenyl)-N-((S)-1-((5-chloro-2-(1H-tetrazol-1-yl)benzyl)amino)-1-oxopropan-2-yl)-1-ethylpiperidine-2-carboxamide was obtained using the procedure described for the synthesis of Example 3 (10 mg, 63% yield).

Example 28

Preparation of (S)-1-((2R,4R)-4-([1,1'-biphenyl]-3-yl)pyrrolidine-2-carbonyl)-N-((6-amino-2-methylpyridin-3-yl)methyl)azetidine-2-carboxamide di-trifluoroacetate salt (Compound 1-16)

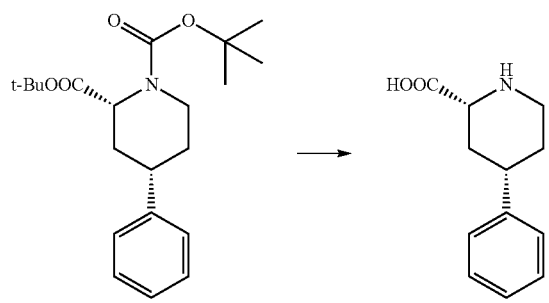

Step 1: (2R,4S)-4-phenylpiperidine-2-carboxylic acid was synthesized according to the procedures described for Example 27 Steps 1-5 with the global deprotection using HCl/IPA instead of dioxane.

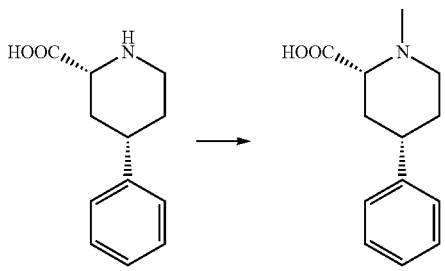 [SMILES: O=C(O)[C@H]1C[C@@H](c2ccccc2)CCN1 ; CN1CC[C@H](c2ccccc2)C[C@@H]1C(=O)O]

Step 2: A solution consisting of (2R,4S)-4-phenylpiperidine-2-carboxylic acid hydrochloride (100 mg, 0.4 mmol, 1 eq.), 10% Pd/C (10 mg, 10 wt %) and formaldehyde (530 µL, 0.78 M) in MeOH (530 µL, 0.78 M) was left over a bed

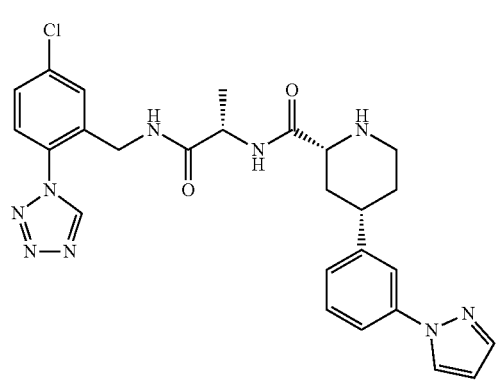

of hydrogen for 16 h, at which point more formaldehyde (265 µL, 1.5 M) was added and reaction mixture was stirred for an additional 7 h.

The reaction mixture was filtered thru a bed of Celite and washed thoroughly with MeOH. The filtrate was then concentrated, redissolved in MeOH, refiltered through a 0.45 micron filter and concentrated in vacuo to afford (2R,4S)-1-methyl-4-phenylpiperidine-2-carboxylic acid hydrochloride (65 mg, 63% yield) as a white solid powder following lyophilization, which was carried forward without further purification.

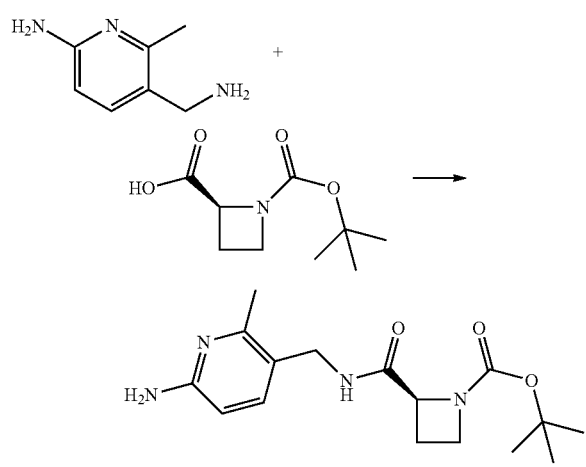

Step 3: tert-butyl (S)-2-(((6-amino-2-methylpyridin-3-yl)methyl)carbamoyl)azetidine-1-carboxylate was synthesized using the conditions described in Example 1 Step 4. (1.29 g, 100%)

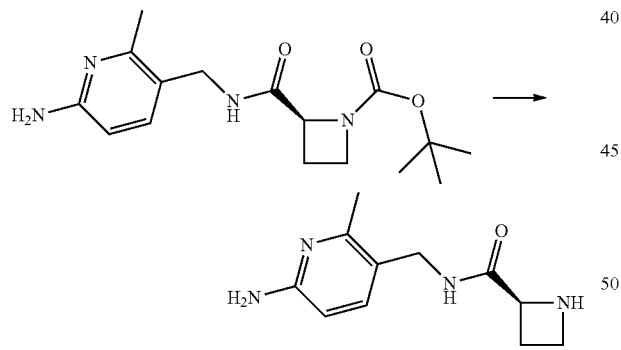

Step 4: (S)—N-((6-amino-2-methylpyridin-3-yl)methyl)azetidine-2-carboxamide hydrochloride was synthesized using the conditions described in Example 8 Step 3 and used without further purification.

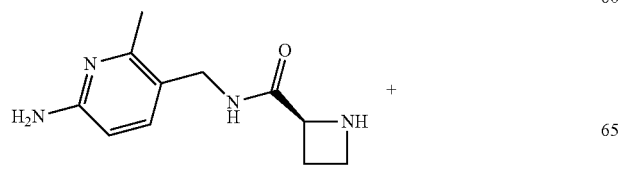

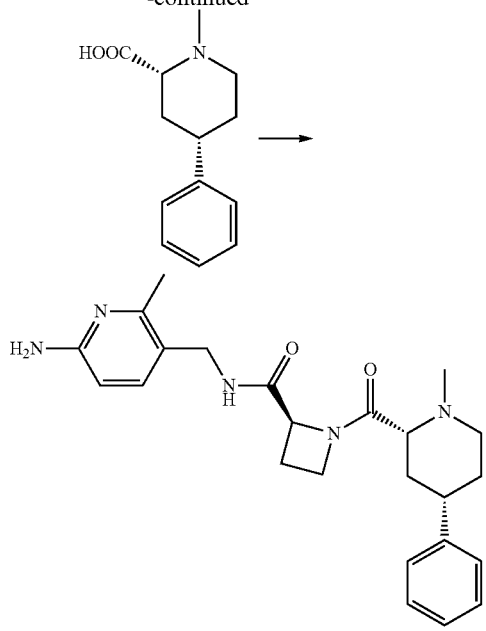

Step 5: To (S)—N-((6-amino-2-methylpyridin-3-yl)methyl)azetidine-2-carboxamide hydrochloride (90 mg, 0.3 mmol, 1.5 eq.), (2R,4S)-1-methyl-4-phenylpiperidine-2-carboxylic acid hydrochloride (0.2 mmol, 1 eq.), DIEA (180 µL, 1 mmol) in DMF (670 µL) was added HATU (114 mg, 0.3 mmol) with stirring at RT while monitoring for the consumption of starting material (16 h). The solution was diluted with EtOAc then washed with sat'd NH₄Cl. After partitioning, the aqueous portion was extracted with EtOAc (2X) and the combined organics washed with H₂O, brine, then dried over Na₂SO₄ and evaporated to dryness. The resulting residue was purified on an amine column using EtOAc followed by MeOH/DCM then further purified by reverse phase HPLC to afford (S)—N-((6-amino-2-methylpyridin-3-yl)methyl)-1-((2R,4S)-1-methyl-4-phenylpiperidine-2-carbonyl)azetidine-2-carboxamide di-trifluoroacetate (9.3 mg, 7% yield) as an off-white film.

Example 29

Preparation of benzyl (imino(4-(((S)-1-((2R,4S)-1-methyl-4-phenylpiperidine-2-carbonyl)azetidine-2-carboxamido)methyl)phenyl)methyl)carbamate (Compound I-18)

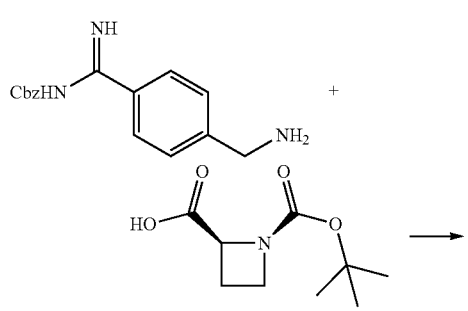

-continued

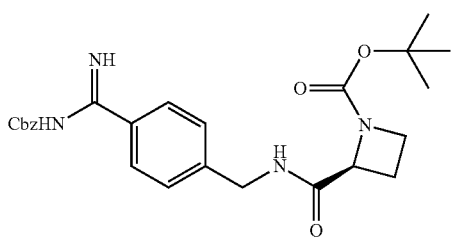

Step 1: tert-butyl (S)-2-((4-(N-((benzyloxy)carbonyl)carbamimidoyl)benzyl)carbamoyl)azetidine-1-carboxylate was synthesized using the procedure described in Example 1 Step 4. (210 mg, 35%)

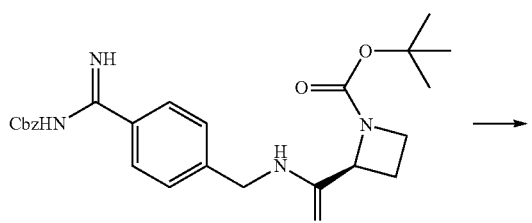

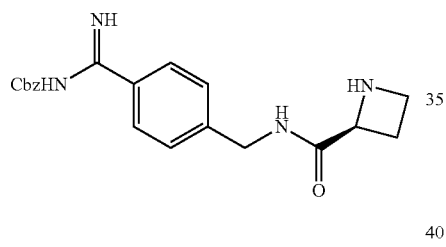

Step 2. benzyl (S)-((4-((azetidine-2-carboxamido)methyl)phenyl)(imino)methyl)carbamate hydrochloride was synthesized using the procedure described in Example 8 Step 3 except the solvent used was dioxane. The isolated material was used without further purification.

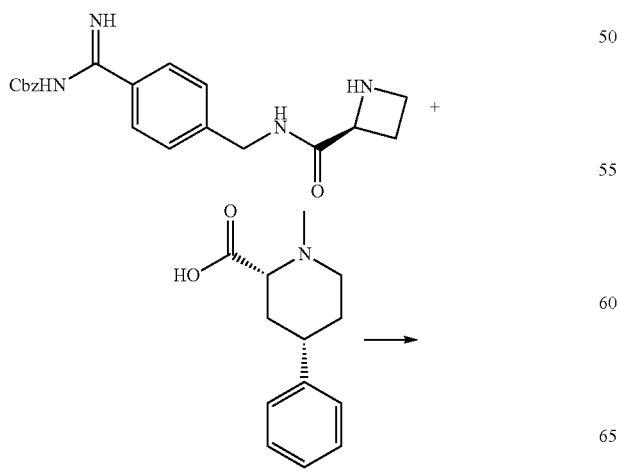

-continued

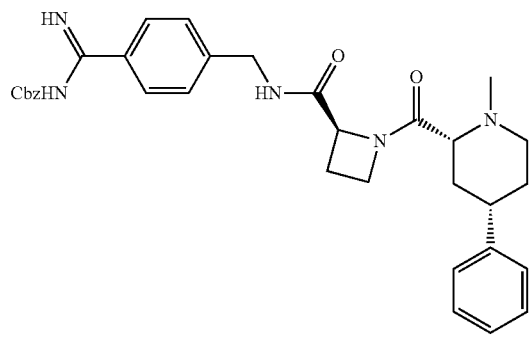

Step 3: benzyl (imino(4-(((S)-1-((2R,4S)-1-methyl-4-phenylpiperidine-2-carbonyl)azetidine-2-carboxamido)methyl)phenyl)methyl)carbamate was synthesized using the procedure described in Example 27 Step 5. 1st batch isolated as free base (43 mg), remaining material purified by reverse phase HPLC (30 mg; 47% combined yield).

Example 30

Preparation of (S)—N-(4-carbamimidoylbenzyl)-1-((2R,4S)-1-methyl-4-phenylpiperidine-2-carbonyl)azetidine-2-carboxamide di-trifluoroacetate SALT (Compound I-17)

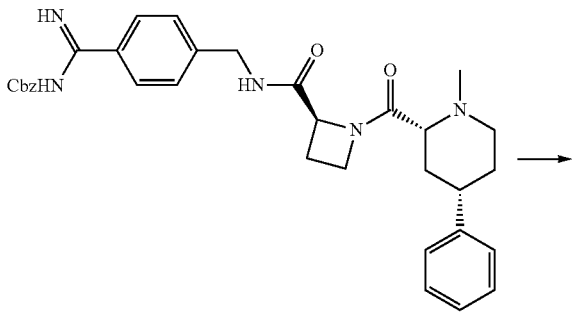

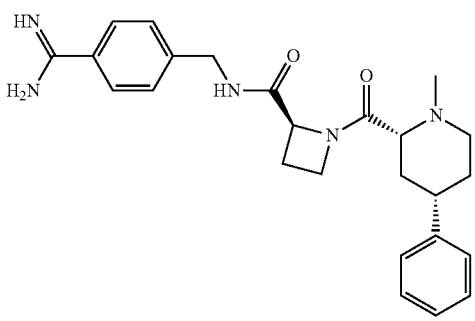

The desired compound was synthesized using the procedure described or Example 27. The final product was purified by reverse phase HPLC (10.5 mg, 20%).

Example 31

Preparation of benzyl (imino(4-(((S)-1-((2R,4S)-4-phenylpiperidine-2-carbonyl)azetidine-2-carboxamido)methyl)phenyl)methyl)carbamate di-trifluoroacetate salt (Compound I-19)

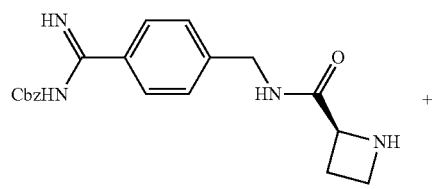

+

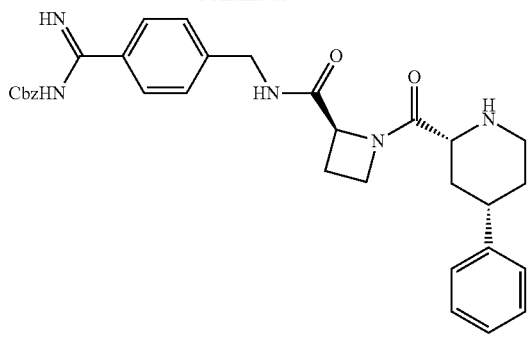

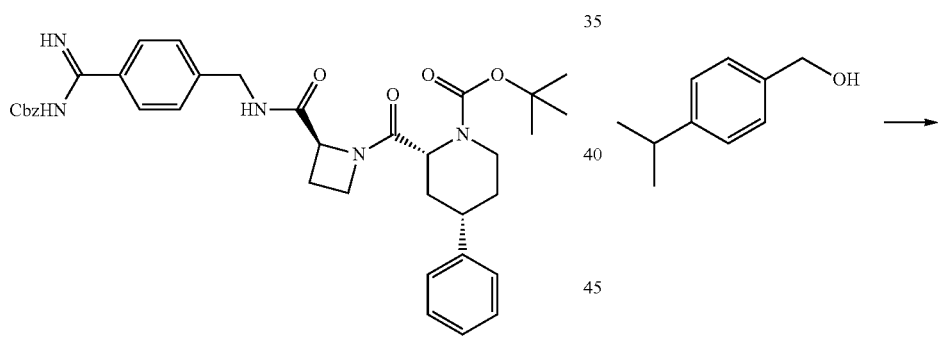

Step 1: tert-butyl (2R,4S)-2-((S)-2-((4-(N-((benzyloxy)carbonyl)carbamimidoyl)benzyl) carbamoyl)azetidine-1-carbonyl)-4-phenylpiperidine-1-carboxylate was obtained using the procedure described in Example 28 Step 5 (100 mg, 47% yield).

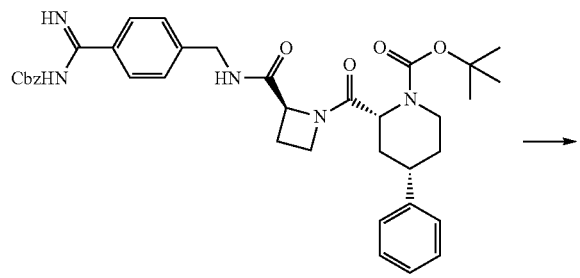

Step 2: benzyl (imino(4-(((S)-1-((2R,4S)-4-phenylpiperidine-2-carbonyl)azetidine-2-carboxamido)methyl)phenyl)methyl)carbamate was synthesized using the procedure described for Example 2 Step 4. The final product was purified by reverse phase HPLC (50.1 mg, 40% yield)

Example 32

Preparation of 4-isopropylbenzyl (imino(4-(((S)-2-((2R,4S)-4-phenylpiperidine-2-carboxamido)propanamido)methyl)phenyl)methyl)carbamate hydrochloride (Compound I-23)

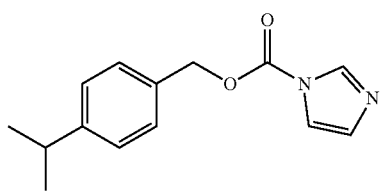

Step 1: To a stirred solution of (4-isopropylphenyl)methanol (100 mg, 0.67 mmol) and DIEA (128 μL, 0.74 mmol) in DCM (5 mL) was added CDI (220 mg, 1.34 mmol) and the reaction was stirred at RT overnight. The reaction was diluted with DCM (50 mL) and washed with water (50 mL) and saturated aqueous NH$_4$Cl (50 mL). The organic portion was dried (MgSO$_4$), filtered and concentrated to afford 4-isopropylbenzyl 1H-imidazole-1-carboxylate (160 mg) as a clear oil. Used as is with no further purification.

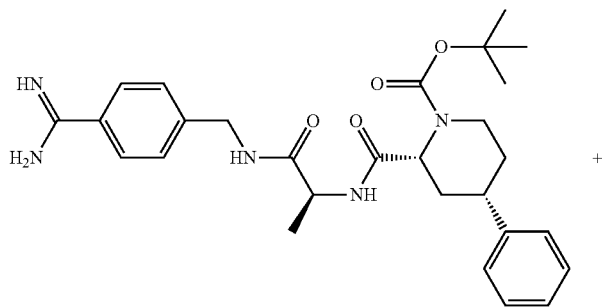

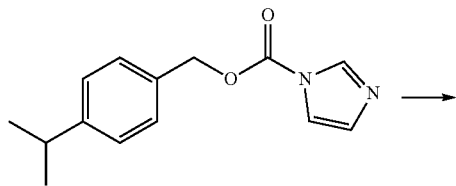

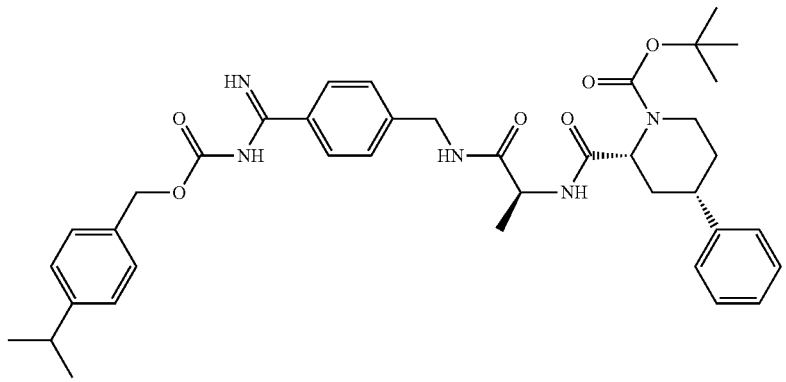

Step 2: To a stirred solution of tert-butyl (2R,4S)-2-(((S)-1-((4-carbamimidoylbenzyl)amino)-1-oxopropan-2-yl)carbamoyl)-4-phenylpiperidine-1-carboxylate (25 mg, 0.049 mmol) and DIEA (17 µL, 0.098 mmol) in DMF (1.0 mL) was added 4-isopropylbenzyl 1H-imidazole-1-carboxylate (24 mg, 0.098 mmol) and the reaction was stirred at RT overnight. The reaction was diluted with ethyl acetate (40 mL) and washed with water (4×20 mL) and brine (20 mL). Organics were dried (Na₂SO₄), filtered and concentrated crude was purified via flash chromatography using an eluent of 0-100% ethyl acetate in heptane to afford tert-butyl (2R,4S)-2-(((S)-1-((4-(N-(((4-isopropylbenzyl)oxy)carbonyl)carbamimidoyl)benzyl)amino)-1-oxopropan-2-yl)carbamoyl)-4-phenylpiperidine-1-carboxylate (34 mg, 100% yield) as a white solid.

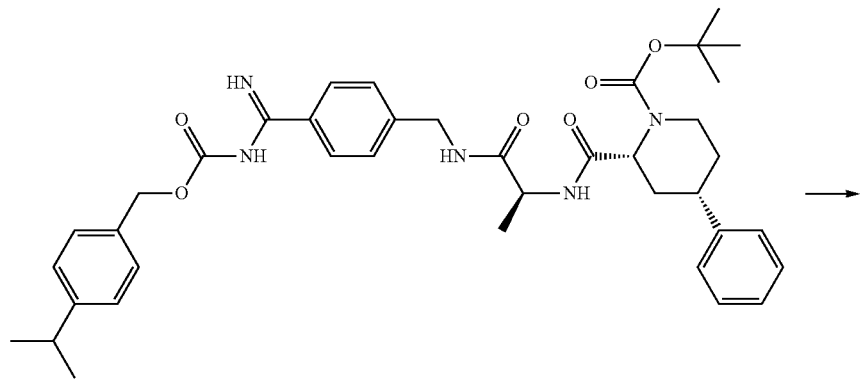

-continued

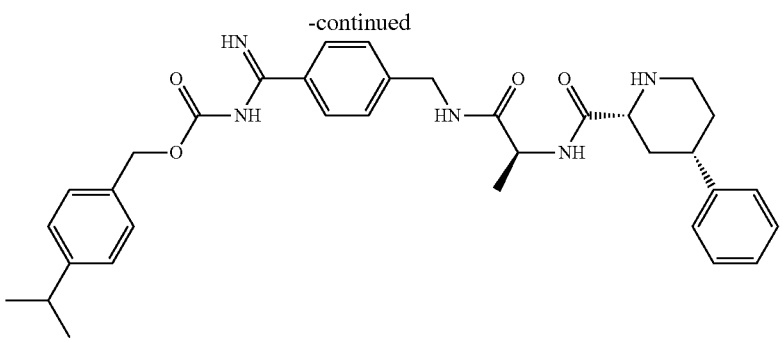

Step 3: A solution of 4-isopropylbenzyl (imino(4-(((S)-2-((2R,4S)-4-phenylpiperidine-2-carboxamido)propanamido)methyl)phenyl)methyl)carbamate (34 mg, 0.047 mmol) in 6M HCl in isopropanol was stirred for 2 h at RT. The reaction was concentrated in vacuo to afford a 4-isopropylbenzyl (imino(4-(((S)-2-((2R,4S)-4-phenylpiperidine-2-carboxamido)propanamido)methyl)phenyl)methyl)carbamate hydrochloride salt (27 mg, 98% yield) as a white solid.

The following compounds were synthesized in a similar fashion as described in Example 32 using the appropriate acylimidazolide. Prep HPLC was used to obtain the final products:

| Example No. | Compound Name | Yield (mass, %) |
|---|---|---|
| 33 | 5-chloro-2-fluorobenzyl (imino(4-(((S)-2-((2R,4S)-4-phenylpiperidine-2-carboxamido)propanamido)methyl)phenyl)methyl)carbamate Di-Trifluoroacetate salt (Compound I-33) | 37.5 mg, 34% |
| 34 | 2,3,4-trifluorobenzyl (imino(4-(((S)-2-((2R,4S)-4-phenylpiperidine-2-carboxamido)propanamido)methyl)phenyl)methyl)carbamate Di-Trifluoroacetate salt (Compound I-34) | 28.5 mg, 42% |
| 35 | 4-chloro-3-fluorobenzyl (imino(4-(((S)-2-((2R,4S)-4-phenylpiperidine-2-carboxamido)propanamido)methyl)phenyl)methyl)carbamate Di-Trifluoroacetate salt (Compound I-35) | 34.5 mg, 32% |
| 36 | 3-methoxybenzyl (imino(4-(((S)-2-((2R,4S)-4-phenylpiperidine-2-carboxamido)propanamido)methyl)phenyl)methyl)carbamate Di-Trifluoroacetate salt (Compound I-36) | 51 mg, 31% |

Table 1 lists compounds of the Examples described above, as well as additional compounds that may be prepared according to methods analogous to those described for the compounds above and other methods known to a person having skill in the art. In some embodiments, the compound is a compound selected from Table 1, or a stereoisomer, tautomer, or pharmaceutically acceptable salt thereof.

TABLE 1

Exemplary compounds of Structure (I)

| Cmp No. | Structure | Salt | Exact Observed Mass (ES+; M + H) | Exact Calc. Mass |
|---|---|---|---|---|
| I-1 | 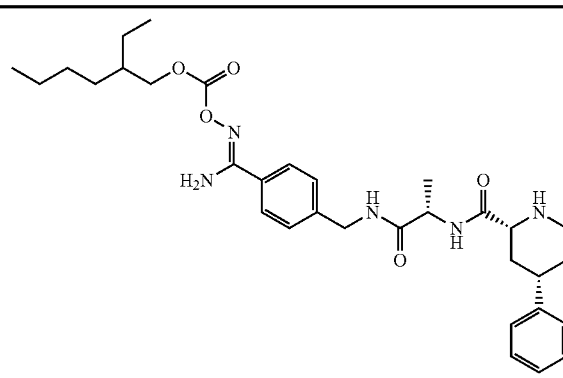 | 2TFA | 580.35 | 579.34 |

TABLE 1-continued

Exemplary compounds of Structure (I)

| Cmp No. | Structure | Salt | Exact Observed Mass (ES+; M + H) | Exact Calc. Mass |
|---|---|---|---|---|
| I-2 | 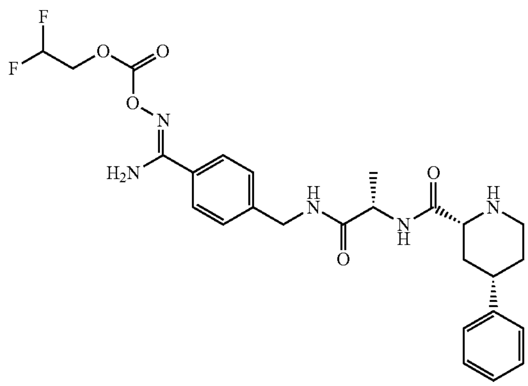 [SMILES: C[C@H](NC(=O)[C@H]1C[C@@H](c2ccccc2)CCN1)C(=O)NCc1ccc(/C(N)=N/OC(=O)OCC(F)F)cc1] | 2TFA | 532.18 | 531.23 |
| I-3 | 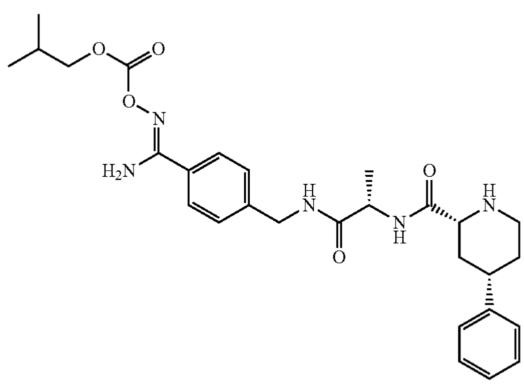 [SMILES: CC(C)COC(=O)O/N=C(\N)c1ccc(CNC(=O)[C@H](C)NC(=O)[C@H]2C[C@@H](c3ccccc3)CCN2)cc1] | 2TFA | 524.24 | 523.28 |
| I-4 | 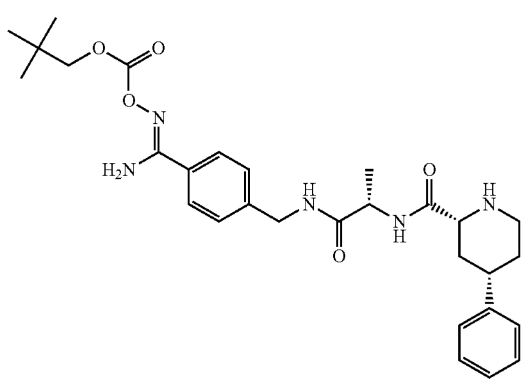 [SMILES: C[C@H](NC(=O)[C@H]1C[C@@H](c2ccccc2)CCN1)C(=O)NCc1ccc(/C(N)=N/OC(=O)OCC(C)(C)C)cc1] | 2TFA | 538.28 | 537.30 |
| I-5 | 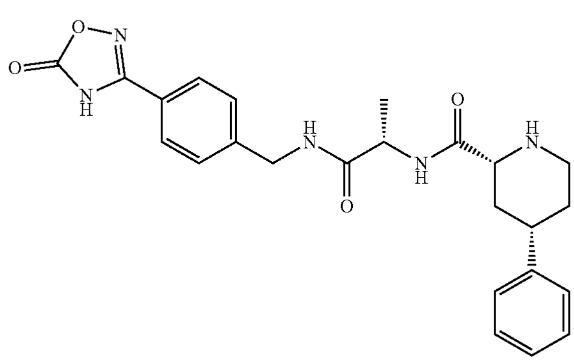 [SMILES: C[C@H](NC(=O)[C@H]1C[C@@H](c2ccccc2)CCN1)C(=O)NCc1ccc(-c2noc(=O)[nH]2)cc1] | 1TFA | 450.17 | 449.21 |

TABLE 1-continued

Exemplary compounds of Structure (I)

| Cmp No. | Structure | Salt | Exact Observed Mass (ES+; M + H) | Exact Calc. Mass |
|---|---|---|---|---|
| I-6 | 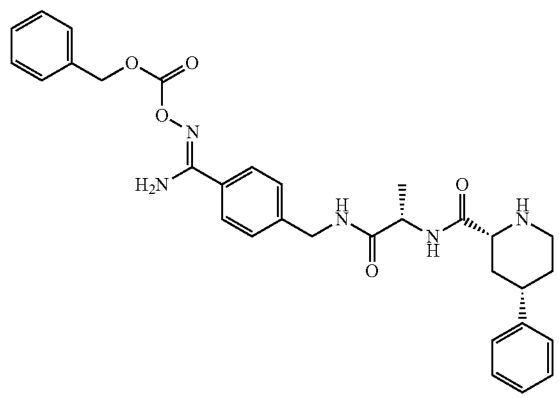 [SMILES: C[C@H](NC(=O)[C@H]1C[C@@H](c2ccccc2)CCN1)C(=O)NCc1ccc(/C(N)=N/OC(=O)OCc2ccccc2)cc1] | 2TFA | 558.24 | 557.26 |
| I-7 | 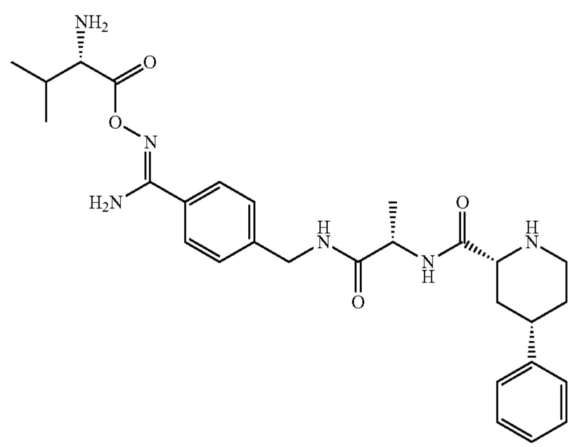 [SMILES: CC(C)[C@H](N)C(=O)O/N=C(\N)c1ccc(CNC(=O)[C@H](C)NC(=O)[C@H]2C[C@@H](c3ccccc3)CCN2)cc1] | 2HCl | 523.50 | 522.30 |
| I-8 | 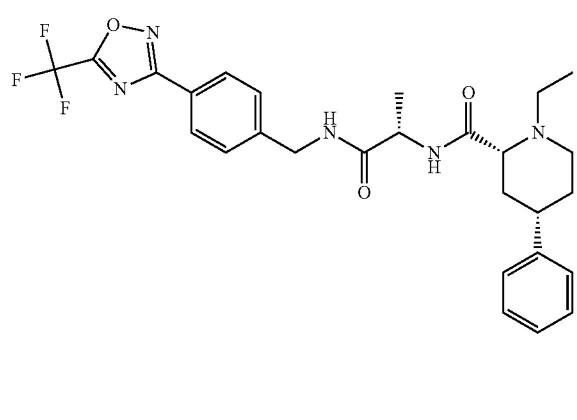 [SMILES: CCN1CC[C@H](c2ccccc2)C[C@@H]1C(=O)N[C@@H](C)C(=O)NCc1ccc(-c2noc(C(F)(F)F)n2)cc1] | 1TFA | 530.44 | 529.23 |

TABLE 1-continued

Exemplary compounds of Structure (I)

| Cmp No. | Structure | Salt | Exact Observed Mass (ES+; M + H) | Exact Calc. Mass |
|---|---|---|---|---|
| I-9 | 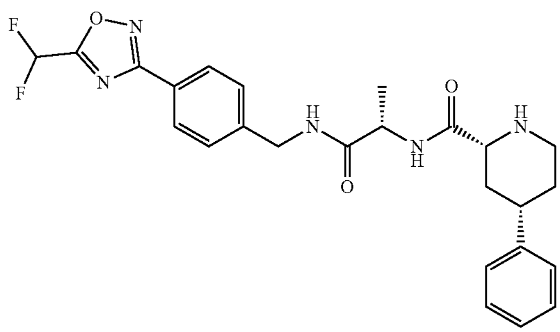 [SMILES: C[C@H](NC(=O)[C@H]1C[C@@H](c2ccccc2)CCN1)C(=O)NCc1ccc(-c2noc(C(F)F)n2)cc1] | 1TFA | 484.24 | 483.21 |
| I-10 | 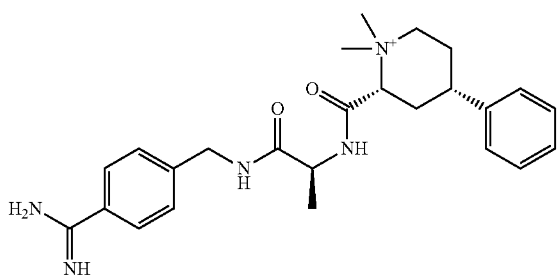 [SMILES: C[C@H](NC(=O)[C@H]1C[C@@H](c2ccccc2)CC[N+]1(C)C)C(=O)NCc1ccc(C(=N)N)cc1] | 2TFA | 436.53 | 436.27 |
| I-11 | 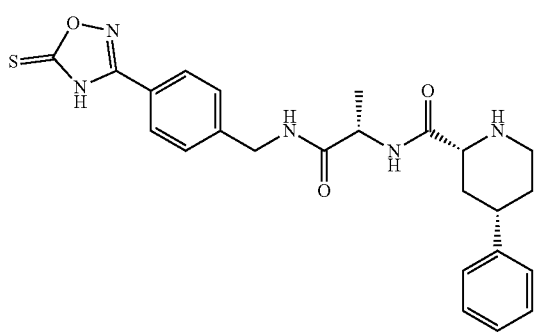 [SMILES: C[C@H](NC(=O)[C@H]1C[C@@H](c2ccccc2)CCN1)C(=O)NCc1ccc(-c2noc(=S)[nH]2)cc1] | 1TFA | 466.17 | 465.18 |
| I-12 | 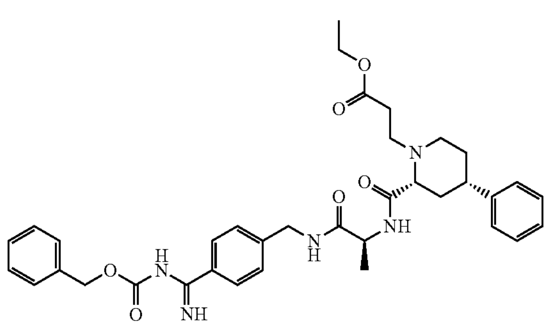 [SMILES: CCOC(=O)CCN1CC[C@H](c2ccccc2)C[C@@H]1C(=O)N[C@@H](C)C(=O)NCc1ccc(C(=N)NC(=O)OCc2ccccc2)cc1] | — | 642.58 | 641.32 |

TABLE 1-continued

Exemplary compounds of Structure (I)

| Cmp No. | Structure | Salt | Exact Observed Mass (ES+; M + H) | Exact Calc. Mass |
|---|---|---|---|---|
| I-13 | 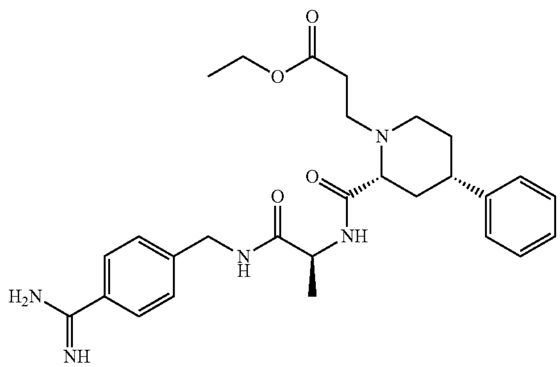 [SMILES: CCOC(=O)CCN1CC[C@H](c2ccccc2)C[C@@H]1C(=O)N[C@@H](C)C(=O)NCc1ccc(C(=N)N)cc1] | — | 508.56 | 507.28 |
| I-14 | 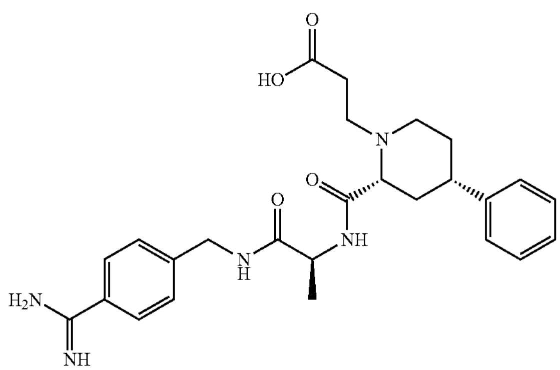 [SMILES: C[C@H](NC(=O)[C@H]1C[C@@H](c2ccccc2)CCN1CCC(=O)O)C(=O)NCc1ccc(C(=N)N)cc1] | 2TFA | 480.61 | 479.25 |
| I-15 | 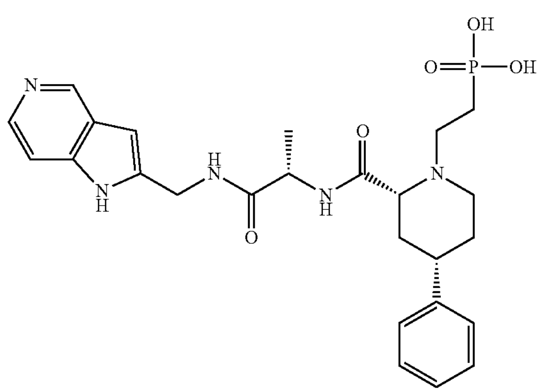 [SMILES: C[C@H](NC(=O)[C@H]1C[C@@H](c2ccccc2)CCN1CCP(=O)(O)O)C(=O)NCc1cc2cnccc2[nH]1] | 2TFA | 514.14 | 513.21 |
| I-16 | 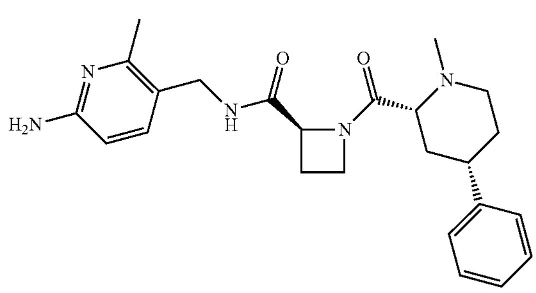 [SMILES: Cc1nc(N)ccc1CNC(=O)[C@@H]1CCN1C(=O)[C@H]1C[C@@H](c2ccccc2)CCN1C] | 2TFA | 422.40 | 421.25 |

TABLE 1-continued

Exemplary compounds of Structure (I)

| Cmp No. | Structure | Salt | Exact Observed Mass (ES+; M + H) | Exact Calc. Mass |
|---|---|---|---|---|
| I-17 | 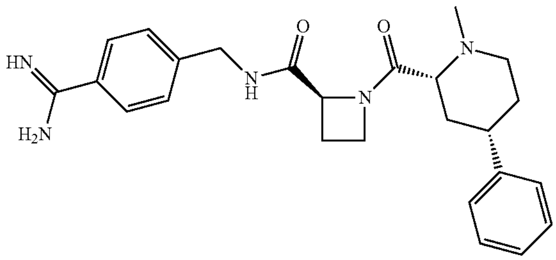 [SMILES: CN1CC[C@H](c2ccccc2)C[C@@H]1C(=O)N1CC[C@H]1C(=O)NCc1ccc(C(=N)N)cc1] | 2TFA | 434.20 | 433.25 |
| I-18 | 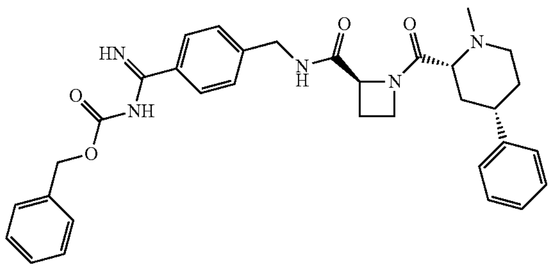 [SMILES: CN1CC[C@H](c2ccccc2)C[C@@H]1C(=O)N1CC[C@H]1C(=O)NCc1ccc(C(=N)NC(=O)OCc2ccccc2)cc1] | 2TFA | 568.21 | 567.28 |
| I-19 | 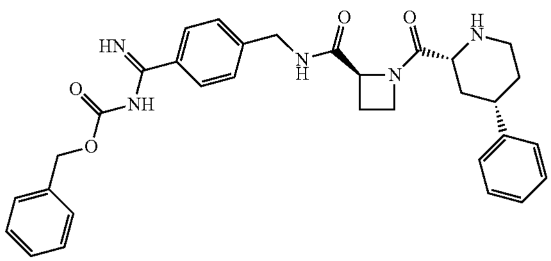 [SMILES: N=C(NC(=O)OCc1ccccc1)c1ccc(CNC(=O)[C@@H]2CCN2C(=O)[C@H]2C[C@@H](c3ccccc3)CCN2)cc1] | 2TFA | 554.50 | 553.27 |
| I-20 | 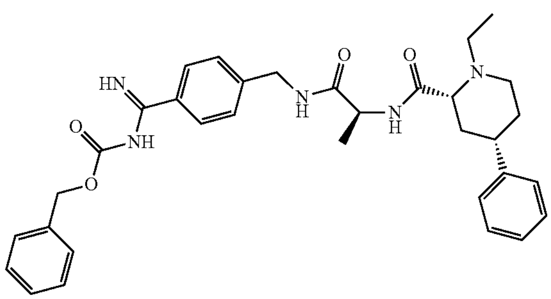 [SMILES: CCN1CC[C@H](c2ccccc2)C[C@@H]1C(=O)N[C@@H](C)C(=O)NCc1ccc(C(=N)NC(=O)OCc2ccccc2)cc1] | — | 570.37 | 569.30 |
| I-21 | 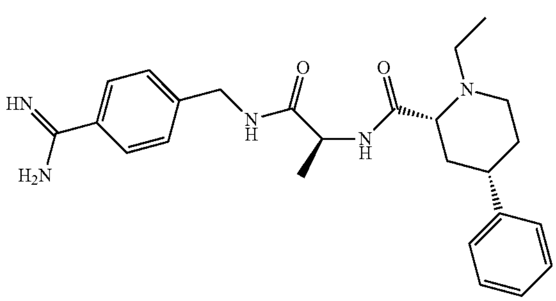 [SMILES: CCN1CC[C@H](c2ccccc2)C[C@@H]1C(=O)N[C@@H](C)C(=O)NCc1ccc(C(=N)N)cc1] | — | 436.53 | 435.26 |

TABLE 1-continued

Exemplary compounds of Structure (I)

| Cmp No. | Structure | Salt | Exact Observed Mass (ES+; M + H) | Exact Calc. Mass |
|---|---|---|---|---|
| I-22 | 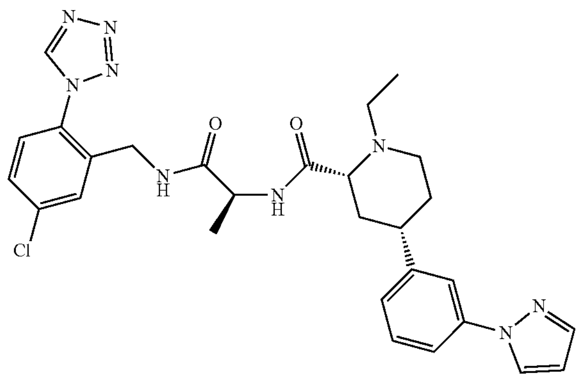 [SMILES: CCN1CC[C@H](c2cccc(-n3cccn3)c2)C[C@@H]1C(=O)N[C@@H](C)C(=O)NCc1cc(Cl)ccc1-n1cnnn1] | — | 562.33 | 561.24 |
| I-23 | 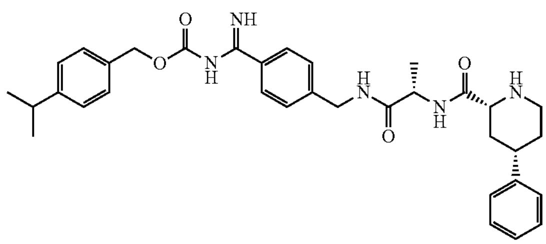 [SMILES: CC(C)c1ccc(COC(=O)NC(=N)c2ccc(CNC(=O)[C@H](C)NC(=O)[C@H]3C[C@@H](c4ccccc4)CCN3)cc2)cc1] | 1HCl | 584.50 | 583.73 |
| I-24 | 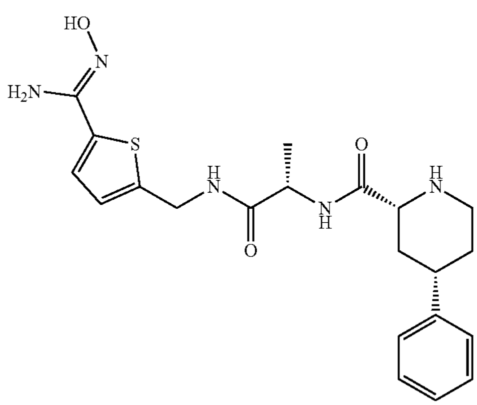 [SMILES: C[C@H](NC(=O)[C@H]1C[C@@H](c2ccccc2)CCN1)C(=O)NCc1ccc(/C(N)=N/O)s1] | 1HCl | 430.44 | 429.54 |
| I-25 | 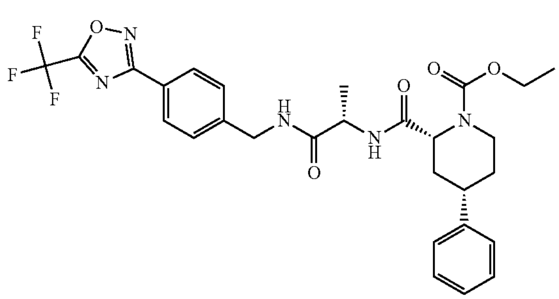 [SMILES: CCOC(=O)N1CC[C@H](c2ccccc2)C[C@@H]1C(=O)N[C@@H](C)C(=O)NCc1ccc(-c2noc(C(F)(F)F)n2)cc1] | — | 574.41 | 573.22 |

TABLE 1-continued

Exemplary compounds of Structure (I)

| Cmp No. | Structure | Salt | Exact Observed Mass (ES+; M + H) | Exact Calc. Mass |
|---|---|---|---|---|
| I-26 | 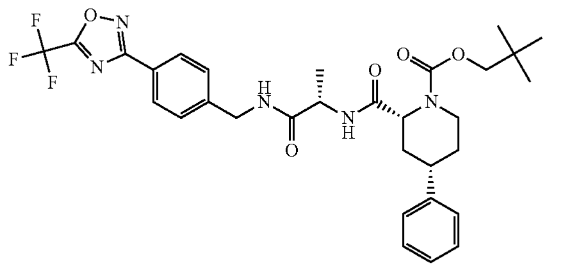 [SMILES: C[C@H](NC(=O)[C@H]1C[C@@H](c2ccccc2)CCN1C(=O)OCC(C)(C)C)C(=O)NCc1ccc(-c2noc(C(F)(F)F)n2)cc1] | — | 616.41 | 615.27 |
| I-27 | 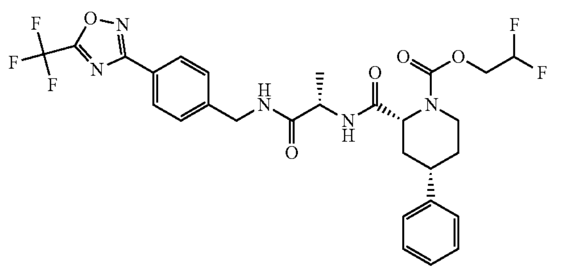 [SMILES: C[C@H](NC(=O)[C@H]1C[C@@H](c2ccccc2)CCN1C(=O)OCC(F)F)C(=O)NCc1ccc(-c2noc(C(F)(F)F)n2)cc1] | — | 610.51 | 609.20 |
| I-28 | 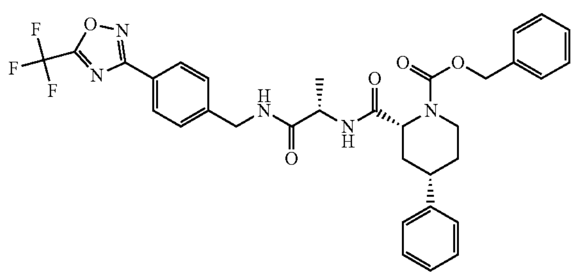 [SMILES: C[C@H](NC(=O)[C@H]1C[C@@H](c2ccccc2)CCN1C(=O)OCc1ccccc1)C(=O)NCc1ccc(-c2noc(C(F)(F)F)n2)cc1] | — | 636.21 | 635.24 |
| I-29 | 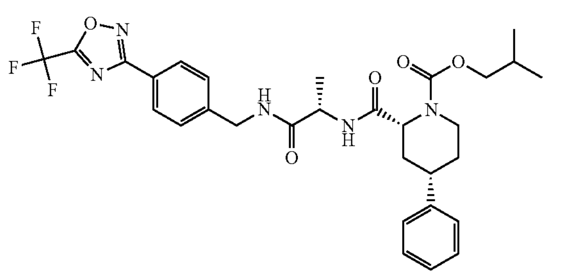 [SMILES: CC(C)COC(=O)N1CC[C@H](c2ccccc2)C[C@@H]1C(=O)N[C@@H](C)C(=O)NCc1ccc(-c2noc(C(F)(F)F)n2)cc1] | — | 602.52 | 601.25 |
| I-30 | 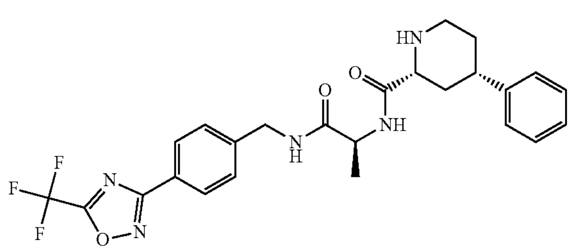 [SMILES: C[C@H](NC(=O)[C@H]1C[C@@H](c2ccccc2)CCN1)C(=O)NCc1ccc(-c2noc(C(F)(F)F)n2)cc1] | 1TFA | 502.17 | 501.20 |

TABLE 1-continued

Exemplary compounds of Structure (I)

| Cmp No. | Structure | Salt | Exact Observed Mass (ES+; M + H) | Exact Calc. Mass |
|---|---|---|---|---|
| I-31 | 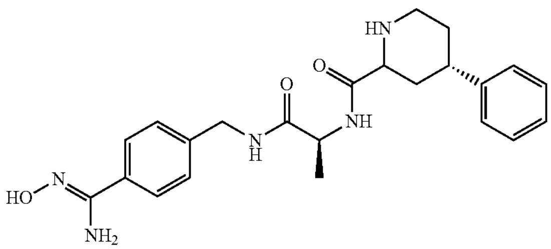 [SMILES: C[C@H](NC(=O)C1C[C@@H](c2ccccc2)CCN1)C(=O)NCc1ccc(/C(N)=N/O)cc1] | 2TFA | 424.16 | 423.23 |
| I-32 | 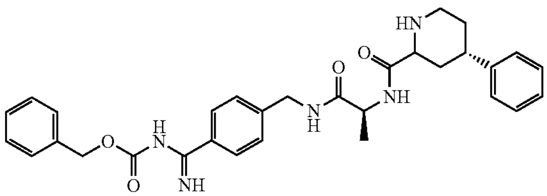 [SMILES: C[C@H](NC(=O)C1C[C@@H](c2ccccc2)CCN1)C(=O)NCc1ccc(C(=N)NC(=O)OCc2ccccc2)cc1] | 2TFA | 542.18 | 541.27 |
| I-33 | 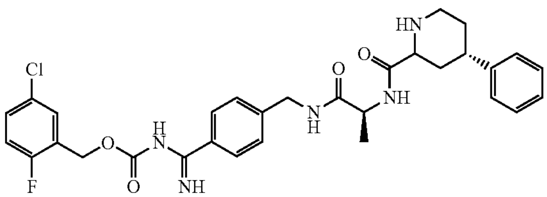 [SMILES: C[C@H](NC(=O)C1C[C@@H](c2ccccc2)CCN1)C(=O)NCc1ccc(C(=N)NC(=O)OCc2cc(Cl)ccc2F)cc1] | 2TFA | 594.18 | 593.22 |
| I-34 | 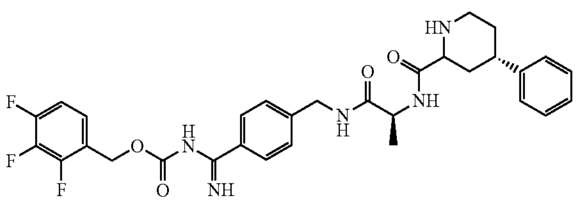 [SMILES: C[C@H](NC(=O)C1C[C@@H](c2ccccc2)CCN1)C(=O)NCc1ccc(C(=N)NC(=O)OCc2ccc(F)c(F)c2F)cc1] | 2TFA | 596.21 | 595.24 |
| I-35 | 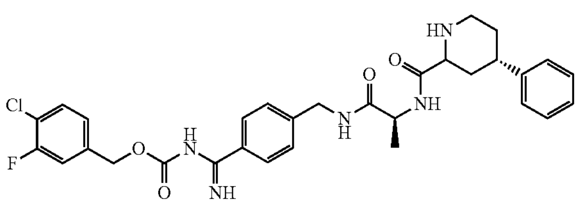 [SMILES: C[C@H](NC(=O)C1C[C@@H](c2ccccc2)CCN1)C(=O)NCc1ccc(C(=N)NC(=O)OCc2ccc(Cl)c(F)c2)cc1] | 2TFA | 594.21 | 593.22 |
| I-36 | 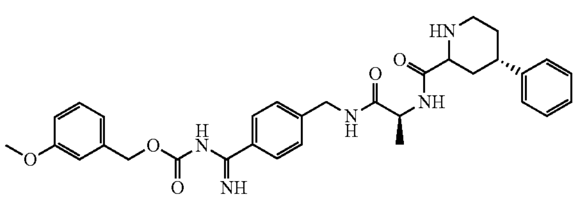 [SMILES: COc1cccc(COC(=O)NC(=N)c2ccc(CNC(=O)[C@H](C)NC(=O)C3C[C@@H](c4ccccc4)CCN3)cc2)c1] | 2TFA | 572.24 | 571.28 |

Example 33

Enzymatic Assay for MASP-2

The MASP-2 assay utilizes a fluorogenic substrate, based on the cleavage site for its natural substrate C2. The assay is run at room temperature in an assay buffer containing 20 mM HEPES, pH 7.4, 140 mM NaCl and 0.1% Tween 20. Assay parameters are adjusted such that the assay is linear with respect to time, enzyme, and substrate concentrations. Under these optimized assays conditions, $IC_{50}$ values are equivalent to Ki values, except in a few cases of "tight binding" inhibitors. Cases of "tight binding" or possible "slow binding" inhibitors are handled by the methods described in Copeland R.A. (2013) Evaluation of Enzyme Inhibitors in Drug Discovery. 2nd Ed., John Wiley and Sons, Inc., Chapters 5-7.

The MASP-2 assay protocol is carried out as follows. Test compounds are serially diluted in DMSO and then 100 nL of each dilution is transferred to the assay plate(s). 10 μL of Assay Buffer is added, followed by 15 μL of Enzyme MASP-2 (CCP1-CCP2-SP) in Assay Buffer. 15 μL of Substrate in Assay Buffer is then added and mixed to start the reactions. After 20 min at room temperature, 15 μL of a stop solution (0.1 M acetic acid) is added, mixed and the plates are read on a SpectraMax i3x Microplate Reader and exported as Excel files. Each assay plate included a "no inhibitor" (DMSO Only) control, a "no enzyme" control and a reference inhibitor control. % Activity values=100*(average test comp. fluorescence−average "no enzyme" fluorescence)/(average "DMSO only" fluorescence−average "no enzyme" fluorescence). $IC_{50}$ and Ki values are very reproducible, falling well within 2-fold.

The results of biological assays for the compounds listed in Table 1 are listed in Table 2, below.

TABLE 2

MASP-2 Inhibition for exemplary compound of Structure (I)

| Compound | MASP-2 $K_i$ (μM) | Compound | MASP-2 $K_i$ (μM) | Compound | MASP-2 $K_i$ (μM) |
| --- | --- | --- | --- | --- | --- |
| I-1 | — | I-2 | — | I-3 | — |
| I-4 | — | I-5 | — | I-6 | — |
| I-7 | **** | I-8 | — | I-9 | — |
| I-10 | **** | I-11 | — | I-12 | — |
| I-13 | **** | I-14 | **** | I-15 | **** |
| I-16 | **** | I-17 | **** | I-18 | — |
| I-19 | *** | I-20 | ** | I-21 | **** |
| I-22 | **** | I-23 | — | I-24 | **** |
| I-25 | — | I-26 | — | I-27 | — |
| I-28 | — | I-29 | — | I-30 | — |
| I-31 | *** | I-32 | — | I-33 | — |
| I-34 | — | I-35 | — | I-36 | — |

MASP-2 Inhibition $K_i$ Values:
* $K_i$ greater than 10 μM
** $K_i$ between 2.5-10 μM
*** $K_i$ between 0.5-2.5 μM
**** $K_i$ of less than 0.5 μM
— not tested It is understood that the examples and embodiments described herein are for illustrative purposes only and that various modifications or changes in light thereof will be suggested to persons skilled in the art and are to be included within the spirit and purview of this application and scope of the appended claims. Each reference, including without limitation all patent, patent applications, and publications, cited in the present application is incorporated herein by reference in its entirety for all purposes.

The invention claimed is:

1. A compound having the following Structure (I):

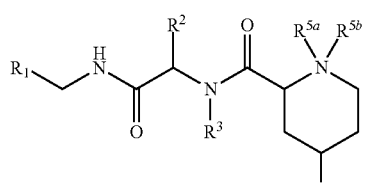

or a stereoisomer, tautomer, or pharmaceutically acceptable salt thereof, wherein:

$R^1$ is a substituted or unsubstituted aryl, substituted or unsubstituted cycloalkyl, a substituted or unsubstituted heterocyclyl, or a substituted or unsubstituted heteroaryl, wherein the heteroaryl is selected from the group consisting of

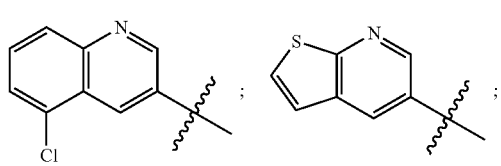

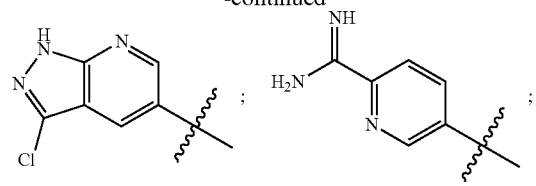

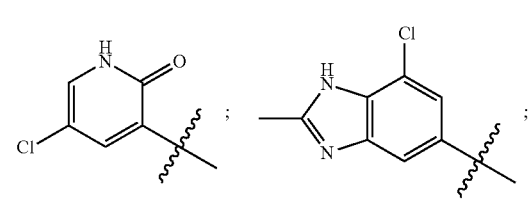

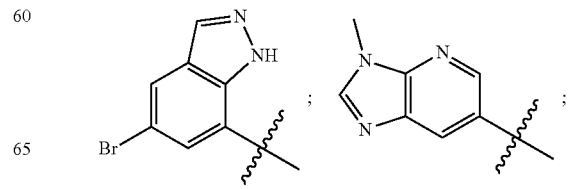

187
-continued
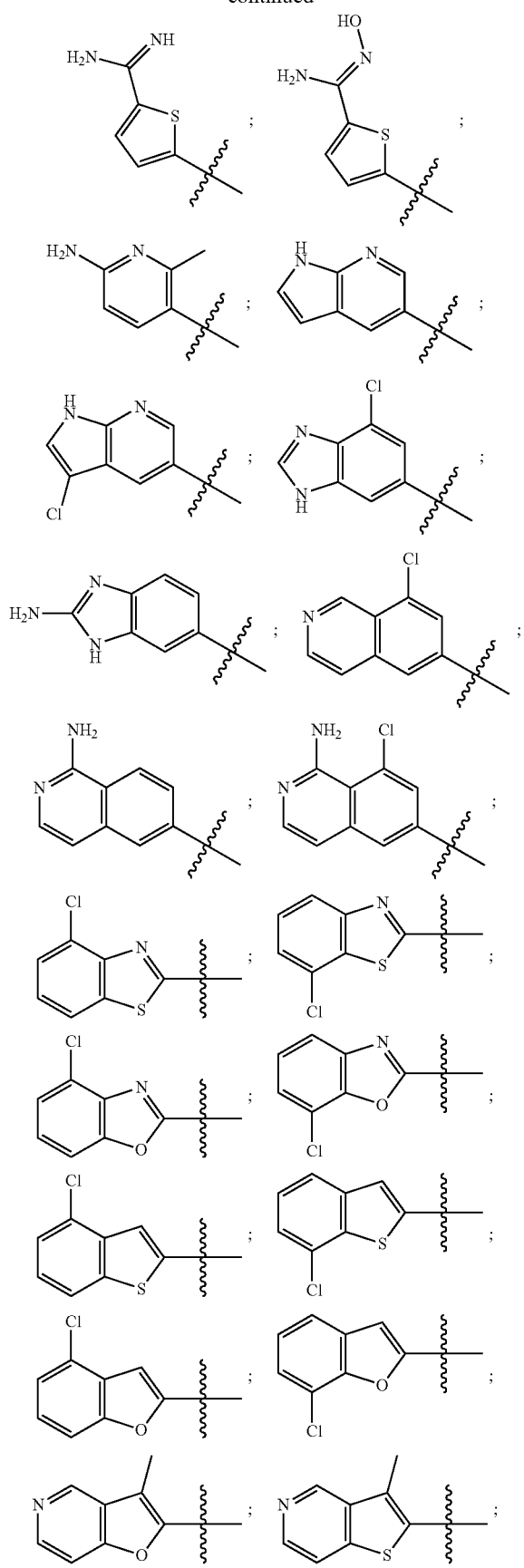
188
-continued
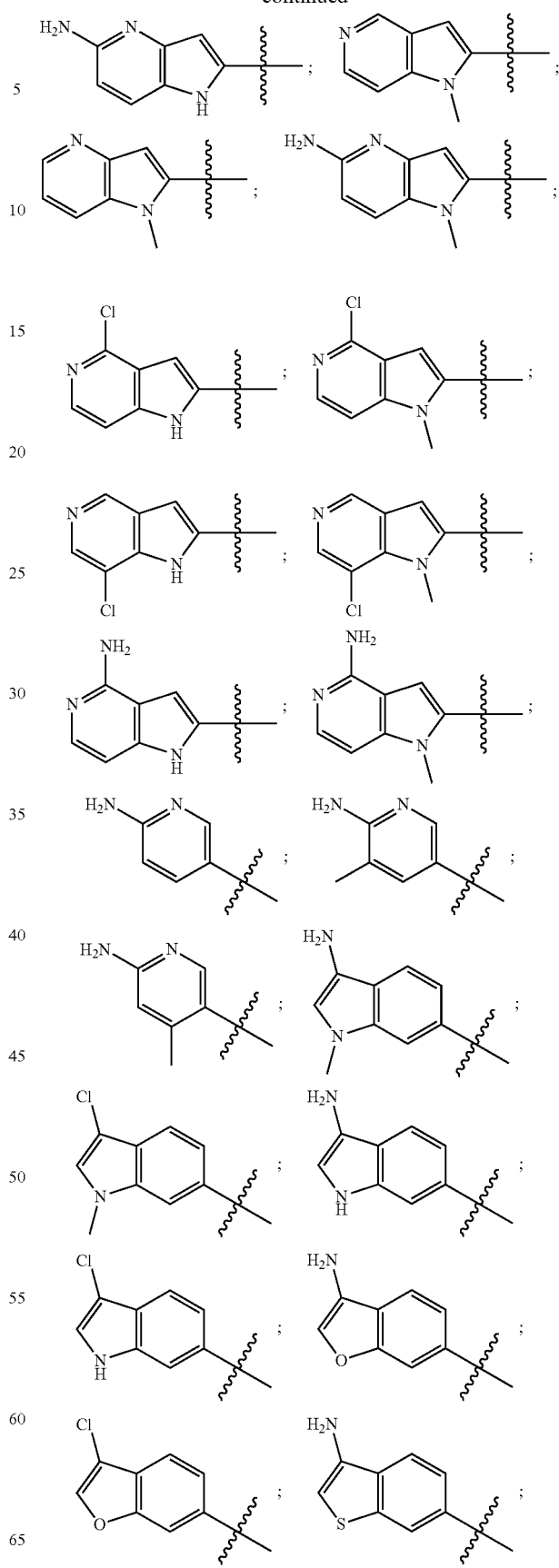

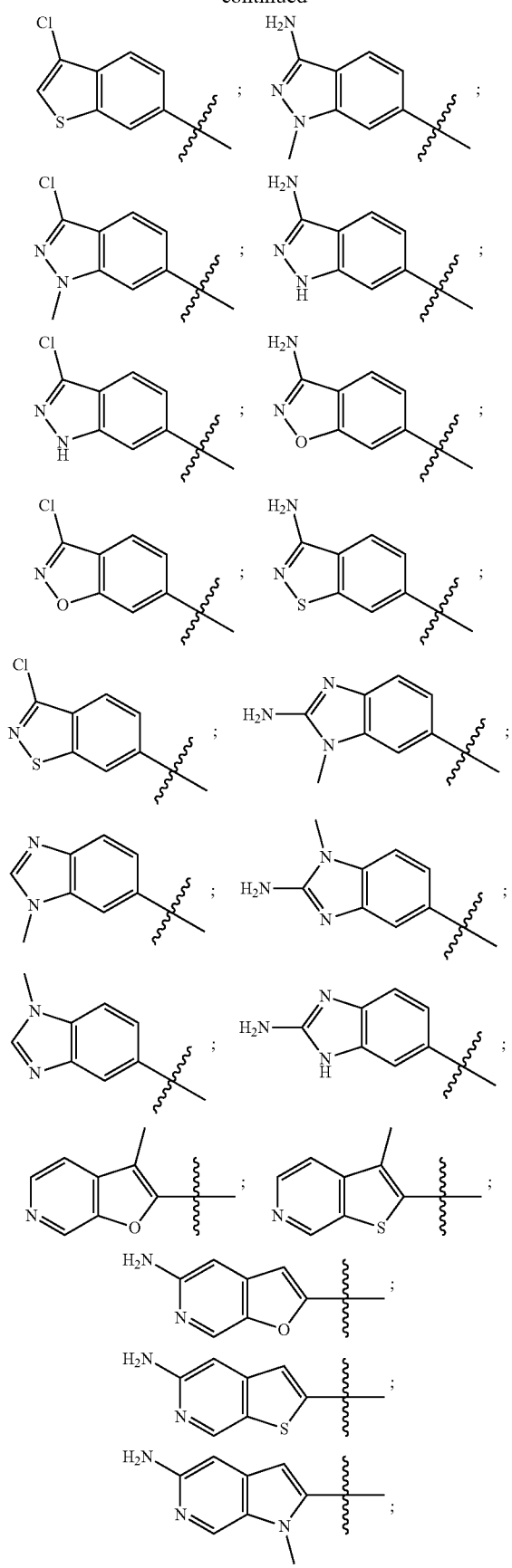
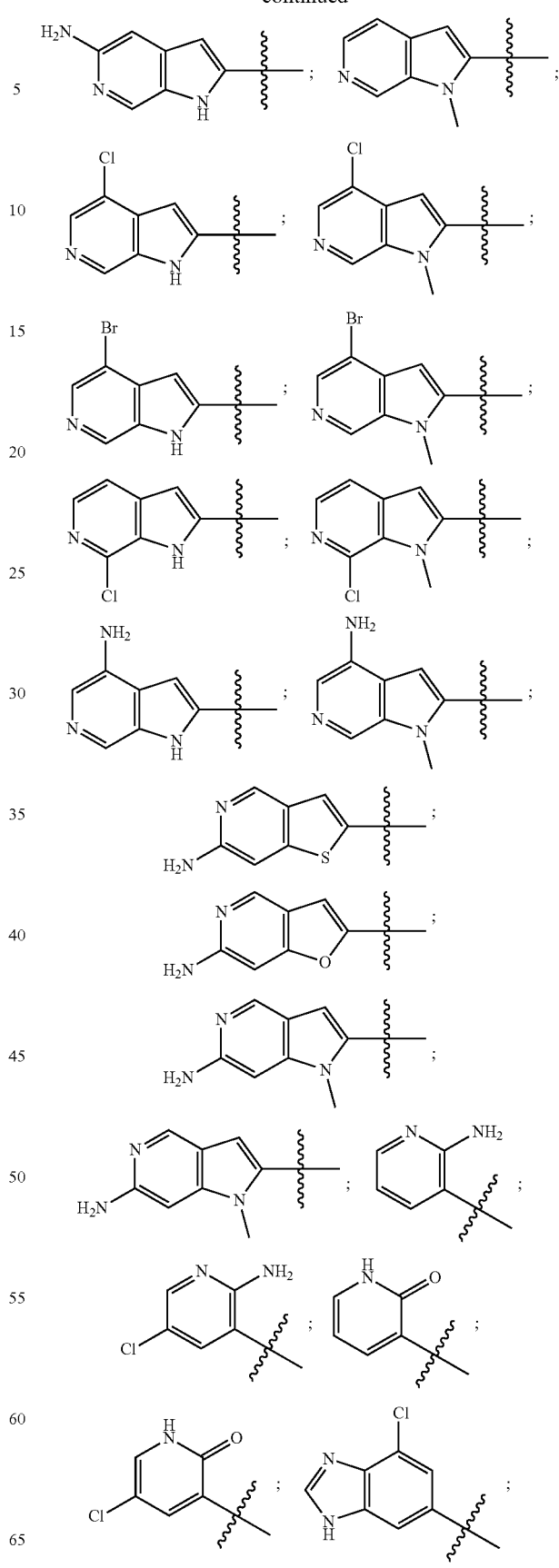

-continued

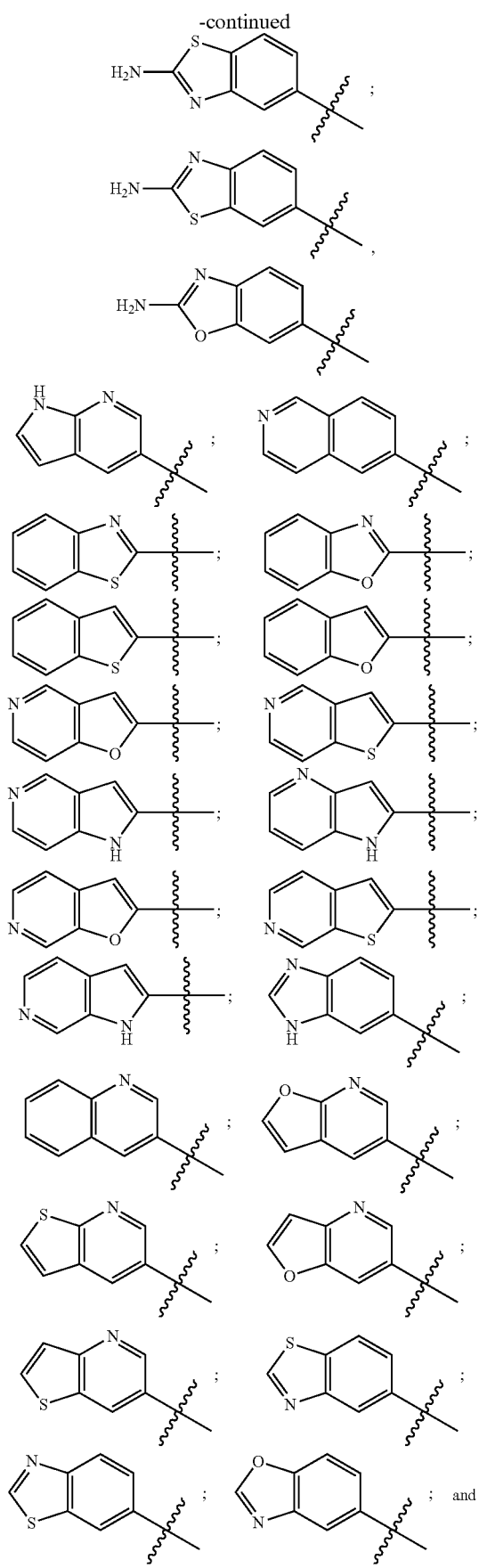

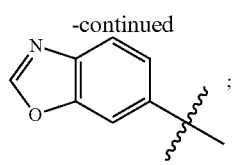

R² is hydrogen, alkyl, alkoxy, haloalkyl, haloalkoxy, or cycloalkyl;

R³ is hydrogen, alkyl, haloalkyl, or cycloalkyl;

or R² and R³, together with the carbon and nitrogen to which they are attached, respectively, form an optionally substituted 4-7 membered heterocyclyl;

R⁴ is a substituted or unsubstituted aryl, substituted or unsubstituted heteroaryl, substituted or unsubstituted cycloalkyl, or a substituted or unsubstituted heterocyclyl;

$R^{5a}$ is hydrogen, alkyl, haloalkyl, cycloalkyl, phosphonalkyl, $(CH_2)_nC(=O)OR^6$, $C(=O)R^6$, $C(=O)OR^6$, or $C(=O)NR^6R^7$;

$R^{5b}$ is an electron pair or alkyl;

R⁶ and R⁷ are, at each occurrence, independently hydrogen, alkyl, haloalkyl, cycloalkyl, or arylalkyl;

R⁸ is alkyl, haloalkyl, aminylalkyl, substituted or unsubstituted arylalkyl; and n is 1, 2, 3, 4, 5, 6, 7, or 8, provided that A) $R^{5a}$ is alkyl, haloalkyl, cycloalkyl, phosphonalkyl, $(CH_2)_nC(=O)OR^6$, $C(=O)R^6$, $C(=O)OR^6$, or $C(=O)NR^6R^7$ or R¹ is substituted with one or more substituents selected from the group consisting of a substituted heteroaryl, $C(=NH)NHC(=O)OR^8$, $C(=NOC(=O)R^8)NH_2$, $C(=NOC(=O)OR^8)NH_2$, and $C(=NOH)NH_2$; and B) when $R^{5a}$ is alkyl or $(CH_2)_nC(=O)OR^6$, R¹ does not have the following structure:

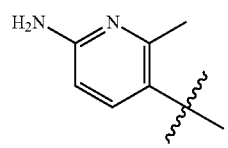

unless R² and R³, together with the carbon and nitrogen to which they are attached, respectively, form an optionally substituted 4-7 membered heterocyclyl.

2. The compound of claim 1, wherein R' is a substituted or unsubstituted phenyl.

3. The compound of claim 1, wherein R¹ has one of the following structures:

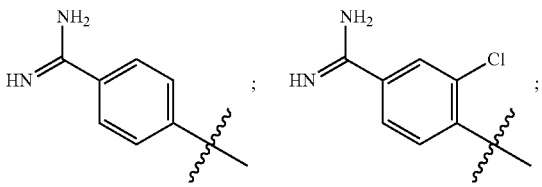

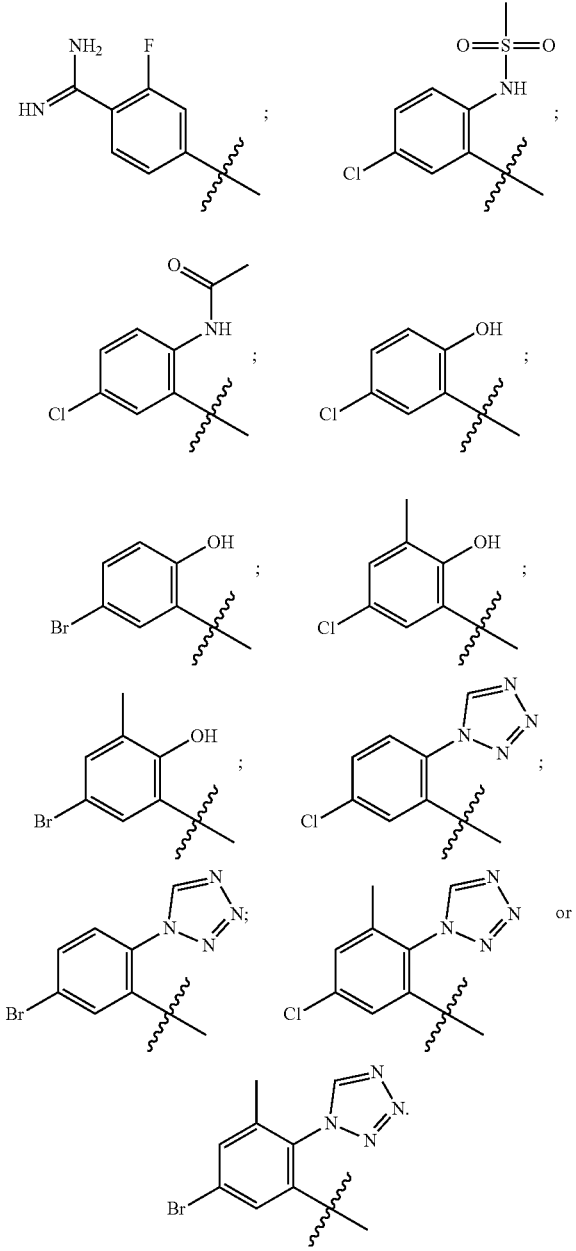

4. The compound of claim 1, wherein $R^1$ is a substituted or unsubstituted heteroaryl.

5. The compound of claim 1, wherein $R^1$ is substituted with one or more substituents selected from the group consisting of a substituted heteroaryl, C(=NH)NHC(=O)OR$^8$, C(=NOC(=O)R$^8$)NH$_2$, C(=NOC(=O)OR$^8$)NH$_2$, and C(=NOH)NH$_2$.

6. The compound of claim 5, wherein $R^1$ is substituted with C(=NH)NHC(=O)OR$^8$ and $R^8$ is a substituted or unsubstituted arylalkyl.

7. The compound of claim 5, wherein $R^1$ is substituted with C(=NOC(=O)R$^8$)NH$_2$ and $R^8$ is an aminylalkyl.

8. The compound of claim 5, wherein $R^1$ is substituted with C(=NOC(=O)OR$^8$)NH$_2$ and $R^8$ is an alkyl, a haloalkyl, or a substituted or unsubstituted arylalkyl.

9. The compound of claim 5, wherein $R^1$ has one of the following structures:

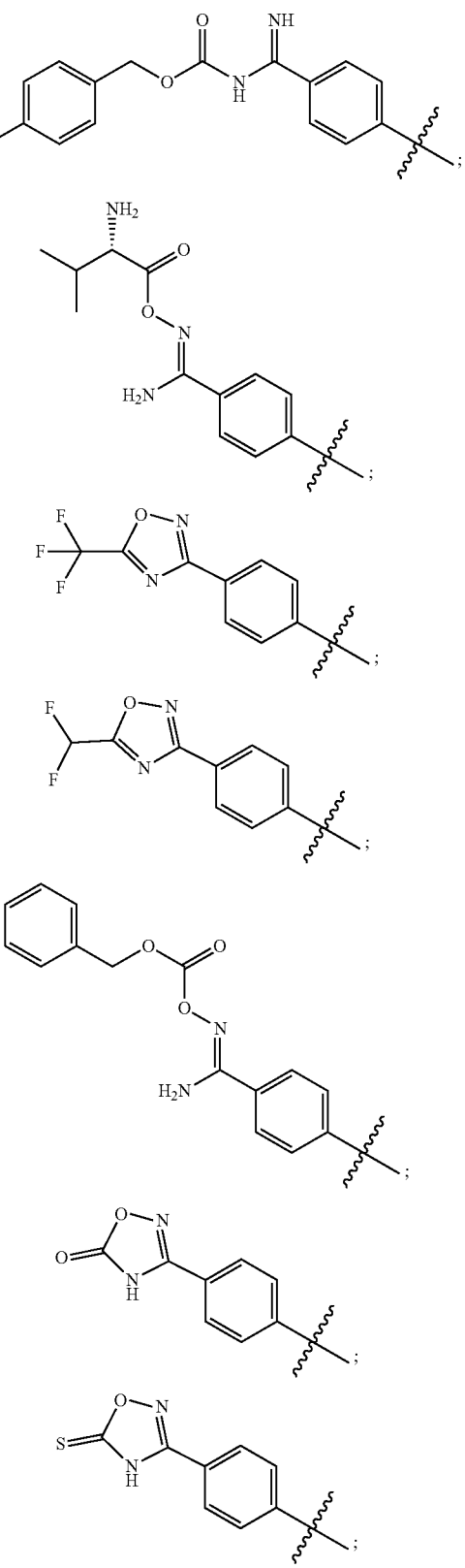

-continued

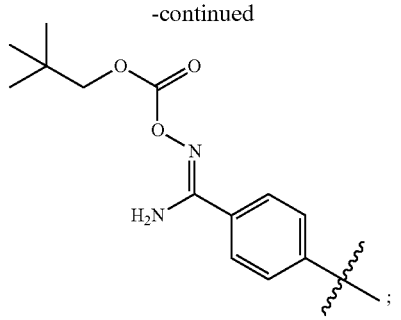

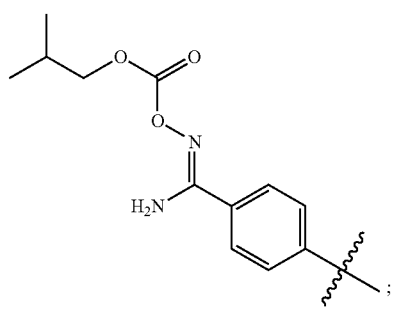

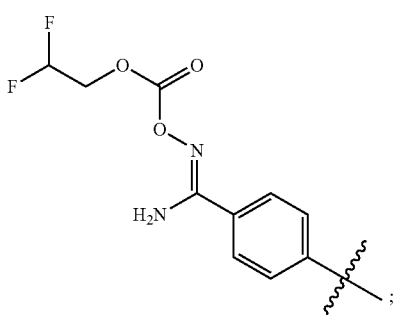

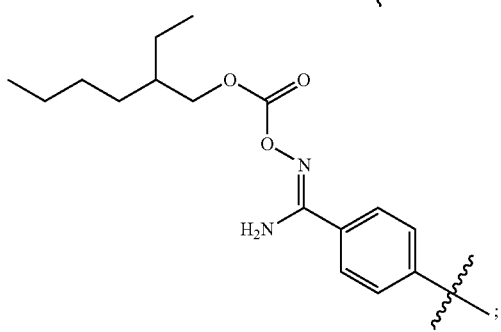

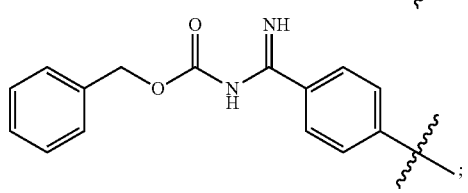

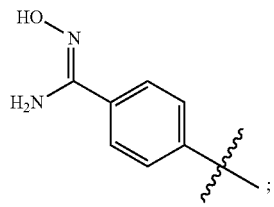

-continued

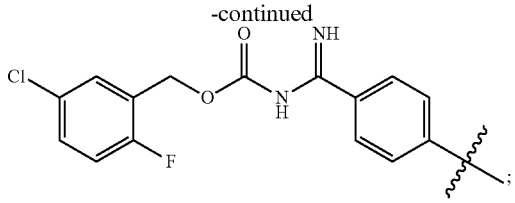

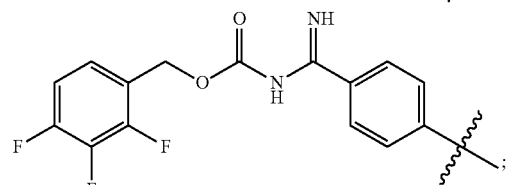

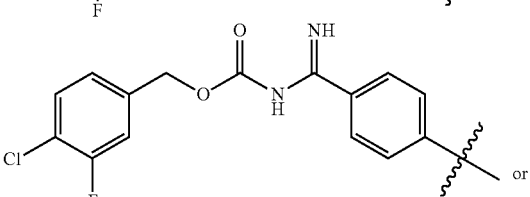

or

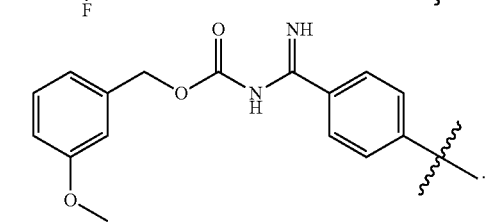

.

10. The compound of claim 1, wherein $R^2$ is hydrogen or $C_1$-$C_6$ alkyl.

11. The compound of claim 1, wherein $R^2$ is —$CH_3$.

12. The compound of claim 1, wherein $R^2$ and $R^3$, together with the carbon and nitrogen to which they are attached, respectively, form an optionally substituted 4, 5, or 6 membered heterocyclyl.

13. The compound of claim 1, wherein $R^4$ is a substituted or unsubstituted aryl.

14. The compound of claim 1, wherein $R^4$ has one of the following structures:

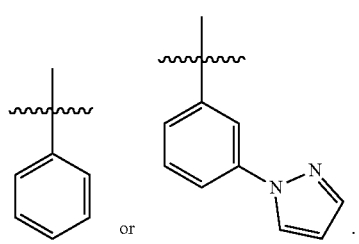 [SMILES: *c1ccccc1 ; *c1cccc(-n2cccn2)c1]

15. The compound of claim 1, wherein $R^{5a}$ is alkyl, C(=O)O$R^6$, phosphonalkyl, or (CH$_2$)$_n$C(=O)O$R^6$.

16. The compound of claim 15, wherein $R^{5a}$ has one of the following structures:

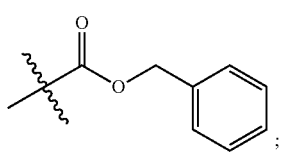

;

197
-continued
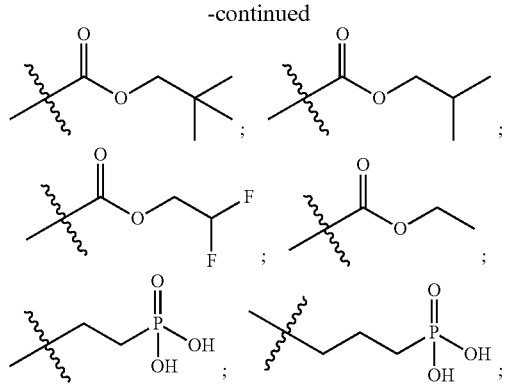
198
-continued
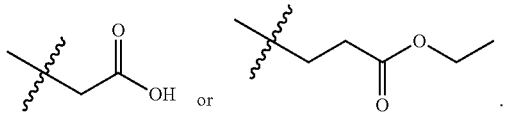
17. The compound of claim 1, wherein $R^{5b}$ is an electron pair.
18. The compound of claim 1, wherein $R^{5b}$ is alkyl.
19. A compound having one of the structures:
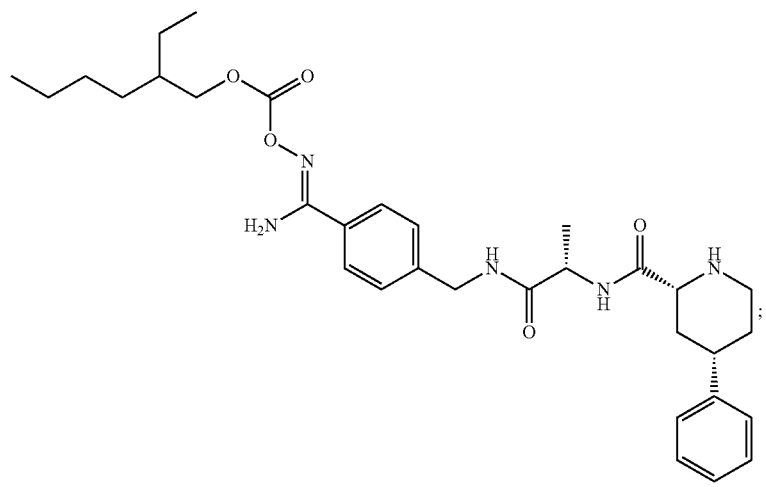
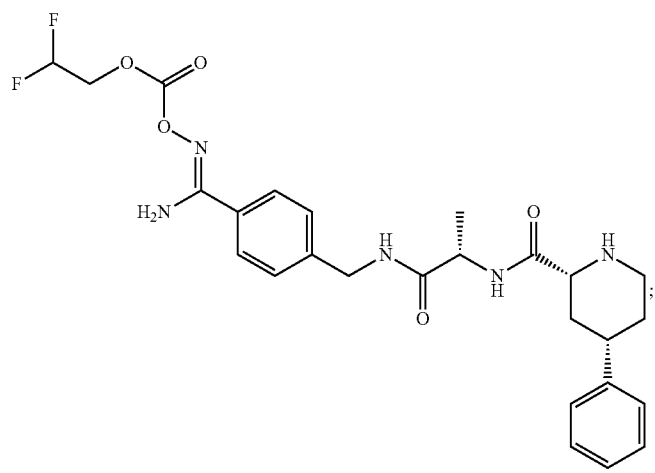

-continued
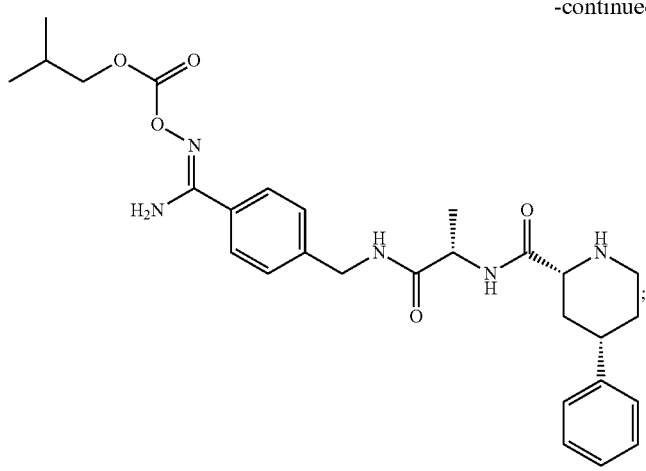
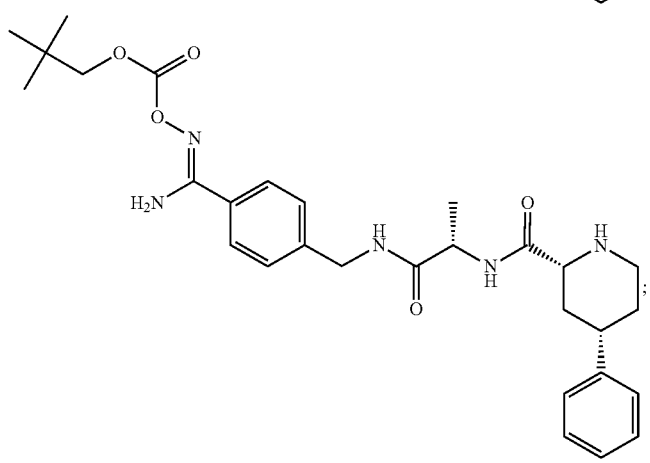
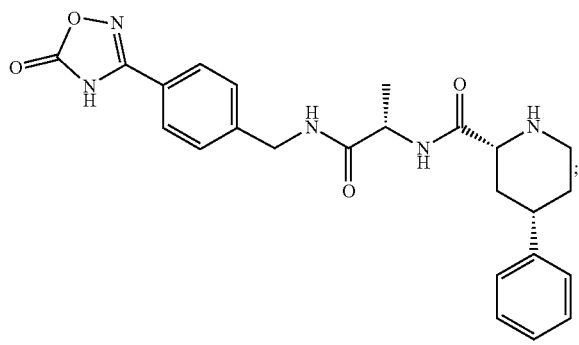
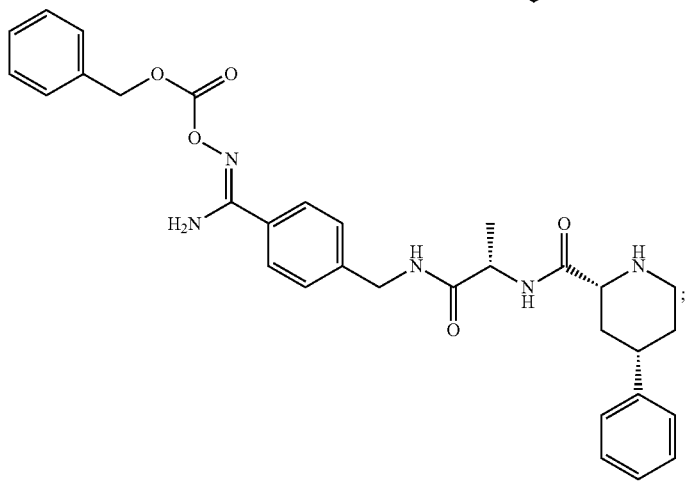

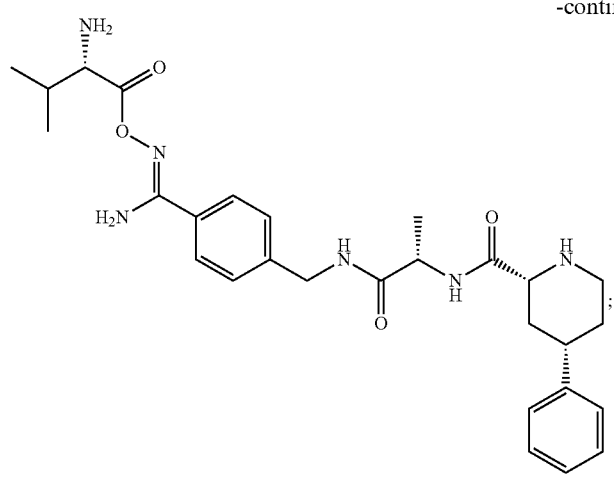
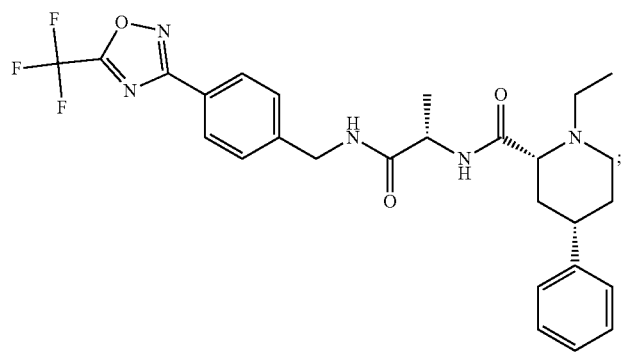
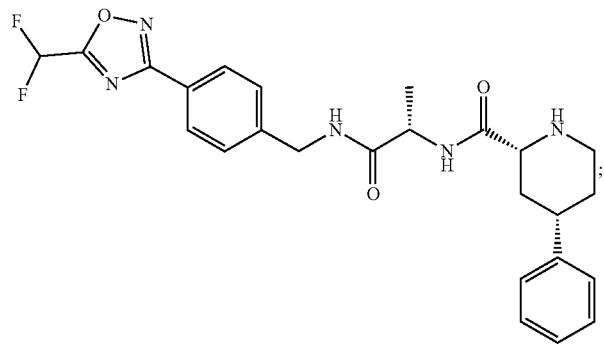
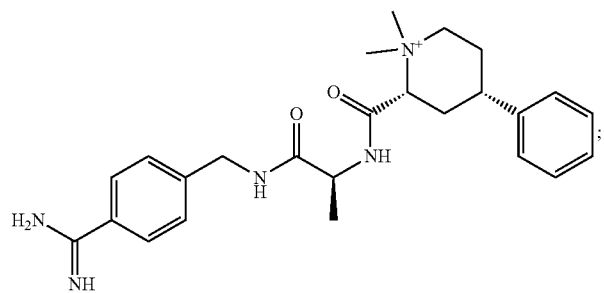

203 204
-continued
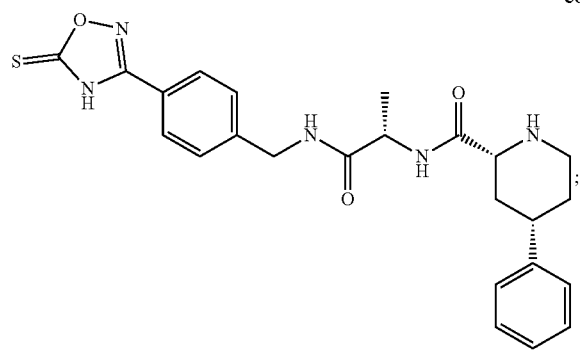
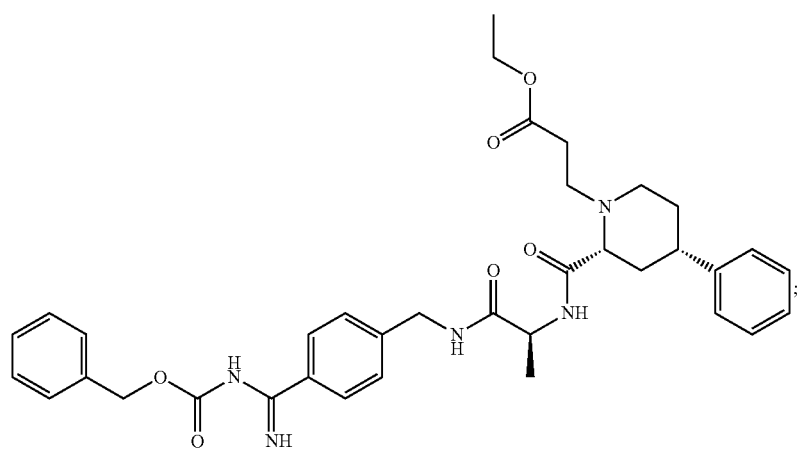
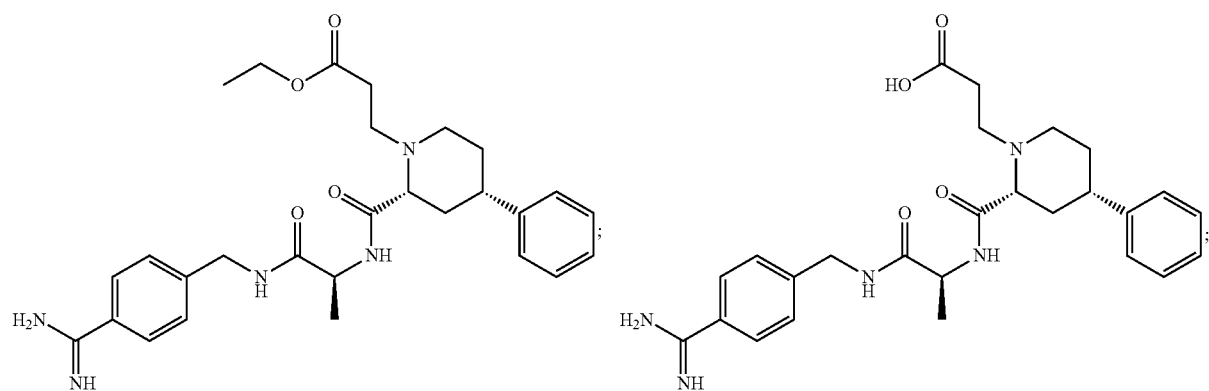
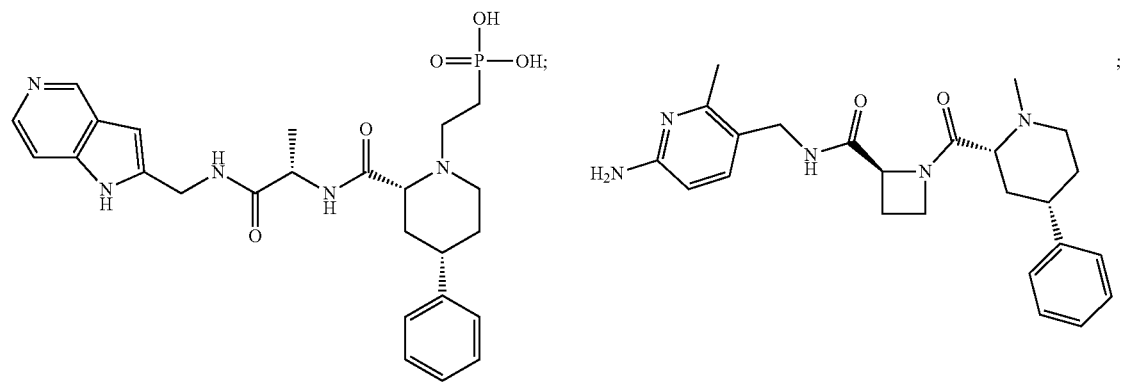

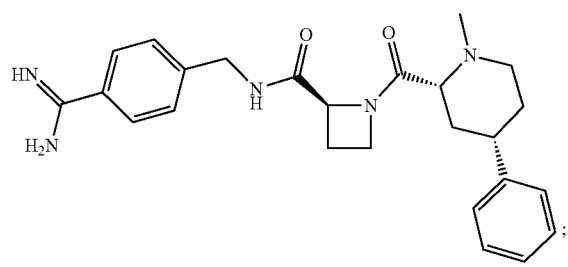
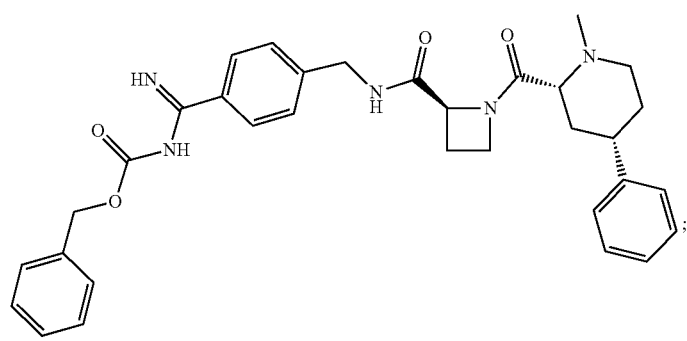
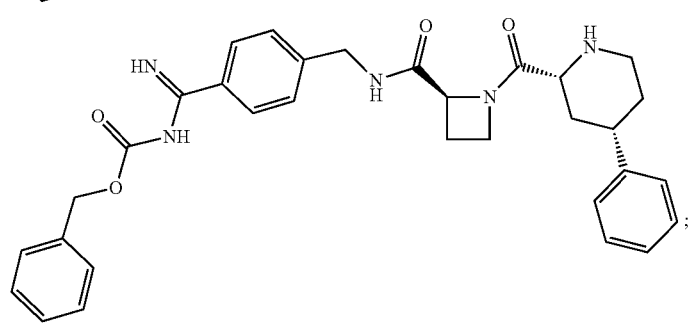
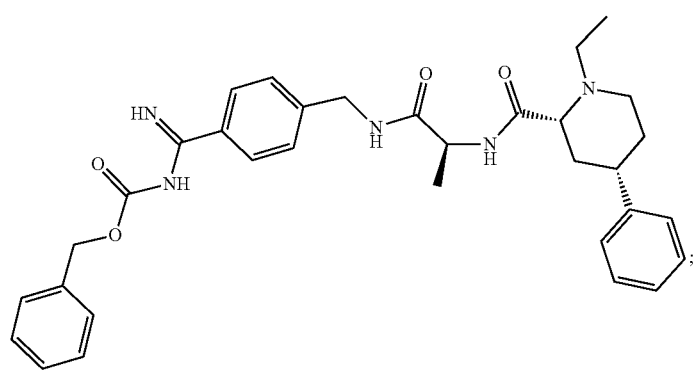
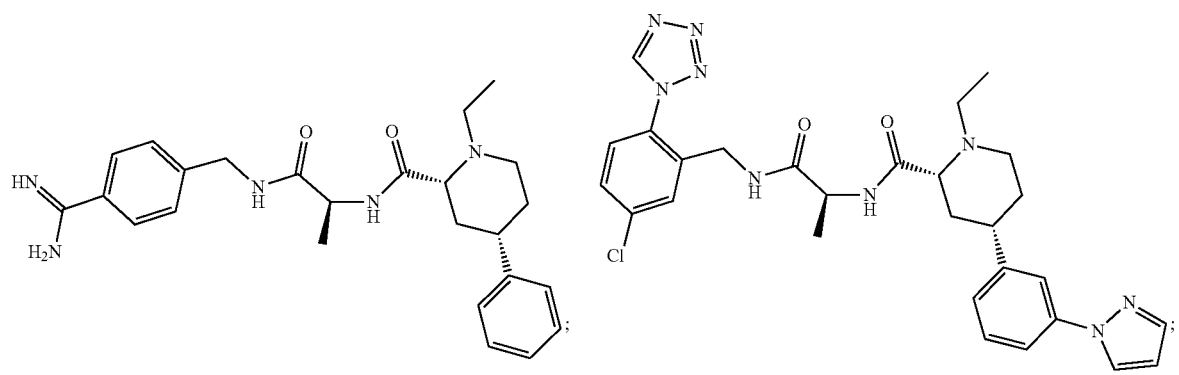

207
-continued
208
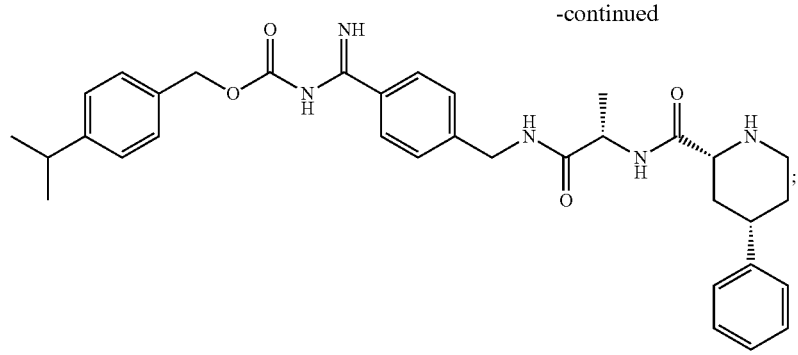
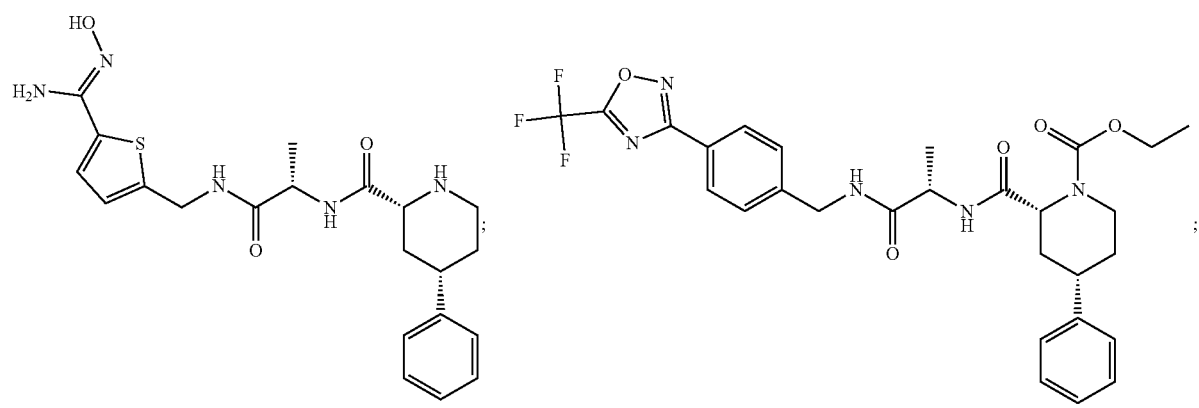
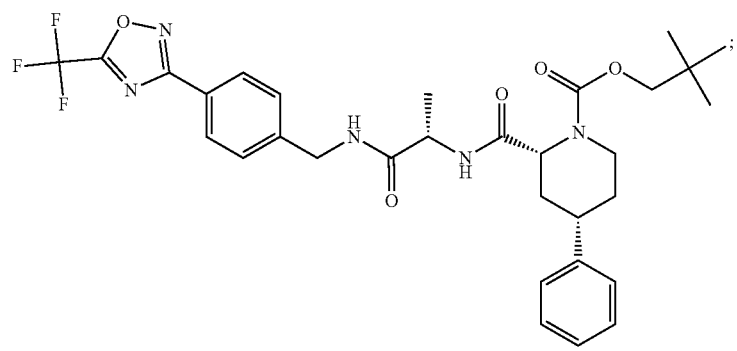
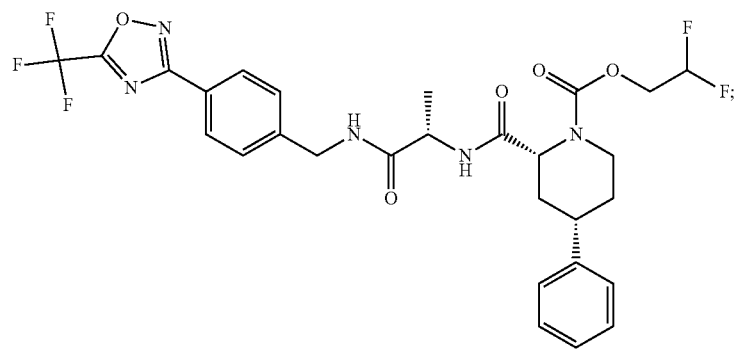

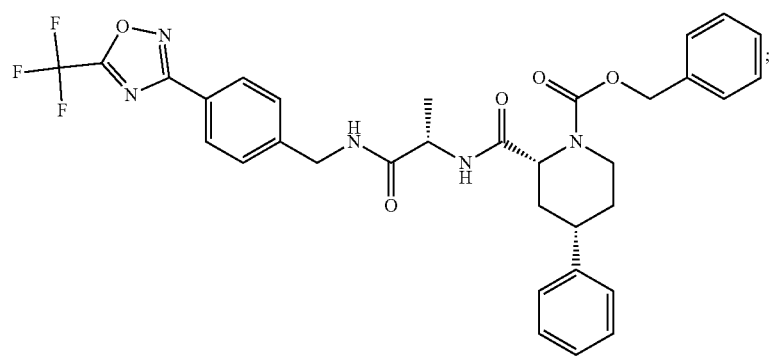
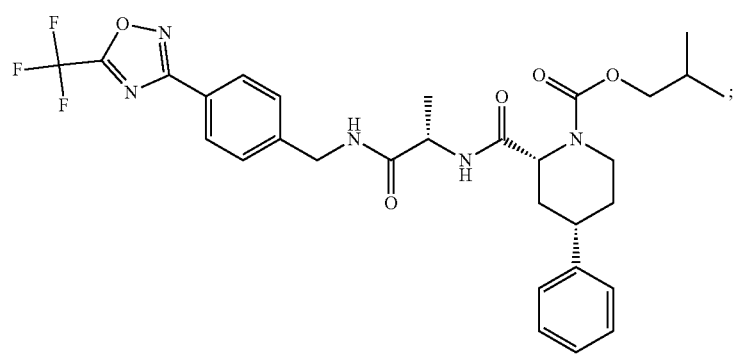
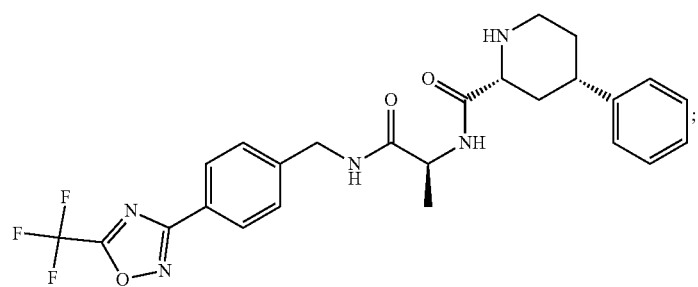
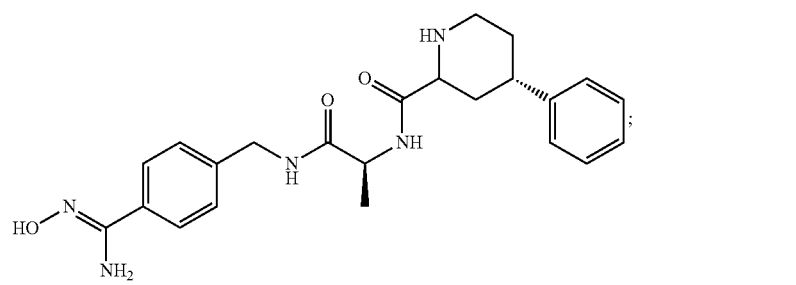
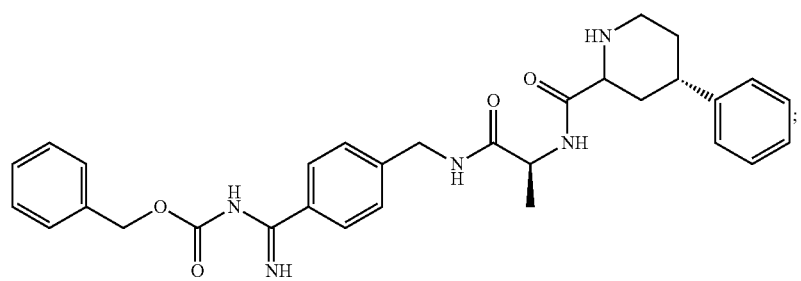

-continued

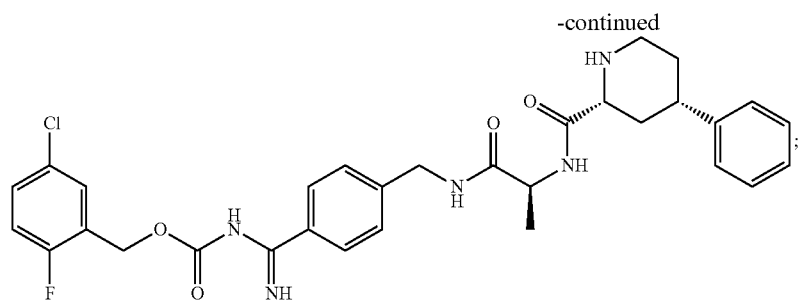

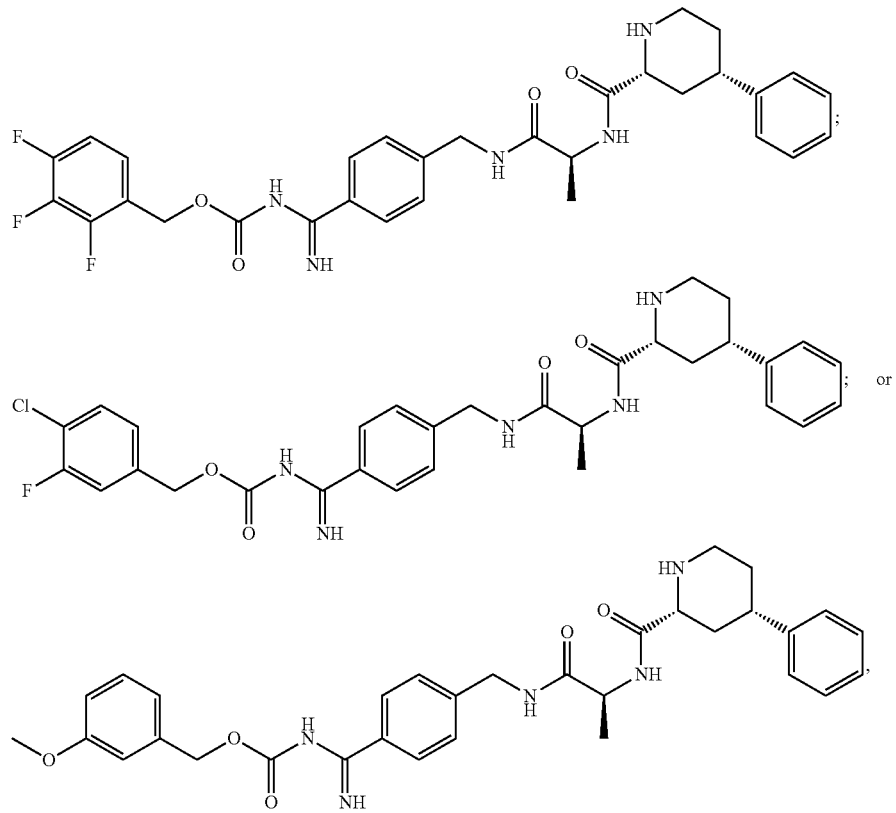

or a stereoisomer, tautomer, or pharmaceutically acceptable salt thereof.

20. A pharmaceutical composition comprising a compound or pharmaceutically acceptable salt thereof of claim 1 and a pharmaceutically acceptable carrier or excipient.

21. A method for treating a MASP-2-associated disease or disorder in a subject in need thereof, the method comprising administering to the subject an effective amount of a compound of claim 1.

* * * * *